US008481267B2

(12) United States Patent
Burns et al.

(10) Patent No.: US 8,481,267 B2
(45) Date of Patent: Jul. 9, 2013

(54) GENETIC FINGERPRINTING AND IDENTIFICATION METHOD

(75) Inventors: Frank R. Burns, Philadelphia, PA (US); Xuan Peng, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 330 days.

(21) Appl. No.: 12/858,508

(22) Filed: Aug. 18, 2010

(65) Prior Publication Data

US 2011/0045478 A1 Feb. 24, 2011

Related U.S. Application Data

(60) Provisional application No. 61/235,999, filed on Aug. 21, 2009.

(51) Int. Cl.
*C12Q 1/68* (2006.01)
*C07H 19/00* (2006.01)
*C07H 21/00* (2006.01)

(52) U.S. Cl.
USPC ........................................ 435/6.12; 536/22.1

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,879,214 | A | 11/1989 | Kornher et al. |
| 5,126,239 | A | 6/1992 | Livak et al. |
| 5,874,215 | A | 2/1999 | Kuiper et al. |
| 6,263,286 | B1 | 7/2001 | Gilmanshin et al. |

OTHER PUBLICATIONS

Benecke, M., Random amplified polymorphic DNA (RAPD) typing of necrophageous insects (diptera, coleopteran) in criminal forensic studies: validation and use in practice; Forensic Science International, vol. 98, No. 3, pp. 157-168, Dec. 21, 1998.*

Healy Mimi, et al., Microbial DNA typing by automated repetitive-sequence based PCR; Journal of Clinical Microbiology, vol. 43, No. 1, pp. 119-207, Jan. 2005.*

Healy, M et al, Use of the Diversi Lab System for species and strain differentiation of Fusadum species isolates, Journal of Clinical Microbiology, Oct. 2005, vol. 43, No. 10, Oct. 2005, pp. 5278-5280.*

Pounder, June et al, Repetitive-sequence-PCR-based DNA fingerprinting using the Diversilab system for identification of commonly encountered dermatophytes, Journal of Clinical Microbiology, May 2005, vol. 43, No. 5, May 2005, pp. 2141-2147.*

Pounder, June et al, Clinical evaluation of repetitive sequence- based polymerase chain reaction using the Diversi-Lab System for strain typing of vancomycin-resistant enterococci, Diagnostic Microbiology and Infectious Disease, Mar. 2006, vol. 54, No. 3, pp. 183-187.*

Shutt, Cheryl et al, Clinical evaluation of the DiversiLab microbial typing system using repetitive-sequence-based PCR for characterization of *Staphylococcus aureus* strains, Journal of Clinical Microbiology, Mar. 2005, vol. 43, No. 3, pp. 1187-1192.*

Benecke, M., "Random amplified polymorphic DNA (RAPD) typing of necrophageous insects . . . ", Forensic Science International, vol. 98, No. 3, pp. 157-168, Dec. 21, 1998.

Healy Mimi, et al., "Microbial DNA typing by automated repetitive-sequence based PCR"; Journal of Clinical Microbiology, vol. 43, No. 1, pp. 119-207, Jan. 2005.

Healy M, et al., "Use of the Diversi Lab Sytem for Species . . . "; Journal of Clinical Microbiology, vol. 43, No. 10, pp. 5278-5280, Oct. 2005.

Hilton AC, et al., "Randon amplification of polymorphic DNA (RAPD) of *Salmonella*..", The Journal of Applied Bacteriology, vol. 81, No. 6, pp. 575-584, Dec. 1996.

Hilton AC, et al., "Optimization of RAPD for fingerprinting *Salmonella*", Letters in Applied Microbiology, vol. 24., No. 4, pp. 243-248, Apr. 1997.

Kuske CR, et al., "Small-scale DNA sample preparation method for field PCR . . . ", Applied and Environmental Microbiology, vol. 64, No. 7, pp. 2463-2472, Jul. 1998.

Pounder, June I. et al., "Repetitive-sequence-PCR-based DNA fingerprinting . . . ", Journal of Clinical Microbiology, vol. 43, No. 5, pp. 2141-2147, May, 2005.

Pounder, June I., et al., "Clinical evaluation of repetiitive sequence-based . . . "; Diagnostic Microbiology and Infectious Disease, vol. 54, No. 3, pp. 183-187, Mar. 2006.

Shutt Cheryl., et al., "Clinical evaluation of the DiversiLab microbial . . . "; Journal of Clinical Microbiology, vol. 43, No. 3, pp. 1187-1192, Mar. 2005.

PCT Search Report and Written Opion for International Application No. PCT/US2010/048004 dated Apr. 11, 2011.

Chan, Eugene, et al., "DNA Mapping Using Microfluidic Stretching and Single-Molecule Detection of Fluorescent Site-Specific Tags", Genome Res. 14:1137-1146 (2004).

Jeffreys, A.J., et al., "Individual-specific 'fingerprints' of human DNA", Nature vol. 316:76-69 (1985).

Louws, D.W., et al., "Specific genomic fingerpritns of phytopathogenic Xanthomonas and Pseudomonas . . . " Appl. Environ. Micro. 60:2286-95 (1994).

Versalovic, James, et al., "Genomic Finjgerprinting of Bacteria Using Repetitive Sequence-Based . . . " Methods Mol. Cell. Biol. 5:25-40 (1994).

Williams, John G.K., et al., "CNA polymorphisms amplified by arbitrary primers are useful as genetic markers", Nucleic Acids Res. 18:6531-35 (1990).

* cited by examiner

*Primary Examiner* — Christopher M Babic
*Assistant Examiner* — Aaron Priest

(57) ABSTRACT

The present disclosure provides methods for molecular fingerprinting for the characterization and identification of organisms. More specifically, in one aspect the present invention provides a method of identifying an organism in a sample by embedding fingerprint bands from any amplification based fingerprinting method within a DNA sequence so that small differences in size are resolvable. Fingerprint output is provided in a text file format that can then be analyzed by bioinformatics tools.

9 Claims, 2 Drawing Sheets

Phylogram

Phylogram

GENETIC FINGERPRINTING AND IDENTIFICATION METHOD

CROSS-REFERENCE TO RELATED APPLICATION

This application claims the benefit of U.S. Provisional Application No. 61/235,999, filed Aug. 21, 2009, which is incorporated by reference herein in its entirety.

FIELD OF THE INVENTION

This invention relates to the field of molecular biology and more specifically to methods for molecular fingerprinting for the characterization and identification of organisms.

BACKGROUND OF THE INVENTION

Central to the field of microbiology is the ability to positively identify microorganisms at the level of genus, species, or serotype. Correct identification is not only an essential tool in the laboratory, but it plays a significant role in the control of microbial contamination in the processing of food stuffs, the production of agricultural products, and the monitoring of environmental media, such as ground water. Of greatest concern is the detection and control of pathogenic microorganisms. Typically, pathogen identification has relied on methods for distinguishing phenotypic aspects, such as growth or motility characteristics, and for immunological and serological characteristics. Selective growth procedures and immunological methods are the traditional methods of choice for bacterial identification and these can be effective for the presumptive detection of a large number of species within a particular genus. However, these methods are time consuming and are subject to error. Selective growth methods require culturing and subculturing in selective media, followed by subjective analysis by an experienced investigator. Immunological detection (e.g., ELISA) is more rapid and specific, however, it still requires growth of a significant population of organisms and isolation of the relevant antigens. For these reasons, interest has turned to detection of bacterial pathogens based on nucleic acid sequence.

Nucleic acid polymorphism provides a means to identify species, serotypes, strains, varieties, breeds, or individuals based on differences in their genetic make up. Nucleic acid polymorphism can be caused by nucleotide substitution, insertion, or deletion. The ability to determine genetic polymorphism has widespread application in areas such as genome mapping, genetic linkage studies, medical diagnosis, epidemiological studies, forensics, and agriculture. Several methods have been developed to compare homogenous segments of DNA to determine if polymorphism exists.

One method for determining genetic polymorphism uses primers of an arbitrary sequence to amplify DNA by the polymerase chain reaction (PCR) (Williams et al., Nucleic Acids Res. 18:6531-35 (1990); U.S. Pat. No. 5,126,239, incorporated herein by reference). Because the primers are not designed to amplify a specific sequence, the technique is called random amplification of polymorphic DNA (RAPD) or arbitrarily primed PCR (APPCR). The primers used are at least seven nucleotides in length. Under the proper conditions, differences as small as a single nucleotide can affect the binding of the primer to the template DNA, thus resulting in differences in the distribution of amplification products produced between genomes.

Another method for identifying and mapping genetic polymorphisms has been termed amplified fragment length polymorphism (AFLP; U.S. Pat. No. 5,874,215, incorporated herein by reference). AFLP combines the use of restriction enzymes with the use of PCR. Briefly, restriction fragments are produced by the digestion of genomic DNA with a single or a pair of restriction enzymes. If a pair of enzymes is used, enzymes are paired based on differences in the frequency of restriction sites in the genome, such that one of the restriction enzymes is a "frequent cutter" while the remaining enzyme is a "rare cutter." The use of two enzymes results in the production of single and double digestion fragments. Next, double stranded synthetic oligonucleotide adaptors of 10-30 bases are ligated onto the fragments generated. Primers are then designed based on the sequence of the adapters and the restriction site. When pairs of restriction enzymes are used, nucleotides extending into the restriction sites are added to the 3' end of the primers such that only fragments generated due to the action of both enzymes (double cut fragments) are amplified. Using this method, any polymorphism present at or near the restriction site will affect the binding of the primer and thus the distribution of the amplification products. In addition, any differences in the nucleotide sequence in the area flanked by the primers will also be detected. AFLP allows for the simultaneous co-amplification of multiple fragments.

A further method is Direct Linear Analysis (DLA), which analyzes individual DNA molecules bound with sequence-specific tags (see Chan et al., Genome Res. 14:1137-46 (2004); U.S. Pat. No. 6,263,286, incorporated herein by reference). The method is intended to identify repetitive information in DNA, which is moved past at least one station, at which labelled units of DNA interact with the station to produce a DNA-dependent impulse. Because the extended objects are similar, or preferably identical, and comprise a similar, or preferably identical, pattern of labelled units, a characteristic signature of interactions is repeated as each extended object moves past a station or a plurality of stations. This repetitive information is extracted from the overall raw data by means of an autocorrelation function and is then used to determine structural information about the DNA.

Another method is amplification of repetitive elements (REP-PCR). This technique is based on families of repetitive DNA sequences present throughout the genome of diverse bacterial species (reviewed by Versalovic et al., Methods Mol. Cell. Biol. 5:25-40 (1994)). Repetitive extragenic palindromic (REP) sequences are thought to play an important role in the organization of the bacterial genome. Genomic organization is believed to be shaped by selection and the differential dispersion of these elements within the genome of closely related bacterial strains can be used to discriminate between strains (see, e.g., Louws et al., Appl. Environ. Micro. 60:2286-95 (1994)). REP-PCR utilizes oligonucleotide primers complementary to these repetitive sequences to amplify the variably sized DNA fragments lying between them. The resulting products are separated by electrophoresis to establish the DNA "fingerprint" for each strain.

The output data of these fingerprinting systems generally is measured by assigning band sizes, though these assignments are somewhat imprecise depending on the sizing ladder used for the comparison. In addition, the output data can be difficult to compare between laboratories and often relies on the use of expensive proprietary software programs (such as BioNumerics, Applied Maths, Austin, Tex.) to handle the data.

SUMMARY OF THE INVENTION

Applicants have solved the aforementioned problems by embedding the fingerprint bands from any amplification based fingerprinting method within a DNA sequence so that small differences in size are resolvable. Fingerprint output is provided in a text file format that can then be analyzed by powerful, freeware bioinformatics tools.

One aspect is for a method of identifying an organism in a sample comprising: (a) providing a sample comprising said organism, said organism comprising at least one nucleic acid; (b) combining said sample or the at least one nucleic acid therefrom with an amplification mix comprising at least one labeled oligonucleotide primer; (c) generating at least one labeled amplification product from the at least one nucleic acid of said organism using a nucleotide amplification technique employing said at least one labeled oligonucleotide primer; (d) combining said at least one labeled amplification product with products of a DNA sequencing reaction to create a separation mix; and (e) separating said separation mix on the basis of oligonucleotide length in a fluorescent DNA sequencing instrument to generate a sequence embedded fingerprint pattern for said organism.

In some aspects, the method comprises after step (e) the further steps of: (f) comparing said sequence embedded fingerprint pattern for said organism to a database containing sequence embedded fingerprint patterns for known organisms; and (g) identifying said organism as a function of said comparison to said database.

Another aspect is for an isolated polynucleotide comprising the nucleic acid sequence set forth in SEQ ID NO:1, SEQ ID NO:2, SEQ ID NO:3, SEQ ID NO:4, or SEQ ID NO:5.

Other objects and advantages will become apparent to those skilled in the art upon reference to the detailed description that hereinafter follows.

SUMMARY OF THE SEQUENCES

SEQ ID NOs:1-4 and 25 are the nucleotide sequences of oligonucleotide primers useful in the present invention. Each primer can be employed alone or in conjunction with one or more other primers. For example, SEQ ID NOs:1-4 can be employed together to create the FB1D1 primer mix, while SEQ ID NO:25 can be employed alone as the FP5 primer.

SEQ ID NOS:5-7, 13, and 14 are the nucleotide sequences resulting from operating the method of the present invention with negative control PCR reactions obtained using the FB1D1 primer set.

SEQ ID NOS:8-12 are the nucleotide sequences resulting from operating the method of the present invention with PCR reactions obtained using the FB1D1 primer set and *Saccharomyces cerevisiae* DNA.

SEQ ID NOS:15-19 are the nucleotide sequences resulting from operating the method of the present invention with PCR reactions obtained using the FB1D1 primer set and *Salmonella enterica* DNA.

SEQ ID NOS:20-24 are the nucleotide sequences resulting from operating the method of the present invention with PCR reactions obtained using the FB1D1 primer set and *Staphylococcus aureus* DNA.

SEQ ID NOS:26-30 are the nucleotide sequences resulting from operating the method of the present invention with negative control PCR reactions obtained using the FP5 primer.

SEQ ID NOS:31-35 are the nucleotide sequences resulting from operating the method of the present invention with PCR reactions obtained using the FP5 primer and *Staphylococcus aureus* DNA.

SEQ ID NOS:36-40 are the nucleotide sequences resulting from operating the method of the present invention with PCR reactions obtained using the FP5 primer and *Salmonella enterica* DNA.

SEQ ID NOS:41-45 are the nucleotide sequences resulting from operating the method of the present invention with PCR reactions obtained using the FP5 primer and *Saccharomyces cerevisiae* DNA.

SEQ ID NO:46 is the consensus nucleotide sequence obtained from a sequence comparison of SEQ ID NOS:21-23.

SEQ ID NO:47 is the consensus nucleotide sequence obtained from a sequence comparison of SEQ ID NOS:33-35.

SEQ ID NO:48 is the consensus nucleotide sequence obtained from a sequence comparison of SEQ ID NOS:9-11.

SEQ ID NO:49 is the consensus nucleotide sequence obtained from a sequence comparison of SEQ ID NOS:41, 43, and 45.

SEQ ID NO:50 is the consensus nucleotide sequence obtained from a sequence comparison of SEQ ID NOS:17-19.

SEQ ID NO:51 is the consensus nucleotide sequence obtained from a sequence comparison of SEQ ID NOS:36-38.

The sequences conform with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. 1.822.

DETAILED DESCRIPTION

Figure 1A:
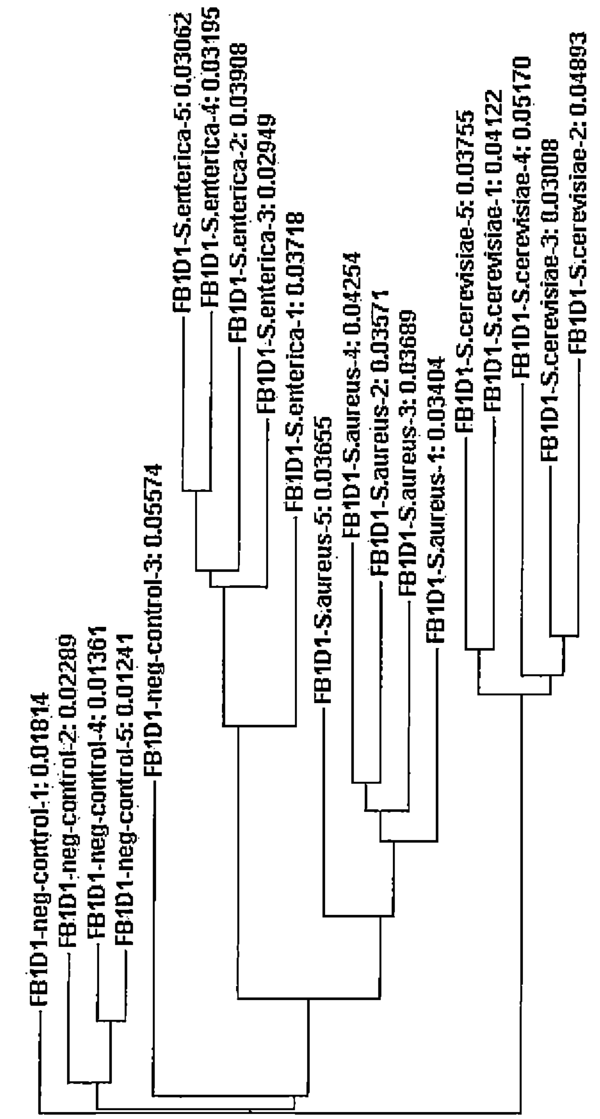
FIG. 1A shows a phylogram generated from a Clustal W alignment of all sequence reads from primer mix FB1D1 of Example 1.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The term "comprising" is intended to include embodiments encompassed by the terms "consisting essentially of" and "consisting of." Similarly, the term "consisting essentially of" is intended to include embodiments encompassed by the term "consisting of."

The term "oligonucleotide" as used herein refers to a molecule comprised of two or more deoxyribonucleotides or ribonucleotides.

The term "primer" as used herein refers to an oligonucleotide of any arbitrary sequence, whether occurring naturally, as in a purified restriction digest, or produced synthetically, that is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. It is preferable that primers are sequences that do not form a secondary structure by base pairing with other copies of the primer or sequences that form a "hair pin" configuration. The sequence conveniently can be generated by computer or selected at random from a gene bank. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide.

In the present disclosure, primers used for amplification based fingerprint methods are labelled with a fluor. Following generation of the fingerprint products by amplification, the fingerprint amplicons are comingled with the product of a previously performed DNA sequencing reaction. The comingled products are then run to produce a DNA sequence from a fluorescent DNA sequencing instrument. The sequence output is perturbed at positions where the fingerprint products are migrating with like-sized DNA sequencing fragments. The perturbations result in an altered DNA sequence output from the instrument. These alterations are reproducible, and comparison of the output sequences can be used to characterize and/or identify the organism whose DNA was subject to the fingerprinting method.

The nucleic acids to be analyzed by a process described herein may be DNA or RNA, and the DNA or RNA may be double stranded or single stranded. Any source of nucleic acid, in purified or nonpurified form, can be utilized as the starting nucleic acid. For example, the nucleic acid may be from a natural DNA or RNA from any source, including virus, bacteria, and higher organisms such as plants, animals, and microbes or from cloned DNA or RNA. Additionally, the nucleic acid may constitute the entire nucleic acid or may be a fraction of a complex mixture of nucleic acids. Preferably, the nucleic acid is deoxyribonucleic acid.

Processes described herein are applicable to any nucleic acid-containing starting material, including foods and allied products, vaccines and milk infected with a virus or a bacterium, whole blood, blood serum, buffy coat, urine, feces, liquor cerebrospinalis, sperm, saliva, tissues, and cell cultures (such as mammalian cell cultures and bacterial cultures). The processes are also applicable to relatively pure input materials, such as the product of a PCR or the product to be purified further of another process for recovering nucleic acids.

The step of generating an amplified nucleic acid product can be performed by, for example, RAPD PCR, AFLP PCR, REP-PCR, or DLA. Using RAPD as an example, the choice of nucleic acid polymerase used in the extension reaction, depends on the nature of the template. For DNA template strands, suitable commercially available DNA polymerase includes DNA polymerase obtained from the thermophilic bacterium *Thermus aquaticus* (Taq polymerase) or other thermostable polymerases. Structural variants and modified forms of this and other DNA polymerases would also be expected to be useful in the process of the present invention. For RNA templates, reverse transcriptase is an example of a DNA polymerase that would also be expected to be useful. In the presence of the nucleoside triphosphate substrates, natural or analogues, the polymerase extends the length of the primer in the 3' direction. The sequence of the extension product will generally be complementary to the corresponding sequence of the template strand.

The nucleoside triphosphate substrates are employed as described in PCR Protocols, A Guide to Methods and Applications, M. A. Innis, D. H. Gelfand, J.-J. Sninsky and T. J. White, eds. pp. 3-12, Academic Press (1989), which is incorporated by reference, and U.S. Pat. Nos. 4,683,195 and 4,683,202, both incorporated by reference. The substrates can be modified for a variety of experimental purposes in ways known to those skilled in the art. As an example, at least one of the natural nucleoside triphosphate substrates may be replaced by a mobility-shifting analogue as taught in U.S. Pat. No. 4,879,214, which is incorporated by reference.

Specifically, U.S. Pat. No. 4,683,202 to Mullis is directed to a process for amplifying any desired specific nucleic acid sequence contained in a nucleic acid or mixture thereof. The process of Mullis comprises treating separate complementary strands of the nucleic acid with a molar excess of two oligonucleotide primers, and extending the primers to form complementary primer extension products, which act as templates for synthesizing the desired nucleic acid sequence. The primers of Mullis are designed to be sufficiently complementary to different strands of each specific sequence to be amplified. The steps of the reaction may be carried out stepwise or simultaneously and can be repeated as often as desired.

In one embodiment, at least one primer of greater than seven nucleotides is provided. Primers can be synthesized by standard techniques known to those skilled in the art. In some embodiments, at least one primer of nine to ten nucleotides in length is employed. Conveniently, one primer is employed. The at least one primer is labelled, preferably with a fluorophore, which can be, for example, dR6G, dR110, dTAMRA, dROX, VIC, NED, PET, LIZ, 6-FAM, TAMRA, DyeMer488/615, DyeMer488/630, PE-TexasRed, ECD, Alexa Fluor 610RPE, FITC, Oregon Green 488, or Qdot525. Other fluorophores can also be employed.

In some embodiments, a nucleic acid is contacted with at least one oligonucleotide primer as described herein. The extension product is dissociated from the complementary random nucleic acid on which it was synthesized to produce a single-stranded molecule; and the random nucleic acid segment is amplified by contacting the single-stranded extension product with a primer from above under conditions as, for example, disclosed in PCR Protocols and U.S. Pat. No. 4,683,202 such that an amplification extension product is synthesized using the single strand produced (i.e., the dissociated extension product) as a template.

The comingled products are then run to produce a DNA sequence from a fluorescent DNA sequencing instrument. The sequence output is perturbed at positions where the fingerprint products are migrating with like-sized DNA sequencing fragments. The perturbations result in an altered DNA sequence output from the instrument. These alterations are reproducible, and comparison of the output sequences can be used to characterize and/or identify the organism whose DNA was subject to the fingerprinting method using powerful freeware sequence analysis tools such as BLAST and Clustal W.

A process disclosed herein can be used to construct a nucleic acid 'fingerprint'. Such fingerprints are specific to individual organisms and can be applied to problems of identification or distinguishing of individual organisms. Such a fingerprint would be constructed using multiple polymorphisms generated by different primers and detected by the present invention, just as the polymorphisms are used to create a fingerprint in Jeffreys, A. J., "Individual-Specific 'Fingerprints' of Human DNA", Nature 316:76-79 (1985), which is incorporated herein by reference. That is, genomes are compared for the presence of absence of polymorphisms.

In some embodiments, the steps of generating amplification products and producing an amplification profile after mixing the amplifications products with the oligonucleotide size ladder can be repeated at different stringency conditions as compared to that of a first pass through the process to generate a different amplification profile as compared to that generated by the first pass. Multiple repetitions are of course possible.

EXAMPLES

The present invention is further defined in the following Examples. It should be understood that these Examples, while indicating preferred embodiments of the invention, are given by way of illustration only. From the above discussion and these Examples, one skilled in the art can ascertain the preferred features of this invention, and without departing from the spirit and scope thereof, can make various changes and modification of the invention to adapt it to various uses and conditions.

Example 1

The hypothesis that labeled amplification based fingerprinting products could be detected and reproducibly placed within a DNA sequence by means of the invention was tested using Random amplification of polymorphic DNA (RAPD) fingerprinting to generate the fingerprinting products. PCR was performed using a mix of four primers labeled at the 5' end with a FAM fluor, collectively known as primer mix FB1D1 and single primer FP5 (see Table 1).

TABLE 1

| Primers | |
|---|---|
| **FB1D1 primer mix** | |
| 1. | 5′ FAM-CGCTTCGCGTTTTAAAAACCGACATGAGTACAATAC (SEQ ID NO: 1) |
| 2. | 5′ FAM-CGCTTCGCGTTTTAAAAACCGACATGAGTACAATCC (SEQ ID NO: 2) |
| 3. | 5′ FAM-CGCTTCGCGTTTTAAAAACCGACATGAGTACAATGC (SEQ ID NO: 3) |
| 4. | 5′ FAM-CGCTTCGCGTTTTAAAAACCGACATGAGTACAATTC (SEQ ID NO: 4) |
| **FP5 primer** | |
| 5. | 5′ FAM-ATCCGGCATATCTCGACATTCCTGATTACAATCC (SEQ ID NO: 25) |

For primer mix FB1D1, each primer was present in the reaction at 0.25 μM concentration in the presence of other components necessary for performing polymerase chain reaction (nucleotides, polymerase, buffer) in a total reaction volume of 30 μl; for single primer FP5, it was present in the reaction at 0.1 μM concentration in a total reaction volume of 30 μl, in the presence of the other components required by polymerase chain reaction.

Reactions were run either with or without (negative controls) the addition of purified microbial DNA from three diverse organisms (one yeast, one gram positive bacterium and one gram negative bacterium (Table 2)) at a concentration of 30 ng per reaction. Five replicates each were run for the negative control and each of the microbial DNA's.

TABLE 2

| Microbial species analyzed | |
|---|---|
| 1. *Salmonella enterica* (serovar Minnesota) MR595 | ATCC 49284D |
| 2. *Staphylococcus aureus* Mu3 | ATCC 700698D-5 |
| 3. *Saccharomyces cerevisiae* S288C | ATCC 204508D-5 |

PCR was carried out using a 2 minute hold at 95° C. followed by 10 cycles of 15 seconds at 95° C., 5 minutes at 40° C. and 1 minute at 70° C., followed by 30 cycles of 95° C. for 15 seconds and 3 minutes at 70° C.

PCR reaction products were cleaned up as appropriate for DNA sequence reactions prior to loading on a capillary electrophoresis sequence apparatus, at which time the PCR products are recovered in a 15 μl volume of $H_2O$.

A 2 μl aliquot of the PCR product is then added to 20 μl of deionized water. A commercial sequence standard (hsp 60, Applied Biosystems, Foster City, Calif.) is prepared as follows. A 1 μl aliquot of the sequence standard is mixed with 9 μl of formamide (HiDi, Applied Biosystems). 1.5 μl of the diluted PCR product is then added to the 10 μl sequence standard/formamide solution. Samples are then mixed, denatured as for a standard sequencing reaction and loaded on to an Applied Biosystems 3730 DNA sequencer and run using standard DNA sequencing conditions. The output sequence files are then analyzed using standard DNA sequence analysis tools.

Figure 1B:
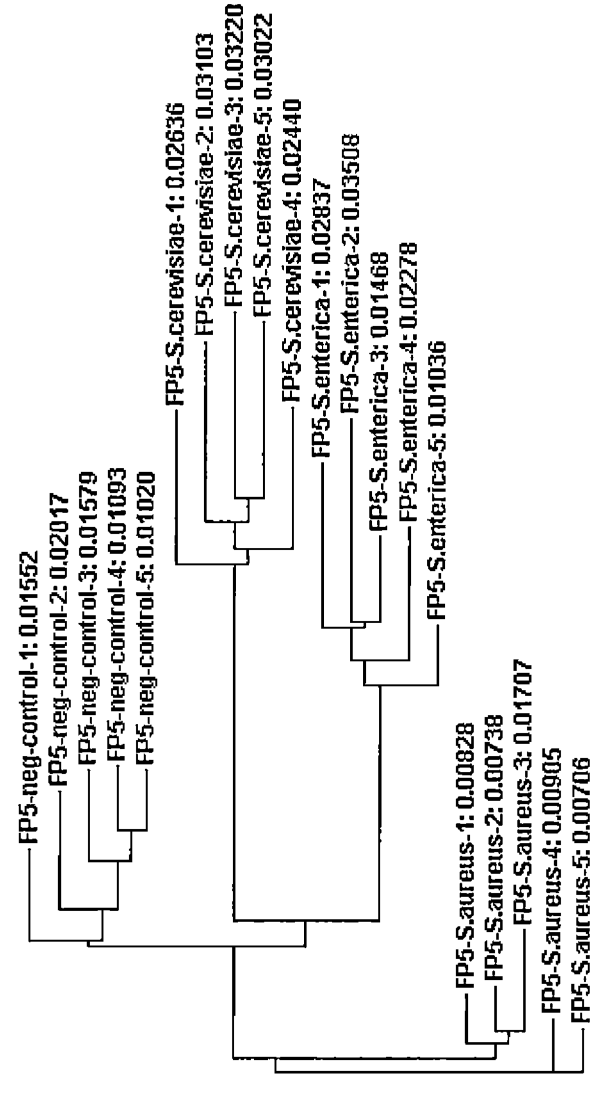
FIG. 1B shows a phylogram generated from a Clustal W alignment of all sequence reads from single primer FP5 of Example 1.

In order to test the ability of this invention to characterize an organism as belonging to a group (characterization) the sequences were examined using the Clustal W program (European Bioinformatics Institute web server). Two sets of alignments of sequences produced from primer mix FB1D1 and single primer FP5 of Example 1 are shown in Tables 3A and 3B and the resulting phylograms are shown in FIGS. 1A and 1B. As hypothesized, the perturbations of the sequence due to the comingling of the PCR products from the RAPD fingerprinting reaction were detected as changes in the sequence output from the instrument. Clustal W alignments show that the replicate samples from a single organism cluster together and are separate from the clusters for non-identical microorganisms.

TABLE 3A

CLUSTAL 2.0.11 multiple sequence alignment of all sequence reads from primer mix FB1D1 of Example 1.

| | | |
|---|---|---|
| SEQ ID NO: 5 FB1D1-neg-control-4 | -------------GTTGNT-CNNCTGCTGACAATGCTGCTGCTGCTTCNCCTCNCTGTCT | 46 |
| SEQ ID NO: 6 FB1D1-neg-control-5 | --------------------TCNCNGCTGACAATGCTGCTGCTGCTTCNCCTCNNNGTCT | 40 |
| SEQ ID NO: 7 FB1D1-neg-control-2 | --------GTNNNGTTGCTACTACTGCTGACAATGCTGCTGCTGCTTCTCCTCNNTGTCT | 52 |
| SEQ ID NO: 8 FB1D1-*S. cerevisiae*-5 | ------------TGTTGCTACTACTGCTGACAATGCTGCTGCTGCTTCTCCTCACTGTCT | 48 |
| SEQ ID NO: 9 FB1D1-*S. cerevisiae*-1 | -----CTGNTAATGTTGCTACTACTGCTGACAATGCTGCTGCTGCTTCTCCTCACTGTCT | 55 |
| SEQ ID NO: 10 FB1D1-*S. cerevisiae*-3 | ----NCNGNNNNNGNTGCTACTACTGCTGACAATGCTGCTGCTGCTTCTCCTCNCTGTCT | 56 |
| SEQ ID NO: 11 FB1D1-*S. cerevisiae*-2 | -----CTGTTAATGTTGCTACTACTGCTGACAATGCTGCTGCTGCTTCNCCTCNCTGTCT | 55 |

TABLE 3A-continued

CLUSTAL 2.0.11 multiple sequence alignment of all sequence reads from primer mix FB1D1 of Example 1.

```
SEQ ID NO: 12            -------------GTTGNT--CNCNGCTGACAATGCTGCTGCTGCTTCTCCTCACTGTCT     45
FB1D1-S. cerevisiae-4
SEQ ID NO: 13            --------GNTANGTTGCTNCTACTGCTGACAATGCTGCTGCTGCTTCNCCTCNCTGTCT     52
FB1D1-neg-control-1
SEQ ID NO: 14            GNTNNCTGTTAATGTTGCTACTACTGCTGACAATGCTGCTGCTGCTTCNCCTCNCTGTCT     60
FB1D1-neg-control-3
SEQ ID NO: 15            ------CNGNNNTGTTNCTCNN-CTGCTGACAATGCTGCTGNNGNNNCNCCTCNCTGTCT     53
FB1D1-S. enterica-5
SEQ ID NO: 16            ------CNGNNNNGTTGCTNCTACTGCTGACAATGCTGCTGNNGNNNCNCCTCNCTGTCT     54
FB1D1-S. enterica-4
SEQ ID NO: 17            ------CNGNNANGTTNNTCNN--NGCTGACAATGCTGCTGCNGCTTCNCCTCNCTGTCT     52
FB1D1-S. enterica-2
SEQ ID NO: 18            -------------GTTNNTCNN--NGCTGACAATGCTGCTGCNGCTTCTCCTCNCTGTCT     45
FB1D1-S. enterica-3
SEQ ID NO: 19            -------------GTTGCTNCTACTGCTGANAATGCTGCTGCTGCTTCTCCTCNCTGTCT     47
FB1D1-S. enterica-1
SEQ ID NO: 20            ----------------GNTCNC--NGNNGANNATGNTGCTGCTGCTTNNNGNNNCTGTCT     42
FB1D1-S. aureus-4
SEQ ID NO: 21            ---------TNNGTTGNTCTAC--NGNTGACNATGCTGCTGCTGCTTNNNNNNNCTGTCT     49
FB1D1-S. aureus-2
SEQ ID NO: 22            ------CNGTTATGTTGCTCTC--NGCTGACNATGCTGCTGCTGCTTCNNGNNNCTGTCT     52
FB1D1-S. aureus-3
SEQ ID NO: 23            -------------GTTGNTCNN--NGCTGACNATGCTGCTGCTGCTTNNNGNNNCTGTCT     45
FB1D1-S. aureus-1
SEQ ID NO: 24            ------CNGNNANGTTGNTCNN--NGCTGANNN-GCTGCTGCTGCTTCNNGTNNCTGTCT     51
FB1D1-S. aureus-5                    *  **    * *****  *            ****


FB1D1-neg-control-4      CCACTTCCTTGAACAATGCGCCGTCATGCTTCTTTTGCCTCCCGCTGCTCCAGAAAGCTA    106
FB1D1-neg-control-5      CCACTTCCTTGAACAATGCGCCGTCATGCTTCTTTTGCCTCCCGCTGCTCCAGAAAGCTA    100
FB1D1-neg-control-2      CCACTTCCTTGAACAATGCGCCGTCATGCTTCTTTTGCCTCCCGCTGCTCCAGAAAGCTA    112
FB1D1-S. cerevisiae-5    CCACTTCCTTGAACAATGCGCCGNCNTGCTTCTTTTGCCTCCCGCTGCTCCNGAGNGNTA    108
FB1D1-S. cerevisiae-1    CCACTTCCTTGAACAATGCGCCGNCNTGCTTCTTTTGCCTCCCGCTGCTCCNGAGNGCTA    115
FB1D1-S. cerevisiae-3    CCACTTCCTTGAACAATGCGCCGTCNTGCTTCTTTTGCCTCCCGCTGCTCCNNANNGNTA    116
FB1D1-S. cerevisiae-2    CCACTTCCTTGAACAATGCGCCGNCNTGCTTCTTTTGCCTCCCGCTGCTCCNGAGNGNTA    115
FB1D1-S. cerevisiae-4    CCACTTCCTTGAACAATGCGCCGNCNTGCTTCTTTTGCCTCCCGCTGCTCCANAGNGCTA    105
FB1D1-neg-control-1      CCACTTCCTTGAACAATGCGCCGTCATGCTTCTTTTGCCTCCCGCTGCTCCAGAAAGCTA    112
FB1D1-neg-control-3      CCACTTCCTTGAACAATGCGCCGTCATGCTTCTTTTGCCTCCCGCTGCTCCAGAAAGCTA    120
FB1D1-S. enterica-5      CCACTTCCTTGAACAATGCGCCGTCATGCTTCTTTTGCCTCCCGCTGCTCCAGAAAGCTA    113
FB1D1-S. enterica-4      CCACTTCCTTGAACAATGCGCCGTCATGCTTCTTTTGCCTCCCGCTGCTCCAGAAAGCTA    114
FB1D1-S. enterica-2      CCACTTCCTTGAACAATGCGCCGTCATGCTTCTTTTGCCTCCCGCTGCTCCAGAAAGCTA    112
FB1D1-S. enterica-3      CCACTTCCTTGAACAATGCGCCGTCATGCTTCTTTTGCCTCCCGCTGCTCCAGAAAGCTA    105
FB1D1-S. enterica-1      CCACTTCCTTGAACAATGCGCCGTCATGCTTCTTTTGCCTCCCGCTGCTCCAGAAAGCTA    107
FB1D1-S. aureus-4        CCACTTCCTTGAACAATGCGCCGTCATGCTTCTTTTGCCTCCCGCTGCTCCAGAAAGCTA    102
FB1D1-S. aureus-2        CCACTTCCTTGAACAATGNGCCGTCATGCTTCTTTTGCCTCCCGCTGCTCCAGAAAGCTA    109
FB1D1-S. aureus-3        CCACTTCCTTGAACAATGNGCCGTCATGCTTCTTTTGCCTCCCGCTGCTCCAGAAAGCTA    112
FB1D1-S. aureus-1        CCACTTCCTTGAACANTGCGCCGTCATGCTTCTTTTGCCTCCCGCTGCTCCAGAAAGCTA    105
FB1D1-S. aureus-5        CCACTTCCTTGAACAATGCGCCGTCATGCTTCTTTTGCCTCCCGCTGCTCCAGAAAGCTA    111
                         *************** ** **** * *************************  *  * **

FB1D1-neg-control-4      GGCCGCAGATCAGAACCACCACAGTCAATATCACCACCTTCCTCTTATAGATTCGGAATC    166
FB1D1-neg-control-5      GGCCGCAGATCAGAACCACCACAGTCAATATCACCACCTTCCTCTTATAGATTCGGAATC    160
FB1D1-neg-control-2      GGCCGCAGATCAGAACCACCACAGTCAATATCACCACCTTCCTCTTATAGATTCGGAATC    172
FB1D1-S. cerevisiae-5    GGCCGCAGATCANAACCACCACAGTCAATATCACCACCTTCNTCTTATAGATTCGGAATC    168
FB1D1-S. cerevisiae-1    GGCCGCAGATCAGAACCACCACAGNCAATATCACCACCNNCNNCTTATAGATTCGGAATC    175
FB1D1-S. cerevisiae-3    GGCCGCAGATCAGAACCACCACAGTCAATATCACCACCTTCCTCTTATAGATTCGGAATC    176
FB1D1-S. cerevisiae-2    GGCCGCAGATCAGAACCACCACAGNCAATATCACCACCNTCNNCTTATANATTCGGAATC    175
FB1D1-S. cerevisiae-4    GGCCGCAGATCANAACCACCACAGNCAATATCACCACCNTCNNCTTATAGATTCGGAATC    165
FB1D1-neg-control-1      GGCCGCAGATCAGAACCACCACAGTCAATATCACCACCTTCCTCTTATAGATTCGGAATC    172
FB1D1-neg-control-3      GGCCGCAGATCAGAACCACCACAGTCAATATCACCACCTTCCTCTTATAGATTCGGAATC    180
FB1D1-S. enterica-5      GGCCGCAGATCAGAACCACCACAGTCAATATCACCNCCTTCCTCTTATAGATTCGGAATC    173
FB1D1-S. enterica-4      GGCCGCAGATCAGAACCACCACAGTCAATATCACCACCTTCCTCTTATAGATTCGGAATC    174
FB1D1-S. enterica-2      GGCCGCAGATCANAACCACCACAGTCAATATCACCACCTTCCTCTTATAGATTCGGAATC    172
FB1D1-S. enterica-3      GGCCGCAGATCANAACCACCACAGTCAATATCACCACCTTCCTCTTATAGATTCGGAATC    165
FB1D1-S. enterica-1      GGCCGCAGATCAGAACCACCACAGTCAATATCACCACCTTCCTCTTATAGATTCGGAATC    167
FB1D1-S. aureus-4        NGNCNNAGATCAGAACCACCACAGTCANNNTCNCCNCCTTCCTCTTATAGATTCGGAATC    162
FB1D1-S. aureus-2        NGNNNNAGATCAGAACCACCACAGNCNNNNTNACCNCCTTCCTCTTATAGATTCGGAATC    169
FB1D1-S. aureus-3        GGNCNNAGATCAGAACCACCACAGNCNNTATCNCCNCCTTCCTCTTATAGATTCGGAATC    172
FB1D1-S. aureus-1        NGNCNNAGATCAGAACCACCACAGNCNNNNTCNCCNCCTTCCTCTTATAGATTCGGAATC    165
FB1D1-S. aureus-5        GGCCGCAGATCAGAACCACCACAGTCNATATCACCNCCTTCCTCTTATAGATTCGGAATC    171
                          *    ****** *********** *    *  ** **  *  ****** **********

FB1D1-neg-control-4      TCATGATAGGGGCTCAGCCTCTGTGCGAGTGGAGAGAAGTTTGCAGGCGAGCTGAGGAGC    226
FB1D1-neg-control-5      TCATGATAGGGGCTCAGCCTCTGTGCGAGTGGAGAGAAGTTTGCAGGCGAGCTGAGGAGC    220
FB1D1-neg-control-2      TCATGATAGGGGCTCAGCCTCTGTGCGAGTGGAGAGAAGTTTGCAGGCGAGCTGAGGAGC    232
FB1D1-S. cerevisiae-5    TCATGATAGGGGCTCAGCCTCTGTGCGAGTGGAGAGAAGTTTGCAGGCGAGCTGAGGAGC    228
FB1D1-S. cerevisiae-1    TCATGATAGGGGCTCAGCCTCTGTGCGAGTGGAGAGAAGTTTGCAGGCGAGCTGAGGAGC    235
```

TABLE 3A-continued

CLUSTAL 2.0.11 multiple sequence alignment of all sequence reads from primer mix FB1D1 of Example 1.

```
FB1D1-S. cerevisiae-3     TCATGATAGGGGCTCAGCCTCTGTGCGAGTGGAGAGAAGTTTGCAGGCGAGCTGAGGAGC    236
FB1D1-S. cerevisiae-2     TCATGATAGGGGCTCAGCCTCTGTGCGAGTGGAGAGAAGTTTGCAGGCGAGCTGAGGAGC    235
FB1D1-S. cerevisiae-4     TCATGATAGGGGCTCAGCCTCTGTGCGAGTGGAGAGAAGTTTGCAGGCGAGCTGAGGAGC    225
FB1D1-neg-control-1       TCATGATAGGGGCTCAGCCTCTGTGCGAGTGGAGAGAAGTTTGCAGGCGAGCTGAGGAGC    232
FB1D1-neg-control-3       TCATGATAGGGGCTCAGCCTCTGTGCGAGTGGAGAGAAGTTTGCAGGCGAGCTGAGGAGC    240
FB1D1-S. enterica-5       TCATGATAGGGGCTCAGCCTCTGTGCGAGTGGAGAGAAGTTNGNNNNNNAGCTGANGAGC    233
FB1D1-S. enterica-4       TCATGATAGGGGCTCAGCCTCTGTGCGAGTGGAGAGAAGTTNNNNNNNNAGCTGANGANC    234
FB1D1-S. enterica-2       TCATGATAGGGGCTCAGCCTCTGTGCGAGTGGAGAGAAGTTNNNNNGNNAGCTGANGANC    232
FB1D1-S. enterica-3       TCATGATAGGGGCTCAGCCTCTGTGCGAGTGGAGAGAAGTTNNNNNNNGAGCTGAGGAGC    225
FB1D1-S. enterica-1       TCATGATAGGGGCTCAGCCTCTGTGCGAGTGGAGAGAAGTTNGCAGGCGAGCTGAGGAGC    227
FB1D1-S. aureus-4         TCATGATAGGGNNTCNNCCTCTGTGCGAGTGGAGAGAAGTTTGCAGGCGAGCTGANGAGC    222
FB1D1-S. aureus-2         TCATGATAGGGNNTCNNCCTCTGTGCGAGTGGAGAGAAGTTTGCAGGCNAGCTGANGAGC    229
FB1D1-S. aureus-3         TCATGATAGGGNNTCNNCCTCTGTGCGAGTGGAGAGAAGTTTGCAGGCGAGCTGANGAGC    232
FB1D1-S. aureus-1         TCATGATAGGGGNTCNNCCTCTGTGCGAGTGGAGAGAAGTTTGCAGGCGAGCTGAGGAGC    225
FB1D1-S. aureus-5         TCATGATAGGGGCTCANCCTCTGTGCGAGTGGAGAGAAGTTTGCAGGCGAGCTGAGGAGC    231
                          ***********  **  ************************        ****** ** *

FB1D1-neg-control-4       AATTGCAGGTGATATGATGTGCTCGGCTCAAGAAGCGGGCCCGNNNNGNNNNNNNNCGTG    286
FB1D1-neg-control-5       AATTGCAGGTGATATGATGTGCTCGGCTCAAGAAGCGGGCCCGGNNNNNNNNNNNNCGTG    280
FB1D1-neg-control-2       AATTGCAGGTGATATGATGTGCTCGGCTCAAGAAGCGGGCCCGGAGAGGAANANNTCGTG    292
FB1D1-S. cerevisiae-5     AATTGCAGGTGATATGATGTGCTCGGCTCNNNGGGCGNGGN-NNNNNNNNNNANGNCNNG    287
FB1D1-S. cerevisiae-1     AATTGCNGGTGATATGATGTGCTCGGCTCNNNGGGNNNGGN-GNNNNNNNNANGNCNNG-    293
FB1D1-S. cerevisiae-3     AATTGCAGGTGATATGATGTGCTCGGCTCANGGGGNNNNNN-NNNNNNNNNNNNNNNNNG    295
FB1D1-S. cerevisiae-2     AATTGCAGGTGATATGATGTGCTCGGCTCANNGGGCNNNNN-NNNNNNNNNNNNNNNNTG    294
FB1D1-S. cerevisiae-4     AATTGCAGGTGATATGATGTGCTCGGCTCNNNGGGCGNNNN-NNNNNNNNNNNNNNNCNNG    284
FB1D1-neg-control-1       AATTGCAGGTGATATGATGTGCTCGGCTCAAGAAGCGGGCCCNNNGAGNAGGANGTCGTG    292
FB1D1-neg-control-3       AATTGCAGGTGATATGATGTGCTCGGCTCAAGAAGCNGNNNNNGNNAGGAAGAAGTCGTG    300
FB1D1-S. enterica-5       AATTGCAGGTGATATGATGTGCTCGGCTCAAGAAGCGGGCCCGGAGAGGAAGAAGNNNNN    293
FB1D1-S. enterica-4       AATTGCAGGTGATATGATGTGCTCGGCTCAAGAAGCGGGCCCGGANANGAANAAGTNNNN    294
FB1D1-S. enterica-2       AATTGCAGGTGATATGATGTGCTCGGCTCAAGAAGCGGGCCCGGAGNNNNNNAAGNNNNN    292
FB1D1-S. enterica-3       AATTGCAGGTGATATGATGTGCTCGGCTCAAGAAGCGGGCCNGGNNAGGAAGAAGNNNNN    285
FB1D1-S. enterica-1       AATTGCAGGTGATATGATGTGCTCGGCTCAAGAAGCGGGCCNGNNNNGNNNGAAGTCNNG    287
FB1D1-S. aureus-4         ANTTGCAGGNGNNNNNNTGTGCTCGGCTCAAGAAGCGGGCCCNGNNNNNANNAAGTCGTG    282
FB1D1-S. aureus-2         ANTTGCAGGNGNNNGNNTGTGCTCGGCTCAAGANGCGGGNCCGGANAGGAAGAAGTCGTG    289
FB1D1-S. aureus-3         AATTGCAGGTGNNNNNATGTGCTCGGCTCAAGAAGCGGGCCCGGAGAGGAAGAAGTCGTG    292
FB1D1-S. aureus-1         ANTTGCAGGTGNNNNNATGTGCTCGGCTCAAGAAGCGGGCCCGGAGAGGAAGAAGTCGTG    285
FB1D1-S. aureus-5         AATTGCAGGTGNNNNNNNGTGCTCGGCTCAAGAAGCGGGCCNNGNNNNNNNNNNAGTCGTG    291
                          * **** ** * *********** *

FB1D1-neg-control-4       CCGGGG-CTAATTATTGGCAAAACGAGCTCTTGTTGTAAACATTGATCCAACTGGAATGN    345
FB1D1-neg-control-5       CCGGGG-CTAATTATTGGCAAAACGAGCTCTTGTTGTAAACATTGATCCAACTGGAANGN    339
FB1D1-neg-control-2       CCGGGG-CTAATTATTGGCAAAACGAGCTCTTGTTGTAAACATTGATCCAACTGGAATGN    351
FB1D1-S. cerevisiae-5     CCGGGG-CTAATTATTGGCAAAACGAGCTCTTGTTGTAAACATTGATCCGGGNGGNATGN    346
FB1D1-S. cerevisiae-1     CCGGGG-CTAATTATTGGCAAAACGAGCTCTTGTTGTAAACATTGATCCNNNNGGNNNGT    352
FB1D1-S. cerevisiae-3     CCGGGG-CTAATTATTGGCAAAACGAGCTCTTGTTGTAAACATTGATCCAACTGGNNGGN    354
FB1D1-S. cerevisiae-2     CCGGGG-CTAATTATTGGCAAAACGAGCTCTTGTTGTAAACATTGATCCAACTGGNNGGN    353
FB1D1-S. cerevisiae-4     CCGGGG-CTAATTATTGGCAAAACGAGCTCTTGTTGTAAACATTGATCCAACTGNNNNGN    343
FB1D1-neg-control-1       CCGGGG-CTAATTATTGGCAAAACGAGCTCTTGTTGTAAACATTGATCCAACTGGNNNGN    351
FB1D1-neg-control-3       CCGGGG-CTAATTATTGGCAAAACGAGCTCTTGTTGTAAACATTGATCCNNCTGGANTNN    359
FB1D1-S. enterica-5       NCGGGGGCTAATTATTGGCAAAACGAGCTCTTGTTNNNNNNNNNNNNNNGNNNNNNNNNN    353
FB1D1-S. enterica-4       NCNNGG-CTAATTATTGGCAAAACGAGCTCTTGTTNNNNNNNNNNNNNNGNNNNNNNNNN    353
FB1D1-S. enterica-2       NNNNNN-NTAATTATTGGCAAAACGAGCTCTTGTTNNNNNNNNNNNNNNGNNNNNNNNNN    351
FB1D1-S. enterica-3       NNNNNN-NTAATTATTGGCAAAACGAGCTCTTGTTGTANNNNNNNNNNNGNNNNNNNNNN    344
FB1D1-S. enterica-1       NCGNGG-CTAATTATTGGCAAAACGAGCTCTTGTTGTANNNNNNNNNNNGNNNNNNNNNN    346
FB1D1-S. aureus-4         CCGGGG-CTAATTATTGGCAAAACGAGCTCTTGTTGTAAACATTGANNNGGGGGGGGGGN    341
FB1D1-S. aureus-2         CCGGGG-CTAATTATTGGCAAAACGAGCTCTTGTTGTAAACATTGNNNNNNNNNNNNNNN    348
FB1D1-S. aureus-3         CCGGGG-CTAATTATTGGCAAAACGAGCTCTTGTTGNAAACNTNGNNNGGGGGGGGNNNN    351
FB1D1-S. aureus-1         CCGGGG-CTAATTATTGGCAAAACGAGCTCTTGTTGTAAACATNGNNNNNNNNNNNNNNN    344
FB1D1-S. aureus-5         CCGGGG-CTAATTATTGGCAAAACGAGCTCTTGTTGTAAACATTGANNNNNNNNNNNNNN    350
                                  ***************************

FB1D1-neg-control-4       CNCTAATNNNNNNNTCAATATTCCATAAGGCATGATGGTTGCTCAGAGGCAGGAGAAGAG    405
FB1D1-neg-control-5       CNCTAANNNNNNAT-CAATATTCCATAAGGCATGATGGTTGCTCAGAGGCAGGAGAAGAG    398
FB1D1-neg-control-2       CNCTAANNNNNNNN-NAATATTCCATAAGGCATGATGGTTGCTCAGAGGCAGGAGAAGAG    410
FB1D1-S. cerevisiae-5     NNNNNANGNNNNNN-NNNNNNGNNNNNNGGNATGATGGTTGCTCAGAGGCAGGAGAAGAG    405
FB1D1-S. cerevisiae-1     NNNNNNNGGNGNNN-GANNNTGNNNNNNGGNATGATGGTTGCTCAGAGGCAGGAGAAGAG    411
FB1D1-S. cerevisiae-3     NNNNNATGGNGNNN-NNNNNTGCCNNNNNGCATGATGGTTGCTCAGAGGCAGGAGAAGAG    413
FB1D1-S. cerevisiae-2     NNNNNATGGNGNNN-GNNNNTGNNNNNNGGGATGATGGTTGCTCAGAGGCAGGAGAAGAG    412
FB1D1-S. cerevisiae-4     NNNNNANGGNGNNN-NNNNGTGNNNNNNGGNATGATGGTTGCTCAGAGGCAGGAGAAGAG    402
FB1D1-neg-control-1       NACTNANNNNNNNN-CAATATTCCATAAGGCATGATGGTTGCTCAGAGGCAGGAGAAGAG    410
FB1D1-neg-control-3       NNNNNATGGCGAAT-CAATATTCCATAAGGCATGATGGTTGCTCAGAGGCAGGAGAAGAG    418
FB1D1-S. enterica-5       NNACNNNNGGNNNNNCAATATTCCNTANNGCATGATGGTTGCTCAGAGGCANNNNNNNAG    413
FB1D1-S. enterica-4       NNNCTNNNNNNGNNCNA-TATTCCNTAANGCATGATGGTTGCTCAGAGGCAGGNNNNNAN    412
FB1D1-S. enterica-2       NA--CTANNGNNGNNCAATATTCCNTANNGCATGATGGTTGCTCAGAGGCAGNNNNNNAG    409
FB1D1-S. enterica-3       NA--CTNNNNGNGNNCAATATTCCNTANNGCATGATGGTTGCTCAGAGGCAGNNNNNNAG    402
FB1D1-S. enterica-1       NC--TANNGNNNNATCNATATTCCNTAANGCATGATGGTTGCTCAGAGGCANGNNNNA-G    403
FB1D1-S. aureus-4         NNN-NNNNNNNA--TCAATATTCCATAAGGCATGATGGTTGCTCAGAGGCAGGAGAAGAG    398
```

TABLE 3A-continued

CLUSTAL 2.0.11 multiple sequence alignment of all sequence reads from primer mix FB1D1 of Example 1.

```
FB1D1-S. aureus-2        NNN-NNNNNNNNA-TCAATATTCCATAAGGCATGATGGTTGCTCAGAGGCAGGAGAAGAG     406
FB1D1-S. aureus-3        NNN-NNNNNNNNA-TCAATATTCCATAAGGCATGATGGTTGCTCAGAGGCAGGAGAAGAG     409
FB1D1-S. aureus-1        NNN-NNNNNNNNGNNCAATATTCCATAAGGCATGATGGTTGCTCAGAGGCAGGAGAAGAG     403
FB1D1-S. aureus-5        NNN-NNNNNNNNNNNCNATATTCCATAAGGCATGATGGTTGCTCAGAGGCAGGAGAAGAG     409
                                                      * ********************

FB1D1-neg-control-4      CAACGAATACGATCCTATAAAAGATAAAACATAAATAAACAGTCTTGATTATATTCTGGG     465
FB1D1-neg-control-5      CAACGAATACGATCCTATAAAAGATAAAACATAAATAAACAGTCTTGATTATATTCTGGG     458
FB1D1-neg-control-2      CAACGAATACGATCCTATAAAAGATAAAACATAAATAAACAGTCTTGATTATATTCTGGG     470
FB1D1-S. cerevisiae-5    CAACGAATACGATCCTATNAAAGATAAAACATAAATAAACAGTCTTGATTATATTCTGGG     465
FB1D1-S. cerevisiae-1    CAACGAATACGATCCTATNAAAGATAAAACATAAATAAACNGTCTTGATTATATTCTGGG     471
FB1D1-S. cerevisiae-3    CAACGAATACGATCCTATAAAAGATAAAACATAAATAAACAGTCTTGATTATATTCTGGG     473
FB1D1-S. cerevisiae-2    CAACGAATACNATCCTATAAAAGATAAAACATAAATAAACAGTCTTGATTATATTCTGGG     472
FB1D1-S. cerevisiae-4    CAACGAATACGATCCTATNAAAGATAAAACATAAATAAACAGTCTTGATTATATTCTGGG     462
FB1D1-neg-control-1      CAACGAATACGATCCTATAAAAGATAAAACATAAATAAACAGTCTTGATTATATTCTGGG     470
FB1D1-neg-control-3      CAACGAATACGATCCTATAAAAGATAAAACATAAATAAACAGTCTTGATTATATTCTGGG     478
FB1D1-S. enterica-5      CAANNNNNNCGATCCTATAAAAGATAAAACATAAATAAACAGTCTTGATTATATTCTGGG     473
FB1D1-S. enterica-4      CAANNNNNNCGATCCTATAAAAGATAAAACATAAATAAACAGTCTTGATTATATTCTGGG     472
FB1D1-S. enterica-2      CAACNNANNCNATCCTATAAAAGATAAAACATAAATAAACAGTCTTGATTATATTCTGGG     469
FB1D1-S. enterica-3      CAANNNANNCGATCCTATAAAAGATAAAACATAAATAAACAGTCTTGATTATATTCTGGG     462
FB1D1-S. enterica-1      CAACNAANACGATCCTATAAAAGATAAAACATAAATAAACAGTCTTGATTATATTCTGGG     463
FB1D1-S. aureus-4        CAACGAATACGATCCTATAAAAGATAAAACATAAATAAACAGTCTTGATTATATTCTGGG     458
FB1D1-S. aureus-2        CAACGAATACGATCCTATAAAAGATAAAACATAAATAAACAGTCTTGATTATATTCTGGG     466
FB1D1-S. aureus-3        CAACGAATACGATCCTATAAAAGATAAAACATAAATAAACAGTCTTGATTATATTCTGGG     469
FB1D1-S. aureus-1        CAACGAATACGATCCTATAAAAGATAAAACATAAATAAACAGTCTTGATTATATTCTGGG     463
FB1D1-S. aureus-5        CAACGAATACGATCCTATAAAAGATAAAACATAAATAAACAGTCTTGATTATATTCTGGG     469
                                  * ******* ********************* *******************

FB1D1-neg-control-4      TATTAAAGCCACAATCAGAACAAATATATGCTTTGTATCTTTTCTTGCCTTCTTCAT-TA     524
FB1D1-neg-control-5      TATTAAAGCCACAATCAGAACAAATATATGCTTTGTATCTTTTCTTGCCTTCTTCAT-TA     517
FB1D1-neg-control-2      TATTAAAGCCACAATCAGAACAAATATATGCTTTGTATCTTTTCTTGCCTTCTTCAT-TA     529
FB1D1-S. cerevisiae-5    TATTAAANNCNCNGNCNGAACAAATATATGCTTTGTNNNNNNTNNNGCCTTNNNNNN-GN     524
FB1D1-S. cerevisiae-1    TATTAAANNCNNNGNNAGAACAAATATATGCTTTNNNNNNNNTCNNGNCNNNNNNNN-NN     530
FB1D1-S. cerevisiae-3    TATTAAAGNCNCAGNCAGAACAAATATATGCTTTGTNNCTNNNCNTGCCTTCTTNNN-NN     532
FB1D1-S. cerevisiae-2    TATTAAANNNNNNGNCAGAACAAATATATGCTTTGNNNNNTNNCNTGNNNNCNNNNG-GN     531
FB1D1-S. cerevisiae-4    TATTAAANNNNNNGTCAGAACAAATATATGCTTTGTNNNNNNNCNNNCCTTCTNNNN-GN     521
FB1D1-neg-control-1      TATTAAAGCCACAATCAGAACAAATATATGCTTTGTATCTTTTCTTGCCTTCTTCATTAC     530
FB1D1-neg-control-3      TATTAAAGCCACAATCAGAACAAATATATGCTTTGTATCTTTTCTTGCCNNNNNNGT-TA     537
FB1D1-S. enterica-5      TATTAAAGCCACAATCAGAACAAATATATGCTTTGTATCTTNNNNNGCCTTCTTCAN-NN     532
FB1D1-S. enterica-4      TATTAAAGCCACAATCAGAACAAATATATGCTTTGTATCTTNNNNNGCCTTCTTCAT-NN     531
FB1D1-S. enterica-2      TATTAAAGCCACAATCAGAACAAATATATGCTTTGTATCTTNNNNNGCCTTCTTCAN-NN     528
FB1D1-S. enterica-3      TATTAAAGCCACAATCAGAACAAATATATGCTTTGTATCTTNNNNNGCCTTCTTCAT-NN     521
FB1D1-S. enterica-1      TATTAAAGCCACAATCAGAACAAATATATGCTTTGTATCTTTNCNNGCCTTCTTCAT-NN     522
FB1D1-S. aureus-4        TATTAAAGCCACAATCAGAACAAATATATGCTTTGTATCTTTTCTTGCCTTCTTCAT-TN     517
FB1D1-S. aureus-2        TATTAAAGCCACAATCAGAACAAATATATGCTTTGTATCTTTTCTTGCCTTCTTCNT-TA     525
FB1D1-S. aureus-3        TATTAAAGCCACAATCAGAACAAATATATGCTTTGTATCTTTTCTTGCCTTCTTCAT-TA     528
FB1D1-S. aureus-1        TATTAAAGCCACAATCAGAACAAATATATGCTTTGTATCTTTTCTTGCCTTCTTCAT-NN     522
FB1D1-S. aureus-5        TATTAAAGCCACAATCAGAACAAATATATGCTTTGTATCTTTTCTTGCCTTCTTCAT-TA     528
                         *******          *****************

FB1D1-neg-control-4      CCAANNGNNTNNNCNNNNNNNNNNAGAGAACTTGTGGTAAGATAAGAAGATATTTTATTC     584
FB1D1-neg-control-5      CCNANNNNNNNNNNNNNNNNNNNTAAGAGAACTTGTGGTAAGATAAGAAGATATTTTATTC     577
FB1D1-neg-control-2      CCAACTGCTTNNNCGGCCNCNTTNAGAGAACTTGTGGTAAGATAAGAAGATATTTTATTC     589
FB1D1-S. cerevisiae-5    NNNNNNNNNNNNNCGGCCANNNNNNNAGAACTTGTGNNNNNATAAGAAGATATTTTATTC     584
FB1D1-S. cerevisiae-1    NNNNNNNNNNNNNNNGGCCACATTAAGAGAACTTGTNNNNNNNNTAAGAAGATATTTTATTC     590
FB1D1-S. cerevisiae-3    NNNNNNNNNNNNNNNGGCCACNNNNNNAGAACTTGNGGNGNNATAAGAAGATATTTTATTC     592
FB1D1-S. cerevisiae-2    NNNNNNNNNNNNNNNGGCCNCNNNNNGAGAACTTGTNNNNNNNNTAAGAAGATATTTTATTC     591
FB1D1-S. cerevisiae-4    NNNNNNNNNNNNNNNGGCCNNNNNNNGAGAACTTGTNNNNNNNNTAAGAAGATATTTTATTC     581
FB1D1-neg-control-1      NNNNNNNNNNCGCGGGCNNNNNNAAGAGAACTTGTGGTAAGATAAGAAGATATTTTATTC     590
FB1D1-neg-control-3      CNNNNTGNTTCCGCGGCCACATTAAGAGAACTTGTGGTAAGATAAGAAGATATTTTATTC     597
FB1D1-S. enterica-5      NNNACTGCTTCCGCGGCCACATTAAGAGAACTTGTGGTAAGATAAGAAGATATTTTATTC     592
FB1D1-S. enterica-4      NNNNNTGCTTCCGCGGNNACATTAAGAGAACTTGTGGTAAGATAAGAAGATATTTTATTC     591
FB1D1-S. enterica-2      NNNANNGCTNNNNNGGCCACATTAAGAGAACTTGTGGTAAGATAAGAAGATATTTTATTC     588
FB1D1-S. enterica-3      NNNNNTGNTTCCGCGGNCACATTAAGAGAACTTGTGGTAAGATAAGAAGATATTTTATTC     581
FB1D1-S. enterica-1      NNNNNNGNTTCCGCGNNNNCATTAAGAGAACTTGTGGTAAGATAAGAAGATATTTTATTC     582
FB1D1-S. aureus-4        NNNNNNGNTNCNGCGGCCACATTAAGAGAACTTGNGNTAAGATAAGAAGATATTTTATTC     577
FB1D1-S. aureus-2        CCAACTGCTTCCGCGGCCACATTAAGAGAACTTGNGNTAAGATAAGAAGATATTTTATTC     585
FB1D1-S. aureus-3        CCAACTGCTTCCGCGGCCACATTAAGAGAACTTGNGGTAAGATAAGAAGATATTTTATTC     588
FB1D1-S. aureus-1        NNNNNTGCTTCCGCGGCCACATTAAGAGAACTTGGGGTAAGATAAGAAGATATTTTATTC     582
FB1D1-S. aureus-5        NNNNCNGCNNNNNNGNCCACATTAAGAGAACTTGNGGTAAGATAAGAAGATATTTTATTC     588
                                                   ********        ******************

FB1D1-neg-control-4      GTTCTGCTGACTTGCTGGATGTCGGGAAATATTCTGCATTTGATAAGAGGCGGTTAATTG     644
FB1D1-neg-control-5      GTTCTGCTGACTTGCTGGATGTCGGGAAATATTCTGCATTTGATAAGAGGCGGTTAATTG     637
FB1D1-neg-control-2      GTTCTGCTGACTTGCTGGATGTCGGGAAATATTCTGCATTTGATAAGAGGCGGTTAATTG     649
FB1D1-S. cerevisiae-5    GNTCTGCTGACTTGCTGGATGTCGGGAAATATTCTGCATTTGATAAGAGGCGGTTAATTG     644
FB1D1-S. cerevisiae-1    GNTCTGCTGACTTGCTGGATGTCGGGAAATATTCTGCATTTGATAAGAGGCGGTTAATTG     650
```

TABLE 3A-continued

CLUSTAL 2.0.11 multiple sequence alignment of all sequence reads from primer mix FB1D1 of Example 1.

| | | |
|---|---|---|
| FB1D1-*S. cerevisiae*-3 | GNTCTGCTGACTTGCTGGATGTCGGGAAATATTCTGCATTTGATAAGAGGCGGTTAATTG | 652 |
| FB1D1-*S. cerevisiae*-2 | GNNCTGCTGACTTGCTGGATGTCGGGAAATATTCTGCATTTGATAAGAGGCGGTTAATTG | 651 |
| FB1D1-*S. cerevisiae*-4 | GNTCTGCTGACTTGCTGGATGTCGGGAAATATTCTGCATTTGATAAGAGGCGGTTAATTG | 641 |
| FB1D1-neg-control-1 | GTTCTGCTGACTTGCTGGATGTCGGGAAATATTCTGCATTTGATAAGAGGCGGTTAATTG | 650 |
| FB1D1-neg-control-3 | GTTCTGCTGACTTGCTGGATGTCGGGAAATATTCTGCATTTGATAAGAGGCGGTTAATTG | 657 |
| FB1D1-*S. enterica*-5 | GTTCTGCTGACTTGCTGGATGTCGGGAAATATTCTGCATTNNNNNNNAGGCGGTTAATTG | 652 |
| FB1D1-*S. enterica*-4 | GTTCTGCTGACTTGCTGGATGTCGGGAAATANTCTGCATTNNANNNNAGGCGGTTAATTG | 651 |
| FB1D1-*S. enterica*-2 | GTTCTGCTGACTTGCTGGATGTCGGGAAATANTCTGCATTTNNNNNNAGGCGGTTAATTG | 648 |
| FB1D1-*S. enterica*-3 | GTTCTGCTGACTTGCTGGATGTCGGGAAATATTCTGCATTTNNNNNNAGGCGGTTAATTG | 641 |
| FB1D1-*S. enterica*-1 | GTTCTGCTGACTTGCTGGATGTCGGGAAATATTCTGCATTTNNNNNGAGGCGGTTAATTG | 642 |
| FB1D1-*S. aureus*-4 | GTTCTGCTGACTTGCTGGATGTCGGGAAATATTCTGCATTTGATAAGAGGCGGTTAATTG | 637 |
| FB1D1-*S. aureus*-2 | GTTCTGCTGACTTGCTGGATGTCGGGAAATATTCTGCATTTGATAAGAGGCGGTTAATTG | 645 |
| FB1D1-*S. aureus*-3 | GTTCTGCTGACTTGCTGGATGTCGGGAAATATTCTGCATTTGATAAGAGGCGGTTAATTG | 648 |
| FB1D1-*S. aureus*-1 | GTTCTGCTGACTTGCTGGATGTCGGGAAATATTCTGCATTTGATAAGAGGCGGTTAATTG | 642 |
| FB1D1-*S. aureus*-5 | GTTCTGCTGACTTGCTGGATGTCGGGAAATATTCTGCATTTGATAAGAGGCGGTTAATTG | 648 |
| | *  **************************** ********       ************* | |
| FB1D1-neg-control-4 | CAGATATAATTGGTAGTGAAAAGGGTCGTTGCTATGGTCACCGTGAAGCGAGTACAGCAG | 704 |
| FB1D1-neg-control-5 | CAGATATAATTGGTAGTGAAAAGGGTCGTTGCTATGGTCACCGTGAAGCGAGTACAGCAG | 697 |
| FB1D1-neg-control-2 | CAGATATAATTGGTAGTGAAAAGGGTCGTTGCTATGGTCACCGTGAAGCGAGTACAGCAG | 709 |
| FB1D1-*S. cerevisiae*-5 | CAGATATAATTGGTAGTGAAAAGGGTCGTTGCTATGGTCACCGTGAAGCGAGTACAGCAG | 704 |
| FB1D1-*S. cerevisiae*-1 | CAGATATAATTGGTAGTGAAAAGGGTCGTTGCTATGGTCACCGTGAAGCGAGTACAGCAG | 710 |
| FB1D1-*S. cerevisiae*-3 | CAGATATAATTGGTAGTGAAAAGGGTCGTTGCTATGGTCACCGTGAAGCGAGTACAGCAG | 712 |
| FB1D1-*S. cerevisiae*-2 | CAGATATAATTGGTAGTGAAAAGGGTCGTTGCTATGGTCACCGTGAAGCGAGTACAGCAG | 711 |
| FB1D1-*S. cerevisiae*-4 | CAGATATAATTGGTAGTGAAAAGGGTCGTTGCTATGGTCACCGTGAAGCGAGTACAGCAG | 701 |
| FB1D1-neg-control-1 | CAGATATAATTGGTAGTGAAAAGGGTCGTTGCTATGGTCACCGTGAAGCGAGTACAGCAG | 710 |
| FB1D1-neg-control-3 | CAGATATAATTGGTAGTGAAAAGGGTCGTTGCTATGGTCACCGTGAAGCGAGTACAGCAG | 717 |
| FB1D1-*S. enterica*-5 | CANATATAATTGGTAGTGAAAAGGGTCGTTGCTATGGTCACCGTGAAGCGAGTACAGCAG | 712 |
| FB1D1-*S. enterica*-4 | CANATATAATTGGTAGTGAAAAGGGNCNNTGCTATGGTCACCGTGAAGCGAGTACAGCAG | 711 |
| FB1D1-*S. enterica*-2 | CANATATAATTGGTAGTGAAAAGGGTCGTTGCTATGGTCACCGTGAAGCGAGTACAGCAG | 708 |
| FB1D1-*S. enterica*-3 | CAGATATAATTGGTAGTGAAAAGGGTCGTTGCTATGGTCACCGTGAAGCGAGTACAGCAG | 701 |
| FB1D1-*S. enterica*-1 | CAGATATAATTGGTAGTGAAAAGGGTCGTTGCTATGGTCACCGTGAAGCGAGTACAGCAG | 702 |
| FB1D1-*S. aureus*-4 | CAGATATAATTGGTAGTGAAAAGGNGNNTTGCTATGGTCACCGTGAAGNGAGTACAGCAG | 697 |
| FB1D1-*S. aureus*-2 | CAGATATAATTGGTAGTGAAAAGGNGCGTTGCTATGGTCACCGTGAAGNGAGTACAGCAG | 705 |
| FB1D1-*S. aureus*-3 | CAGATATAATTGGTAGTGAAAAGGNNNNTTGCTATGGTCACCGTGAAGCGAGTACAGCAG | 708 |
| FB1D1-*S. aureus*-1 | CAGATATAATTGGTAGTGAAAAGGNNNNTTGCTATGGTCACCGTGAAGCGAGTACAGCAG | 702 |
| FB1D1-*S. aureus*-5 | CAGATATAATTGGTAGTGAAAAGGNNNNTTGCTATGGTCACCGTGAAGCGAGTACAGCAG | 708 |
| | ** *********************     ******************* *********** | |
| FB1D1-neg-control-4 | CACAAGAATGTGTGCCGTTCTCAGTTAATATTGTTTGAATATGGTAACCTGTTTTAGTCG | 764 |
| FB1D1-neg-control-5 | CACAAGAATGTGTGCCGTTCTCAGTTAATATTGTTTGAATATGGTAACCTGTTTTAGTCG | 757 |
| FB1D1-neg-control-2 | CACAAGAATGTGTGCCGTTCTCAGTTAATATTGTTTGAATATGGTAACCTGNTTTAGTCG | 769 |
| FB1D1-*S. cerevisiae*-5 | CACAAGAATGTGTGCCGNTCTCAGTTAATATTGTTTGAATATGGNAACCTGTTTTAGTCG | 764 |
| FB1D1-*S. cerevisiae*-1 | CACAAGAATGTGTGCCGTTCTCAGTTAATATTGTNTGAATATGGTAACCTGNTTTAGTCG | 770 |
| FB1D1-*S. cerevisiae*-3 | CACAAGANNGTGTGCCGTTCTCAGTTAATATNGNNNGAATATGGTAACCTGNTTTAGTCG | 772 |
| FB1D1-*S. cerevisiae*-2 | CACANGANNGTGTGCCGTTCTCAGTTAATATTGNTTGAATATGGTAACCTGTTTTAGTCG | 771 |
| FB1D1-*S. cerevisiae*-4 | CACAANANNGNGTGCCGTTCTCAGTTNNNNNNGTTTGAATATGGTAACCTGTTTTAGTCG | 761 |
| FB1D1-neg-control-1 | CACAAGAATGTGTGCCGTTCTCAGTTAATATTGTTTGAATATGGTAACCTGTTTTAGTCG | 770 |
| FB1D1-neg-control-3 | CACAAGAATGTGTGCCGTTCTCAGTTAATATTGTTTGAATATGGTAACCTGTTTTAGTCG | 777 |
| FB1D1-*S. enterica*-5 | CACAAGAATGTGNGCCGTTCTCNNNNNNTATTGTTTGAATATNNNNNACCTGTTTTAGTCG | 772 |
| FB1D1-*S. enterica*-4 | CACAAGAATGTGNGCCGTTCTCNNNNNNTATTGTTTGAATATGNNNACCTGNTTTAGTCG | 771 |
| FB1D1-*S. enterica*-2 | CACAAGAATGNGTGCCGTTCTCNGNNNNTATTGTTTGAATATGGNAACCTGTTTTAGTCG | 768 |
| FB1D1-*S. enterica*-3 | CACAAGAATGTGTGCCGTTCTCNNNNNNTATTGTTTGAATATGGNAACCTGTTTTAGTCG | 761 |
| FB1D1-*S. enterica*-1 | CACAAGAATGTGTGCCGTTCTCNNNNNNTATTGTTTGAATATGGTAACCTGTTTTAGTCG | 762 |
| FB1D1-*S. aureus*-4 | CACAAGAATGTGTGCCGTTCTCAGTTAATATTGTTTGAATATGGTAACCTGTTTTAGTCG | 757 |
| FB1D1-*S. aureus*-2 | CACAAGAATGTGTGCCGTTCTCAGTTAATATTGTTTGAATATGGTAACCTGTTTTAGTCG | 765 |
| FB1D1-*S. aureus*-3 | CACAAGAATGTGTGCCGTTCTCAGTTAATATTGTTTGAATATGGTAACCTGTTTTAGTCG | 768 |
| FB1D1-*S. aureus*-1 | CACAAGAATGTGTGCCGTTCTCAGTTAATATTGTTTGAATATGGTAACCTGTTTTAGTCG | 762 |
| FB1D1-*S. aureus*-5 | CACAAGAATGTGTGCCGTTCTCAGTTAATATTGTTTGAATATGGTAACCTGTTTTAGTCG | 768 |
| | ****  *  * * **** ****          *   ******    ***** ******** | |
| FB1D1-neg-control-4 | GTTTAAAGGTAAGAAGANCTAACCAAAAACAAC-ACTGCAGTGACTG--ANNGTAGTATT | 821 |
| FB1D1-neg-control-5 | GTTTAAAGGNAAGAAGATCTAACCAAAAACAAC-ACTGCAGTGACTG--ATTG------- | 807 |
| FB1D1-neg-control-2 | GTTTAAAGGTAAGAAGATCTAACCNAAAACAAC-ACTGCAGTGACTG--ATT-------- | 818 |
| FB1D1-*S. cerevisiae*-5 | GTTTAAAGGTAAGAAGATCTAACCNAAAACAAN-NNNNNNNGNCNNN--NNGNNGNNNNN | 821 |
| FB1D1-*S. cerevisiae*-1 | GTTTAAAGGTAAGAAGATCTAACCAAAAACAAC-ACTGCNNGNCNGN--NNNNNNGGNNN | 827 |
| FB1D1-*S. cerevisiae*-3 | GTTTAAAGGTAAGAAGANCTAACCAAAAACAAC-ACTGCNNNNNNNN--NNGGGGGNNNN | 829 |
| FB1D1-*S. cerevisiae*-2 | GTTTAAAGGTAAGAAGANCTAACCNAAAACAAC-ACTGCNNNNNNGN--GGGGGGNNNNN | 828 |
| FB1D1-*S. cerevisiae*-4 | GTTTAAAGGNAAGAAGATCTAACCAAAAACAAC-ACTGCANTGNCNG--NGNNGGNNNNN | 818 |
| FB1D1-neg-control-1 | GTTTAAAGGTAAGAAGATCTAACCNAAAACAAC-ACTGCAGTGACTG--A---------- | 817 |
| FB1D1-neg-control-3 | GTTTAAAGGTAAGAAGATCTANNNNNNNNNNNNCACTGCAGNGACTG--ANNGNAGTATT | 835 |
| FB1D1-*S. enterica*-5 | GTTTAANNNNNNNNNNNTCTAACCNAAAAC-AACACTGCAGNGACTG--ANNGTAGTATT | 829 |
| FB1D1-*S. enterica*-4 | GTTTAANNNNNNNNNNNTCTAACNNAAAAC-AACACTGCNGNGACTG--ANTGNNNNATT | 828 |
| FB1D1-*S. enterica*-2 | GNTTAANNNNNNNNNNNTCTAACCAAAAAC-AACACTGNNGNGACTG--ANTGTAGTATT | 825 |
| FB1D1-*S. enterica*-3 | GTTTAAANGNNNNNNNT-CTAACCNAAAAC-AACACTGCAGTGACNG--ANNNNNGTANT | 817 |
| FB1D1-*S. enterica*-1 | GTTTAANNNNNNNNNNNTCTAACCAAAAAC-AACACTGCAGNGGNNNGGNNNGTAGTATT | 821 |
| FB1D1-*S. aureus*-4 | GTTTAAAGGTAAGAAGATCTAACCAAAAAC-AACACTGNNNNGNNNG--ATTGTAGNNNN | 814 |

TABLE 3A-continued

CLUSTAL 2.0.11 multiple sequence alignment of all sequence reads from primer mix FB1D1 of Example 1.

| | | |
|---|---|---|
| FB1D1-*S. aureus*-2 | GTTTAAAGGTAAGAAGATCTAACCAAAAAC-AACACNGCAGTGACTG--ATTGNNGNNNN | 822 |
| FB1D1-*S. aureus*-3 | GNTTAAAGGTAAGAAGATCTAACNNAAANNCAACACTGCANNGACTG--NNNNNNNNNAT | 826 |
| FB1D1-*S. aureus*-1 | GTTTAAAGGTNAGAAGATCTAACCAAAAAC-AACACTGCAGNGACTG--ATTGTAGTATT | 819 |
| FB1D1-*S. aureus*-5 | GTTTAAAGGTAAGAAGATCTAACCAAAANC-AACACTGCAGTGACNG--NNNNGNNGNAT | 825 |
| | * ****            *** | |
| FB1D1-neg-control-4 | ------------------------------------------------------------ | |
| FB1D1-neg-control-5 | ------------------------------------------------------------ | |
| FB1D1-neg-control-2 | ------------------------------------------------------------ | |
| FB1D1-*S. cerevisiae*-5 | NNNNNNTT--A--CTTNNNNNNNATTTTGGNNGNA--AACATCAACGG-NNNNNNTCAAC | 874 |
| FB1D1-*S. cerevisiae*-1 | NNNNNNNNTTA--CTNNNNNNNNATTTTGGNN-TA--AACATCAACGG-NNNNNNNCANC | 881 |
| FB1D1-*S. cerevisiae*-3 | NNNNNNNTT-A--CTNNNNGNNNNTTNNNGGNGNA--AACATCNACGN-NNNNNNNCAAC | 883 |
| FB1D1-*S. cerevisiae*-2 | NNNNNNNNT-A--CTTNNNNNNNNNNNNNNNNNNN----ACATCNNCGN-NNNNNNNCAAC | 880 |
| FB1D1-*S. cerevisiae*-4 | NNNNNNNNNTA--CTTANNNNNNNNNNNNNNNGGNGTAAACATCAACGN-NNNNNTCNACC | 875 |
| FB1D1-neg-control-1 | ------------------------------------------------------------ | |
| FB1D1-neg-control-3 | TATTTTTTT-A--CTTAATCTNNATTTTGGTGNAA---ACATCNACGG-CNN-------- | 880 |
| FB1D1-*S. enterica*-5 | TATTTTTNNNN--CNNNNNCTTNANTTT-GGTGTA--AACATCAACGG-CGCACTT---- | 879 |
| FB1D1-*S. enterica*-4 | TATTTTTTTAC--NNNNNNNNNNNTTT--GGTGTA--AACATCAACGG-CGCACTTCNN- | 880 |
| FB1D1-*S. enterica*-2 | TATTTTNNNNN--NNNNNCTTAATTTT--GGTGNA--AACATCNACGG-CGCACTTCAAC | 878 |
| FB1D1-*S. enterica*-3 | TATTTTTTTAC--TNNNNNNNNNNNNTTTGGTGNA--AACATCAACGG-CGCACTTC--- | 869 |
| FB1D1-*S. enterica*-1 | TATTTTNNNNN--NNNNNNCTTAATTTT-GGNGNA--AACATCNACGG-CGCACNTNNN- | 874 |
| FB1D1-*S. aureus*-4 | NANNNNNTTT--ACNTAATCNTANTTTT-GGTGNA--AACATCAACGG-CGCACTTCAAC | 868 |
| FB1D1-*S. aureus*-2 | NNNNNTTTTTT-ANNTNATCTTAATTTT-GGTGTA--AACATCNACGG-CGCACTTCAA- | 876 |
| FB1D1-*S. aureus*-3 | TNNNNNNTTTTTACTTAATCTTAATTTT-GGTGTA--AACATCAACNGGCGCACTTN--- | 880 |
| FB1D1-*S. aureus*-1 | TATTTTTNNN---NNNNNNCTNNATTTT-GGTGTA--AACATCAACGG-CGCACNN---- | 868 |
| FB1D1-*S. aureus*-5 | TTATTTTTNN--NNNNNNNNTTAATTTT-GGNGNA--AACATCAACGG-CGCACTTCN-- | 877 |

TABLE 3B

CLUSTAL 2.0.11 multiple sequence alignment of all sequence reads from single primer FP5 of Example 1.

| | | |
|---|---|---|
| SEQ ID NO: 26<br>FP5-neg-control-4 | -----------NNNNNNNATTACTGTTAATGTTGCTACTACTGCTGACAATGCTGCTGCT | 49 |
| SEQ ID NO: 27<br>FP5-neg-control-5 | ---------NNNNTTNNNATTACTGTTAATGNTGCTACTACTGCTGACAATGCTGCTGCT | 51 |
| SEQ ID NO: 28<br>FP5-neg-control-3 | ---------NNGNNNNTGATTACTGTTAATGTTGCTACTACTGCTGACAATGCTGCTGCT | 51 |
| SEQ ID NO: 29<br>FP5-neg-control-2 | --------NCTGGTNNNNNNNACTGTTAATGTTGCTACTACTGCTGACAATGCTGCTGCT | 52 |
| SEQ ID NO: 30<br>FP5-neg-control-1 | --------NCNGNNNATGANTACTGTTAATGTTGCTACTACTGCTGACAATGCTGCTGCT | 52 |
| SEQ ID NO: 31<br>FP5-*S. aureus*-4 | --------NCCNGNNNNNNNTACTGTTAATGTTGCTACTACTGCTGACAATGCTGCTGCT | 52 |
| SEQ ID NO: 32<br>FP5-*S. aureus*-5 | --------------------TACTGTTAATGTTGNNNCNNNNGCTGACAATGCTGCTGCT | 40 |
| SEQ ID NO: 33<br>FP5-*S. aureus*-2 | -NNNGCNGCCNGGTTNTGATTACTGTTAATGTTGCTACTACTGCTGACAATGCTGCTGCT | 59 |
| SEQ ID NO: 34<br>FP5-*S. aureus*-3 | ------NNNCTGGTTNTGANTACTGNNNNNGTTGCTACTACTGCTGACAATGCTGCTGCT | 54 |
| SEQ ID NO: 35<br>FP5-*S. aureus*-1 | -----NNNNCTGGTTNTGANTACTGTTAANGTTGCTACTACTGCTGACAATGCTGCTGCT | 55 |
| SEQ ID NO: 36<br>FP5-*S. enterica*-2 | ------------NTTNTGATTACTGTTNNNNNTGCTACTACTGCTGACAATGCTGCTGCT | 48 |
| SEQ ID NO: 37<br>FP5-*S. enterica*-3 | -----NNNNNNGGTTNTGATTACTGTTAATGTTGCTACTACTGCTGACAATGCTGCTGCT | 55 |
| SEQ ID NO: 38<br>FP5-*S. enterica*-1 | ---------CTGNNNNTGATTACTGTNNNNGTTGCTACTACTGCTGACAATGCTGCTGCT | 51 |
| SEQ ID NO: 39<br>FP5-*S. enterica*-4 | --NNNNNNCCTGGTNATGANTACTGTTAATGTTGCTACTACTGCTGACAATGCTGCTGCT | 58 |
| SEQ ID NO: 40<br>FP5-*S. enterica*-5 | -------------NNNNNATTNCTGTTAATGTTGCTACTACTGCTGACAATGCTGCTGCT | 47 |
| SEQ ID NO: 41<br>FP5-*S. cerevisiae*-3 | -------------NNNNNATNNCTGTTNATGTTGCTNCTACTGCTGACAATGCTGCTGCT | 47 |
| SEQ ID NO: 42<br>FP5-*S. cerevisiae*-5 | ------------NTTNNGATTACTGTTAATNNTNNTNCTACTGCTGACAATGCTGCTGCT | 48 |
| SEQ ID NO: 43<br>FP5-*S. cerevisiae*-2 | NNNTGNNGCCTGNTTNTGATTACTGTTAATGTTGCTACTACTGCTGACAATGCTGCTGCT | 60 |
| SEQ ID NO: 44<br>FP5-*S. cerevisiae*-4 | --------CCTGGTTANGANTACTGNTNNNGNTGCTACTACTGCTGACAATGCTGCTGCT | 52 |
| SEQ ID NO: 45<br>FP5-*S. cerevisiae*-1 | --------CCTGNNNNNGATTACTGTTAATGTTGCTACTACTGCTGACAATGCTGCTGCT | 52 |
| | ***        *    *     ****************** | |

TABLE 3B-continued

CLUSTAL 2.0.11 multiple sequence alignment of all sequence reads from single primer FP5 of Example 1.

| | | |
|---|---|---|
| FP5-neg-control-4 | GCTTCNCCTCNCTGTCTCCACTTCCTTGAACAATGCGCCGTCATGCTTCTTTTGCCTCCC | 109 |
| FP5-neg-control-5 | GCTTCTCCTCNCTGTCTCCACTTCCTTGAACAATGCGCCGTCATGCTTCTTTTGCCTCCC | 111 |
| FP5-neg-control-3 | GCTTCTCCTCNCTGTCTCCACTTCCTTGAACAATGCGCCGTCATGCTTCTTTTGCCTCCC | 111 |
| FP5-neg-control-2 | GCTTCTCCTNNCTGTCTCCACTTCCTTGAACAATGCGCCGTCATGCTTCTTTTGCCTCCC | 112 |
| FP5-neg-control-1 | GCTTCTCCTCNCTGTCTCCACTTCCTTGAACAATGCGCCGTCATGCTTCTTTTGCCTCCC | 112 |
| FP5-*S. aureus*-4 | GCTTCTCCTCNNTGTCTCCACTTCCTTGAACAATGCGCCGTCATGCTTCTTTTGCCTCCC | 112 |
| FP5-*S. aureus*-5 | GCTTCTCCTCNCTGTCTCCACTTCCTTGAACAATGCGCCGTCATGCTTCTTTTGCCTCCC | 100 |
| FP5-*S. aureus*-2 | GCTTCTCCTNNCTGTCTCCACTTCCTTGAACAATGCGCCGTCATGCTTCTTTTGCCTCCC | 119 |
| FP5-*S. aureus*-3 | GCTTCTCNTNNCTGTCTCCACTTCCTTGAACAATGCGCCGTCATGCTTCTTTTGCCTCCC | 114 |
| FP5-*S. aureus*-1 | GCTTCTCCTCNCTGTCTCCACTTCCTTGAACAATGCGCCGTCATGCTTCTTTTGCCTCCC | 115 |
| FP5-*S. enterica*-2 | GCTTCTCCTCNCTGTCTCCACTTCCTTGAACAATGCGCCGTCATGCTTCTTTTGCCTCCC | 108 |
| FP5-*S. enterica*-3 | GCTTCTCCTNNCTGTCTCCACTTCCTTGAACAATGCGCCGTCATGCTTCTTTTGCCTCCC | 115 |
| FP5-*S. enterica*-1 | GCTTCTCCTNNCTGTCTCCACTTCCTTGAACAATGCGCCGTCATGCTTCTTTTGCCTCCC | 111 |
| FP5-*S. enterica*-4 | GCTTCTCCTNNCTGTCTCCACTTCCTTGAACAATGCGCCGTCATGCTTCTTTTGCCTCCC | 118 |
| FP5-*S. enterica*-5 | GCTTCTCCTCNCTGTCTCCACTTCCTTGAACAATGCGCCGTCATGCTTCTTTTGCCTCCC | 107 |
| FP5-*S. cerevisiae*-3 | GCTTCTCCTCNNTGTCTCCACTTCCTTGAACAATGCGCCGTCATGCTTCTTTTGCCTCCC | 107 |
| FP5-*S. cerevisiae*-5 | GCTTCTCCTNNCTGTCTCCACTTCCTTGAACAATGCGCCGTCATGCTTCTTTTGCCTCCC | 108 |
| FP5-*S. cerevisiae*-2 | GCTTCTCCTCNCTGTCTCCACTTCCTTGAACAATGCGCCGTCATGCTTCTTTTGCCTCCC | 120 |
| FP5-*S. cerevisiae*-4 | GCTTCTCCTCNCTGTCTCCACTTCCTTGAACAATGCGCCGTCATGCTTCTTTTGCCTCCC | 112 |
| FP5-*S. cerevisiae*-1 | GCTTCTCCTCNCTGTCTCCACTTCCTTGAACAATGCGCCGTCATGCTTCTTTTGCCTCCC | 112 |
| | ***** * * * ************************************************ | |
| FP5-neg-control-4 | GCTGCTCCAGAAAGCTAGGCCGCAGATCAGAACCACCACAGTCAATATCACCACCTTCCT | 169 |
| FP5-neg-control-5 | GCTGCTCCAGAAAGCTAGGCCGCAGATCAGAACCACCACAGTCAATATCACCACCTTCCT | 171 |
| FP5-neg-control-3 | GCTGCTCCAGAAAGCTAGGCCGCAGATCAGAACCACCACAGTCAATATCACCACCTTCCT | 171 |
| FP5-neg-control-2 | GCTGCTCCAGAAAGCTAGGCCGCAGATCAGAACCACCACAGTCAATATCACCACCTTCCT | 172 |
| FP5-neg-control-1 | GCTGCTCCAGAAAGCTAGGCCGCAGATCAGAACCACCACAGTCAATATCACCACCTTCCT | 172 |
| FP5-*S. aureus*-4 | GCTGCTCCAGAAAGCTAGGCCGCAGATCAGAACCACCACAGTCAATATCACCACCTTCCT | 172 |
| FP5-*S. aureus*-5 | GCTGCTCCAGAAAGCTAGGCCGCAGATCAGAACCACCACAGTCAATATCACCACCTTCCT | 160 |
| FP5-*S. aureus*-2 | GCTGCTCCAGAAAGCTAGGCCGCAGATCAGAACCACCACAGTCAATATCACCACCTTCCT | 179 |
| FP5-*S. aureus*-3 | GCTGCTCCAGAAAGCTAGGCCGCAGATCAGAACCACCACAGTCAATATCACCACCTTCCT | 174 |
| FP5-*S. aureus*-1 | GCTGCTCCAGAAAGCTAGGCCGCAGATCAGAACCACCACAGTCAATATCACCACCTTCCT | 175 |
| FP5-*S. enterica*-2 | GCTGCTCCAGAAAGCTAGGCCGCAGATCAGAACCACCACAGTCAATATCACCACCTTCCT | 168 |
| FP5-*S. enterica*-3 | GCTGCTCCAGAAAGCTAGGCCGCAGATCAGAACCACCACAGTCAATATCACCACCTTCCT | 175 |
| FP5-*S. enterica*-1 | GCTGCTCCAGAAAGCTAGGCCGCAGATCAGAACCACCACAGTCAATATCACCACCTTCCT | 171 |
| FP5-*S. enterica*-4 | GCTGCTCCAGAAAGCTAGGCCGCAGATCAGAACCACCACAGTCAATATCACCACCTTCCT | 178 |
| FP5-*S. enterica*-5 | GCTGCTCCAGAAAGCTAGGCCGCAGATCAGAACCACCACAGTCAATATCACCACCTTCCT | 167 |
| FP5-*S. cerevisiae*-3 | GCTGCTCCAGAAAGCTAGGCCGCAGATCAGAACCACCACAGTCAATATCACCACCTTCCT | 167 |
| FP5-*S. cerevisiae*-5 | GCTGCTCCAGAAAGCTAGGCCGCAGATCAGAACCACCACAGTCAATATCACCACCTTCCT | 168 |
| FP5-*S. cerevisiae*-2 | GCTGCTCCAGAAAGCTAGGCCGCAGATCAGAACCACCACAGTCAATATCACCACCTTCCT | 180 |
| FP5-*S. cerevisiae*-4 | GCTGCTCCAGAAAGCTAGGCCGCAGATCAGAACCACCACAGTCAATATCACCACCTTCCT | 172 |
| FP5-*S. cerevisiae*-1 | GCTGCTCCAGAAAGCTAGGCCGCAGATCAGAACCACCACAGTCAATATCACCACCTTCCT | 172 |
| | ************************************************************ | |
| FP5-neg-control-4 | CTTATAGATTCGGAATCTCATGATAGGGGCTCAGCCTCTGTGCGAGTGGAGAGAAGTTTG | 229 |
| FP5-neg-control-5 | CTTATAGATTCGGAATCTCATGATAGGGGCTCAGCCTCTGTGCGAGTGGAGAGAAGTTTG | 231 |
| FP5-neg-control-3 | CTTATAGATTCGGAATCTCATGATAGGGGCTCAGCCTCTGTGCGAGTGGAGAGAAGTTTG | 231 |
| FP5-neg-control-2 | CTTATAGATTCGGAATCTCATGATAGGGGCTCAGCCTCTGTGCGAGTGGAGAGAAGTTTG | 232 |
| FP5-neg-control-1 | CTTATAGATTCGGAATCTCATGATAGGGGCTCAGCCTCTGTGCGAGTGGAGAGAAGTTTG | 232 |
| FP5-*S. aureus*-4 | CTTATAGATTCGGAATCTCATGATAGGGGCTCAGCCTCTGTGCGAGTGGAGAGAAGTTTG | 232 |
| FP5-*S. aureus*-5 | CTTATAGATTCGGAATCTCATGATAGGGGCTCAGCCTCTGTGCGAGTGGAGAGAAGTTTG | 220 |
| FP5-*S. aureus*-2 | CTTATAGATTCGGAATCTCATGATAGGGGCTCAGCCTCTGTGCGAGTGGAGAGAAGTTTG | 239 |
| FP5-*S. aureus*-3 | CTTATAGATTCGGAATCTCATGATAGGGGCTCAGCCTCTGTGCGAGTGGAGAGAAGTTTG | 234 |
| FP5-*S. aureus*-1 | CTTATAGATTCGGAATCTCATGATAGGGGCTCAGCCTCTGTGCGAGTGGAGAGAAGTTTG | 235 |
| FP5-*S. enterica*-2 | CTTATAGATTCGGAATCTCATGATAGGGGCTCAGCCTCTGTGCGAGTGGAGAGAAGTTTG | 228 |
| FP5-*S. enterica*-3 | CTTATAGATTCGGAATCTCATGATAGGGGCTCAGCCTCTGTGCGAGTGGAGAGAAGTTTG | 235 |
| FP5-*S. enterica*-1 | CTTATAGATTCGGAATCTCATGATAGGGGCTCAGCCTCTGTGCGAGTGGAGAGAAGTTTG | 231 |
| FP5-*S. enterica*-4 | CTTATAGATTCGGAATCTCATGATAGGGGCTCAGCCTCTGTGCGAGTGGAGAGAAGTTTG | 238 |
| FP5-*S. enterica*-5 | CTTATAGATTCGGAATCTCATGATAGGGGCTCAGCCTCTGTGCGAGTGGAGAGAAGTTTG | 227 |
| FP5-*S. cerevisiae*-3 | CTTATAGATTCGGAATCTCATGATAGGGGCTCAGCCTCTGTGCGAGTGGAGAGAAGTTTG | 227 |
| FP5-*S. cerevisiae*-5 | CTTATAGATTCGGAATCTCATGATAGGGGCTCAGCCTCTGTGCGAGTGGAGAGAAGTTTG | 228 |
| FP5-*S. cerevisiae*-2 | CTTATAGATTCGGAATCTCATGATAGGGGCTCAGCCTCTGTGCGAGTGGAGAGAAGTTTG | 240 |
| FP5-*S. cerevisiae*-4 | CTTATAGATTCGGAATCTCATGATAGGGGCTCAGCCTCTGTGCGAGTGGAGAGAAGTTTG | 232 |
| FP5-*S. cerevisiae*-1 | CTTATAGATTCGGAATCTCATGATAGGGGCTCAGCCTCTGTGCGAGTGGAGAGAAGTTTG | 232 |
| | ************************************************************ | |
| FP5-neg-control-4 | CAGGCGAGCTGAGGAGCAATTGCAGGTGATATGATGTGCTCGGCTCAAGAAGCGGGCCCG | 289 |
| FP5-neg-control-5 | CAGGCGAGCTGAGGAGCAATTGCAGGTGATATGATGTGCTCGGCTCAAGAAGCGGGCCCG | 291 |
| FP5-neg-control-3 | CAGGCGAGCTGAGGAGCAATTGCAGGTGATATGATGTGCTCGGCTCAAGAAGCGGGCCCG | 291 |
| FP5-neg-control-2 | CAGGCGAGCTGAGGAGCAATTGCAGGTGATATGATGTGCTCGGCTCAAGAAGCGGGCCCG | 292 |
| FP5-neg-control-1 | CAGGCGAGCTGAGGAGCAATTGCAGGTGATATGATGTGCTCGGCTCAAGAAGCGGGCCCG | 292 |
| FP5-*S. aureus*-4 | CAGGCGAGCTGAGGAGCAATTGCAGGTGATATGATGTGCTCGGCTCAAGAAGCGGGCCCG | 292 |
| FP5-*S. aureus*-5 | CAGGCGAGCTGAGGAGCAATTGCAGGTGATATGATGTGCTCGGCTCAAGAAGCGGGCCCG | 280 |
| FP5-*S. aureus*-2 | CAGGCGAGCTGAGGAGCAATTGCAGGTGATATGATGTGCTCGGCTCAAGAAGCGGGCCCG | 299 |
| FP5-*S. aureus*-3 | CAGGCGAGCTGAGGAGCAATTGCAGGTGATATGATGTGCTCGGCTCAAGAAGCGGGCCCG | 294 |
| FP5-*S. aureus*-1 | CAGGCGAGCTGAGGAGCAATTGCAGGTGATATGATGTGCTCGGCTCAAGAAGCGGGCCCG | 295 |
| FP5-*S. enterica*-2 | CAGGCGAGCTGAGGAGCAATTGCAGGTGATATGATGTGCTCGGCTCAAGAAGCGGGCCCG | 288 |

TABLE 3B-continued

CLUSTAL 2.0.11 multiple sequence alignment of all sequence reads from single primer FP5 of Example 1.

```
FP5-S. enterica-3   CAGGCGAGCTGAGGAGCAATTGCAGGTGATATGATGTGCTCGGCTCAAGAAGCGGGCCCG    295
FP5-S. enterica-1   CAGGCGAGCTGAGGAGCAATTGCAGGTGATATGATGTGCTCGGCTCAAGAAGCGGGCCCG    291
FP5-S. enterica-4   CAGGCGAGCTGAGGAGCAATTGCAGGTGATATGATGTGCTCGGCTCAAGAAGCGGGCCCG    298
FP5-S. enterica-5   CAGGCGAGCTGAGGAGCAATTGCAGGTGATATGATGTGCTCGGCTCAAGAAGCGGGCCCG    287
FP5-S. cerevisiae-3 CAGGCGAGCTGAGGAGNNNTTGCAGGTGATATGATGTGCTCGGCTCAAGAAGCGGGCCCG    287
FP5-S. cerevisiae-5 CAGGCGAGCTGAGGAGCAATTGCAGGTGATATGATGTGCTCGGCTCAAGAAGCGGGCCCG    288
FP5-S. cerevisiae-2 CAGGCGAGCTGAGGAGCANTTGCAGGTGATATGATGTGCTCGGCTCAAGAAGCGGGCCCG    300
FP5-S. cerevisiae-4 CAGGCGAGCTGAGGAGCAATTGCAGGTGATATGATGTGCTCGGCTCAAGAAGCGGGCCCG    292
FP5-S. cerevisiae-1 CAGGCGAGCTGAGGAGCAATTGCAGGTGATATGATGTGCTCGGCTCAAGAAGCGGGCCCG    292
                    ****************   *****************************************

FP5-neg-control-4   GAGAGGAAGAAGTCGTGCCGGGGCTAATTATTGGCAAAACGAGCTCTTGTTGTAAACATT    349
FP5-neg-control-5   GAGAGGAAGAAGTCGTGCCGGGGCTAATTATTGGCAAAACGAGCTCTTGTTGTAAACATT    351
FP5-neg-control-3   GAGAGGAANAAGNCGTGCCGGGGCTAATTATTGGCAAAACGAGCTCTTGTTGTAAACATT    351
FP5-neg-control-2   GAGAGGAAGAAGTCGTGCCGGGGCTAATTATTGGCAAAACGAGCTCTTGTTGTAAACATT    352
FP5-neg-control-1   GAGAGGAAGAAGTCGTGCCGGGGCTAATTATTGGCAAAACGAGCTCTTGTTGTAAACATT    352
FP5-S. aureus-4     GAGAGGAAGAAGTCGTGCCGGGGCTAATTATTGGCAAAACGAGCTCTTGTTGTAAACATT    352
FP5-S. aureus-5     GAGAGGAAGAAGTCGTGCCGGGGCTAATTATTGGCAAAACGAGCTCTTGTTGTAAACATT    340
FP5-S. aureus-2     GAGAGGAAGAAGTCGTGCCGGGGCTAATTATTGGCAAAACGAGCTCTTGTTGTAAACATT    359
FP5-S. aureus-3     GAGAGGAAGAAGTCGTGCCGGGGCTAATTATTGGCAAAACGAGCTCTTGTTGTAAACATT    354
FP5-S. aureus-1     GAGAGGAAGAAGTCGTGCCGGGGCTAATTATTGGCAAAACCAGCTCTTGTTGTAAACNTT    355
FP5-S. enterica-2   GAGAGGAAGAAGTCGTGCCGGGGCTAATTATTGGCAAAACGAGCTCTTGTTGTAAACATT    348
FP5-S. enterica-3   GAGAGGAAGAAGTCGTGCCGGGGCTAATTATTGGCAAAACGAGCTCTTGTTGTAAACATT    355
FP5-S. enterica-1   GAGAGGAAGAAGTCGTGCCGGGGCTAATTATTGGCAAAACGAGCTCTTGTTGTAAACATT    351
FP5-S. enterica-4   GAGAGGAAGAAGTCGTGCCGGGGCTAATTATTGGCAAAACGAGCTCTTGTTGTAAACATT    358
FP5-S. enterica-5   GAGAGGAAGAAGTCGTGCCGGGGCTAATTATTGGCAAAACGAGCTCTTGTTGTAAACATT    347
FP5-S. cerevisiae-3 GAGAGGAAGAAGTCGTGCCGGGGCTAATTATTGGCAAAACGAGCTCTTGTTGTAAACATN    347
FP5-S. cerevisiae-5 GAGAGGAAGAAGTCGTGCCGGGGCTAATTATTGGCAAAACGAGCTCTTGTTGTAAACATN    348
FP5-S. cerevisiae-2 GAGAGGAAGAAGTCGTGCCGGGGCTAATTATTGGCAAAACGAGCTCTTGTTGTAAACATN    360
FP5-S. cerevisiae-4 GAGAGGAAGAAGTCGTGCCGGGGCTAATTATTGGCAAAACGAGCTCTTGTTGTAAACNTN    352
FP5-S. cerevisiae-1 GAGAGGAAGAAGTCGTGCCGGGGCTAATTATTGGCAAAACGAGCTCTTGTTGTAAACATN    352
                    ******** *** ******************************************** *

FP5-neg-control-4   GATCCAACTGGAANNNNNNNNNNGGNNNNNNNNNNNNNCATAAGGCATGATGGTTGCTCA    409
FP5-neg-control-5   GATCCAACTGGANNGNNNNNNATGGNNNNNNNNNNNTCCATAAGGCATGATGGTTGCTCA    411
FP5-neg-control-3   GATCCAACTGGAANNNNNNNNNTGNNNNNNNNNNNNTTCCATAAGGCATGATGGTTGCTCA    411
FP5-neg-control-2   GATCCAACTGGNANGNCACNNNNGNNNNNNNAATATTCCATAAGGCATGATGGTTGCTCA    412
FP5-neg-control-1   GATCCAACTGGAATGTCACTAANGGNNNNNNNATATTCCATAAGGCATGATGGTTGCTCA    412
FP5-S. aureus-4     GATCCAACTGGAATGTCACTAATGGCGAATCAATATTCCATAAGGCATGATGGTTGCTCA    412
FP5-S. aureus-5     GATCCAACTGGAATGTCACTAATGGCGAATCAATATTCCATAAGGCATGATGGTTGCTCA    400
FP5-S. aureus-2     GATCCAACTGGAATGTCACTAATGGCGAATCAATATTCCATAAGGCATGATGGTTGCTCA    419
FP5-S. aureus-3     GATCCAACTGGAATGTCACTAATGGCGAATCAATATTCCATAAGGCATGATGGTTGCTCA    414
FP5-S. aureus-1     GNTNCAACTGGAATGTCACTAATGGCGAATCAATATTCCATAAGGCATGATGGTTGCTCA    415
FP5-S. enterica-2   GATCCAACTGGAATGTCACTAANNNNNNNNNNATATTCCATAAGGCATGATGGTTGCTCA    408
FP5-S. enterica-3   GATCCAACTGGAATGTCACTAANNNNNNNNNNNNTATTCCATAAGGCATGATGGTTGCTCA    415
FP5-S. enterica-1   GATCCAACTGGAATGTCACTAANNNNNNNNNAN-TATTCCATAAGGCATGATGGTTGCTCA    410
FP5-S. enterica-4   GATCCAACTGGAATGTCACTAANNNNNNNNNAA-TATTCCATAAGGCATGATGGTTGCTCA    417
FP5-S. enterica-5   GATCCAACTGGAATGTCACTAANNNNNNNNNNAATATTCCATAAGGCATGATGGTTGCTCA    407
FP5-S. cerevisiae-3 NNNNNNNNTGGNATGTCACTAATGGCGAATNNNNANNNNNTAAGGNNTGATGGTTGCTCA    407
FP5-S. cerevisiae-5 NNNNNNNNNGGAATGTCACTAATGGCGAATCNNNNNNNCNTAAGGNNNGNTGGTTGCTCA    408
FP5-S. cerevisiae-2 NNNNNNNNNNNNANGTCACTAATGGCGAANNNNNANNNNNTAAGGNNTGATGGTTGCTCA    420
FP5-S. cerevisiae-4 NNNNNNNNNGGAATGTCACTAATGGCGAATNNNNNNNNNNTAAGGCATGATGGTTGCTCA    412
FP5-S. cerevisiae-1 NNNNNNNNNGGAATGTCACTAATGGCGAANNNNNNNNNNNTAAGGNATGATGGTTGCTCA    412
                                                            *****   * **********

FP5-neg-control-4   GAGGCAGGAGAAGAGCAACGAATACGATCCTATAAAAGATAAAACATAAATAAACAGTCT    469
FP5-neg-control-5   GAGGCAGGAGAAGAGCAACGAATACGATCCTATAAAAGATAAAACATAAATAAACAGTCT    471
FP5-neg-control-3   GAGGCAGGAGAAGAGCAACGAATACGATCCTATAAAAGATAAAACATAAATAAACAGTCT    471
FP5-neg-control-2   GAGGCAGGAGAAGAGCAACGAATACGATCCTATAAAAGATAAAACATAAATAAACAGTCT    472
FP5-neg-control-1   GAGGCAGGAGAAGAGCAACGAATACGATCCTATAAAAGATAAAACATAAATAAACAGTCT    472
FP5-S. aureus-4     GAGGCAGGAGAAGAGCAACGAATACGATCCTATAAAAGATAAAACATAAATAAACAGTCT    472
FP5-S. aureus-5     GAGGCAGGAGAAGAGCAACGAATACGATCCTATAAAAGATAAAACATAAATAAACAGTCT    460
FP5-S. aureus-2     GAGGCAGGAGAAGAGCAACGAATACGATCCTATAAAAGATAAAACATAAATAAACAGTCT    479
FP5-S. aureus-3     GAGGCAGGAGAAGAGCAACGAATACGATCCTATAAAAGATAAAACATAAATAAACAGTCT    474
FP5-S. aureus-1     GAGGCAGGAGAAGAGCAACGAATACGATCCTATAAAAGATAAAACATAAATAAACAGTCT    475
FP5-S. enterica-2   GAGGCAGGAGAAGAGCAACGAATACGATCCTATAAAAGATAAAACATAAATAAACAGTCT    468
FP5-S. enterica-3   GAGGCAGGAGAAGAGCAACGAATACGATCCTATAAAAGATAAAACATAAATAAACAGTCT    475
FP5-S. enterica-1   GAGGCNGGAGAAGAGCAACGAATACGATCCTATAAAAGATAAAACATAAATAAACAGTCT    470
FP5-S. enterica-4   GAGGCAGGAGAAGAGCAACGAATACGATCCTATAAAAGATAAAACATAAATAAACAGTCT    477
FP5-S. enterica-5   GAGGCAGGAGAAGAGCAACGAATACGATCCTATAAAAGATAAAACATAAATAAACAGTCT    467
FP5-S. cerevisiae-3 GAGGCAGGAGAAGAGCNNNGNATACNNNNNTATAAAAGATAAAACATAAATAAACAGTCT    467
FP5-S. cerevisiae-5 GAGGCAGGAGAAGAGCNNNGNATACGNNNNTATAAAAGATAAAACATAAATAAACAGTCT    468
FP5-S. cerevisiae-2 GAGGCAGGAGAAGAGNNNNGNATACNNNNNNATAAAAGATAAAACATAAATAAACAGTCT    480
FP5-S. cerevisiae-4 GAGGCAGGAGAAGAGCAACGAATACNNNNNNATAAAAGATAAAACATAAATAAACAGTCT    472
FP5-S. cerevisiae-1 GAGGCAGGAGAAGAGCAACGAATACGANGCNNTAAAAGATAAAACATAAATAAACAGTCT    472
                    ***** *********    * ****       ****************************
```

TABLE 3B-continued

CLUSTAL 2.0.11 multiple sequence alignment of all sequence reads from single primer FP5 of Example 1.

```
FP5-neg-control-4   TGATTATATTCTGGGTATTAAAGCCACAATCAGAACAAATATATGCTTTGTATCTTTTCT   529
FP5-neg-control-5   TGATTATATTCTGGGTATTAAAGCCACAATCAGAACAAATATATGCTTTGTATCTTTTCT   531
FP5-neg-control-3   TGATTATATTCTGGGTATTAAAGCCACAATCAGAACAAATATATGCTTTGTATCTTTTCT   531
FP5-neg-control-2   TGATTATATTCTGGGTATTAAAGCCACAATCAGAACAAATATATGCTTTGTATCTTTTCT   532
FP5-neg-control-1   TGATTATATTCTGGGTATTAAAGCCACAATCAGAACAAATATATGCTTTGTATCTTTTCT   532
FP5-S. aureus-4     TGATTATATTCTGGGTATTAAAGCCACAATCAGAACAAATATATGCTTTGTATCTTTTCT   532
FP5-S. aureus-5     TGATTATATTCTGGGTATTAAAGCCACAATCAGAACAAATATATGCTTTGTATCTTTTCT   520
FP5-S. aureus-2     TGATTATATTCTGGGTATTAAAGCCACAATCAGAACAAATATATGCTTTGTATCTTTTCT   539
FP5-S. aureus-3     TGATTATATTCTGGGTATTAAAGCCACAATCAGAACAAATATATGCTTTGTATCTTTTCT   534
FP5-S. aureus-1     TGATTATATTCTGGGTATTAAAGCCACAATCAGAACAAATATATGCTTTGTATCTTTTCT   535
FP5-S. enterica-2   TGATTATATTCTGGGTATTAAAGCCACAANNNNNNNNNNNNNTNTGCTTTGTATCTTTNNN   528
FP5-S. enterica-3   TGATTATATTCTGGGTATTAAAGCCACANNNNNNNNNNNNNNTATGCTTTGTATCTTNNNN   535
FP5-S. enterica-1   TGATTATATTCTGGGTATTAAAGCCACANNNNNNNNNNGANNTATGCTTTGTATCTTNNNN   530
FP5-S. enterica-4   TGATTATATTCTGGGTATTAAAGCCACAANGNGNNNNNANNTATGCTTTGTATCTTNNNN   537
FP5-S. enterica-5   TGATTATATTCTGGGTATTAAAGCCACANNNNNNNNNNGANNTATGCTTTGTATCTTTTCT   527
FP5-S. cerevisiae-3 TGATTATATTCTGGGTATTAAAGCCNCAATCNNANNAAATATATGCTTTGTATCTTTTCT   527
FP5-S. cerevisiae-5 TGATTATATTCTGGGTATTAAAGCCACAATCAGAACAAATATATGCTTTGTATCTTTTCT   528
FP5-S. cerevisiae-2 TGATTATATTCTGGGTATTAAAGCCACAATCAGAACAAATATATGCTTTGTATCTTTTCT   540
FP5-S. cerevisiae-4 TGATTATATTCTGGGTATTAAAGCCACAATCAGAACAAATATATGCTTTGTATCTTTTCT   532
FP5-S. cerevisiae-1 TGATTATATTCTGGGTATTAAAGCCACAATCAGAACAAATATATGCTTTGTATCTTTTCT   532
                    ************************* **             * *************

FP5-neg-control-4   TGCCTTCTTCATTACCAACTGCTTCCGCGGCCACATTANNAGAACTTGTGGTAAGATAAG   589
FP5-neg-control-5   TGCCTTCTTCATTACCAACTGCTTCCGCGGCCACATTAAGAGAACTTGTGGTAAGATAAG   591
FP5-neg-control-3   TGCCTTCTTCATTACCAACTGNTTCCGCGGNCACNTTAAGAGAACTTGTGGTAAGATAAG   591
FP5-neg-control-2   TGCCTTCTTCATTACCAACTGCTTCCGCGGCCACATTAAGAGAACTTGTGGTAAGATAAG   592
FP5-neg-control-1   TGCCTTCTTCATTACCAACTGCTTCCGCGGCCACATTAAGAGAACTTGTGGTAAGATAAG   592
FP5-S. aureus-4     TGCCTTCTTCATTACCAACTGCTTCCGCGGCCACATTAAGAGAACTTGTGGTAAGATAAG   592
FP5-S. aureus-5     TGCCTTCTTCATTACCAACTGCTTCCGCGGCCACATTAAGAGAACTTGTGGTAAGATAAG   580
FP5-S. aureus-2     TGCCTTCTTCATTACCAACTGCTTCCGCGGCCACATTAAGAGAACTTGTGGTAAGATAAG   599
FP5-S. aureus-3     TGCCTTCTTCATTACCAACTGCTTCCGCGGCCACATTAAGAGAACTTGTGGTAAGATAAG   594
FP5-S. aureus-1     TGCCTTCTTCATTACCAACTGCTTCCGCGGCCACATTAAGAGAACTTGTGGTAAGATAAG   595
FP5-S. enterica-2   NGCCTTCTTCATTACCAACTGCTTCCGCGGCCACATTAAGAGAACTTGTGGTAAGATAAN   588
FP5-S. enterica-3   NGNCNTCTTCATTACCAACTGCTTCCGCGGCCACATTAAGAGAACTTGTGGTAAGATAAG   595
FP5-S. enterica-1   NGNCTTCTTCATTACCAACTGCTTCCGCGGCCACATTAAGAGAACTTGTGGTAAGATAAG   590
FP5-S. enterica-4   NNNCTTCTTCATTACCAACTGCTTCCGCGGCCACATTAAGAGAACTTGTGGTAAGATAAN   597
FP5-S. enterica-5   TGNCTTCTTCATTACCAACTGCTTCCGCGGCCACATTAAGAGAACTTGTGGTAAGATAAG   587
FP5-S. cerevisiae-3 TGCCTNNNNNNNNNNNNNNNNNNNTCCGCGGCCACATTAAGAGAACTTGTGGTAAGATAAG   587
FP5-S. cerevisiae-5 TGCCTNNNNNNNNNNNNNNNNNNNTCCGCGGCCACATTAAGAGAACTTGTGGNAAGATAAG   588
FP5-S. cerevisiae-2 TGCCTNNNNNNNNNNNNNNNNNNNTCCGCGGCCACATTAAGAGAACTTGTGGTAAGATAAG   600
FP5-S. cerevisiae-4 TGCCTTNNNNNNNNNNNNNNNNNNTCCGCGGCCACATTAAGAGAACTTGTGNTAAGATAAG   592
FP5-S. cerevisiae-1 TGCCTTNNNNNNNNNNNNNNNNNNTCCGCGGCCACATTAAGAGAACTTGTGGTAAGATAAG   592
                       *                   ******* *** ***  **********  *******

FP5-neg-control-4   AAGATATTTTATTCGTTCTGCTGACTTGCTGGATGTCGGGAAATATTCTGCATTTGATAA   649
FP5-neg-control-5   AAGATATTTTATTCGTTCTGCTGACTTGCTGGATGTCGGGAAATATTCTGCATTTGATAA   651
FP5-neg-control-3   AAGATATTTTATTCGTTCTGCTGACTTGCTGGATGTCGGGAAATATTCTGCATTTGATAA   651
FP5-neg-control-2   AAGATATTTTATTCGTTCTGCTGACTTGCTGGATGTCGGGAAATATTCTGCATTTGATAA   652
FP5-neg-control-1   AAGATATTTTATTCGTTCTGCTGACTTGCTGGATGTCGGGAAATATTCTGCATTTGATAA   652
FP5-S. aureus-4     AAGATATTTTATTCGTTCTGCTGACTTGCTGGATGTCGGGAAATATTCTGCATTTGATAA   652
FP5-S. aureus-5     AAGATATTTTATTCGTTCTGCTGACTTGCTGGATGTCGGGAAATATTCTGCATTTGATAA   640
FP5-S. aureus-2     AAGATATTTTATTCGTTCTGCTGACTTGCTGGATGTCGGGAAATATTCTGCATTTGATAA   659
FP5-S. aureus-3     AAGATATTTTATTCGTTCTGCTGACTTGCTGGATGTCGGGAAATATTCTGCATTTGATAA   654
FP5-S. aureus-1     AAGATATTTTATTCGTTCTGCTGACTTGCTGGATGTCGGGAAATATTCTGCATTTGATAA   655
FP5-S. enterica-2   AANATATTTTATTCNNNNNNNTGACTTGCTGGATGTCGGGAAATATTCTGCATTTGATAA   648
FP5-S. enterica-3   AAGATATTTTATTCNNNNNNNTGACTTGCTGGATGTCGGGAAATATTCTGCATTTGATAA   655
FP5-S. enterica-1   AAGATATTTTATTCNNNNNNNTGACTTGCTGGATGTCGGGAAATATTCTGCATTTGATAA   650
FP5-S. enterica-4   ANNANNTTTTATTCGNNNNGNTGACTTGCTGGATGTCGGGAAATATTCTGCATTTGATAA   657
FP5-S. enterica-5   AAGATATTTTATTCGNNCNNNTGACTTGCTGGATGTCGGGAAATATTCTGCATTTGATAA   647
FP5-S. cerevisiae-3 AAGATATTTTATTCNNNNNNNTGNNNNNNTGGATGTCGGGAAATATTCTGCATTTGATAA   647
FP5-S. cerevisiae-5 AAGATATTTTATTCNNNNNNNTNNNNNNNTGGATGTCGGGAAATATTCTGCATTTGATAA   648
FP5-S. cerevisiae-2 AAGATATTTTATTCGNNNNNNTGNNNNNNTGGATGTCGGGAAATATTCTGCATTTGATAA   660
FP5-S. cerevisiae-4 AAGATATTTTATTCNNNNNNNTGNNNNNNTGGATGTCGGGAAATATTCTGCATTTGATAA   652
FP5-S. cerevisiae-1 AAGATATTTTATTCGNNNNNNTGNNNNNNTGGATGTCGGGAAATATTCTGCATTTGATAA   652
                    *  *  ********       *       *******************************

FP5-neg-control-4   GAGGCGGTTAATTGCAGATATAATTGGTAGTGAAAAGGGTCGTTGCTATGGTCACCGTGA   709
FP5-neg-control-5   GAGGCGGTTAATTGCAGATATAATTGGTAGTGAAAAGGGTCGTTGCTATGGTCACCGTGA   711
FP5-neg-control-3   GAGGCGGTTAATTGCAGATATAATTGGTAGTGAAAAGGGTCGTTGCTATGGTCACCGTGA   711
FP5-neg-control-2   GAGGCGGTTAATTGCAGATATAATTGGTAGTGAAAAGGGTCGTTGCTATGGTCACCGTGA   712
FP5-neg-control-1   GAGGCGGTTAATTGCAGATATAATTGGTAGTGAAAAGGGTCGTTGCTATGGTCACCGTGA   712
FP5-S. aureus-4     GAGGCGGTTAATTGCAGATATAATTGGTAGTGAAAAGGGTCGTTGCTATGGTCACCGTGA   712
FP5-S. aureus-5     GAGGCGGTTAATTGCAGATATAATTGGTAGTGAAAAGGGTCGTTGCTATGGTCACCGTGA   700
FP5-S. aureus-2     GAGGCGGTTAATTGCAGATATAATTGGTAGTGAAAAGGGTCGTTGCTATGGTCACCGTGA   719
FP5-S. aureus-3     GAGGCGGTTAATTGCAGATATAATTGGTAGTGAAAAGGGTCGTTGCTATGGTCACCGTGA   714
FP5-S. aureus-1     GAGGCGGTTAATTGCAGATATAATTGGTAGTGAAAAGGGTCGTTGCTATGGTCACCGTGA   715
FP5-S. enterica-2   GAGGCGGTTAATTGCAGATATAATTNNNNNNNNNNNNGGTCGTTGCTATGGTCACCGTGA   708
```

TABLE 3B-continued

CLUSTAL 2.0.11 multiple sequence alignment of all sequence reads from single primer FP5 of Example 1.

```
FP5-S. enterica-3   GAGGCGGTTAATTGCAGATATAATTGGNNNNNNNNNNGNTCGTTGCTATGGTCACCGTGA   715
FP5-S. enterica-1   GAGGCGGTTAATTGCAGATATAATTGGNNGTNNNNNNGNNCGTTGCTATGGTCACCGTGA   710
FP5-S. enterica-4   GAGGCGGNTAATTGCAGATATAATTGGNNGTNNNNNNGGTCGTTGCTATGGTCACCGTGA   717
FP5-S. enterica-5   GAGGCGGTTAATTGCAGATATAATTGGNNGTNNNNNNGGTCGTTGCTATGGTCACCGTGA   707
FP5-S. cerevisiae-3 GAGGCGGTTAANTGCAGATATAATTGNNNNNNNNNNNGGTCGTTGCTATGGTCACCGTGA   707
FP5-S. cerevisiae-5 GAGGCGGTTAANTGCAGATATAATTGGTAGTGAAAAGGGTCGTTGCTATGGTCACCGTGA   708
FP5-S. cerevisiae-2 GANGCGGNTAANTGNANATATNATTGGNNGNGAAA-------------------------   695
FP5-S. cerevisiae-4 GAGGCGGTTAATTGCAGATATAATTGGTAGTGAAAAGGGTCGTTGCTATGGTCACCGTGA   712
FP5-S. cerevisiae-1 GAGGCGGTTNNNTGNAGATATAATTGGTAGTGAAAAGGGTCGTTGCTATGGTCACCGTGA   712
                    ** **** *   ** * **** ***

FP5-neg-control-4   AGCGAGTACAGCAGCACAAGAATGTGTGCCGTTCTCAGTTAATATTGNTTGAATATGGTA   769
FP5-neg-control-5   AGCGAGTACAGCAGCACAAGAATGTGTGCCGNTCTCAGTTAATATTGTTTGAATATGGTA   771
FP5-neg-control-3   AGCGAGTACAGCAGCACAAGAATGTGTGCCGTTCTCAGTTAATATTGNTTGAATATGGTA   771
FP5-neg-control-2   AGCGAGTACAGCAGCACAAGAATGTGTGCCGTTCTCAGTTAATATTGNTTGAATATGGNA   772
FP5-neg-control-1   AGCGAGTACAGCAGCACAAGAATGNGTGCCGTTCTCAGTTAATATTGTTTGAATATGGNA   772
FP5-S. aureus-4     AGCGAGTACAGCAGCACAAGAATGTGTGCCGTTCTCAGTNNGNNNNNNNNGAATATGGTA   772
FP5-S. aureus-5     AGCGAGTACAGCAGCACAAGAATGTGTGCCGTTCTCAGNNNNNNNNNNNNNGAATATGGTA   760
FP5-S. aureus-2     AGCGAGTACAGCAGCACAAGAATGTGTGCCGTTCTCAGNNNNNNNNNNNNNGAATATGGTA   779
FP5-S. aureus-3     AGCGAGTACAGCAGCACAAGAATGTGTGCCGTTCTCAGNNNGNANNNNNNGAATATGGTA   774
FP5-S. aureus-1     AGCGAGTACAGCAGCACAAGAATGTGTGCCGTTCTCAGNNNNNNNNNNNNNGAATATGGTA   775
FP5-S. enterica-2   AGCGAGTNNNGCNNNNNNAGANTGNGNGGNNGNNNNNNNNNATATTGNTTGAATATGGNN   768
FP5-S. enterica-3   AGCGAGTACAGCAGCACAAGAATGTGTGNNNNNNNNNNNNNAATATTGNTTGAATATGGTA   775
FP5-S. enterica-1   AGCGAGTACNNCAGCACAAGAATGTGTGNNNNNNNNNNNNTAATATNGTTTGAATATGGTA   770
FP5-S. enterica-4   AGCGAGTACAGCAGCACAAGAATGTGTGNNGNNNNNNNNTAATATTGTTTGAATATGGTA   777
FP5-S. enterica-5   AGCGAGTACAGCAGCACAAGAATGTGTNNNNNNNNNNNNNTAATATTGTTTGAATATGGTA   767
FP5-S. cerevisiae-3 AGCGAGTACAGCNNNNNNNNNATGTGTGCCGTTCTCAGTTAATATTGTTTGAATATGGTA   767
FP5-S. cerevisiae-5 AGCGAGTACNNNGNNNNNNNNNATGTGTGCCGTTCTCAGTTAATATTGTTTGAATATGGTA   768
FP5-S. cerevisiae-2 ------------------------------------------------------------
FP5-S. cerevisiae-4 AGCGAGTACNNNNNNNNNNNNNATGTGTGCCGTTCTCAGTTAATATTGNNTGAATATGGTA   772
FP5-S. cerevisiae-1 AGCGAGTACAGCNGNNNNNNNATGTGTGCCGTTCTCAGTTAATATTGTTTGAATANGGNN   772

FP5-neg-control-4   ACCTGTTTTAGTCGGNTTAAAGGTAAGAAGATCTAACCNAAAACAACACTGCAGTGACTG   829
FP5-neg-control-5   ACCTGTTTTAGTCGGTTTAAAGGTAAGAAGATCTAACCNAAAACAACACTGCAGTGACTG   831
FP5-neg-control-3   ACCTGTTTTAGTCGGTTTAAAGGTAAGAAGATCTAACCAAAAACAACACTGCAGTGACTG   831
FP5-neg-control-2   ACCTGNTTTAGTCGGTTTAAAGGTAAGAAGATCTAACCNAAAACAACACTGCAGNGACTG   832
FP5-neg-control-1   ACCTGNTTTAGTCGGTTTAAAGGTAAGAAGATCTAACCAAAAACAACACTGCAGTGACTG   832
FP5-S. aureus-4     ACCTGNTTTAGTCGGTTTAAAGGTAAGAAGATCTAACCAAAAACNNNNNNGCAGTGACTG   832
FP5-S. aureus-5     ACCTGNTTTAGTCGGNTTAAAGGNAAGAAGANCTAACCAAAAACNNN-------------   807
FP5-S. aureus-2     ACCTGTTTTAGTCGGTTTAAAGGTAAGAAGATCTAACCAAAAANNNNNNTGCAGTGACTG   839
FP5-S. aureus-3     ACCTGTTTTAGTCGGTTTANANNNNAGAAGATCTAACCNNAAAA----------------   818
FP5-S. aureus-1     ACCTGNTTTAGTCGGNTTAAAGGTAAGAAGATCTAACCAAANACANN-------------   822
FP5-S. enterica-2   NCCTGNTTTAGTCGGNTTAAAGGTAAGAAGATCTAACCNAAAACAACACTGCAGTGACTG   828
FP5-S. enterica-3   ACCTGTTTTAGTCGGTTTAAAGGTAAGAAGATCTAACCNAAAACNACACTGCAGTGACTG   835
FP5-S. enterica-1   ACCTGTTTTAGTCGGNTTAAAGGTAAGAAGATCTAACCAAAAACAACACTGCAGTGACNN   830
FP5-S. enterica-4   ACCTGTTTTAGTCGGTTTAAAGGTAAGAAGATCTAACCAAAAACAACACTGCAGTGACTG   837
FP5-S. enterica-5   ACCTGTTTTAGTCGGTTTAAAGGTAAGAAGATCTAACCNAAAACAACACTGCAGTGACTG   827
FP5-S. cerevisiae-3 ACCTGTTTTAGTCGGTTTAAAGGTAAGAAGANCTAACCAAAAACAACACTGCAGTGACTG   827
FP5-S. cerevisiae-5 ACCTGTTTTAGTCGGTTTAAAGGTAAGANNANNTAACCAAAAACAACACTGCAGTGACTG   828
FP5-S. cerevisiae-2 ------------------------------------------------------------
FP5-S. cerevisiae-4 ACCTGTTTTAGTCGGNTTAAAGGTAAGAAGATCTAACCAAAAACAACACTGCAGNGACTG   832
FP5-S. cerevisiae-1 NNNNGTTTTAGTCGGTTTAAAGGTAAGAAGATCTAACCAAAAACAACACTGCAGNGACTG   832

FP5-neg-control-4   ATTGNAGTANTTATTTTTNNACT-------------------------------------   852
FP5-neg-control-5   ATTGTAGTANTTATTTTTTTACTTAATCTTAANNNNNNG---------------------   870
FP5-neg-control-3   ATTGNAGTATTTNNNNNTNN----------------------------------------   851
FP5-neg-control-2   ATTGNANNATTTATTTNNNNNCNNNNTCNTNNNNNNNGNGTAAACATCNACGGCGCACTT   892
FP5-neg-control-1   ATTGTAGTATTTATTTTTTTACNNNNNCTTAANNNNNNNGNANACNTCAACGGCGCACTT   892
FP5-S. aureus-4     ATTGNNG-----------------------------------------------------   839
FP5-S. aureus-5     ------------------------------------------------------------
FP5-S. aureus-2     ANNGNAGTATTTATTTTTTTACTTAA----------------------------------   865
FP5-S. aureus-3     ------------------------------------------------------------
FP5-S. aureus-1     ------------------------------------------------------------
FP5-S. enterica-2   ATTGTAGNANNNNNNN--------------------------------------------   844
FP5-S. enterica-3   ATTGNAGTATNNNNNN--------------------------------------------   851
FP5-S. enterica-1   NNNNNAGTATNNNNNNTTTTACTTANNNNNAATTNTGGTGTAAACATCANCGGCGCACTT   890
FP5-S. enterica-4   ATTGTAGTANNNNNNNTTTTACTTAATCTTAATTTTGG----------------------   875
FP5-S. enterica-5   ATTGNNGNANN-------------------------------------------------   838
FP5-S. cerevisiae-3 ATTGNAGNANTTATTTTTTTACTTAATCTTAANTTNNG----------------------   865
FP5-S. cerevisiae-5 ATNGNAGTATTTATTTTTTTACTTAATCTTAATTTNGNNGNAAACATCANCGGNNNGNTT   888
FP5-S. cerevisiae-2 ------------------------------------------------------------
FP5-S. cerevisiae-4 ATTGNAGTATTTATTTTTTTACTTAATCTTAATTTTGGGGN-------------------   873
FP5-S. cerevisiae-1 ATTGTAGTATTTATTTTNNNNNNNNATCTT------------------------------   862
```

In order to test the ability of the invention to provide a means of identification by comparison to a database, the first three sequence embedded fingerprints (Numbers 1-3) generated for each microorganism were used to produce a consensus fingerprint sequence for that organism (Tables 4-6). These consensus sequences were then used to create a BLAST database (NCBI BLAST web server). The fifth sequence embedded fingerprint (number 5) for each organism was used to query the database. The resultant blast scores (Tables 7-9) show that the comparison of BLAST program identifies each microorganisms sequence embedded fingerprint as belonging to the correct species (highest total score).

TABLE 4A

CLUSTAL 2.0.11 muultiple sequence alignment
First three *Staphylococcus aureus* MU3 sequence embedded fingerprints by primer mix FB1D1 were aligned and used to generate a consensus sequence

```
SEQ ID NO: 46       -------GTTGCTCT-CNGCTGACNATGCTGCTGCTGCTTNNNGNNNCTGTCTCCACTTC
consensus
SEQ ID NO: 22       CNGTTATGTTGCTCT-CNGCTGACNATGCTGCTGCTGCTTCNNGNNNCTGTCTCCACTTC          59
FB1D1 S. aureus 3
SEQ ID NO: 21       ----TNNGTTGNTCTACNGNTGACNATGCTGCTGCTGCTTNNNNNNNCTGTCTCCACTTC          56
FB1D1 S. aureus 2
SEQ ID NO: 23       -------GTTGNTCN-NNGCTGACNATGCTGCTGCTGCTTNNNGNNNCTGTCTCCACTTC          52
FB1D1 S. aureus 1
                           **** **   ** ******************** ** ****************

consensus           CTTGAACAATGNGCCGTCATGCTTCTTTTGCCTCCCGCTGCTCCAGAAAGCTANGNCNNA
FB1D1 S. aureus 3   CTTGAACAATGNGCCGTCATGCTTCTTTTGCCTCCCGCTGCTCCAGAAAGCTAGGNCNNA         119
FB1D1 S. aureus 2   CTTGAACAATGNGCCGTCATGCTTCTTTTGCCTCCCGCTGCTCCAGAAAGCTANGNNNNA         116
FB1D1 S. aureus 1   CTTGAACANTGCGCCGTCATGCTTCTTTTGCCTCCCGCTGCTCCAGAAAGCTANGNCNNA         112
                    ******** ** ***************************************** ** ***

consensus           CATCAGAACCACCACAGNCNNTNTCNCCNCCTTCCTCTTATAGATTCGGAATCTCATGAT
FB1D1 S. aureus 3   GATCAGAACCACCACAGNCNNTATCNCCNCCTTCCTCTTATAGATTCGGAATCTCATGAT         179
FB1D1 S. aureus 2   GATCAGAACCACCACAGNCNNNNTNACCNCCTTCCTCTTATAGATTCGGAATCTCATGAT         176
FB1D1 S. aureus 1   GATCAGAACCACCACAGNCNNNNTCNCCNCCTTCCTCTTATAGATTCGGAATCTCATGAT         172
                    *********************  *  **********************************

consensus           AGGGNNTCNNCCTCTGTGCGAGTGGAGAGAAGTTTGCAGGCGAGCTGANGAGCANTTGCA
FB1D1 S. aureus 3   AGGGNNTCNNCCTCTGTGCGAGTGGAGAGAAGTTTGCAGGCGAGCTGANGAGCAATTGCA         239
FB1D1 S. aureus 2   AGGGNNTCNNCCTCTGTGCGAGTGGAGAGAAGTTTGCAGGCNAGCTGANGAGCANTTGCA         236
FB1D1 S. aureus 1   AGGGGNTCNNCCTCTGTGCGAGTGGAGAGAAGTTTGCAGGCGAGCTGAGGAGCANTTGCA         232
                    **** ************************************ ****** ***** *****

consensus           GGTGNNNNNATGTGCTCGGCTCAAGAAGCGGGCCCGGAGAGGAAGAAGTCGTGCCGGGGC
FB1D1 S. aureus 3   GGTGNNNNNATGTGCTCGGCTCAAGAAGCGGGCCCGGAGAGGAAGAAGTCGTGCCGGGGC         299
FB1D1 S. aureus 2   GGNGNNNGNNTGTGCTCGGCTCAAGANGCGGGNCCGGANAGGAAGAAGTCGTGCCGGGGC         296
FB1D1 S. aureus 1   GGTGNNNNNATGTGCTCGGCTCAAGAAGCGGGCCCGGAGAGGAAGAAGTCGTGCCGGGGC         292
                    ** **** * **************** ***** ***** *********************

consensus           TAATTATTGGCAAAACGAGCTCTTGTTGTAAACATNGNNNNNNNNNNNNNNNNNNNNNNN
FB1D1 S. aureus 3   TAATTATTGGCAAAACGAGCTCTTGTTGNAAACNTNGNNNGGGGGGGNNNNNNNNNNNNN         359
FB1D1 S. aureus 2   TAATTATTGGCAAAACGAGCTCTTGTTGTAAACATTGNNNNNNNNNNNNNNNNNNNNNNN         356
FB1D1 S. aureus 1   TAATTATTGGCAAAACGAGCTCTTGTTGTAAACATNGNNNNNNNNNNNNNNNNNNNNNNN         352
                    **************************** **** * ****        ************

consensus           NNN-ATCAATATTCCATAAGGCATGATGGTTGCTCAGAGGCAGGAGAAGAGCAACGAATA
FB1D1 S. aureus 3   NNN-ATCAATATTCCATAAGGCATGATGGTTGCTCAGAGGCAGGAGAAGAGCAACGAATA         418
FB1D1 S. aureus 2   NNN-ATCAATATTCCATAAGGCATGATGGTTGCTCAGAGGCAGGAGAAGAGCAACGAATA         415
FB1D1 S. aureus 1   NNNGNNCAATATTCCATAAGGCATGATGGTTGCTCAGAGGCAGGAGAAGAGCAACGAATA         412
                    ***   ******************************************************

consensus           CGATCCTATAAAAGATAAAACATAAATAAACAGTCTTGATTATATTCTGGGTATTAAAGC
FB1D1 S. aureus 3   CGATCCTATAAAAGATAAAACATAAATAAACAGTCTTGATTATATTCTGGGTATTAAAGC         478
FB1D1 S. aureus 2   CGATCCTATAAAAGATAAAACATAAATAAACAGTCTTGATTATATTCTGGGTATTAAAGC         475
FB1D1 S. aureus 1   CGATCCTATAAAAGATAAAACATAAATAAACAGTCTTGATTATATTCTGGGTATTAAAGC         472
                    ************************************************************

consensus           CACAATCAGAACAAATATATGCTTTGTATCTTTTCTTGCCTTCTTCATTACCAACTGCTT
FB1D1 S. aureus 3   CACAATCAGAACAAATATATGCTTTGTATCTTTTCTTGCCTTCTTCATTACCAACTGCTT         538
FB1D1 S. aureus 2   CACAATCAGAACAAATATATGCTTTGTATCTTTTCTTGCCTTCTTCNTTACCAACTGCTT         535
FB1D1 S. aureus 1   CACAATCAGAACAAATATATGCTTTGTATCTTTTCTTGCCTTCTTCATNNNNNNNTGCTT         532
                    ********************************************** *       *****

consensus           CCGCGGCCACATTAAGAGAACTTGNGGTAAGATAAGAAGATATTTTATTCGTTCTGCTGA
FB1D1 S. aureus 3   CCGCGGCCACATTAAGAGAACTTGNGGTAAGATAAGAAGATATTTTATTCGTTCTGCTGA         598
FB1D1 S. aureus 2   CCGCGGCCACATTAAGAGAACTTGNGNTAAGATAAGAAGATATTTTATTCGTTCTGCTGA         595
FB1D1 S. aureus 1   CCGCGGCCACATTAAGAGAACTTGGGGTAAGATAAGAAGATATTTTATTCGTTCTGCTGA         592
                    ************************ * *********************************

consensus           CTTGCTGGATGTCGGGAAATATTCTGCATTTGATAAGAGGCGGTTAATTGCAGATATAAT
FB1D1 S. aureus 3   CTTGCTGGATGTCGGGAAATATTCTGCATTTGATAAGAGGCGGTTAATTGCAGATATAAT         658
FB1D1 S. aureus 2   CTTGCTGGATGTCGGGAAATATTCTGCATTTGATAAGAGGCGGTTAATTGCAGATATAAT         655
FB1D1 S. aureus 1   CTTGCTGGATGTCGGGAAATATTCTGCATTTGATAAGAGGCGGTTAATTGCAGATATAAT         652
                    ************************************************************
```

TABLE 4A-continued

CLUSTAL 2.0.11 muultiple sequence alignment
First three *Staphylococcus aureus* MU3 sequence embedded fingerprints by primer mix
FB1D1 were aligned and used to generate a consensus sequence

```
consensus            TGGTAGTGAAAAGGNNNNTTGCTATGGTCACCGTGAAGCGAGTACAGCAGCACAAGAATG
FB1D1 S. aureus 3    TGGTAGTGAAAAGGNNNNTTGCTATGGTCACCGTGAAGCGAGTACAGCAGCACAAGAATG   718
FB1D1 S. aureus 2    TGGTAGTGAAAAGGNGCGTTGCTATGGTCACCGTGAAGNGAGTACAGCAGCACAAGAATG   715
FB1D1 S. aureus 1    TGGTAGTGAAAAGGNNNNTTGCTATGGTCACCGTGAAGCGAGTACAGCAGCACAAGAATG   712
                     ***************   ******************** *********************

consensus            TGTGCCGTTCTCAGTTAATATTGTTTGAATATGGTAACCTGTTTTAGTCGGNTTAAAGGT
FB1D1 S. aureus 3    TGTGCCGTTCTCAGTTAATATTGTTTGAATATGGTAACCTGTTTTAGTCGGNTTAAAGGT   778
FB1D1 S. aureus 2    TGTGCCGTTCTCAGTTAATATTGTTTGAATATGGTAACCTGTTTTAGTCGGTTTAAAGGT   775
FB1D1 S. aureus 1    TGTGCCGTTCTCAGTTAATATTGTTTGAATATGGTAACCTGTTTTAGTCGGTTTAAAGGT   772

consensus            AAGAAGATCTAACCAAAAAC-AACACTGCAGNGACTGATTGNNGNN-TTNNNNNTTTTTT
FB1D1 S. aureus 3    AAGAAGATCTAACNNAAANNCAACACTGCANNGACTGNNNNNNNNNATTNNNNNNTTTTT   838
FB1D1 S. aureus 2    AAGAAGATCTAACCAAAAAC-AACACNGCAGTGACTGATTGNNGNN-NNNNNNNTTTTTT   833
FB1D1 S. aureus 1    NAGAAGATCTAACCAAAAAC-AACACTGCAGNGACTGATTGTAGTA---TTTATTTTTNN   828
                      ************  ***   ***** ***  *****                 ***

consensus            ACTTAATCTTAATTTTGGTGTAAACATCAACGG-CGCAC-----
FB1D1 S. aureus 3    ACTTAATCTTAATTTTGGTGTAAACATCAACNGGCGCACTTN--                   880
FB1D1 S. aureus 2    ANNTNATCTTAATTTTGGTGTAAACATCNACGG-CGCACTTCAA                   876
FB1D1 S. aureus 1    NNNNNNNCTNNATTTTGGTGTAAACATCAACGG-CGCACNN---                   868
                            **  ***************** ** * *****
```

TABLE 4B

CLUSTAL 2.0.11 multiple sequence alignment
First three *Staphylococcus aureus* MU3 sequence embedded fingerprints by primer
FP5 were aligned and used to generate a consensus sequence

```
SEQ ID NO: 47     -----NNNCTGGTTNTGANTACTGTTAANGTTGCTACTACTGCTGACAATGCTGCTGCTG      55
Consensus
SEQ ID NO: 33     NNNGCNGCCNGGTTNTGATTACTGTTAATGTTGCTACTACTGCTGACAATGCTGCTGCTG      60
FP5-S. aureus-2
SEQ ID NO: 35     ----NNNNCTGGTTNTGANTACTGTTAANGTTGCTACTACTGCTGACAATGCTGCTGCTG      56
FP5-S. aureus-1
SEQ ID ND: 34     -----NNNCTGGTTNTGANTACTGNNNNNGTTGCTACTACTGCTGACAATGCTGCTGCTG      55
FP5-S. aureus-3
                       *  * ******** *****     *******************************

Consensus         CTTCTCCTNNCTGTCTCCACTTCCTTGAACAATGCGCCGTCATGCTTCTTTTGCCTCCCG     115
FP5-S. aureus-2   CTTCTCCTNNCTGTCTCCACTTCCTTGAACAATGCGCCGTCATGCTTCTTTTGCCTCCCG     120
FP5-S. aureus-1   CTTCTCCTCNCTGTCTCCACTTCCTTGAACAATGCGCCGTCATGCTTCTTTTGCCTCCCG     116
FP5-S. aureus-3   CTTCTCNTNNCTGTCTCCACTTCCTTGAACAATGCGCCGTCATGCTTCTTTTGCCTCCCG     115
                  ****** * **************************************************

Consensus         CTGCTCCAGAAAGCTAGGCCGCAGATCAGAACCACCACAGTCAATATCACCACCTTCCTC     175
FP5-S. aureus-2   CTGCTCCAGAAAGCTAGGCCGCAGATCAGAACCACCACAGTCAATATCACCACCTTCCTC     180
FP5-S. aureus-1   CTGCTCCAGAAAGCTAGGCCGCAGATCAGAACCACCACAGTCAATATCACCACCTTCCTC     176
FP5-S. aureus-3   CTGCTCCAGAAAGCTAGGCCGCAGATCAGAACCACCACAGTCAATATCACCACCTTCCTC     175
                  ************************************************************

Consensus         TTATAGATTCGGAATCTCATGATAGGGGCTCAGCCTCTGTGCGAGTGGAGAGAAGTTTGC     235
FP5-S. aureus-2   TTATAGATTCGGAATCTCATGATAGGGGCTCAGCCTCTGTGCGAGTGGAGAGAAGTTTGC     240
FP5-S. aureus-1   TTATAGATTCGGAATCTCATGATAGGGGCTCAGCCTCTGTGCGAGTGGAGAGAAGTTTGC     236
FP5-S. aureus-3   TTATAGATTCGGAATCTCATGATAGGGGCTCAGCCTCTGTGCGAGTGGAGAGAAGTTTGC     235
                  ************************************************************

Consensus         AGGCGAGCTGAGGAGCAATTGCAGGTGATATGATGTGCTCGGCTCAAGAAGCGGGCCCGG     295
FP5-S. aureus-2   AGGCGAGCTGAGGAGCAATTGCAGGTGATATGATGTGCTCGGCTCAAGAAGCGGGCCCGG     300
FP5-S. aureus-1   AGGCGAGCTGAGGAGCAATTGCAGGTGATATGATGTGCTCGGCTCAAGAAGCGGGCCCGG     296
FP5-S. aureus-3   AGGCGAGCTGAGGAGCAATTGCAGGTGATATGATGTGCTCGGCTCAAGAAGCGGGCCCGG     295
                  ************************************************************

Consensus         AGAGGAAGAAGTCGTGCCGGGGCTAATTATTGGCAAAACGAGCTCTTGTTGTAAACATTG     355
FP5-S. aureus-2   AGAGGAAGAAGTCGTGCCGGGGCTAATTATTGGCAAAACGAGCTCTTGTTGTAAACATTG     360
FP5-S. aureus-1   AGAGGAAGAAGTCGTGCCGGGGCTAATTATTGGCAAAACGAGCTCTTGTTGTAAACNTTG     356
FP5-S. aureus-3   AGAGGAAGAAGTCGTGCCGGGGCTAATTATTGGCAAAACGAGCTCTTGTTGTAAACATTG     355
                  ******************************************************** ***

Consensus         ATCCAACTGGAATGTCACTAATGGCGAATCAATATTCCATAAGGCATGATGGTTGCTCAG     415
FP5-S. aureus-2   ATCCAACTGGAATGTCACTAATGGCGAATCAATATTCCATAAGGCATGATGGTTGCTCAG     420
FP5-S. aureus-1   NTNCAACTGGAATGTCACTAATGGCGAATCAATATTCCATAAGGCATGATGGTTGCTCAG     416
FP5-S. aureus-3   ATCCAACTGGAATGTCACTAATGGCGAATCAATATTCCATAAGGCATGATGGTTGCTCAG     415
                   * *********************************************************
```

TABLE 4B-continued

CLUSTAL 2.0.11 multiple sequence alignment
First three *Staphylococcus aureus* MU3 sequence embedded fingerprints by primer FP5 were aligned and used to generate a consensus sequence

```
Consensus          AGGCAGGAGAAGAGCAACGAATACGATCCTATAAAAGATAAAACATAAATAAACAGTCTT     475
FP5-S. aureus-2    AGGCAGGAGAAGAGCAACGAATACGATCCTATAAAAGATAAAACATAAATAAACAGTCTT     480
FP5-S. aureus-1    AGGCAGGAGAAGAGCAACGAATACGATCCTATAAAAGATAAAACATAAATAAACAGTCTT     476
FP5-S. aureus-3    AGGCAGGAGAAGAGCAACGAATACGATCCTATAAAAGATAAAACATAAATAAACAGTCTT     475
                   ************************************************************

Consensus          GATTATATTCTGGGTATTAAAGCCACAATCAGAACAAATATATGCTTTGTATCTTTTCTT     535
FP5-S. aureus-2    GATTATATTCTGGGTATTAAAGCCACAATCAGAACAAATATATGCTTTGTATCTTTTCTT     540
FP5-S. aureus-1    GATTATATTCTGGGTATTAAAGCCACAATCAGAACAAATATATGCTTTGTATCTTTTCTT     536
FP5-S. aureus-3    GATTATATTCTGGGTATTAAAGCCACAATCAGAACAAATATATGCTTTGTATCTTTTCTT     535
                   ************************************************************

Consensus          GCCTTCTTCATTACCAACTGCTTCCGCGGCCACATTAAGAGAACTTGTGGTAAGATAAGA     595
FP5-S. aureus-2    GCCTTCTTCATTACCAACTGCTTCCGCGGCCACATTAAGAGAACTTGTGGTAAGATAAGA     600
FP5-S. aureus-1    GCCTTCTTCATTACCAACTGCTTCCGCGGCCACATTAAGAGAACTTGTGGTAAGATAAGA     596
FP5-S. aureus-3    GCCTTCTTCATTACCAACTGCTTCCGCGGCCACATTAAGAGAACTTGTGGTAAGATAAGA     595
                   ************************************************************

Consensus          AGATATTTTATTCGTTCTGCTGACTTGCTGGATGTCGGGAAATATTCTGCATTTGATAAG     655
FP5-S. aureus-2    AGATATTTTATTCGTTCTGCTGACTTGCTGGATGTCGGGAAATATTCTGCATTTGATAAG     660
FP5-S. aureus-1    AGATATTTTATTCGTTCTGCTGACTTGCTGGATGTCGGGAAATATTCTGCATTTGATAAG     656
FP5-S. aureus-3    AGATATTTTATTCGTTCTGCTGACTTGCTGGATGTCGGGAAATATTCTGCATTTGATAAG     655
                   ************************************************************

Consensus          AGGCGGTTAATTGCAGATATAATTGGTAGTGAAAAGGGTCGTTGCTATGGTCACCGTGAA     715
FP5-S. aureus-2    AGGCGGTTAATTGCAGATATAATTGGTAGTGAAAAGGGTCGTTGCTATGGTCACCGTGAA     720
FP5-S. aureus-1    AGGCGGTTAATTGCAGATATAATTGGTAGTGAAAAGGGTCGTTGCTATGGTCACCGTGAA     716
FP5-S. aureus-3    AGGCGGTTAATTGCAGATATAATTGGTAGTGAAAAGGGTCGTTGCTATGGTCACCGTGAA     715
                   ************************************************************

Consensus          GCGAGTACAGCAGCACAAGAATGTGTGCCGTTCTCAGNNNNNNNNNNNNNGAATATGGTAA     775
FP5-S. aureus-2    GCGAGTACAGCAGCACAAGAATGTGTGCCGTTCTCAGNNNNNNNNNNNNNGAATATGGTAA     780
FP5-S. aureus-1    GCGAGTACAGCAGCACAAGAATGTGTGCCGTTCTCAGNNNNNNNNNNNNNGAATATGGTAA     776
FP5-S. aureus-3    GCGAGTACAGCAGCACAAGAATGTGTGCCGTTCTCAGNNNGNANNNNNNGAATATGGTAA     775
                   **************************************** * *****************

Consensus          CCTGTTTTAGTCGGTTTAAAGGTAAGAAGATCTAACCAAAAANN----------------     819
FP5-S. aureus-2    CCTGTTTTAGTCGGTTTAAAGGTAAGAAGATCTAACCAAAAANNNNNNTGCAGTGACTGA     840
FP5-S. aureus-1    CCTGNTTTAGTCGGNTTAAAGGTAAGAAGATCTAACCAAANACANN--------------     822
FP5-S. aureus-3    CCTGTTTTAGTCGGTTTANANNNNAGAAGATCTAACCNNAAAA-----------------     818
                   **** ********* *** *    *************  * *
```

TABLE 5A

CLUSTAL 2.0.11 multiple sequence alignment
First Three *Saccharomyces cerevisiae* S288C sequence embedded fingerprints by primer mix FB1D1 were aligned and used to generate a consensus sequence

```
SEQ ID NO: 48             CTGNTAATGTTGCTACTACTGCTGACAATGCTGCTGCTGCTTCNCCTCNCTGTCTCCAC
Consensus
SEQ ID NO: 10            NCNGNNNNNGNTGCTACTACTGCTGACAATGCTGCTGCTGCTTCTCCTCNCTGTCTCCAC      60
FB1D1 S. cerevisiae 3
SEQ ID NO: 11            -CTGTTAATGTTGCTACTACTGCTGACAATGCTGCTGCTGCTTCNCCTCNCTGTCTCCAC      59
FB1D1 S. cerevisiae 2
SEQ ID NO: 9             -CTGNTAATGTTGCTACTACTGCTGACAATGCTGCTGCTGCTTCTCCTCACTGTCTCCAC      59
FB1D1 S. cerevisiae 1
                          * *     * ********************************* **** **********

Consensus                TTCCTTGAACAATGCGCCGNCNTGCTTCTTTTGCCTCCCGCTGCTCCNGAGNGNTAGGCC
FB1D1 S. cervisiae 3     TTCCTTGAACAATGCGCCGTCNTGCTTCTTTTGCCTCCCGCTGCTCCNNANNGNTAGGCC     120
FB1D1 S. cervisiae 2     TTCCTTGAACAATGCGCCGNCNTGCTTCTTTTGCCTCCCGCTGCTCCNGAGNGNTAGGCC     119
FB1D1 S. cervisiae 1     TTCCTTGAACAATGCGCCGNCNTGCTTCTTTTGCCTCCCGCTGCTCCNGAGNGCTAGGCC     119
                         ******************* **************************** * ** ******

Consensus                GCAGATCAGAACCACCACAGNCAATATCACCACCNTCNNCTTATAGATTCGGAATCTCAT
FB1D1 S. cervisiae 3     GCAGATCAGAACCACCACAGTCAATATCACCACCTTCCTCTTATAGATTCGGAATCTCAT     180
FB1D1 S. cervisiae 2     GCAGATCAGAACCACCACAGNCAATATCACCACCNTCNNCTTATANATTCGGAATCTCAT     179
FB1D1 S. cervisiae 1     GCAGATCAGAACCACCACAGNCAATATCACCACCNNCNNCTTATAGATTCGGAATCTCAT     179
                         ******************** *************  *  ****** **************

Consensus                GATAGGGGCTCAGCCTCTGTGCGAGTGGAGAGAAGTTTGCAGGCGAGCTGAGGAGCAATT
FB1D1 S. cervisiae 3     GATAGGGGCTCAGCCTCTGTGCGAGTGGAGAGAAGTTTGCAGGCGAGCTGAGGAGCAATT     240
```

TABLE 5A-continued

CLUSTAL 2.0.11 multiple sequence alignment
First Three *Saccharomyces cerevisiae* S288C sequence embedded fingerprints by primer mix FB1D1 were aligned and used to generate a consensus sequence

```
FB1D1 S. cervisiae 2  GATAGGGGCTCAGCCTCTGTGCGAGTGGAGAGAAGTTTGCAGGCGAGCTGAGGAGCAATT   239
FB1D1 S. cervisiae 1  GATAGGGGCTCAGCCTCTGTGCGAGTGGAGAGAAGTTTGCAGGCGAGCTGAGGAGCAATT   239
                      ************************************************************

Consensus             GCAGGTGATATGATGTGCTCGGCTCANNGGGNNNNNNNNNNNNNNNNNNNNNNNTGCCGGG
FB1D1 S. cervisiae 3  GCAGGTGATATGATGTGCTCGGCTCANGGGGNNNNNNNNNNNNNNNNNNNNNNNGCCGGG   300
FB1D1 S. cervisiae 2  GCAGGTGATATGATGTGCTCGGCTCANNGGGCNNNNNNNNNNNNNNNNNNNNNTGCCGGG   299
FB1D1 S. cervisiae 1  GCNGGTGATATGATGTGCTCGGCTCNNNGGGNNNGGNGNNNNNNNNNANGNCNN-GCCGGG   298
                      ** ********************* * *** **  * ******** * * ** ******

Consensus             GCTAATTATTGGCAAAACGAGCTCTTGTTGTAAACATTGATCCAACTGGNNGGNNNNNNA
FB1D1 S. cervisiae 3  GCTAATTATTGGCAAAACGAGCTCTTGTTGTAAACATTGATCCAACTGGNNGGNNNNNNA   360
FB1D1 S. cervisiae 2  GCTAATTATTGGCAAAACGAGCTCTTGTTGTAAACATTGATCCAACTGGNNGGNNNNNNA   359
FB1D1 S. cervisiae 1  GCTAATTATTGGCAAAACGAGCTCTTGTTGTAAACATTGATCCNNNNGGNNNGTNNNNNN   358
                      *******************************************    **** * *****

Consensus             TGGNGNNNGNNNNTGNCNNNNGGCATGATGGTTGCTCAGAGGCAGGAGAAGAGCAACGAA
FB1D1 S. cervisiae 3  TGGNGNNNNNNNNTGCCNNNNNGCATGATGGTTGCTCAGAGGCAGGAGAAGAGCAACGAA   420
FB1D1 S. cervisiae 2  TGGNGNNNGNNNNTGNNNNNNNGGATGATGGTTGCTCAGAGGCAGGAGAAGAGCAACGAA   419
FB1D1 S. cervisiae 1  NGGNGNNNGANNNTGNNNNNNNGGNATGATGGTTGCTCAGAGGCAGGAGAAGAGCAACGAA   418
                       *******  *****  **** * *  ********************************

Consensus             TACGATCCTATAAAAGATAAAACATAAATAAACAGTCTTGATTATATTCTGGGTATTAAA
FB1D1 S. cervisiae 3  TACGATCCTATAAAAGATAAAACATAAATAAACAGTCTTGATTATATTCTGGGTATTAAA   480
FB1D1 S. cervisiae 2  TACNATCCTATAAAAGATAAAACATAAATAAACAGTCTTGATTATATTCTGGGTATTAAA   479
FB1D1 S. cervisiae 1  TACGATCCTATNAAAGATAAAACATAAATAAACNGTCTTGATTATATTCTGGGTATTAAA   478
                      *** ******* ********************* **************************

Consensus             NNCNNNGNCAGAACAAATATATGCTTTGNNNNNNNNCNTGNCNNCNNNNNNNNNNNNNNN
FB1D1 S. cervisiae 3  GNCNCAGNCAGAACAAATATATGCTTTGTNNCTNNNCNTGCCTTCTTNNNNNNNNNNNNN   540
FB1D1 S. cervisiae 2  NNNNNNGNCAGAACAAATATATGCTTTGNNNNNTNNCNTGNNNNCNNNNGGNNNNNNNNN   539
FB1D1 S. cervisiae 1  NNCNNNGNNAGAACAAATATATGCTTTNNNNNNNNNTCNNGNCNNNNNNNNNNNNNNNNN   538
                       * *  ** *****************  **    * ** *       **  *********

Consensus             NNNNNNGGCCACNNNNNGAGAACTTGTNNNNNNNTAAGAAGATATTTTATTCGNTCTGCT
FB1D1 S. cervisiae 3  NNNNNNGGCCACNNNNNNAGAACTTGNGGNGNNATAAGAAGATATTTTATTCGNTCTGCT   600
FB1D1 S. cervisiae 2  NNNNNNGGCCNCNNNNNGAGAACTTGTNNNNNNNTAAGAAGATATTTTATTCGNNCTGCT   599
FB1D1 S. cervisiae 1  NNNNNNGGCCACATTAAGAGAACTTGTNNNNNNNTAAGAAGATATTTTATTCGNTCTGCT   598
                      ********** *      ********    * ** ******************* *****

Consensus             GACTTGCTGGATGTCGGGAAATATTCTGCATTTGATAAGAGGCGGTTAATTGCAGATATA
FB1D1 S. cervisiae 3  GACTTGCTGGATGTCGGGAAATATTCTGCATTTGATAAGAGGCGGTTAATTGCAGATATA   660
FB1D1 S. cervisiae 2  GACTTGCTGGATGTCGGGAAATATTCTGCATTTGATAAGAGGCGGTTAATTGCAGATATA   659
FB1D1 S. cervisiae 1  GACTTGCTGGATGTCGGGAAATATTCTGCATTTGATAAGAGGCGGTTAATTGCAGATATA   658
                      ************************************************************

Consensus             ATTGGTAGTGAAAAGGGTCGTTGCTATGGTCACCGTGAAGCGAGTACAGCAGCACAAGAN
FB1D1 S. cervisiae 3  ATTGGTAGTGAAAAGGGTCGTTGCTATGGTCACCGTGAAGCGAGTACAGCAGCACAAGAN   720
FB1D1 S. cervisiae 2  ATTGGTAGTGAAAAGGGTCGTTGCTATGGTCACCGTGAAGCGAGTACAGCAGCACANGAN   719
FB1D1 S. cervisiae 1  ATTGGTAGTGAAAAGGGTCGTTGCTATGGTCACCGTGAAGCGAGTACAGCAGCACAAGAA   718
                      ******************************************************** **

Consensus             NGTGTGCCGTTCTCAGTTAATATTGNNTGAATATGGTAACCTGNTTTAGTCGGTTTAAAG
FB1D1 S. cervisiae 3  NGTGTGCCGTTCTCAGTTAATATNGNNNGAATATGGTAACCTGNTTTAGTCGGTTTAAAG   780
FB1D1 S. cervisiae 2  NGTGTGCCGTTCTCAGTTAATATTGNTTGAATATGGTAACCTGTTTTAGTCGGTTTAAAG   779
FB1D1 S. cervisiae 1  TGTGTGCCGTTCTCAGTTAATATTGTNTGAATATGGTAACCTGNTTTAGTCGGTTTAAAG   778
                       ********************** *   *************** ****************

Consensus             GTAAGAAGANCTAACCAAAAACAACACTGCNNNNNNGNNNGGGGGNNNNNNNNNNNNTAC
FB1D1 S. cervisiae 3  GTAAGAAGANCTAACCAAAAACAACACTGCNNNNNNNNNNGGGGGNNNNNNNNNNNNTTAC   840
FB1D1 S. cervisiae 2  GTAAGAAGANCTAACCNAAAACAACACTGCNNNNNNGNGGGGGGNNNNNNNNNNNNNTAC   839
FB1D1 S. cervisiae 1  GTAAGAAGATCTAACCAAAAACAACACTGCNNGNCNGNNNNNNNGGNNNNNNNNNNNNTTA   838
                      ********* ****** *************** * * *        ********** *

Consensus             TNNNNNNNNNTTNNNGGNGNAAACATCNACGNNNNNNNNNCAACCAATN
FB1D1 S. cervisiae 3  TNNNNGNNNNTTNNNGGNGNAAACATCNACGNNNNNNNNNCAACCNATNNN   890
FB1D1 S. cervisiae 2  TTNNNNNNNNNNNNNNNNNN--ACATCNNCGNNNNNNNNNCAACCAATAN-   886
FB1D1 S. cervisiae 1  CTNNNNNNNNATTTTGGNNTAAACATCAACGGNNNNNNNNCANCCANNN--   886
                        *** ****       *    *****  ** ********* **
```

TABLE 5B

CLUSTAL 2.0.11 multiple sequence alignment
First Three *Saccharomyces cerevisiae* S288C sequence embedded fingerprints by primer FP5 were aligned and used to generate a consensus sequence

```
SEQ ID NO: 49       --------CCTGNNNNNGATTACTGTTAATGTTGCTACTACTGCTGACAATGCTGCTGCT      52
Consensus
SEQ ID NO: 45       --------CCTGNNNNNGATTACTGTTAATGTTGCTACTACTGCTGACAATGCTGCTGCT      52
FP5-S. cerevisiae-1
SEQ ID NO: 43       NNNTGNNGCCTGNTTNTGATTACTGTTAATGTTGCTACTACTGCTGACAATGCTGCTGCT      60
FP5-S. cerevisiae-2
SEQ ID NO: 41       -------------NNNNNATNNCTGTTNATGTTGCTNCTACTGCTGACAATGCTGCTGCT      47
FP5-S. cerevisiae-3
                                   *  **  ***** ******** ***********************

Consensus           GCTTCTCCTCNCTGTCTCCACTTCCTTGAACAATGCGCCGTCATGCTTCTTTTGCCTCCC     112
FP5-S. cerevisiae-1 GCTTCTCCTCNCTGTCTCCACTTCCTTGAACAATGCGCCGTCATGCTTCTTTTGCCTCCC     112
FP5-S. cerevisiae-2 GCTTCTCCTCNCTGTCTCCACTTCCTTGAACAATGCGCCGTCATGCTTCTTTTGCCTCCC     120
FP5-S. cerevisiae-3 GCTTCTCCTCNNTGTCTCCACTTCCTTGAACAATGCGCCGTCATGCTTCTTTTGCCTCCC     107
                    *********** ************************************************

Consensus           GCTGCTCCAGAAAGCTAGGCCGCAGATCAGAACCACCACAGTCAATATCACCACCTTCCT     172
FP5-S. cerevisiae-1 GCTGCTCCAGAAAGCTAGGCCGCAGATCAGAACCACCACAGTCAATATCACCACCTTCCT     172
FP5-S. cerevisiae-2 GCTGCTCCAGAAAGCTAGGCCGCAGATCAGAACCACCACAGTCAATATCACCACCTTCCT     180
FP5-S. cerevisiae-3 GCTGCTCCAGAAAGCTAGGCCGCAGATCAGAACCACCACAGTCAATATCACCACCTTCCT     167
                    ************************************************************

Consensus           CTTATAGATTCGGAATCTCATGATAGGGGCTCAGCCTCTGTGCGAGTGGAGAGAAGTTTG     232
FP5-S. cerevisiae-1 CTTATAGATTCGGAATCTCATGATAGGGGCTCAGCCTCTGTGCGAGTGGAGAGAAGTTTG     232
FP5-S. cerevisiae-2 CTTATAGATTCGGAATCTCATGATAGGGGCTCAGCCTCTGTGCGAGTGGAGAGAAGTTTG     240
FP5-S. cerevisiae-3 CTTATAGATTCGGAATCTCATGATAGGGGCTCAGCCTCTGTGCGAGTGGAGAGAAGTTTG     227
                    ************************************************************

Consensus           CAGGCGAGCTGAGGAGCANTTGCAGGTGATATGATGTGCTCGGCTCAAGAAGCGGGCCCG     292
FP5-S. cerevisiae-1 CAGGCGAGCTGAGGAGCAATTGCAGGTGATATGATGTGCTCGGCTCAAGAAGCGGGCCCG     292
FP5-S. cerevisiae-2 CAGGCGAGCTGAGGAGCANTTGCAGGTGATATGATGTGCTCGGCTCAAGAAGCGGGCCCG     300
FP5-S. cerevisiae-3 CAGGCGAGCTGAGGAGNNNTTGCAGGTGATATGATGTGCTCGGCTCAAGAAGCGGGCCCG     287
                    ****************   *****************************************

Consensus           GAGAGGAAGAAGTCGTGCCGGGGCTAATTATTGGCAAAACGAGCTCTTGTTGTAAACATN     352
FP5-S. cerevisiae-1 GAGAGGAAGAAGTCGTGCCGGGGCTAATTATTGGCAAAACGAGCTCTTGTTGTAAACATN     352
FP5-S. cerevisiae-2 GAGAGGAAGAAGTCGTGCCGGGGCTAATTATTGGCAAAACGAGCTCTTGTTGTAAACATN     360
FP5-S. cerevisiae-3 GAGAGGAAGAAGTCGTGCCGGGGCTAATTATTGGCAAAACGAGCTCTTGTTGTAAACATN     347
                    ************************************************************

Consensus           NNNNNNNNNGGNATGTCACTAATGGCGAANNNNNANNNNNTAAGGNNTGATGGTTGCTCA     412
FP5-S. cerevisiae-1 NNNNNNNNNGGAATGTCACTAATGGCGAANNNNNNNNNNNTAAGGNATGATGGTTGCTCA     412
FP5-S. cerevisiae-2 NNNNNNNNNNNNANGTCACTAATGGCGAANNNNNANNNNNTAAGGNNTGATGGTTGCTCA     420
FP5-S. cerevisiae-3 NNNNNNNNTGGNATGTCACTAATGGCGAATNNNNANNNNNTAAGGNNTGATGGTTGCTCA     407
                    ********    * *************** **** *********** *************

Consensus           GAGGCAGGAGAAGAGCNNNGNATACNNNNNNATAAAAGATAAAACATAAATAAACAGTCT     472
FP5-S. cerevisiae-1 GAGGCAGGAGAAGAGCAACGAATACGANGCNNTAAAAGATAAAACATAAATAAACAGTCT     472
FP5-S. cerevisiae-2 GAGGCAGGAGAAGAGNNNNGNATACNNNNNNATAAAAGATAAAACATAAATAAACAGTCT     480
FP5-S. cerevisiae-3 GAGGCAGGAGAAGAGCNNNGNATACNNNNNTATAAAAGATAAAACATAAATAAACAGTCT     467
                    ***************    * ****  *    ****************************

Consensus           TGATTATATTCTGGGTATTAAAGCCACAATCAGAACAAATATATGCTTTGTATCTTTTCT     532
FP5-S. cerevisiae-1 TGATTATATTCTGGGTATTAAAGCCACAATCAGAACAAATATATGCTTTGTATCTTTTCT     532
FP5-S. cerevisiae-2 TGATTATATTCTGGGTATTAAAGCCACAATCAGAACAAATATATGCTTTGTATCTTTTCT     540
FP5-S. cerevisiae-3 TGATTATATTCTGGGTATTAAAGCCNCAATCNNANNAAATATATGCTTTGTATCTTTTCT     527
                    ************************* *****  *  ************************

Consensus           TGCCTNNNNNNNNNNNNNNNNNNNTCCGCGGCCACATTAAGAGAACTTGTGGTAAGATAAG     592
FP5-S. cerevisiae-1 TGCCTTNNNNNNNNNNNNNNNNNNTCCGCGGCCACATTAAGAGAACTTGTGGTAAGATAAG     592
FP5-S. cerevisiae-2 TGCCTNNNNNNNNNNNNNNNNNNNTCCGCGGCCACATTAAGAGAACTTGTGGTAAGATAAG     600
FP5-S. cerevisiae-3 TGCCTNNNNNNNNNNNNNNNNNNNTCCGCGGCCACATTAAGAGAACTTGTGGTAAGATAAG     587
                    ***** ******************************************************

Consensus           AAGATATTTTATTCGNNNNNNTGNNNNNNTGGATGTCGGGAAATATTCTGCATTTGATAA     652
FP5-S. cerevisiae-1 AAGATATTTTATTCGNNNNNNTGNNNNNNTGGATGTCGGGAAATATTCTGCATTTGATAA     652
FP5-S. cerevisiae-2 AAGATATTTTATTCGNNNNNNTGNNNNNNTGGATGTCGGGAAATATTCTGCATTTGATAA     660
FP5-S. cerevisiae-3 AAGATATTTTATTCNNNNNNNTGNNNNNNTGGATGTCGGGAAATATTCTGCATTTGATAA     647
                    ************** *********************************************

Consensus           GAGGCGGTTAANTGNAGATATAATTGGNNGNGAAA-------------------------     687
FP5-S. cerevisiae-1 GAGGCGGTTNNNTGNAGATATAATTGGTAGTGAAAAGGGTCGTTGCTATGGTCACCGTGA     712
FP5-S. cerevisiae-2 GANGCGGNTAANTGNANATATNATTGGNNGNGAAA-------------------------     695
FP5-S. cerevisiae-3 GAGGCGGTTAANTGCAGATATAATTGNNNNNNNNNNNGGTCGTTGCTATGGTCACCGTGA     707
                    ** **** *  *** * **** ****
```

TABLE 5B-continued

CLUSTAL 2.0.11 multiple sequence alignment
First Three *Saccharomyces cerevisiae* S288C sequence embedded fingerprints by primer FP5 were aligned and used to generate a consensus sequence

```
Consensus           ------------------------------------------------------------
FP5-S. cerevisiae-1 AGCGAGTACAGCNGNNNNNNNATGTGTGCCGTTCTCAGTTAATATTGTTTGAATANGGNN     772
FP5-S. cerevisiae-2 ------------------------------------------------------------
FP5-S. cerevisiae-3 AGCGAGTACAGCNNNNNNNNNATGTGTGCCGTTCTCAGTTAATATTGTTTGAATATGGTA     767

Consensus           ------------------------------------------------------------
FP5-S. cerevisiae-1 NNNNGTTTTAGTCGGTTTAAAGGTAAGAAGATCTAACCAAAAACAACACTGCAGNGACTG     832
FP5-S. cerevisiae-2 ------------------------------------------------------------
FP5-S. cerevisiae-3 ACCTGTTTTAGTCGGTTTAAAGGTAAGAAGANCTAACCAAAAACAACACTGCAGTGACTG     827

Consensus           --------------------------------------
FP5-S. cerevisiae-1 ATTGTAGTATTTATTTTNNNNNNNNATCTT--------                           862
FP5-S. cerevisiae-2 --------------------------------------
FP5-S. cerevisiae-3 ATTGNAGNANTTATTTTTTACTTAATCTTAANTTNNG                            865
```

TABLE 6A

CLUSTAL 2.0.11 multiple sequence alignment
First Three *Salmonella enterica* MR595 sequence embedded fingerprints by primer mix FB1D1 were aligned and used to generate a consensus sequence

```
SEQ ID NO: 50       GCTGACAATGCTGCTGCNGCTTCTCCTCNCTGTCTCCACTT
Consensus
SEQ ID NO: 18       -------GTTNNTCNNN--GCTGACAATGCTGCTGCNGCTTCTCCTCNCTGTCTCCACTT           51
FB1D1 S. enterica 3
SEQ ID NO: 17       CNGNNANGTTNNTCNNN--GCTGACAATGCTGCTGCNGCTTCNCCTCNCTGTCTCCACTT           58
FB1D1 S. enterica 2
SEQ ID NO: 19       -------GTTGCTNCTACTGCTGANAATGCTGCTGCTGCTTCTCCTCNCTGTCTCCACTT           53
FB1D1 S. enterica 1        ***  *      ***** *********** ***** *****************


Consensus           CCTTGAACAATGCGCCGTCATGCTTCTTTTGCCTCCCGCTGCTCCAGAAAGCTAGGCCGC
FB1D1 S. enterica 3 CCTTGAACAATGCGCCGTCATGCTTCTTTTGCCTCCCGCTGCTCCAGAAAGCTAGGCCGC          111
FB1D1 S. enterica 2 CCTTGAACAATGCGCCGTCATGCTTCTTTTGCCTCCCGCTGCTCCAGAAAGCTAGGCCGC          118
FB1D1 S. enterica 1 CCTTGAACAATGCGCCGTCATGCTTCTTTTGCCTCCCGCTGCTCCAGAAAGCTAGGCCGC          113
                    ************************************************************

Consensus           AGATCANAACCACCACAGTCAATATCACCACCTTCCTCTTATAGATTCGGAATCTCATGA
FB1D1 S. enterica 3 AGATCANAACCACCACAGTCAATATCACCACCTTCCTCTTATAGATTCGGAATCTCATGA          171
FB1D1 S. enterica 2 AGATCANAACCACCACAGTCAATATCACCACCTTCCTCTTATAGATTCGGAATCTCATGA          178
FB1D1 S. enterica 1 AGATCAGAACCACCACAGTCAATATCACCACCTTCCTCTTATAGATTCGGAATCTCATGA          173
                    ****** *****************************************************

Consensus           TAGGGGCTCAGCCTCTGTGCGAGTGGAGAGAAGTTNNNNNNNGAGCTGAGGAGCAATTGC
FB1D1 S. enterica 3 TAGGGGCTCAGCCTCTGTGCGAGTGGAGAGAAGTTNNNNNNNGAGCTGAGGAGCAATTGC          231
FB1D1 S. enterica 2 TAGGGGCTCAGCCTCTGTGCGAGTGGAGAGAAGTTNNNNNGNNAGCTGANGANCAATTGC          238
FB1D1 S. enterica 1 TAGGGGCTCAGCCTCTGTGCGAGTGGAGAGAAGTTNGCAGGCGAGCTGAGGAGCAATTGC          233
                    ************************************  ******   **    *******

Consensus           AGGTGATATGATGTGCTCGGCTCAAGAAGCGGGCCNGGNNNGNNNGAAGNNNNNNNNNNN
FB1D1 S. enterica 3 AGGTGATATGATGTGCTCGGCTCAAGAAGCGGGCCNGGNNAGGAAGAAGNNNNNNNNNNN          291
FB1D1 S. enterica 2 AGGTGATATGATGTGCTCGGCTCAAGAAGCGGGCCCGGAGNNNNNNAAGNNNNNNNNNNN          298
FB1D1 S. enterica 1 AGGTGATATGATGTGCTCGGCTCAAGAAGCGGGCCNGNNNNGNNNGAAGTCNNGNCGNGG          293
                    ********************************** *          ***  ** *  *

Consensus           NTAATTATTGGCAAAACGAGCTCTTGTTGTANNNNNNNNNNNGNNNNNNNNNNNACTNNN
FB1D1 S. enterica 3 NTAATTATTGGCAAAACGAGCTCTTGTTGTANNNNNNNNNNNGNNNNNNNNNNNACTNNN          351
FB1D1 S. enterica 2 NTAATTATTGGCAAAACGAGCTCTTGTTNNNNNNNNNNNNNNGNNNNNNNNNNNACTANN          358
FB1D1 S. enterica 1 CTAATTATTGGCAAAACGAGCTCTTGTTGTANNNNNNNNNNNGNNNNNNNNNNNCTANNG          353
                     ***************************   ***********************    *

Consensus           NNNGNNCAATATTCCNTANNGCATGATGGTTGCTCAGAGGCAGNNNNNNAGCAANNNANN
FB1D1 S. enterica 3 NGNGNNCAATATTCCNTANNGCATGATGGTTGCTCAGAGGCAGNNNNNNAGCAANNNANN          411
FB1D1 S. enterica 2 GNNGNNCAATATTCCNTANNGCATGATGGTTGCTCAGAGGCAGNNNNNNAGCAACNNANN          418
FB1D1 S. enterica 1 NNNNATCNATATTCCNTAANGCATGATGGTTGCTCAGAGGCANGNNNN-AGCAACNAANA          412
                      *   * ********** ***********************  **** **** * **

Consensus           CGATCCTATAAAAGATAAAACATAAATAAACAGTCTTGATTATATTCTGGGTATTAAAGC
FB1D1 S. enterica 3 CGATCCTATAAAAGATAAAACATAAATAAACAGTCTTGATTATATTCTGGGTATTAAAGC          471
FB1D1 S. enterica 2 CNATCCTATAAAAGATAAAACATAAATAAACAGTCTTGATTATATTCTGGGTATTAAAGC          478
FB1D1 S. enterica 1 CGATCCTATAAAAGATAAAACATAAATAAACAGTCTTGATTATATTCTGGGTATTAAAGC          472
                    * **********************************************************
```

TABLE 6A-continued

CLUSTAL 2.0.11 multiple sequence alignment
First Three *Salmonella enterica* MR595 sequence embedded fingerprints by primer mix FB1D1 were aligned and used to generate a consensus sequence

```
Consensus            CACAATCAGAACAAATATATGCTTTGTATCTTNNNNNGCCTTCTTCATNNNNNNNNNGNTT
FB1D1 S. enterica 3  CACAATCAGAACAAATATATGCTTTGTATCTTNNNNNGCCTTCTTCATNNNNNNNNTGNTT     531
FB1D1 S. enterica 2  CACAATCAGAACAAATATATGCTTTGTATCTTNNNNNGCCTTCTTCANNNNNNNANNGCTN     538
FB1D1 S. enterica 1  CACAATCAGAACAAATATATGCTTTGTATCTTTNCNNGCCTTCTTCATNNNNNNNNNGNTT     532
                     ******************************** * ************ ***** * * *

Consensus            CCGCGGNCACATTAAGAGAACTTGTGGTAAGATAAGAAGATATTTTATTCGTTCTGCTGA
FB1D1 S. enterica 3  CCGCGGNCACATTAAGAGAACTTGTGGTAAGATAAGAAGATATTTTATTCGTTCTGCTGA     591
FB1D1 S. enterica 2  NNNNGGCCACATTAAGAGAACTTGTGGTAAGATAAGAAGATATTTTATTCGTTCTGCTGA     598
FB1D1 S. enterica 1  CCGCGNNNNCATTAAGAGAACTTGTGGTAAGATAAGAAGATATTTTATTCGTTCTGCTGA     592
                         *    ***************************************************

Consensus            CTTGCTGGATGTCGGGAAATATTCTGCATTTNNNNNNAGGCGGTTAATTGCAGATATAAT
FB1D1 S. enterica 3  CTTGCTGGATGTCGGGAAATATTCTGCATTTNNNNNNAGGCGGTTAATTGCAGATATAAT     651
FB1D1 S. enterica 2  CTTGCTGGATGTCGGGAAATANTCTGCATTTNNNNNNAGGCGGTTAATTGCANATATAAT     658
FB1D1 S. enterica 1  CTTGCTGGATGTCGGGAAATATTCTGCATTTNNNNNGAGGCGGTTAATTGCAGATATAAT     652
                     ********************* ************** *************** *******

Consensus            TGGTAGTGAAAAGGGTCGTTGCTATGGTCACCGTGAAGCGAGTACAGCAGCACAAGAATG
FB1D1 S. enterica 3  TGGTAGTGAAAAGGGTCGTTGCTATGGTCACCGTGAAGCGAGTACAGCAGCACAAGAATG     711
FB1D1 S. enterica 2  TGGTAGTGAAAAGGGTCGTTGCTATGGTCACCGTGAAGCGAGTACAGCAGCACAAGAATG     718
FB1D1 S. enterica 1  TGGTAGTGAAAAGGGTCGTTGCTATGGTCACCGTGAAGCGAGTACAGCAGCACAAGAATG     712
                     ************************************************************

Consensus            TGTGCCGTTCTCNNNNNNTATTGTTTGAATATGGNAACCTGTTTTAGTCGGTTTAAANNN
FB1D1 S. enterica 3  TGTGCCGTTCTCNNNNNNTATTGTTTGAATATGGNAACCTGTTTTAGTCGGTTTAAANGN     771
FB1D1 S. enterica 2  NGTGCCGTTCTCNGNNNNTATTGTTTGAATATGGNAACCTGTTTTAGTCGGNTTAANNNN     778
FB1D1 S. enterica 1  TGTGCCGTTCTCNNNNNNTATTGTTTGAATATGGTAACCTGTTTTAGTCGGTTTAANNNN     772
                      ************ ******************* **************** **** * *

Consensus            NNNNNNNTCTAACCNAAAACAACACTGCAGNGACNG--ANNGTAGTATTTATTTTNNNNN
FB1D1 S. enterica 3  NNNNNNT-CTAACCNAAAACAACACTGCAGTGACNG--ANNNNNGTANTTATTTTTTTAC     828
FB1D1 S. enterica 2  NNNNNNNTCTAACCAAAAACAACACTGNNGNGACTG--ANTGTAGTATTTATTTTNNNNN     836
FB1D1 S. enterica 1  NNNNNNNTCTAACCAAAAACAACACTGCAGNGGNNNGGNNNGTAGTATTTATTTTNNNNN     832
                     ******  ****** ************  * *       *    *** *******

Consensus            NNNNNNCTTAATTTT-GGTGNAAACATCNACGGCGCACTTC
FB1D1 S. enterica 3  TNNNNNNNNNNNNTTTGGTGNAAACATCAACGGCGCACTTC--------                 869
FB1D1 S. enterica 2  NNNNN-CTTAATTTT-GGTGNAAACATCNACGGCGCACTTCAACCANNN                 883
FB1D1 S. enterica 1  NNNNNNCTTAATTTT-GGNGNAAACATCNACGGCGCACNTNNN------                 874
                      ****        *  ** ********* ********* *
```

TABLE 6B

CLUSTAL 2.0.11 multiple sequence alignment
First Three *Salmonella enterica* MR595 sequence embedded fingerprints by primer FP5 were aligned and used to generate a consensus sequence

```
SEQ ID NO: 51        ------GNTTNTGATTACTGTTNNNGTTGCTACTACTGCTGACAATGCTGCTGCTGCTTC     54
Consensus
SEQ ID NO: 38        ----CTGNNNNTGATTACTGTNNNNGTTGCTACTACTGCTGACAATGCTGCTGCTGCTTC     56
FP5-S. enterica-1
SEQ ID NO: 37        NNNNNNGGTTNTGATTACTGTTAATGTTGCTACTACTGCTGACAATGCTGCTGCTGCTTC     60
FP5-S. enterica-3
SEQ ID NO: 36        -------NTTNTGATTACTGTTNNNNNTGCTACTACTGCTGACAATGCTGCTGCTGCTTC     53
FP5-S. enterica-2
                               ***********      *********************************

Consensus            TCCTNNCTGTCTCCACTTCCTTGAACAATGCGCCGTCATGCTTCTTTTGCCTCCCGCTGC    114
FP5-S. enterica-1    TCCTNNCTGTCTCCACTTCCTTGAACAATGCGCCGTCATGCTTCTTTTGCCTCCCGCTGC    116
FP5-S. enterica-3    TCCTNNCTGTCTCCACTTCCTTGAACAATGCGCCGTCATGCTTCTTTTGCCTCCCGCTGC    120
FP5-S. enterica-2    TCCTCNCTGTCTCCACTTCCTTGAACAATGCGCCGTCATGCTTCTTTTGCCTCCCGCTGC    113
                     **** *******************************************************

Consensus            TCCAGAAAGCTAGGCCGCAGATCAGAACCACCACAGTCAATATCACCACCTTCCTCTTAT    174
FP5-S. enterica-1    TCCAGAAAGCTAGGCCGCAGATCAGAACCACCACAGTCAATATCACCACCTTCCTCTTAT    176
FP5-S. enterica-3    TCCAGAAAGCTAGGCCGCAGATCAGAACCACCACAGTCAATATCACCACCTTCCTCTTAT    180
FP5-S. enterica-2    TCCAGAAAGCTAGGCCGCAGATCAGAACCACCACAGTCAATATCACCACCTTCCTCTTAT    173
                     ************************************************************

Consensus            AGATTCGGAATCTCATGATAGGGGCTCAGCCTCTGTGCGAGTGGAGAGAAGTTTGCAGGC    234
FP5-S. enterica-1    AGATTCGGAATCTCATGATAGGGGCTCAGCCTCTGTGCGAGTGGAGAGAAGTTTGCAGGC    236
```

TABLE 6B-continued

CLUSTAL 2.0.11 multiple sequence alignment
First Three *Salmonella enterica* MR595 sequence embedded fingerprints by primer FP5 were aligned and used to generate a consensus sequence

```
FP5-S. enterica-3    AGATTCGGAATCTCATGATAGGGGCTCAGCCTCTGTGCGAGTGGAGAGAAGTTTGCAGGC   240
FP5-S. enterica-2    AGATTCGGAATCTCATGATAGGGGCTCAGCCTCTGTGCGAGTGGAGAGAAGTTTGCAGGC   233
                     ************************************************************

Consensus            GAGCTGAGGAGCAATTGCAGGTGATATGATGTGCTCGGCTCAAGAAGCGGGCCCGGAGAG   294
FP5-S. enterica-1    GAGCTGAGGAGCAATTGCAGGTGATATGATGTGCTCGGCTCAAGAAGCGGGCCCGGAGAG   296
FP5-S. enterica-3    GAGCTGAGGAGCAATTGCAGGTGATATGATGTGCTCGGCTCAAGAAGCGGGCCCGGAGAG   300
FP5-S. enterica-2    GAGCTGAGGAGCAATTGCAGGTGATATGATGTGCTCGGCTCAAGAAGCGGGCCCGGAGAG   293
                     ************************************************************

Consensus            GAAGAAGTCGTGCCGGGGCTAATTATTGGCAAAACGAGCTCTTGTTGTAAACATTGATCC   354
FP5-S. enterica-1    GAAGAAGTCGTGCCGGGGCTAATTATTGGCAAAACGAGCTCTTGTTGTAAACATTGATCC   356
FP5-S. enterica-3    GAAGAAGTCGTGCCGGGGCTAATTATTGGCAAAACGAGCTCTTGTTGTAAACATTGATCC   360
FP5-S. enterica-2    GAAGAAGTCGTGCCGGGGCTAATTATTGGCAAAACGAGCTCTTGTTGTAAACATTGATCC   353
                     ************************************************************

Consensus            AACTGGAATGTCACTAANNNNNNNNNNT-ATTCCATAAGGCATGATGGTTGCTCAGAGGC   413
FP5-S. enterica-1    AACTGGAATGTCACTAANNNNNNNNANT-ATTCCATAAGGCATGATGGTTGCTCAGAGGC   415
FP5-S. enterica-3    AACTGGAATGTCACTAANNNNNNNNNNNTATTCCATAAGGCATGATGGTTGCTCAGAGGC   420
FP5-S. enterica-2    AACTGGAATGTCACTAANNNNNNNNNNATATTCCATAAGGCATGATGGTTGCTCAGAGGC   413
                     ************************* *  *******************************

Consensus            AGGAGAAGAGCAACGAATACGATCCTATAAAAGATAAAACATAAATAAACAGTCTTGATT   473
FP5-S. enterica-1    NGGAGAAGAGCAACGAATACGATCCTATAAAAGATAAAACATAAATAAACAGTCTTGATT   475
FP5-S. enterica-3    AGGAGAAGAGCAACGAATACGATCCTATAAAAGATAAAACATAAATAAACAGTCTTGATT   480
FP5-S. enterica-2    AGGAGAAGAGCAACGAATACGATCCTATAAAAGATAAAACATAAATAAACAGTCTTGATT   473
                      ***********************************************************

Consensus            ATATTCTGGGTATTAAAGCCACANNNNNNNNNNNNNTATGCTTTGTATCTTNNNNNGNCT   533
FP5-S. enterica-1    ATATTCTGGGTATTAAAGCCACANNNNNNNNNGANNTATGCTTTGTATCTTNNNNNGNCT   535
FP5-S. enterica-3    ATATTCTGGGTATTAAAGCCACANNNNNNNNNNNNNTATGCTTTGTATCTTNNNNNGNCN   540
FP5-S. enterica-2    ATATTCTGGGTATTAAAGCCACAANNNNNNNNNNNNTNTGCTTTGTATCTTTNNNNGCCT   533
                     *********************** ********  *** ************* ***** *

Consensus            TCTTCATTACCAACTGCTTCCGCGGCCACATTAAGAGAACTTGTGGTAAGATAAGAAGAT   593
FP5-S. enterica-1    TCTTCATTACCAACTGCTTCCGCGGCCACATTAAGAGAACTTGTGGTAAGATAAGAAGAT   595
FP5-S. enterica-3    TCTTCATTACCAACTGCTTCCGCGGCCACATTAAGAGAACTTGTGGTAAGATAAGAAGAT   600
FP5-S. enterica-2    TCTTCATTACCAACTGCTTCCGCGGCCACATTAAGAGAACTTGTGGTAAGATAANAANAT   593
                     ****************************************************** ** **

Consensus            ATTTTATTCNNNNNNNTGACTTGCTGGATGTCGGGAAATATTCTGCATTTGATAAGAGGC   653
FP5-S. enterica-1    ATTTTATTCNNNNNNNTGACTTGCTGGATGTCGGGAAATATTCTGCATTTGATAAGAGGC   655
FP5-S. enterica-3    ATTTTATTCNNNNNNNTGACTTGCTGGATGTCGGGAAATATTCTGCATTTGATAAGAGGC   660
FP5-S. enterica-2    ATTTTATTCNNNNNNNTGACTTGCTGGATGTCGGGAAATATTCTGCATTTGATAAGAGGC   653
                     ************************************************************

Consensus            GGTTAATTGCAGATATAATTGGNNNNNNNNNNGNTCGTTGCTATGGTCACCGTGAAGCGA   713
FP5-S. enterica-1    GGTTAATTGCAGATATAATTGGNNGTNNNNNNGNNCGTTGCTATGGTCACCGTGAAGCGA   715
FP5-S. enterica-3    GGTTAATTGCAGATATAATTGGNNNNNNNNNNGNTCGTTGCTATGGTCACCGTGAAGCGA   720
FP5-S. enterica-2    GGTTAATTGCAGATATAATTNNNNNNNNNNNNGGTCGTTGCTATGGTCACCGTGAAGCGA   713
                     ********************  **  *******  *************************

Consensus            GTACNGCAGCACAAGAATGTGTGNNNNNNNNNNNNAATATTGNTTGAATATGGTAACCTG   773
FP5-S. enterica-1    GTACNNCAGCACAAGAATGTGTGNNNNNNNNNNNTAATATNGTTTGAATATGGTAACCTG   775
FP5-S. enterica-3    GTACAGCAGCACAAGAATGTGTGNNNNNNNNNNNNAATATTGNTTGAATATGGTAACCTG   780
FP5-S. enterica-2    GTNNNGCNNNNNNAGANTGNGNGGNNGNNNNNNNNNATATTGNTTGAATATGGNNNCCTG   773
                     **    *      *** ** * * ** *******  **** * **********   ****

Consensus            TTTTAGTCGGNTTAAAGGTAAGAAGATCTAACCNAAAACAACACTGCAGTGACTGATTGN   833
FP5-S. enterica-1    TTTTAGTCGGNTTAAAGGTAAGAAGATCTAACCAAAAACAACACTGCAGTGACNNNNNNN   835
FP5-S. enterica-3    TTTTAGTCGGTTTAAAGGTAAGAAGATCTAACCNAAAACNACACTGCAGTGACTGATTGN   840
FP5-S. enterica-2    NTTTAGTCGGNTTAAAGGTAAGAAGATCTAACCNAAAACAACACTGCAGTGACTGATTGT   833
                      ********* ********************** ***** *************

Consensus            AGTATNNNNNN-------------------------------------------------   844
FP5-S. enterica-1    AGTATNNNNNNTTTTACTTANNNNNAATTNTGGTGTAAACATCANCGGCGCACTTCNACC   895
FP5-S. enterica-3    AGTATNNNNNN-------------------------------------------------   851
FP5-S. enterica-2    AGNANNNNNNN-------------------------------------------------   844
                     ** * ******

Consensus            ------------------------------
FP5-S. enterica-1    NATACTCCAATGNTTTATCCATCGACATGN                                 925
FP5-S. enterica-3    ------------------------------
FP5-S. enterica-2    ------------------------------
```

TABLE 7

*Staphylococcus aureus* MU3 sequence embedded fingerprint #5 was run as query sequence. Using BLASTN, low complexity filter on, with values of +2 for a match and −3 for a mismatch against the consensus sequence for all three organisms.
Sequences producing significant alignments:

| Accession | Description | Max score | Total score | Query coverage | E value | Max ident Links |
|---|---|---|---|---|---|---|
| | | by primer mix FB1D1: | | | | |
| 25817 | *Staphalococcus aureus* MU3 | 922 | 989 | 91% | 0.0 | 92% |
| 25816 | *Salmonella enterica* MR595 | 892 | 892 | 97% | 0.0 | 85% |
| 25815 | *Saccharomyces cervisiae* S288C | 820 | 820 | 89% | 0.0 | 84% |
| | | by single primer FP5: | | | | |
| 8382 | *Staphalococcus aureus* MU3 | 1355 | 1355 | 99% | 0.0 | 98% |
| 8381 | *Salmonella enterica* MR595 | 1128 | 1128 | 99% | 0.0 | 89% |
| 8383 | *Saccharomyces cervisiae* S288C | 940 | 940 | 83% | 0.0 | 88% |

TABLE 8

*Saccharomyces cerevisiae* S288C MU3 sequence embedded fingerprint #5 was run as query sequence. Using BLASTN, low complexity filter on, with values of +2 for a match and −3 for a mismatch against the consensus sequences for all three organisms
Sequences producing significant alignments:

| Accession | Description | Max score | Total score | Query coverage | E value | Max ident Links |
|---|---|---|---|---|---|---|
| | | by primer mix FB1D1: | | | | |
| 36125 | *Saccharomyces cervisiae* S288C | 594 | 963 | 82% | 8e−174 | 96% |
| 36126 | *Salmonella enterica* MR595 | 439 | 756 | 79% | 4e−127 | 93% |
| 36127 | *Staphalococcus aureus* MU3 | 459 | 736 | 75% | 4e−133 | 100% |
| | | by single primer FP5: | | | | |
| 39539 | *Saccharomyces cervisiae* S288C | 928 | 928 | 73% | 0.0 | 96% |
| 39538 | *Staphalococcus aureus* MU3 | 1088 | 1088 | 87% | 0.0 | 87% |
| 39537 | *Salmonella enterica* MR595 | 971 | 971 | 90% | 0.0 | 84% |

TABLE 9

*Salmonella enterica* MR595 sequence embedded fingerprint #5 was run as query sequence. Using BLASTN, low complexity filter on, with values of +2 for a match and −3 for a mismatch against the consensus sequence for all three organisms.
Sequences producing significant alignments:

| Accession | Description | Max score | Total score | Query coverage | E value | Max ident Links |
|---|---|---|---|---|---|---|
| | | by primer mix FB1D1: | | | | |
| 49678 | *Salmonella enterica* MR595 | 928 | 928 | 97% | 0.0 | 92% |
| 49679 | *Staphalococcus aureus* MU3 | 760 | 830 | 91% | 0.0 | 84% |
| 49677 | *Saccharomyces cervisiae* S288C | 607 | 607 | 91% | 1e−177 | 75% |
| | | by single primer FP5: | | | | |
| 20645 | *Salmonella enterica* MR595 | 1229 | 1229 | 98% | 0.0 | 96% |
| 20646 | *Staphalococcus aureus* MU3 | 1220 | 1220 | 95% | 0.0 | 92% |
| 20647 | *Saccharomyces cervisiae* S288C | 888 | 888 | 79% | 0.0 | 88% |

We claim:

1. A method of generating a sequence embedded fingerprint pattern for identifying an organism in a sample comprising:

(a) providing a sample comprising said organism, said organism comprising at least one nucleic acid;

(b) combining said sample or the at least one nucleic acid therefrom with an amplification mix comprising at least one labeled oligonucleotide primer;

(c) generating at least one labeled amplification product from the at least one nucleic acid of said organism using a nucleotide amplification technique employing said at least one labeled oligonucleotide primer;

(d) combining said at least one labeled amplification product with products from a previously performed DNA sequencing reaction of a known organism to create a separation mix; and (e) separating said separation mix on the basis of oligonucleotide length in a fluorescent DNA sequencing instrument to generate a sequence embedded fingerprint pattern for said organism, wherein the sequence embedded fingerprint pattern is generated by perturbing sequence output at positions where fingerprint products are migrating with like-sized DNA sequence fragments.

2. The method of claim 1, comprising after step (e) the further steps of:

(f) comparing said sequence embedded fingerprint pattern for said organism to a database containing sequence embedded fingerprint patterns for known organisms; and (g) identifying said organism as a function of said comparison to said database.

3. The method of claim 1, wherein said organism is a microorganism.

4. The method of claim 1, wherein said organism is unknown.

5. The method of claim 1, wherein said nucleotide amplification technique is a random amplification of polymorphic DNA (RAPD) polymerase chain reaction (PCR).

6. The method of claim 1, wherein said at least one nucleic acid is DNA.

7. The method of claim 1, comprising after step (e) the further step of repeating steps (c)-(e) at different stringency conditions as compared to that of a first pass through steps (c)-(e) to generate a different amplification profile as compared to that generated by the first pass through steps (c)-(e).

8. The method of claim 1, wherein step (e) is performed by capillary gel electrophoresis.

9. The method of claim 1, wherein steps (b)-(c) are performed by one or more primers comprising nucleic acid sequences selected from the group consisting of SEQ ID NO:1, SEQ ID NO:2, SEQ ID NO:3, SEQ ID NO:4, SEQ ID NO:25, and a combination thereof.

* * * * *

SEQUENCE LISTING

```
<160> NUMBER OF SEQ ID NOS: 51

<210> SEQ ID NO 1
<211> LENGTH: 36
<212> TYPE: DNA
<213> ORGANISM: Artificial Sequence
<220> FEATURE:
<223> OTHER INFORMATION: Primer
```

<400> SEQUENCE: 1
cgcttcgcgt tttaaaaacc gacatgagta caatac 36

<210> SEQ ID NO 2
<211> LENGTH: 36
<212> TYPE: DNA
<213> ORGANISM: Artificial Sequence
<220> FEATURE:
<223> OTHER INFORMATION: Primer

<400> SEQUENCE: 2
cgcttcgcgt tttaaaaacc gacatgagta caatcc 36

<210> SEQ ID NO 3
<211> LENGTH: 36
<212> TYPE: DNA
<213> ORGANISM: Artificial Sequence
<220> FEATURE:
<223> OTHER INFORMATION: Primer

<400> SEQUENCE: 3
cgcttcgcgt tttaaaaacc gacatgagta caatgc 36

<210> SEQ ID NO 4
<211> LENGTH: 36
<212> TYPE: DNA
<213> ORGANISM: Artificial Sequence
<220> FEATURE:
<223> OTHER INFORMATION: Primer

<400> SEQUENCE: 4
cgcttcgcgt tttaaaaacc gacatgagta caattc 36

<210> SEQ ID NO 5
<211> LENGTH: 821
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (5)..(5)
<223> OTHER INFORMATION: n is unknown
<220> FEATURE:
<221> NAME/KEY: misc_feature
<222> LOCATION: (8)..(9)
<223> OTHER INFORMATION: n is unknown
<220> FEATURE:
<221> NAME/KEY: misc_feature
<222> LOCATION: (35)..(35)
<223> OTHER INFORMATION: n is unknown
<220> FEATURE:
<221> NAME/KEY: misc_feature
<222> LOCATION: (40)..(40)
<223> OTHER INFORMATION: n is unknown
<220> FEATURE:
<221> NAME/KEY: misc_feature
<222> LOCATION: (270)..(273)
<223> OTHER INFORMATION: n is unknown
<220> FEATURE:
<221> NAME/KEY: misc_feature
<222> LOCATION: (275)..(282)
<223> OTHER INFORMATION: n is unknown
<220> FEATURE:
<221> NAME/KEY: misc_feature
<222> LOCATION: (345)..(345)
<223> OTHER INFORMATION: n is unknown
<220> FEATURE:
<221> NAME/KEY: misc_feature
<222> LOCATION: (347)..(347)
<223> OTHER INFORMATION: n is unknown
<220> FEATURE:

<221> NAME/KEY: misc_feature
<222> LOCATION: (353)..(359)
<223> OTHER INFORMATION: n is unknown
<220> FEATURE:
<221> NAME/KEY: misc_feature
<222> LOCATION: (529)..(530)
<223> OTHER INFORMATION: n is unknown
<220> FEATURE:
<221> NAME/KEY: misc_feature
<222> LOCATION: (532)..(533)
<223> OTHER INFORMATION: n is unknown
<220> FEATURE:
<221> NAME/KEY: misc_feature
<222> LOCATION: (535)..(537)
<223> OTHER INFORMATION: n is unknown
<220> FEATURE:
<221> NAME/KEY: misc_feature
<222> LOCATION: (539)..(548)
<223> OTHER INFORMATION: n is unknown
<220> FEATURE:
<221> NAME/KEY: misc_feature
<222> LOCATION: (782)..(782)
<223> OTHER INFORMATION: n is unknown
<220> FEATURE:
<221> NAME/KEY: misc_feature
<222> LOCATION: (812)..(813)
<223> OTHER INFORMATION: n is unknown

<400> SEQUENCE: 5
gttgntcnnc tgctgacaat gctgctgctg cttcncctcn ctgtctccac ttccttgaac 60
aatgcgccgt catgcttctt ttgcctcccg ctgctccaga aagctaggcc gcagatcaga 120
accaccacag tcaatatcac caccttcctc ttatagattc ggaatctcat gataggggct 180
cagcctctgt gcgagtggag agaagtttgc aggcgagctg aggagcaatt gcaggtgata 240
tgatgtgctc ggctcaagaa gcgggcccgn nnngnnnnnn nncgtgccgg ggctaattat 300
tggcaaaacg agctcttgtt gtaaacattg atccaactgg aatgncncta atnnnnnnnt 360
caatattcca taaggcatga tggttgctca gaggcaggag aagagcaacg aatacgatcc 420
tataaaagat aaaacataaa taaacagtct tgattatatt ctgggtatta aagccacaat 480
cagaacaaat atatgctttg tatcttttct tgccttcttc attaccaann gnntnnncnn 540
nnnnnnnnag agaacttgtg gtaagataag aagatatttt attcgttctg ctgacttgct 600
ggatgtcggg aaatattctg catttgataa gaggcggtta attgcagata taattggtag 660
tgaaaagggt cgttgctatg gtcaccgtga agcgagtaca gcagcacaag aatgtgtgcc 720
gttctcagtt aatattgttt gaatatggta acctgtttta gtcggtttaa aggtaagaag 780
anctaaccaa aaacaacact gcagtgactg anngtagtat t 821

<210> SEQ ID NO 6
<211> LENGTH: 807
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (3)..(3)
<223> OTHER INFORMATION: n is unknown
<220> FEATURE:
<221> NAME/KEY: misc_feature
<222> LOCATION: (5)..(5)
<223> OTHER INFORMATION: n is unknown
<220> FEATURE:
<221> NAME/KEY: misc_feature
<222> LOCATION: (29)..(29)
<223> OTHER INFORMATION: n is unknown
<220> FEATURE:
<221> NAME/KEY: misc_feature
<222> LOCATION: (34)..(36)

-continued

<223> OTHER INFORMATION: n is unknown
<220> FEATURE:
<221> NAME/KEY: misc_feature
<222> LOCATION: (265)..(276)
<223> OTHER INFORMATION: n is unknown
<220> FEATURE:
<221> NAME/KEY: misc_feature
<222> LOCATION: (337)..(337)
<223> OTHER INFORMATION: n is unknown
<220> FEATURE:
<221> NAME/KEY: misc_feature
<222> LOCATION: (339)..(339)
<223> OTHER INFORMATION: n is unknown
<220> FEATURE:
<221> NAME/KEY: misc_feature
<222> LOCATION: (341)..(341)
<223> OTHER INFORMATION: n is unknown
<220> FEATURE:
<221> NAME/KEY: misc_feature
<222> LOCATION: (346)..(351)
<223> OTHER INFORMATION: n is unknown
<220> FEATURE:
<221> NAME/KEY: misc_feature
<222> LOCATION: (520)..(520)
<223> OTHER INFORMATION: n is unknown
<220> FEATURE:
<221> NAME/KEY: misc_feature
<222> LOCATION: (522)..(539)
<223> OTHER INFORMATION: n is unknown
<220> FEATURE:
<221> NAME/KEY: misc_feature
<222> LOCATION: (767)..(767)
<223> OTHER INFORMATION: n is unknown

<400> SEQUENCE: 6

```
tcncngctga caatgctgct gctgcttcnc ctcnnngtct ccacttcctt gaacaatgcg      60

ccgtcatgct tcttttgcct cccgctgctc cagaaagcta ggccgcagat cagaaccacc     120

acagtcaata tcaccacctt cctcttatag attcggaatc tcatgatagg ggctcagcct     180

ctgtgcgagt ggagagaagt ttgcaggcga gctgaggagc aattgcaggt gatatgatgt     240

gctcggctca agaagcgggc ccggnnnnnn nnnnnncgtg ccggggctaa ttattggcaa     300

aacgagctct tgttgtaaac attgatccaa ctggaangnc nctaannnnn natcaatatt     360

ccataaggca tgatggttgc tcagaggcag gagaagagca acgaatacga tcctataaaa     420

gataaaacat aaataaacag tcttgattat attctgggta ttaaagccac aatcagaaca     480

aatatatgct ttgtatcttt tcttgccttc ttcattaccn annnnnnnnn nnnnnnnnnt     540

aagagaactt gtggtaagat aagaagatat tttattcgtt ctgctgactt gctggatgtc     600

gggaaatatt ctgcatttga taagaggcgg ttaattgcag atataattgg tagtgaaaag     660

ggtcgttgct atggtcaccg tgaagcgagt acagcagcac aagaatgtgt gccgttctca     720

gttaatattg tttgaatatg gtaacctgtt ttagtcggtt taaaggnaag aagatctaac     780

caaaaacaac actgcagtga ctgattg                                         807
```

<210> SEQ ID NO 7
<211> LENGTH: 818
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (3)..(5)
<223> OTHER INFORMATION: n is unknown
<220> FEATURE:
<221> NAME/KEY: misc_feature
<222> LOCATION: (46)..(47)
<223> OTHER INFORMATION: n is unknown
<220> FEATURE:

```
<221> NAME/KEY: misc_feature
<222> LOCATION: (284)..(284)
<223> OTHER INFORMATION: n is unknown
<220> FEATURE:
<221> NAME/KEY: misc_feature
<222> LOCATION: (286)..(287)
<223> OTHER INFORMATION: n is unknown
<220> FEATURE:
<221> NAME/KEY: misc_feature
<222> LOCATION: (351)..(351)
<223> OTHER INFORMATION: n is unknown
<220> FEATURE:
<221> NAME/KEY: misc_feature
<222> LOCATION: (353)..(353)
<223> OTHER INFORMATION: n is unknown
<220> FEATURE:
<221> NAME/KEY: misc_feature
<222> LOCATION: (358)..(366)
<223> OTHER INFORMATION: n is unknown
<220> FEATURE:
<221> NAME/KEY: misc_feature
<222> LOCATION: (540)..(542)
<223> OTHER INFORMATION: n is unknown
<220> FEATURE:
<221> NAME/KEY: misc_feature
<222> LOCATION: (548)..(548)
<223> OTHER INFORMATION: n is unknown
<220> FEATURE:
<221> NAME/KEY: misc_feature
<222> LOCATION: (550)..(550)
<223> OTHER INFORMATION: n is unknown
<220> FEATURE:
<221> NAME/KEY: misc_feature
<222> LOCATION: (553)..(553)
<223> OTHER INFORMATION: n is unknown
<220> FEATURE:
<221> NAME/KEY: misc_feature
<222> LOCATION: (761)..(761)
<223> OTHER INFORMATION: n is unknown
<220> FEATURE:
<221> NAME/KEY: misc_feature
<222> LOCATION: (794)..(794)
<223> OTHER INFORMATION: n is unknown

<400> SEQUENCE: 7

gtnnngttgc tactactgct gacaatgctg ctgctgcttc tcctcnntgt ctccacttcc      60

ttgaacaatg cgccgtcatg cttcttttgc ctcccgctgc tccagaaagc taggccgcag    120

atcagaacca ccacagtcaa tatcaccacc ttcctcttat agattcggaa tctcatgata    180

ggggctcagc ctctgtgcga gtggagagaa gtttgcaggc gagctgagga gcaattgcag    240

gtgatatgat gtgctcggct caagaagcgg gcccggagag gaananntcg tgccggggct    300

aattattggc aaaacgagct cttgttgtaa acattgatcc aactggaatg ncnctaannn    360

nnnnnnaata ttccataagg catgatggtt gctcagaggc aggagaagag caacgaatac    420

gatcctataa aagataaaac ataaataaac agtcttgatt atattctggg tattaaagcc    480

acaatcagaa caaatatatg ctttgtatct tttcttgcct tcttcattac caactgcttn    540

nncggccncn ttnagagaac ttgtggtaag ataagaagat attttattcg ttctgctgac    600

ttgctggatg tcgggaaata ttctgcattt gataagaggc ggttaattgc agatataatt    660

ggtagtgaaa agggtcgttg ctatggtcac cgtgaagcga gtacagcagc acaagaatgt    720

gtgccgttct cagttaatat tgtttgaata tggtaacctg ntttagtcgg tttaaaggta    780

agaagatcta accnaaaaca acactgcagt gactgatt                            818

<210> SEQ ID NO 8
<211> LENGTH: 874
<212> TYPE: DNA
<213> ORGANISM: Artificial Sequence
<220> FEATURE:
```

<223> OTHER INFORMATION: S. cerevisiae PCR reaction /DNA sequence
standard
<220> FEATURE:
<221> NAME/KEY: misc_feature
<222> LOCATION: (72)..(72)
<223> OTHER INFORMATION: n is unknown
<220> FEATURE:
<221> NAME/KEY: misc_feature
<222> LOCATION: (74)..(74)
<223> OTHER INFORMATION: n is unknown
<220> FEATURE:
<221> NAME/KEY: misc_feature
<222> LOCATION: (100)..(100)
<223> OTHER INFORMATION: n is unknown
<220> FEATURE:
<221> NAME/KEY: misc_feature
<222> LOCATION: (104)..(104)
<223> OTHER INFORMATION: n is unknown
<220> FEATURE:
<221> NAME/KEY: misc_feature
<222> LOCATION: (106)..(106)
<223> OTHER INFORMATION: n is unknown
<220> FEATURE:
<221> NAME/KEY: misc_feature
<222> LOCATION: (121)..(121)
<223> OTHER INFORMATION: n is unknown
<220> FEATURE:
<221> NAME/KEY: misc_feature
<222> LOCATION: (150)..(150)
<223> OTHER INFORMATION: n is unknown
<220> FEATURE:
<221> NAME/KEY: misc_feature
<222> LOCATION: (258)..(260)
<223> OTHER INFORMATION: n is unknown
<220> FEATURE:
<221> NAME/KEY: misc_feature
<222> LOCATION: (266)..(266)
<223> OTHER INFORMATION: n is unknown
<220> FEATURE:
<221> NAME/KEY: misc_feature
<222> LOCATION: (269)..(279)
<223> OTHER INFORMATION: n is unknown
<220> FEATURE:
<221> NAME/KEY: misc_feature
<222> LOCATION: (281)..(281)
<223> OTHER INFORMATION: n is unknown
<220> FEATURE:
<221> NAME/KEY: misc_feature
<222> LOCATION: (283)..(283)
<223> OTHER INFORMATION: n is unknown
<220> FEATURE:
<221> NAME/KEY: misc_feature
<222> LOCATION: (285)..(286)
<223> OTHER INFORMATION: n is unknown
<220> FEATURE:
<221> NAME/KEY: misc_feature
<222> LOCATION: (339)..(339)
<223> OTHER INFORMATION: n is unknown
<220> FEATURE:
<221> NAME/KEY: misc_feature
<222> LOCATION: (342)..(342)
<223> OTHER INFORMATION: n is unknown
<220> FEATURE:
<221> NAME/KEY: misc_feature
<222> LOCATION: (346)..(351)
<223> OTHER INFORMATION: n is unknown
<220> FEATURE:
<221> NAME/KEY: misc_feature
<222> LOCATION: (353)..(353)
<223> OTHER INFORMATION: n is unknown
<220> FEATURE:
<221> NAME/KEY: misc_feature
<222> LOCATION: (355)..(366)
<223> OTHER INFORMATION: n is unknown
<220> FEATURE:
<221> NAME/KEY: misc_feature
<222> LOCATION: (368)..(373)
<223> OTHER INFORMATION: n is unknown
<220> FEATURE:
<221> NAME/KEY: misc_feature
<222> LOCATION: (376)..(376)
<223> OTHER INFORMATION: n is unknown
<220> FEATURE:
<221> NAME/KEY: misc_feature
<222> LOCATION: (424)..(424)
<223> OTHER INFORMATION: n is unknown
<220> FEATURE:
<221> NAME/KEY: misc_feature
<222> LOCATION: (473)..(474)
<223> OTHER INFORMATION: n is unknown
<220> FEATURE:
<221> NAME/KEY: misc_feature
<222> LOCATION: (476)..(476)
<223> OTHER INFORMATION: n is unknown
<220> FEATURE:
<221> NAME/KEY: misc_feature
<222> LOCATION: (478)..(478)
<223> OTHER INFORMATION: n is unknown
<220> FEATURE:
<221> NAME/KEY: misc_feature
<222> LOCATION: (480)..(480)
<223> OTHER INFORMATION: n is unknown
<220> FEATURE:
<221> NAME/KEY: misc_feature
<222> LOCATION: (482)..(482)
<223> OTHER INFORMATION: n is unknown
<220> FEATURE:
<221> NAME/KEY: misc_feature
<222> LOCATION: (502)..(507)
<223> OTHER INFORMATION: n is unknown
<220> FEATURE:
<221> NAME/KEY: misc_feature
<222> LOCATION: (509)..(511)
<223> OTHER INFORMATION: n is unknown
<220> FEATURE:
<221> NAME/KEY: misc_feature
<222> LOCATION: (517)..(522)
<223> OTHER INFORMATION: n is unknown
<220> FEATURE:
<221> NAME/KEY: misc_feature
<222> LOCATION: (524)..(537)
<223> OTHER INFORMATION: n is unknown
<220> FEATURE:
<221> NAME/KEY: misc_feature
<222> LOCATION: (544)..(550)
<223> OTHER INFORMATION: n is unknown
<220> FEATURE:
<221> NAME/KEY: misc_feature
<222> LOCATION: (561)..(565)
<223> OTHER INFORMATION: n is unknown
<220> FEATURE:
<221> NAME/KEY: misc_feature
<222> LOCATION: (586)..(586)
<223> OTHER INFORMATION: n is unknown
<220> FEATURE:
<221> NAME/KEY: misc_feature
<222> LOCATION: (722)..(722)
<223> OTHER INFORMATION: n is unknown
<220> FEATURE:
<221> NAME/KEY: misc_feature
<222> LOCATION: (749)..(749)
<223> OTHER INFORMATION: n is unknown
<220> FEATURE:
<221> NAME/KEY: misc_feature
<222> LOCATION: (789)..(789)
<223> OTHER INFORMATION: n is unknown
<220> FEATURE:
<221> NAME/KEY: misc_feature
<222> LOCATION: (797)..(804)
<223> OTHER INFORMATION: n is unknown
<220> FEATURE:
<221> NAME/KEY: misc_feature
<222> LOCATION: (806)..(806)
<223> OTHER INFORMATION: n is unknown
<220> FEATURE:
<221> NAME/KEY: misc_feature
<222> LOCATION: (808)..(812)
<223> OTHER INFORMATION: n is unknown
<220> FEATURE:
<221> NAME/KEY: misc_feature -continued
<222> LOCATION: (814)..(815)
<223> OTHER INFORMATION: n is unknown
<220> FEATURE:
<221> NAME/KEY: misc_feature
<222> LOCATION: (817)..(827)
<223> OTHER INFORMATION: n is unknown
<220> FEATURE:
<221> NAME/KEY: misc_feature
<222> LOCATION: (834)..(840)
<223> OTHER INFORMATION: n is unknown
<220> FEATURE:
<221> NAME/KEY: misc_feature
<222> LOCATION: (848)..(849)
<223> OTHER INFORMATION: n is unknown
<220> FEATURE:
<221> NAME/KEY: misc_feature
<222> LOCATION: (851)..(851)
<223> OTHER INFORMATION: n is unknown
<220> FEATURE:
<221> NAME/KEY: misc_feature
<222> LOCATION: (864)..(869)
<223> OTHER INFORMATION: n is unknown

<400> SEQUENCE: 8
tgttgctact actgctgaca atgctgctgc tgcttctcct cactgtctcc acttccttga 60
acaatgcgcc gncntgcttc ttttgcctcc cgctgctccn gagngntagg ccgcagatca 120
naaccaccac agtcaatatc accaccttcn tcttatagat tcggaatctc atgatagggg 180
ctcagcctct gtgcgagtgg agagaagttt gcaggcgagc tgaggagcaa ttgcaggtga 240
tatgatgtgc tcggctcnnn gggcgnggnn nnnnnnnnna ngncnngccg gggctaatta 300
ttggcaaaac gagctcttgt tgtaaacatt gatccgggng gnatgnnnnn nangnnnnnn 360
nnnnnngnnn nnnggnatga tggttgctca gaggcaggag aagagcaacg aatacgatcc 420
tatnaaagat aaaacataaa taaacagtct tgattatatt ctgggtatta aanncncngn 480
cngaacaaat atatgctttg tnnnnnntnn ngccttnnnn nngnnnnnnn nnnnnnncgg 540
ccannnnnnn agaacttgtg nnnnnataag aagatatttt attcgntctg ctgacttgct 600
ggatgtcggg aaatattctg catttgataa gaggcggtta attgcagata taattggtag 660
tgaaaagggt cgttgctatg gtcaccgtga agcgagtaca gcagcacaag aatgtgtgcc 720
gntctcagtt aatattgttt gaatatggna acctgtttta gtcggtttaa aggtaagaag 780
atctaaccna aaacaannnn nnnngncnnn nngnngnnnn nnnnnnntta cttnnnnnnn 840
attttggnng naaacatcaa cggnnnnnnt caac 874

<210> SEQ ID NO 9
<211> LENGTH: 881
<212> TYPE: DNA
<213> ORGANISM: Artificial Sequence
<220> FEATURE:
<223> OTHER INFORMATION: S. cerevisiae PCR reaction /DNA sequence standard
<220> FEATURE:
<221> NAME/KEY: misc_feature
<222> LOCATION: (4)..(4)
<223> OTHER INFORMATION: n is unknown
<220> FEATURE:
<221> NAME/KEY: misc_feature
<222> LOCATION: (79)..(79)
<223> OTHER INFORMATION: n is unknown
<220> FEATURE:
<221> NAME/KEY: misc_feature
<222> LOCATION: (81)..(81)
<223> OTHER INFORMATION: n is unknown
<220> FEATURE:
<221> NAME/KEY: misc_feature
<222> LOCATION: (107)..(107)
<223> OTHER INFORMATION: n is unknown
<220> FEATURE:

<221> NAME/KEY: misc_feature
<222> LOCATION: (111)..(111)
<223> OTHER INFORMATION: n is unknown
<220> FEATURE:
<221> NAME/KEY: misc_feature
<222> LOCATION: (140)..(140)
<223> OTHER INFORMATION: n is unknown
<220> FEATURE:
<221> NAME/KEY: misc_feature
<222> LOCATION: (154)..(155)
<223> OTHER INFORMATION: n is unknown
<220> FEATURE:
<221> NAME/KEY: misc_feature
<222> LOCATION: (157)..(158)
<223> OTHER INFORMATION: n is unknown
<220> FEATURE:
<221> NAME/KEY: misc_feature
<222> LOCATION: (242)..(242)
<223> OTHER INFORMATION: n is unknown
<220> FEATURE:
<221> NAME/KEY: misc_feature
<222> LOCATION: (265)..(267)
<223> OTHER INFORMATION: n is unknown
<220> FEATURE:
<221> NAME/KEY: misc_feature
<222> LOCATION: (271)..(273)
<223> OTHER INFORMATION: n is unknown
<220> FEATURE:
<221> NAME/KEY: misc_feature
<222> LOCATION: (276)..(276)
<223> OTHER INFORMATION: n is unknown
<220> FEATURE:
<221> NAME/KEY: misc_feature
<222> LOCATION: (278)..(285)
<223> OTHER INFORMATION: n is unknown
<220> FEATURE:
<221> NAME/KEY: misc_feature
<222> LOCATION: (287)..(287)
<223> OTHER INFORMATION: n is unknown
<220> FEATURE:
<221> NAME/KEY: misc_feature
<222> LOCATION: (289)..(289)
<223> OTHER INFORMATION: n is unknown
<220> FEATURE:
<221> NAME/KEY: misc_feature
<222> LOCATION: (291)..(292)
<223> OTHER INFORMATION: n is unknown
<220> FEATURE:
<221> NAME/KEY: misc_feature
<222> LOCATION: (342)..(345)
<223> OTHER INFORMATION: n is unknown
<220> FEATURE:
<221> NAME/KEY: misc_feature
<222> LOCATION: (348)..(350)
<223> OTHER INFORMATION: n is unknown
<220> FEATURE:
<221> NAME/KEY: misc_feature
<222> LOCATION: (353)..(359)
<223> OTHER INFORMATION: n is unknown
<220> FEATURE:
<221> NAME/KEY: misc_feature
<222> LOCATION: (362)..(362)
<223> OTHER INFORMATION: n is unknown
<220> FEATURE:
<221> NAME/KEY: misc_feature
<222> LOCATION: (364)..(366)
<223> OTHER INFORMATION: n is unknown
<220> FEATURE:
<221> NAME/KEY: misc_feature
<222> LOCATION: (369)..(371)
<223> OTHER INFORMATION: n is unknown
<220> FEATURE:
<221> NAME/KEY: misc_feature
<222> LOCATION: (374)..(379)
<223> OTHER INFORMATION: n is unknown
<220> FEATURE:
<221> NAME/KEY: misc_feature
<222> LOCATION: (382)..(382)
<223> OTHER INFORMATION: n is unknown
<220> FEATURE:

<221> NAME/KEY: misc_feature
<222> LOCATION: (430)..(430)
<223> OTHER INFORMATION: n is unknown
<220> FEATURE:
<221> NAME/KEY: misc_feature
<222> LOCATION: (452)..(452)
<223> OTHER INFORMATION: n is unknown
<220> FEATURE:
<221> NAME/KEY: misc_feature
<222> LOCATION: (479)..(480)
<223> OTHER INFORMATION: n is unknown
<220> FEATURE:
<221> NAME/KEY: misc_feature
<222> LOCATION: (482)..(484)
<223> OTHER INFORMATION: n is unknown
<220> FEATURE:
<221> NAME/KEY: misc_feature
<222> LOCATION: (486)..(487)
<223> OTHER INFORMATION: n is unknown
<220> FEATURE:
<221> NAME/KEY: misc_feature
<222> LOCATION: (506)..(513)
<223> OTHER INFORMATION: n is unknown
<220> FEATURE:
<221> NAME/KEY: misc_feature
<222> LOCATION: (516)..(517)
<223> OTHER INFORMATION: n is unknown
<220> FEATURE:
<221> NAME/KEY: misc_feature
<222> LOCATION: (519)..(519)
<223> OTHER INFORMATION: n is unknown
<220> FEATURE:
<221> NAME/KEY: misc_feature
<222> LOCATION: (521)..(544)
<223> OTHER INFORMATION: n is unknown
<220> FEATURE:
<221> NAME/KEY: misc_feature
<222> LOCATION: (566)..(572)
<223> OTHER INFORMATION: n is unknown
<220> FEATURE:
<221> NAME/KEY: misc_feature
<222> LOCATION: (592)..(592)
<223> OTHER INFORMATION: n is unknown
<220> FEATURE:
<221> NAME/KEY: misc_feature
<222> LOCATION: (745)..(745)
<223> OTHER INFORMATION: n is unknown
<220> FEATURE:
<221> NAME/KEY: misc_feature
<222> LOCATION: (762)..(762)
<223> OTHER INFORMATION: n is unknown
<220> FEATURE:
<221> NAME/KEY: misc_feature
<222> LOCATION: (809)..(810)
<223> OTHER INFORMATION: n is unknown
<220> FEATURE:
<221> NAME/KEY: misc_feature
<222> LOCATION: (812)..(812)
<223> OTHER INFORMATION: n is unknown
<220> FEATURE:
<221> NAME/KEY: misc_feature
<222> LOCATION: (814)..(814)
<223> OTHER INFORMATION: n is unknown
<220> FEATURE:
<221> NAME/KEY: misc_feature
<222> LOCATION: (816)..(822)
<223> OTHER INFORMATION: n is unknown
<220> FEATURE:
<221> NAME/KEY: misc_feature
<222> LOCATION: (825)..(835)
<223> OTHER INFORMATION: n is unknown
<220> FEATURE:
<221> NAME/KEY: misc_feature
<222> LOCATION: (841)..(848)
<223> OTHER INFORMATION: n is unknown
<220> FEATURE:
<221> NAME/KEY: misc_feature
<222> LOCATION: (856)..(857)
<223> OTHER INFORMATION: n is unknown
<220> FEATURE:

<221> NAME/KEY: misc_feature
<222> LOCATION: (871)..(877)
<223> OTHER INFORMATION: n is unknown
<220> FEATURE:
<221> NAME/KEY: misc_feature
<222> LOCATION: (880)..(880)
<223> OTHER INFORMATION: n is unknown

<400> SEQUENCE: 9

```
ctgntaatgt tgctactact gctgacaatg ctgctgctgc ttctcctcac tgtctccact     60

tccttgaaca atgcgccgnc ntgcttcttt tgcctcccgc tgctccngag ngctaggccg    120

cagatcagaa ccaccacagn caatatcacc accnncnnct tatagattcg gaatctcatg    180

ataggggctc agcctctgtg cgagtggaga gaagtttgca ggcgagctga ggagcaattg    240

cnggtgatat gatgtgctcg gctcnnnggg nnnggngnnn nnnnnangnc nngccggggc    300

taattattgg caaaacgagc tcttgttgta aacattgatc cnnnnggnnn gtnnnnnnng    360

gngnnngann ntgnnnnnng gnatgatggt tgctcagagg caggagaaga gcaacgaata    420

cgatcctatn aaagataaaa cataaataaa cngtcttgat tatattctgg gtattaaann    480

cnnngnnaga acaaatatat gctttnnnnn nnntcnngnc nnnnnnnnnn nnnnnnnnnn    540

nnnnggccac attaagagaa cttgtnnnnn nntaagaaga tattttattc gntctgctga    600

cttgctggat gtcgggaaat attctgcatt tgataagagg cggttaattg cagatataat    660

tggtagtgaa aagggtcgtt gctatggtca ccgtgaagcg agtacagcag cacaagaatg    720

tgtgccgttc tcagttaata ttgtntgaat atggtaacct gntttagtcg gtttaaaggt    780

aagaagatct aaccaaaaac aacactgcnn gncngnnnnn nnggnnnnnn nnnnnttact    840

nnnnnnnnat tttggnntaa acatcaacgg nnnnnnncan c                        881
```

<210> SEQ ID NO 10
<211> LENGTH: 883
<212> TYPE: DNA
<213> ORGANISM: Artificial Sequence
<220> FEATURE:
<223> OTHER INFORMATION: S. cerevisiae PCR reaction /DNA sequence standard
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (3)..(3)
<223> OTHER INFORMATION: n is unknown
<220> FEATURE:
<221> NAME/KEY: misc_feature
<222> LOCATION: (5)..(9)
<223> OTHER INFORMATION: n is unknown
<220> FEATURE:
<221> NAME/KEY: misc_feature
<222> LOCATION: (11)..(11)
<223> OTHER INFORMATION: n is unknown
<220> FEATURE:
<221> NAME/KEY: misc_feature
<222> LOCATION: (50)..(50)
<223> OTHER INFORMATION: n is unknown
<220> FEATURE:
<221> NAME/KEY: misc_feature
<222> LOCATION: (82)..(82)
<223> OTHER INFORMATION: n is unknown
<220> FEATURE:
<221> NAME/KEY: misc_feature
<222> LOCATION: (108)..(109)
<223> OTHER INFORMATION: n is unknown
<220> FEATURE:
<221> NAME/KEY: misc_feature
<222> LOCATION: (111)..(112)
<223> OTHER INFORMATION: n is unknown
<220> FEATURE:
<221> NAME/KEY: misc_feature
<222> LOCATION: (114)..(114)
<223> OTHER INFORMATION: n is unknown
<220> FEATURE:
<221> NAME/KEY: misc_feature
<222> LOCATION: (267)..(267)
<223> OTHER INFORMATION: n is unknown
<220> FEATURE:
<221> NAME/KEY: misc_feature
<222> LOCATION: (272)..(294)
<223> OTHER INFORMATION: n is unknown
<220> FEATURE:
<221> NAME/KEY: misc_feature
<222> LOCATION: (350)..(351)
<223> OTHER INFORMATION: n is unknown
<220> FEATURE:
<221> NAME/KEY: misc_feature
<222> LOCATION: (354)..(359)
<223> OTHER INFORMATION: n is unknown
<220> FEATURE:
<221> NAME/KEY: misc_feature
<222> LOCATION: (364)..(364)
<223> OTHER INFORMATION: n is unknown
<220> FEATURE:
<221> NAME/KEY: misc_feature
<222> LOCATION: (366)..(373)
<223> OTHER INFORMATION: n is unknown
<220> FEATURE:
<221> NAME/KEY: misc_feature
<222> LOCATION: (378)..(382)
<223> OTHER INFORMATION: n is unknown
<220> FEATURE:
<221> NAME/KEY: misc_feature
<222> LOCATION: (482)..(482)
<223> OTHER INFORMATION: n is unknown
<220> FEATURE:
<221> NAME/KEY: misc_feature
<222> LOCATION: (484)..(484)
<223> OTHER INFORMATION: n is unknown
<220> FEATURE:
<221> NAME/KEY: misc_feature
<222> LOCATION: (488)..(488)
<223> OTHER INFORMATION: n is unknown
<220> FEATURE:
<221> NAME/KEY: misc_feature
<222> LOCATION: (510)..(511)
<223> OTHER INFORMATION: n is unknown
<220> FEATURE:
<221> NAME/KEY: misc_feature
<222> LOCATION: (514)..(516)
<223> OTHER INFORMATION: n is unknown
<220> FEATURE:
<221> NAME/KEY: misc_feature
<222> LOCATION: (518)..(518)
<223> OTHER INFORMATION: n is unknown
<220> FEATURE:
<221> NAME/KEY: misc_feature
<222> LOCATION: (528)..(546)
<223> OTHER INFORMATION: n is unknown
<220> FEATURE:
<221> NAME/KEY: misc_feature
<222> LOCATION: (553)..(558)
<223> OTHER INFORMATION: n is unknown
<220> FEATURE:
<221> NAME/KEY: misc_feature
<222> LOCATION: (567)..(567)
<223> OTHER INFORMATION: n is unknown
<220> FEATURE:
<221> NAME/KEY: misc_feature
<222> LOCATION: (570)..(570)
<223> OTHER INFORMATION: n is unknown
<220> FEATURE:
<221> NAME/KEY: misc_feature
<222> LOCATION: (572)..(573)
<223> OTHER INFORMATION: n is unknown
<220> FEATURE:
<221> NAME/KEY: misc_feature
<222> LOCATION: (594)..(594)
<223> OTHER INFORMATION: n is unknown
<220> FEATURE:
<221> NAME/KEY: misc_feature
<222> LOCATION: (720)..(721)
<223> OTHER INFORMATION: n is unknown
<220> FEATURE:
<221> NAME/KEY: misc_feature
<222> LOCATION: (744)..(744)
<223> OTHER INFORMATION: n is unknown
<220> FEATURE:
<221> NAME/KEY: misc_feature
<222> LOCATION: (746)..(748)
<223> OTHER INFORMATION: n is unknown
<220> FEATURE:
<221> NAME/KEY: misc_feature
<222> LOCATION: (764)..(764)
<223> OTHER INFORMATION: n is unknown
<220> FEATURE:
<221> NAME/KEY: misc_feature
<222> LOCATION: (790)..(790)
<223> OTHER INFORMATION: n is unknown
<220> FEATURE:
<221> NAME/KEY: misc_feature
<222> LOCATION: (811)..(820)
<223> OTHER INFORMATION: n is unknown
<220> FEATURE:
<221> NAME/KEY: misc_feature
<222> LOCATION: (826)..(836)
<223> OTHER INFORMATION: n is unknown
<220> FEATURE:
<221> NAME/KEY: misc_feature
<222> LOCATION: (842)..(845)
<223> OTHER INFORMATION: n is unknown
<220> FEATURE:
<221> NAME/KEY: misc_feature
<222> LOCATION: (847)..(850)
<223> OTHER INFORMATION: n is unknown
<220> FEATURE:
<221> NAME/KEY: misc_feature
<222> LOCATION: (853)..(855)
<223> OTHER INFORMATION: n is unknown
<220> FEATURE:
<221> NAME/KEY: misc_feature
<222> LOCATION: (858)..(858)
<223> OTHER INFORMATION: n is unknown
<220> FEATURE:
<221> NAME/KEY: misc_feature
<222> LOCATION: (860)..(860)
<223> OTHER INFORMATION: n is unknown
<220> FEATURE:
<221> NAME/KEY: misc_feature
<222> LOCATION: (868)..(868)
<223> OTHER INFORMATION: n is unknown
<220> FEATURE:
<221> NAME/KEY: misc_feature
<222> LOCATION: (872)..(879)
<223> OTHER INFORMATION: n is unknown

<400> SEQUENCE: 10
ncngnnnnng ntgctactac tgctgacaat gctgctgctg cttctcctcn ctgtctccac 60
ttccttgaac aatgcgccgt cntgcttctt ttgcctcccg ctgctccnna nngntaggcc 120
gcagatcaga accaccacag tcaatatcac caccttcctc ttatagattc ggaatctcat 180
gataggggct cagcctctgt gcgagtggag agaagtttgc aggcgagctg aggagcaatt 240
gcaggtgata tgatgtgctc ggctcanggg gnnnnnnnnn nnnnnnnnnn nnnngccggg 300
gctaattatt ggcaaaacga gctcttgttg taaacattga tccaactggn nggnnnnnna 360
tggngnnnnn nnntgccnnn nngcatgatg gttgctcaga ggcaggagaa gagcaacgaa 420
tacgatccta taaaagataa aacataaata aacagtcttg attatattct gggtattaaa 480
gncncagnca gaacaaatat atgctttgtn nctnnncntg ccttcttnnn nnnnnnnnnn 540
nnnnnnggcc acnnnnnnag aacttgnggn gnnataagaa gatattttat tcgntctgct 600
gacttgctgg atgtcgggaa atattctgca tttgataaga ggcggttaat tgcagatata 660
attggtagtg aaaagggtcg ttgctatggt caccgtgaag cgagtacagc agcacaagan 720
ngtgtgccgt tctcagttaa tatngnnnga atatggtaac ctgntttagt cggtttaaag 780
gtaagaagan ctaaccaaaa acaacactgc nnnnnnnnnn gggggnnnnn nnnnnnttac 840
tnnnngnnnn ttnnnggngn aaacatcnac gnnnnnnnnc aac 883

<210> SEQ ID NO 11
<211> LENGTH: 880
<212> TYPE: DNA
<213> ORGANISM: Artificial Sequence
<220> FEATURE:
<223> OTHER INFORMATION: S. cerevisiae PCR reaction /DNA sequence standard
<220> FEATURE:
<221> NAME/KEY: misc_feature
<222> LOCATION: (44)..(44)
<223> OTHER INFORMATION: n is unknown
<220> FEATURE:
<221> NAME/KEY: misc_feature
<222> LOCATION: (49)..(49)
<223> OTHER INFORMATION: n is unknown
<220> FEATURE:
<221> NAME/KEY: misc_feature
<222> LOCATION: (79)..(79)
<223> OTHER INFORMATION: n is unknown
<220> FEATURE:
<221> NAME/KEY: misc_feature
<222> LOCATION: (81)..(81)
<223> OTHER INFORMATION: n is unknown
<220> FEATURE:
<221> NAME/KEY: misc_feature
<222> LOCATION: (107)..(107)
<223> OTHER INFORMATION: n is unknown
<220> FEATURE:
<221> NAME/KEY: misc_feature
<222> LOCATION: (111)..(111)
<223> OTHER INFORMATION: n is unknown
<220> FEATURE:
<221> NAME/KEY: misc_feature
<222> LOCATION: (113)..(113)
<223> OTHER INFORMATION: n is unknown
<220> FEATURE:
<221> NAME/KEY: misc_feature
<222> LOCATION: (140)..(140)
<223> OTHER INFORMATION: n is unknown
<220> FEATURE:
<221> NAME/KEY: misc_feature
<222> LOCATION: (154)..(154)
<223> OTHER INFORMATION: n is unknown
<220> FEATURE:
<221> NAME/KEY: misc_feature
<222> LOCATION: (157)..(158)
<223> OTHER INFORMATION: n is unknown
<220> FEATURE:
<221> NAME/KEY: misc_feature
<222> LOCATION: (165)..(165)
<223> OTHER INFORMATION: n is unknown
<220> FEATURE:
<221> NAME/KEY: misc_feature
<222> LOCATION: (266)..(267)
<223> OTHER INFORMATION: n is unknown
<220> FEATURE:
<221> NAME/KEY: misc_feature
<222> LOCATION: (272)..(292)
<223> OTHER INFORMATION: n is unknown
<220> FEATURE:
<221> NAME/KEY: misc_feature
<222> LOCATION: (349)..(350)
<223> OTHER INFORMATION: n is unknown
<220> FEATURE:
<221> NAME/KEY: misc_feature
<222> LOCATION: (353)..(358)
<223> OTHER INFORMATION: n is unknown
<220> FEATURE:
<221> NAME/KEY: misc_feature
<222> LOCATION: (363)..(363)

<223> OTHER INFORMATION: n is unknown
<220> FEATURE:
<221> NAME/KEY: misc_feature
<222> LOCATION: (365)..(367)
<223> OTHER INFORMATION: n is unknown
<220> FEATURE:
<221> NAME/KEY: misc_feature
<222> LOCATION: (369)..(372)
<223> OTHER INFORMATION: n is unknown
<220> FEATURE:
<221> NAME/KEY: misc_feature
<222> LOCATION: (375)..(380)
<223> OTHER INFORMATION: n is unknown
<220> FEATURE:
<221> NAME/KEY: misc_feature
<222> LOCATION: (423)..(423)
<223> OTHER INFORMATION: n is unknown
<220> FEATURE:
<221> NAME/KEY: misc_feature
<222> LOCATION: (480)..(485)
<223> OTHER INFORMATION: n is unknown
<220> FEATURE:
<221> NAME/KEY: misc_feature
<222> LOCATION: (487)..(487)
<223> OTHER INFORMATION: n is unknown
<220> FEATURE:
<221> NAME/KEY: misc_feature
<222> LOCATION: (508)..(512)
<223> OTHER INFORMATION: n is unknown
<220> FEATURE:
<221> NAME/KEY: misc_feature
<222> LOCATION: (514)..(515)
<223> OTHER INFORMATION: n is unknown
<220> FEATURE:
<221> NAME/KEY: misc_feature
<222> LOCATION: (517)..(517)
<223> OTHER INFORMATION: n is unknown
<220> FEATURE:
<221> NAME/KEY: misc_feature
<222> LOCATION: (520)..(523)
<223> OTHER INFORMATION: n is unknown
<220> FEATURE:
<221> NAME/KEY: misc_feature
<222> LOCATION: (525)..(528)
<223> OTHER INFORMATION: n is unknown
<220> FEATURE:
<221> NAME/KEY: misc_feature
<222> LOCATION: (531)..(545)
<223> OTHER INFORMATION: n is unknown
<220> FEATURE:
<221> NAME/KEY: misc_feature
<222> LOCATION: (550)..(550)
<223> OTHER INFORMATION: n is unknown
<220> FEATURE:
<221> NAME/KEY: misc_feature
<222> LOCATION: (552)..(556)
<223> OTHER INFORMATION: n is unknown
<220> FEATURE:
<221> NAME/KEY: misc_feature
<222> LOCATION: (567)..(573)
<223> OTHER INFORMATION: n is unknown
<220> FEATURE:
<221> NAME/KEY: misc_feature
<222> LOCATION: (593)..(594)
<223> OTHER INFORMATION: n is unknown
<220> FEATURE:
<221> NAME/KEY: misc_feature
<222> LOCATION: (716)..(716)
<223> OTHER INFORMATION: n is unknown
<220> FEATURE:
<221> NAME/KEY: misc_feature
<222> LOCATION: (719)..(720)
<223> OTHER INFORMATION: n is unknown
<220> FEATURE:
<221> NAME/KEY: misc_feature
<222> LOCATION: (745)..(745)
<223> OTHER INFORMATION: n is unknown
<220> FEATURE:
<221> NAME/KEY: misc_feature
<222> LOCATION: (789)..(789)

<223> OTHER INFORMATION: n is unknown
<220> FEATURE:
<221> NAME/KEY: misc_feature
<222> LOCATION: (796)..(796)
<223> OTHER INFORMATION: n is unknown
<220> FEATURE:
<221> NAME/KEY: misc_feature
<222> LOCATION: (810)..(815)
<223> OTHER INFORMATION: n is unknown
<220> FEATURE:
<221> NAME/KEY: misc_feature
<222> LOCATION: (817)..(817)
<223> OTHER INFORMATION: n is unknown
<220> FEATURE:
<221> NAME/KEY: misc_feature
<222> LOCATION: (824)..(836)
<223> OTHER INFORMATION: n is unknown
<220> FEATURE:
<221> NAME/KEY: misc_feature
<222> LOCATION: (842)..(859)
<223> OTHER INFORMATION: n is unknown
<220> FEATURE:
<221> NAME/KEY: misc_feature
<222> LOCATION: (865)..(866)
<223> OTHER INFORMATION: n is unknown
<220> FEATURE:
<221> NAME/KEY: misc_feature
<222> LOCATION: (869)..(876)
<223> OTHER INFORMATION: n is unknown

<400> SEQUENCE: 11

```
ctgttaatgt tgctactact gctgacaatg ctgctgctgc ttcncctcnc tgtctccact     60

tccttgaaca atgcgccgnc ntgcttcttt tgcctcccgc tgctccngag ngntaggccg    120

cagatcagaa ccaccacagn caatatcacc accntcnnct tatanattcg gaatctcatg    180

ataggggctc agcctctgtg cgagtggaga gaagtttgca ggcgagctga ggagcaattg    240

caggtgatat gatgtgctcg gctcannggg cnnnnnnnnn nnnnnnnnnn nntgccgggg    300

ctaattattg gcaaaacgag ctcttgttgt aaacattgat ccaactggnn ggnnnnnnat    360

ggngnnngnn nntgnnnnnn gggatgatgg ttgctcagag gcaggagaag agcaacgaat    420

acnatcctat aaaagataaa acataaataa acagtcttga ttatattctg ggtattaaan    480

nnnnngncag aacaaatata tgctttgnnn nntnncntgn nnncnnnngg nnnnnnnnnn    540

nnnnnggccn cnnnnngaga acttgtnnnn nnntaagaag atattttatt cgnnctgctg    600

acttgctgga tgtcgggaaa tattctgcat ttgataagag gcggttaatt gcagatataa    660

ttggtagtga aaagggtcgt tgctatggtc accgtgaagc gagtacagca gcacangann    720

gtgtgccgtt ctcagttaat attgnttgaa tatggtaacc tgttttagtc ggtttaaagg    780

taagaaganc taaccnaaaa caacactgcn nnnnngnggg gggnnnnnnn nnnnnnntact    840

tnnnnnnnnn nnnnnnnnna catcnncgnn nnnnnncaac                          880
```

<210> SEQ ID NO 12
<211> LENGTH: 875
<212> TYPE: DNA
<213> ORGANISM: Artificial Sequence
<220> FEATURE:
<223> OTHER INFORMATION: S. cerevisiae PCR reaction /DNA sequence standard
<220> FEATURE:
<221> NAME/KEY: misc_feature
<222> LOCATION: (5)..(5)
<223> OTHER INFORMATION: n is unknown
<220> FEATURE:
<221> NAME/KEY: misc_feature
<222> LOCATION: (8)..(8)
<223> OTHER INFORMATION: n is unknown
<220> FEATURE:
<221> NAME/KEY: misc_feature
<222> LOCATION: (10)..(10)
<223> OTHER INFORMATION: n is unknown
<220> FEATURE:
<221> NAME/KEY: misc_feature
<222> LOCATION: (69)..(69)
<223> OTHER INFORMATION: n is unknown
<220> FEATURE:
<221> NAME/KEY: misc_feature
<222> LOCATION: (71)..(71)
<223> OTHER INFORMATION: n is unknown
<220> FEATURE:
<221> NAME/KEY: misc_feature
<222> LOCATION: (98)..(98)
<223> OTHER INFORMATION: n is unknown
<220> FEATURE:
<221> NAME/KEY: misc_feature
<222> LOCATION: (101)..(101)
<223> OTHER INFORMATION: n is unknown
<220> FEATURE:
<221> NAME/KEY: misc_feature
<222> LOCATION: (118)..(118)
<223> OTHER INFORMATION: n is unknown
<220> FEATURE:
<221> NAME/KEY: misc_feature
<222> LOCATION: (130)..(130)
<223> OTHER INFORMATION: n is unknown
<220> FEATURE:
<221> NAME/KEY: misc_feature
<222> LOCATION: (144)..(144)
<223> OTHER INFORMATION: n is unknown
<220> FEATURE:
<221> NAME/KEY: misc_feature
<222> LOCATION: (147)..(148)
<223> OTHER INFORMATION: n is unknown
<220> FEATURE:
<221> NAME/KEY: misc_feature
<222> LOCATION: (255)..(257)
<223> OTHER INFORMATION: n is unknown
<220> FEATURE:
<221> NAME/KEY: misc_feature
<222> LOCATION: (263)..(280)
<223> OTHER INFORMATION: n is unknown
<220> FEATURE:
<221> NAME/KEY: misc_feature
<222> LOCATION: (282)..(283)
<223> OTHER INFORMATION: n is unknown
<220> FEATURE:
<221> NAME/KEY: misc_feature
<222> LOCATION: (338)..(341)
<223> OTHER INFORMATION: n is unknown
<220> FEATURE:
<221> NAME/KEY: misc_feature
<222> LOCATION: (343)..(348)
<223> OTHER INFORMATION: n is unknown
<220> FEATURE:
<221> NAME/KEY: misc_feature
<222> LOCATION: (350)..(350)
<223> OTHER INFORMATION: n is unknown
<220> FEATURE:
<221> NAME/KEY: misc_feature
<222> LOCATION: (353)..(353)
<223> OTHER INFORMATION: n is unknown
<220> FEATURE:
<221> NAME/KEY: misc_feature
<222> LOCATION: (355)..(361)
<223> OTHER INFORMATION: n is unknown
<220> FEATURE:
<221> NAME/KEY: misc_feature
<222> LOCATION: (365)..(370)
<223> OTHER INFORMATION: n is unknown
<220> FEATURE:
<221> NAME/KEY: misc_feature
<222> LOCATION: (373)..(373)
<223> OTHER INFORMATION: n is unknown
<220> FEATURE:
<221> NAME/KEY: misc_feature
<222> LOCATION: (421)..(421)
<223> OTHER INFORMATION: n is unknown
<220> FEATURE:
<221> NAME/KEY: misc_feature
<222> LOCATION: (470)..(475)
<223> OTHER INFORMATION: n is unknown
<220> FEATURE:
<221> NAME/KEY: misc_feature
<222> LOCATION: (499)..(505)
<223> OTHER INFORMATION: n is unknown
<220> FEATURE:
<221> NAME/KEY: misc_feature
<222> LOCATION: (507)..(509)
<223> OTHER INFORMATION: n is unknown
<220> FEATURE:
<221> NAME/KEY: misc_feature
<222> LOCATION: (516)..(519)
<223> OTHER INFORMATION: n is unknown
<220> FEATURE:
<221> NAME/KEY: misc_feature
<222> LOCATION: (521)..(535)
<223> OTHER INFORMATION: n is unknown
<220> FEATURE:
<221> NAME/KEY: misc_feature
<222> LOCATION: (540)..(546)
<223> OTHER INFORMATION: n is unknown
<220> FEATURE:
<221> NAME/KEY: misc_feature
<222> LOCATION: (557)..(563)
<223> OTHER INFORMATION: n is unknown
<220> FEATURE:
<221> NAME/KEY: misc_feature
<222> LOCATION: (583)..(583)
<223> OTHER INFORMATION: n is unknown
<220> FEATURE:
<221> NAME/KEY: misc_feature
<222> LOCATION: (707)..(707)
<223> OTHER INFORMATION: n is unknown
<220> FEATURE:
<221> NAME/KEY: misc_feature
<222> LOCATION: (709)..(710)
<223> OTHER INFORMATION: n is unknown
<220> FEATURE:
<221> NAME/KEY: misc_feature
<222> LOCATION: (712)..(712)
<223> OTHER INFORMATION: n is unknown
<220> FEATURE:
<221> NAME/KEY: misc_feature
<222> LOCATION: (728)..(733)
<223> OTHER INFORMATION: n is unknown
<220> FEATURE:
<221> NAME/KEY: misc_feature
<222> LOCATION: (771)..(771)
<223> OTHER INFORMATION: n is unknown
<220> FEATURE:
<221> NAME/KEY: misc_feature
<222> LOCATION: (801)..(801)
<223> OTHER INFORMATION: n is unknown
<220> FEATURE:
<221> NAME/KEY: misc_feature
<222> LOCATION: (804)..(804)
<223> OTHER INFORMATION: n is unknown
<220> FEATURE:
<221> NAME/KEY: misc_feature
<222> LOCATION: (806)..(806)
<223> OTHER INFORMATION: n is unknown
<220> FEATURE:
<221> NAME/KEY: misc_feature
<222> LOCATION: (808)..(808)
<223> OTHER INFORMATION: n is unknown
<220> FEATURE:
<221> NAME/KEY: misc_feature
<222> LOCATION: (810)..(811)
<223> OTHER INFORMATION: n is unknown
<220> FEATURE:
<221> NAME/KEY: misc_feature
<222> LOCATION: (814)..(827)
<223> OTHER INFORMATION: n is unknown
<220> FEATURE:
<221> NAME/KEY: misc_feature
<222> LOCATION: (834)..(847)
<223> OTHER INFORMATION: n is unknown
<220> FEATURE:
<221> NAME/KEY: misc_feature
<222> LOCATION: (850)..(850)
<223> OTHER INFORMATION: n is unknown
<220> FEATURE:
<221> NAME/KEY: misc_feature
<222> LOCATION: (864)..(869)
<223> OTHER INFORMATION: n is unknown
<220> FEATURE:
<221> NAME/KEY: misc_feature
<222> LOCATION: (872)..(872)
<223> OTHER INFORMATION: n is unknown

<400> SEQUENCE: 12

```
gttgntcncn gctgacaatg ctgctgctgc ttctcctcac tgtctccact tccttgaaca     60

atgcgccgnc ntgcttcttt tgcctcccgc tgctccanag ngctaggccg cagatcanaa    120

ccaccacagn caatatcacc accntcnnct tatagattcg gaatctcatg ataggggctc    180

agcctctgtg cgagtggaga gaagtttgca ggcgagctga ggagcaattg caggtgatat    240

gatgtgctcg gctcnnnggg cgnnnnnnnn nnnnnnnnnn cnngccgggg ctaattattg    300

gcaaaacgag ctcttgttgt aaacattgat ccaactgnnn ngnnnnnnan ggngnnnnnn    360

ngtgnnnnnn ggnatgatgg ttgctcagag gcaggagaag agcaacgaat acgatcctat    420

naaagataaa acataaataa acagtcttga ttatattctg ggtattaaan nnnnngtcag    480

aacaaatata tgctttgtnn nnnnncnnnc cttctnnnng nnnnnnnnnn nnnnnggccn    540

nnnnnngaga acttgtnnnn nnntaagaag atattttatt cgntctgctg acttgctgga    600

tgtcgggaaa tattctgcat ttgataagag gcggttaatt gcagatataa ttggtagtga    660

aaagggtcgt tgctatggtc accgtgaagc gagtacagca gcacaanann gngtgccgtt    720

ctcagttnnn nnngtttgaa tatggtaacc tgttttagtc ggtttaaagg naagaagatc    780

taaccaaaaa caacactgca ntgncngngn nggnnnnnnn nnnnnnntac ttannnnnnn    840

nnnnnnnggn gtaaacatca acgnnnnnnt cnacc                               875
```

<210> SEQ ID NO 13
<211> LENGTH: 817
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (5)..(5)
<223> OTHER INFORMATION: n is unknown
<220> FEATURE:
<221> NAME/KEY: misc_feature
<222> LOCATION: (12)..(12)
<223> OTHER INFORMATION: n is unknown
<220> FEATURE:
<221> NAME/KEY: misc_feature
<222> LOCATION: (41)..(41)
<223> OTHER INFORMATION: n is unknown
<220> FEATURE:
<221> NAME/KEY: misc_feature
<222> LOCATION: (46)..(46)
<223> OTHER INFORMATION: n is unknown
<220> FEATURE:
<221> NAME/KEY: misc_feature
<222> LOCATION: (215)..(217)
<223> OTHER INFORMATION: n is unknown
<220> FEATURE:
<221> NAME/KEY: misc_feature
<222> LOCATION: (221)..(221)
<223> OTHER INFORMATION: n is unknown
<220> FEATURE:
<221> NAME/KEY: misc_feature
<222> LOCATION: (226)..(226)
<223> OTHER INFORMATION: n is unknown
<220> FEATURE:
<221> NAME/KEY: misc_feature
<222> LOCATION: (347)..(349)
<223> OTHER INFORMATION: n is unknown
<220> FEATURE:
<221> NAME/KEY: misc_feature
<222> LOCATION: (351)..(352)
<223> OTHER INFORMATION: n is unknown
<220> FEATURE:
<221> NAME/KEY: misc_feature
<222> LOCATION: (356)..(356)
<223> OTHER INFORMATION: n is unknown
<220> FEATURE:
<221> NAME/KEY: misc_feature
<222> LOCATION: (358)..(365)
<223> OTHER INFORMATION: n is unknown
<220> FEATURE:
<221> NAME/KEY: misc_feature
<222> LOCATION: (531)..(540)
<223> OTHER INFORMATION: n is unknown
<220> FEATURE:
<221> NAME/KEY: misc_feature
<222> LOCATION: (548)..(553)
<223> OTHER INFORMATION: n is unknown
<220> FEATURE:
<221> NAME/KEY: misc_feature
<222> LOCATION: (795)..(795)
<223> OTHER INFORMATION: n is unknown

<400> SEQUENCE: 13
gntangttgc tnctactgct gacaatgctg ctgctgcttc ncctcnctgt ctccacttcc 60
ttgaacaatg cgccgtcatg cttcttttgc ctcccgctgc tccagaaagc taggccgcag 120
atcagaacca ccacagtcaa tatcaccacc ttcctcttat agattcggaa tcaattgcag 180
gtgatatgat gtgctcggct caagaagcgg gcccnnngag naggangtcg tgtcatgata 240
ggggctcagc ctctgtgcga gtggagagaa gtttgcaggc gagctgagga gcccggggct 300
aattattggc aaaacgagct cttgttgtaa acattgatcc aactggnnng nnactnannn 360
nnnnncaata ttccataagg catgatggtt gctcagaggc aggagaagag caacgaatac 420
gatcctataa aagataaaac ataaataaac agtcttgatt atattctggg tattaaagcc 480
acaatcagaa caaatatatg ctttgtatct tttcttgcct tcttcattac nnnnnnnnnn 540
cgcgggcnnn nnnaagagaa cttgtggtaa gataagaaga tattttattc gttctgctga 600
cttgctggat gtcgggaaat attctgcatt tgataagagg cggttaattg cagatataat 660
tggtagtgaa aagggtcgtt gctatggtca ccgtgaagcg agtacagcag cacaagaatg 720
tgtgccgttc tcagttaata ttgtttgaat atggtaacct gttttagtcg gtttaaaggt 780
aagaagatct aaccnaaaac aacactgcag tgactga 817

<210> SEQ ID NO 14
<211> LENGTH: 880
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (4)..(5)
<223> OTHER INFORMATION: n is unknown
<220> FEATURE:
<221> NAME/KEY: misc_feature
<222> LOCATION: (49)..(49)
<223> OTHER INFORMATION: n is unknown
<220> FEATURE:
<221> NAME/KEY: misc_feature
<222> LOCATION: (54)..(54)
<223> OTHER INFORMATION: n is unknown
<220> FEATURE:
<221> NAME/KEY: misc_feature
<222> LOCATION: (277)..(277)
<223> OTHER INFORMATION: n is unknown
<220> FEATURE:
<221> NAME/KEY: misc_feature
<222> LOCATION: (279)..(283)
<223> OTHER INFORMATION: n is unknown
<220> FEATURE:
<221> NAME/KEY: misc_feature
<222> LOCATION: (285)..(286)
<223> OTHER INFORMATION: n is unknown
<220> FEATURE:
<221> NAME/KEY: misc_feature
<222> LOCATION: (349)..(350)
<223> OTHER INFORMATION: n is unknown
<220> FEATURE:
<221> NAME/KEY: misc_feature
<222> LOCATION: (356)..(356)
<223> OTHER INFORMATION: n is unknown
<220> FEATURE:
<221> NAME/KEY: misc_feature
<222> LOCATION: (358)..(364)
<223> OTHER INFORMATION: n is unknown
<220> FEATURE:
<221> NAME/KEY: misc_feature
<222> LOCATION: (528)..(533)
<223> OTHER INFORMATION: n is unknown
<220> FEATURE:
<221> NAME/KEY: misc_feature
<222> LOCATION: (539)..(542)
<223> OTHER INFORMATION: n is unknown
<220> FEATURE:
<221> NAME/KEY: misc_feature
<222> LOCATION: (545)..(545)
<223> OTHER INFORMATION: n is unknown
<220> FEATURE:
<221> NAME/KEY: misc_feature
<222> LOCATION: (799)..(810)
<223> OTHER INFORMATION: n is unknown
<220> FEATURE:
<221> NAME/KEY: misc_feature
<222> LOCATION: (819)..(819)
<223> OTHER INFORMATION: n is unknown
<220> FEATURE:
<221> NAME/KEY: misc_feature
<222> LOCATION: (826)..(827)
<223> OTHER INFORMATION: n is unknown
<220> FEATURE:
<221> NAME/KEY: misc_feature
<222> LOCATION: (829)..(829)
<223> OTHER INFORMATION: n is unknown
<220> FEATURE:
<221> NAME/KEY: misc_feature
<222> LOCATION: (854)..(855)
<223> OTHER INFORMATION: n is unknown
<220> FEATURE:
<221> NAME/KEY: misc_feature
<222> LOCATION: (865)..(865)
<223> OTHER INFORMATION: n is unknown
<220> FEATURE:
<221> NAME/KEY: misc_feature
<222> LOCATION: (873)..(873)
<223> OTHER INFORMATION: n is unknown
<220> FEATURE:
<221> NAME/KEY: misc_feature
<222> LOCATION: (879)..(880)
<223> OTHER INFORMATION: n is unknown

<400> SEQUENCE: 14
gntnnctgtt aatgttgcta ctactgctga caatgctgct gctgcttcnc ctcnctgtct 60
ccacttcctt gaacaatgcg ccgtcatgct tcttttgcct cccgctgctc cagaaagcta 120
ggccgcagat cagaaccacc acagtcaata tcaccacctt cctcttatag attcggaatc 180
tcatgatagg ggctcagcct ctgtgcgagt ggagagaagt ttgcaggcga gctgaggagc 240
aattgcaggt gatatgatgt gctcggctca agaagcngnn nnngnnagga agaagtcgtg 300
ccggggctaa ttattggcaa aacgagctct tgttgtaaac attgatccnn ctggantnnn 360
nnnnatggcg aatcaatatt ccataaggca tgatggttgc tcagaggcag gagaagagca 420
acgaatacga tcctataaaa gataaaacat aaataaacag tcttgattat attctgggta 480
ttaaagccac aatcagaaca aatatatgct ttgtatcttt tcttgccnnn nnngttacnn 540
nntgnttccg cggccacatt aagagaactt gtggtaagat aagaagatat tttattcgtt 600
ctgctgactt gctggatgtc gggaaatatt ctgcatttga taagaggcgg ttaattgcag 660
atataattgg tagtgaaaag ggtcgttgct atggtcaccg tgaagcgagt acagcagcac 720
aagaatgtgt gccgttctca gttaatattg tttgaatatg gtaacctgtt ttagtcggtt 780
taaaggtaag aagatctann nnnnnnnnnn cactgcagng actganngna gtatttattt 840
ttttacttaa tctnnatttt ggtgnaaaca tcnacggcnn 880

<210> SEQ ID NO 15
<211> LENGTH: 879
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (4)..(6)
<223> OTHER INFORMATION: n is unknown
<220> FEATURE:
<221> NAME/KEY: misc_feature
<222> LOCATION: (11)..(11)
<223> OTHER INFORMATION: n is unknown
<220> FEATURE:
<221> NAME/KEY: misc_feature
<222> LOCATION: (15)..(16)
<223> OTHER INFORMATION: n is unknown
<220> FEATURE:
<221> NAME/KEY: misc_feature
<222> LOCATION: (35)..(36)
<223> OTHER INFORMATION: n is unknown
<220> FEATURE:
<221> NAME/KEY: misc_feature
<222> LOCATION: (38)..(40)
<223> OTHER INFORMATION: n is unknown
<220> FEATURE:
<221> NAME/KEY: misc_feature
<222> LOCATION: (42)..(42)
<223> OTHER INFORMATION: n is unknown
<220> FEATURE:
<221> NAME/KEY: misc_feature
<222> LOCATION: (47)..(47)
<223> OTHER INFORMATION: n is unknown
<220> FEATURE:
<221> NAME/KEY: misc_feature
<222> LOCATION: (149)..(149)
<223> OTHER INFORMATION: n is unknown
<220> FEATURE:
<221> NAME/KEY: misc_feature
<222> LOCATION: (215)..(215)
<223> OTHER INFORMATION: n is unknown
<220> FEATURE:
<221> NAME/KEY: misc_feature
<222> LOCATION: (217)..(222)
<223> OTHER INFORMATION: n is unknown
<220> FEATURE:
<221> NAME/KEY: misc_feature
<222> LOCATION: (229)..(229)
<223> OTHER INFORMATION: n is unknown
<220> FEATURE:
<221> NAME/KEY: misc_feature
<222> LOCATION: (289)..(294)
<223> OTHER INFORMATION: n is unknown
<220> FEATURE:
<221> NAME/KEY: misc_feature
<222> LOCATION: (329)..(342)
<223> OTHER INFORMATION: n is unknown
<220> FEATURE:
<221> NAME/KEY: misc_feature
<222> LOCATION: (344)..(355)
<223> OTHER INFORMATION: n is unknown
<220> FEATURE:
<221> NAME/KEY: misc_feature
<222> LOCATION: (358)..(361)
<223> OTHER INFORMATION: n is unknown
<220> FEATURE:
<221> NAME/KEY: misc_feature
<222> LOCATION: (364)..(368)
<223> OTHER INFORMATION: n is unknown
<220> FEATURE:
<221> NAME/KEY: misc_feature
<222> LOCATION: (378)..(378)
<223> OTHER INFORMATION: n is unknown
<220> FEATURE:
<221> NAME/KEY: misc_feature
<222> LOCATION: (381)..(382)
<223> OTHER INFORMATION: n is unknown
<220> FEATURE:
<221> NAME/KEY: misc_feature
<222> LOCATION: (405)..(411)
<223> OTHER INFORMATION: n is unknown
<220> FEATURE:
<221> NAME/KEY: misc_feature
<222> LOCATION: (414)..(422)
<223> OTHER INFORMATION: n is unknown
<220> FEATURE:
<221> NAME/KEY: misc_feature
<222> LOCATION: (515)..(519)
<223> OTHER INFORMATION: n is unknown
<220> FEATURE:
<221> NAME/KEY: misc_feature
<222> LOCATION: (530)..(535)
<223> OTHER INFORMATION: n is unknown
<220> FEATURE:
<221> NAME/KEY: misc_feature
<222> LOCATION: (633)..(639)
<223> OTHER INFORMATION: n is unknown
<220> FEATURE:
<221> NAME/KEY: misc_feature
<222> LOCATION: (655)..(655)
<223> OTHER INFORMATION: n is unknown
<220> FEATURE:
<221> NAME/KEY: misc_feature
<222> LOCATION: (725)..(725)
<223> OTHER INFORMATION: n is unknown
<220> FEATURE:
<221> NAME/KEY: misc_feature
<222> LOCATION: (735)..(740)
<223> OTHER INFORMATION: n is unknown
<220> FEATURE:
<221> NAME/KEY: misc_feature
<222> LOCATION: (755)..(758)
<223> OTHER INFORMATION: n is unknown
<220> FEATURE:
<221> NAME/KEY: misc_feature
<222> LOCATION: (779)..(789)
<223> OTHER INFORMATION: n is unknown
<220> FEATURE:
<221> NAME/KEY: misc_feature
<222> LOCATION: (797)..(797)
<223> OTHER INFORMATION: n is unknown
<220> FEATURE:
<221> NAME/KEY: misc_feature
<222> LOCATION: (813)..(813)
<223> OTHER INFORMATION: n is unknown
<220> FEATURE:
<221> NAME/KEY: misc_feature
<222> LOCATION: (820)..(821)
<223> OTHER INFORMATION: n is unknown
<220> FEATURE:
<221> NAME/KEY: misc_feature
<222> LOCATION: (837)..(840)
<223> OTHER INFORMATION: n is unknown
<220> FEATURE:
<221> NAME/KEY: misc_feature
<222> LOCATION: (842)..(846)
<223> OTHER INFORMATION: n is unknown
<220> FEATURE:
<221> NAME/KEY: misc_feature
<222> LOCATION: (850)..(850)
<223> OTHER INFORMATION: n is unknown
<220> FEATURE:
<221> NAME/KEY: misc_feature
<222> LOCATION: (852)..(852)
<223> OTHER INFORMATION: n is unknown

<400> SEQUENCE: 15
cngnnntgtt nctcnnctgc tgacaatgct gctgnngnnn cncctcnctg tctccacttc 60
cttgaacaat gcgccgtcat gcttcttttg cctcccgctg ctccagaaag ctaggccgca 120
gatcagaacc accacagtca atatcaccnc cttcctctta tagattcgga atctcatgat 180
aggggctcag cctctgtgcg agtggagaga agttngnnnn nnagctgang agcaattgca 240
ggtgatatga tgtgctcggc tcaagaagcg ggcccggaga ggaagaagnn nnnncggggg 300
ctaattattg gcaaaacgag ctcttgttnn nnnnnnnnnn nngnnnnnnn nnnnnacnnn 360
nggnnnnnca atattccnta nngcatgatg gttgctcaga ggcannnnnn nagnnnnnnn 420
nncgatccta taaaagataa aacataaata aacagtcttg attatattct gggtattaaa 480
gccacaatca gaacaaatat atgctttgta tcttnnnnng ccttcttcan nnnnnactgc 540
ttccgcggcc acattaagag aacttgtggt aagataagaa gatattttat tcgttctgct 600
gacttgctgg atgtcgggaa atattctgca ttnnnnnnna ggcggttaat tgcanatata 660
attggtagtg aaaagggtcg ttgctatggt caccgtgaag cgagtacagc agcacaagaa 720
tgtgngccgt tctcnnnnnn tattgtttga atatnnnnac ctgttttagt cggtttaann 780
nnnnnnnnnt ctaaccnaaa acaacactgc agngactgan ngtagtattt atttttnnnn 840
cnnnnncttn antttggtgt aaacatcaac ggcgcactt 879

<210> SEQ ID NO 16
<211> LENGTH: 879
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (4)..(7)
<223> OTHER INFORMATION: n is unknown
<220> FEATURE:
<221> NAME/KEY: misc_feature
<222> LOCATION: (14)..(14)
<223> OTHER INFORMATION: n is unknown
<220> FEATURE:
<221> NAME/KEY: misc_feature
<222> LOCATION: (36)..(37)
<223> OTHER INFORMATION: n is unknown
<220> FEATURE:
<221> NAME/KEY: misc_feature
<222> LOCATION: (39)..(41)
<223> OTHER INFORMATION: n is unknown
<220> FEATURE:
<221> NAME/KEY: misc_feature
<222> LOCATION: (43)..(43)
<223> OTHER INFORMATION: n is unknown
<220> FEATURE:
<221> NAME/KEY: misc_feature
<222> LOCATION: (48)..(48)
<223> OTHER INFORMATION: n is unknown
<220> FEATURE:
<221> NAME/KEY: misc_feature
<222> LOCATION: (216)..(223)
<223> OTHER INFORMATION: n is unknown
<220> FEATURE:
<221> NAME/KEY: misc_feature
<222> LOCATION: (230)..(230)
<223> OTHER INFORMATION: n is unknown
<220> FEATURE:
<221> NAME/KEY: misc_feature
<222> LOCATION: (233)..(233)
<223> OTHER INFORMATION: n is unknown
<220> FEATURE:
<221> NAME/KEY: misc_feature
<222> LOCATION: (280)..(280)
<223> OTHER INFORMATION: n is unknown
<220> FEATURE:
<221> NAME/KEY: misc_feature
<222> LOCATION: (282)..(282)
<223> OTHER INFORMATION: n is unknown
<220> FEATURE:
<221> NAME/KEY: misc_feature
<222> LOCATION: (286)..(286)
<223> OTHER INFORMATION: n is unknown
<220> FEATURE:
<221> NAME/KEY: misc_feature
<222> LOCATION: (291)..(295)
<223> OTHER INFORMATION: n is unknown
<220> FEATURE:
<221> NAME/KEY: misc_feature
<222> LOCATION: (297)..(298)
<223> OTHER INFORMATION: n is unknown
<220> FEATURE:
<221> NAME/KEY: misc_feature
<222> LOCATION: (301)..(303)
<223> OTHER INFORMATION: n is unknown
<220> FEATURE:
<221> NAME/KEY: misc_feature
<222> LOCATION: (306)..(311)
<223> OTHER INFORMATION: n is unknown
<220> FEATURE:
<221> NAME/KEY: misc_feature
<222> LOCATION: (313)..(314)
<223> OTHER INFORMATION: n is unknown
<220> FEATURE:
<221> NAME/KEY: misc_feature
<222> LOCATION: (316)..(316)
<223> OTHER INFORMATION: n is unknown
<220> FEATURE:
<221> NAME/KEY: misc_feature
<222> LOCATION: (324)..(324)
<223> OTHER INFORMATION: n is unknown
<220> FEATURE:
<221> NAME/KEY: misc_feature
<222> LOCATION: (328)..(328)
<223> OTHER INFORMATION: n is unknown
<220> FEATURE:
<221> NAME/KEY: misc_feature
<222> LOCATION: (353)..(357)
<223> OTHER INFORMATION: n is unknown
<220> FEATURE:
<221> NAME/KEY: misc_feature
<222> LOCATION: (359)..(359)
<223> OTHER INFORMATION: n is unknown
<220> FEATURE:
<221> NAME/KEY: misc_feature
<222> LOCATION: (388)..(401)
<223> OTHER INFORMATION: n is unknown
<220> FEATURE:
<221> NAME/KEY: misc_feature
<222> LOCATION: (403)..(412)
<223> OTHER INFORMATION: n is unknown
<220> FEATURE:
<221> NAME/KEY: misc_feature
<222> LOCATION: (416)..(421)
<223> OTHER INFORMATION: n is unknown
<220> FEATURE:
<221> NAME/KEY: misc_feature
<222> LOCATION: (514)..(518)
<223> OTHER INFORMATION: n is unknown
<220> FEATURE:
<221> NAME/KEY: misc_feature
<222> LOCATION: (530)..(536)
<223> OTHER INFORMATION: n is unknown
<220> FEATURE:
<221> NAME/KEY: misc_feature
<222> LOCATION: (548)..(549)
<223> OTHER INFORMATION: n is unknown
<220> FEATURE:
<221> NAME/KEY: misc_feature
<222> LOCATION: (623)..(623)
<223> OTHER INFORMATION: n is unknown
<220> FEATURE:
<221> NAME/KEY: misc_feature
<222> LOCATION: (632)..(633)
<223> OTHER INFORMATION: n is unknown
<220> FEATURE:
<221> NAME/KEY: misc_feature
<222> LOCATION: (635)..(638)
<223> OTHER INFORMATION: n is unknown
<220> FEATURE:
<221> NAME/KEY: misc_feature
<222> LOCATION: (654)..(654)
<223> OTHER INFORMATION: n is unknown
<220> FEATURE:
<221> NAME/KEY: misc_feature
<222> LOCATION: (677)..(677)
<223> OTHER INFORMATION: n is unknown
<220> FEATURE:
<221> NAME/KEY: misc_feature
<222> LOCATION: (679)..(680)
<223> OTHER INFORMATION: n is unknown
<220> FEATURE:
<221> NAME/KEY: misc_feature
<222> LOCATION: (723)..(723)
<223> OTHER INFORMATION: n is unknown
<220> FEATURE:
<221> NAME/KEY: misc_feature
<222> LOCATION: (733)..(738)
<223> OTHER INFORMATION: n is unknown
<220> FEATURE:
<221> NAME/KEY: misc_feature
<222> LOCATION: (754)..(756)
<223> OTHER INFORMATION: n is unknown
<220> FEATURE:
<221> NAME/KEY: misc_feature
<222> LOCATION: (762)..(762)
<223> OTHER INFORMATION: n is unknown
<220> FEATURE:
<221> NAME/KEY: misc_feature
<222> LOCATION: (777)..(787)
<223> OTHER INFORMATION: n is unknown
<220> FEATURE:
<221> NAME/KEY: misc_feature
<222> LOCATION: (794)..(795)
<223> OTHER INFORMATION: n is unknown
<220> FEATURE:
<221> NAME/KEY: misc_feature
<222> LOCATION: (809)..(809)
<223> OTHER INFORMATION: n is unknown
<220> FEATURE:
<221> NAME/KEY: misc_feature
<222> LOCATION: (811)..(811)
<223> OTHER INFORMATION: n is unknown
<220> FEATURE:
<221> NAME/KEY: misc_feature
<222> LOCATION: (818)..(818)
<223> OTHER INFORMATION: n is unknown
<220> FEATURE:
<221> NAME/KEY: misc_feature
<222> LOCATION: (821)..(824)
<223> OTHER INFORMATION: n is unknown
<220> FEATURE:
<221> NAME/KEY: misc_feature
<222> LOCATION: (839)..(849)
<223> OTHER INFORMATION: n is unknown
<220> FEATURE:
<221> NAME/KEY: misc_feature
<222> LOCATION: (878)..(879)
<223> OTHER INFORMATION: n is unknown

<400> SEQUENCE: 16

```
cngnnnngtt gctnctactg ctgacaatgc tgctgnngnn ncncctcnct gtctccactt     60

ccttgaacaa tgcgccgtca tgcttctttt gcctcccgct gctccagaaa gctaggccgc    120

agatcagaac caccacagtc aatatcacca ccttcctctt atagattcgg aatctcatga    180

taggggctca gcctctgtgc gagtggagag aagttnnnnn nnnagctgan gancaattgc    240

aggtgatatg atgtgctcgg ctcaagaagc gggcccggan angaanaagt nnnnncnngg    300

nnnctnnnnn ngnncnatat tccntaangc atgatggttg ctcagaggca ggnnnnnanc    360

taattattgg caaaacgagc tcttgttnnn nnnnnnnnnn ngnnnnnnnn nncaannnnn    420

ncgatcctat aaaagataaa acataaataa acagtcttga ttatattctg ggtattaaag    480

ccacaatcag aacaaatata tgctttgtat cttnnnnngc cttcttcatn nnnnnntgct    540

tccgcggnna cattaagaga acttgtggta agataagaag atattttatt cgttctgctg    600

acttgctgga tgtcgggaaa tantctgcat tnnannnnag gcggttaatt gcanatataa    660

ttggtagtga aaagggncnn tgctatggtc accgtgaagc gagtacagca gacaagaatg    720

tgngccgttc tcnnnnnnta ttgtttgaat atgnnnacct gntttagtcg gtttaannnn    780

nnnnnnntct aacnnaaaac aacactgcng ngactgantg nnnnatttat ttttttacnn    840

nnnnnnnnnt ttggtgtaaa catcaacggc gcacttcnn                           879
```

<210> SEQ ID NO 17
<211> LENGTH: 878
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (4)..(5)
<223> OTHER INFORMATION: n is unknown
<220> FEATURE:
<221> NAME/KEY: misc_feature
<222> LOCATION: (7)..(7)
<223> OTHER INFORMATION: n is unknown
<220> FEATURE:
<221> NAME/KEY: misc_feature
<222> LOCATION: (11)..(12)
<223> OTHER INFORMATION: n is unknown
<220> FEATURE:
<221> NAME/KEY: misc_feature
<222> LOCATION: (15)..(17)
<223> OTHER INFORMATION: n is unknown
<220> FEATURE:
<221> NAME/KEY: misc_feature
<222> LOCATION: (35)..(35)
<223> OTHER INFORMATION: n is unknown
<220> FEATURE:
<221> NAME/KEY: misc_feature
<222> LOCATION: (41)..(41)
<223> OTHER INFORMATION: n is unknown
<220> FEATURE:
<221> NAME/KEY: misc_feature
<222> LOCATION: (46)..(46)
<223> OTHER INFORMATION: n is unknown
<220> FEATURE:
<221> NAME/KEY: misc_feature
<222> LOCATION: (125)..(125)
<223> OTHER INFORMATION: n is unknown

```
<220> FEATURE:
<221> NAME/KEY: misc_feature
<222> LOCATION: (214)..(218)
<223> OTHER INFORMATION: n is unknown
<220> FEATURE:
<221> NAME/KEY: misc_feature
<222> LOCATION: (220)..(221)
<223> OTHER INFORMATION: n is unknown
<220> FEATURE:
<221> NAME/KEY: misc_feature
<222> LOCATION: (228)..(228)
<223> OTHER INFORMATION: n is unknown
<220> FEATURE:
<221> NAME/KEY: misc_feature
<222> LOCATION: (231)..(231)
<223> OTHER INFORMATION: n is unknown
<220> FEATURE:
<221> NAME/KEY: misc_feature
<222> LOCATION: (279)..(284)
<223> OTHER INFORMATION: n is unknown
<220> FEATURE:
<221> NAME/KEY: misc_feature
<222> LOCATION: (288)..(299)
<223> OTHER INFORMATION: n is unknown
<220> FEATURE:
<221> NAME/KEY: misc_feature
<222> LOCATION: (327)..(340)
<223> OTHER INFORMATION: n is unknown
<220> FEATURE:
<221> NAME/KEY: misc_feature
<222> LOCATION: (342)..(352)
<223> OTHER INFORMATION: n is unknown
<220> FEATURE:
<221> NAME/KEY: misc_feature
<222> LOCATION: (357)..(358)
<223> OTHER INFORMATION: n is unknown
<220> FEATURE:
<221> NAME/KEY: misc_feature
<222> LOCATION: (360)..(361)
<223> OTHER INFORMATION: n is unknown
<220> FEATURE:
<221> NAME/KEY: misc_feature
<222> LOCATION: (363)..(364)
<223> OTHER INFORMATION: n is unknown
<220> FEATURE:
<221> NAME/KEY: misc_feature
<222> LOCATION: (374)..(374)
<223> OTHER INFORMATION: n is unknown
<220> FEATURE:
<221> NAME/KEY: misc_feature
<222> LOCATION: (377)..(378)
<223> OTHER INFORMATION: n is unknown
<220> FEATURE:
<221> NAME/KEY: misc_feature
<222> LOCATION: (402)..(407)
<223> OTHER INFORMATION: n is unknown
<220> FEATURE:
<221> NAME/KEY: misc_feature
<222> LOCATION: (414)..(415)
<223> OTHER INFORMATION: n is unknown
<220> FEATURE:
<221> NAME/KEY: misc_feature
<222> LOCATION: (417)..(418)
<223> OTHER INFORMATION: n is unknown
<220> FEATURE:
<221> NAME/KEY: misc_feature
<222> LOCATION: (420)..(420)
<223> OTHER INFORMATION: n is unknown
<220> FEATURE:
<221> NAME/KEY: misc_feature
<222> LOCATION: (511)..(515)
<223> OTHER INFORMATION: n is unknown
<220> FEATURE:
<221> NAME/KEY: misc_feature
<222> LOCATION: (526)..(531)
<223> OTHER INFORMATION: n is unknown
<220> FEATURE:
<221> NAME/KEY: misc_feature
<222> LOCATION: (533)..(534)
<223> OTHER INFORMATION: n is unknown
```

<220> FEATURE:
<221> NAME/KEY: misc_feature
<222> LOCATION: (538)..(542)
<223> OTHER INFORMATION: n is unknown
<220> FEATURE:
<221> NAME/KEY: misc_feature
<222> LOCATION: (620)..(620)
<223> OTHER INFORMATION: n is unknown
<220> FEATURE:
<221> NAME/KEY: misc_feature
<222> LOCATION: (630)..(635)
<223> OTHER INFORMATION: n is unknown
<220> FEATURE:
<221> NAME/KEY: misc_feature
<222> LOCATION: (651)..(651)
<223> OTHER INFORMATION: n is unknown
<220> FEATURE:
<221> NAME/KEY: misc_feature
<222> LOCATION: (719)..(719)
<223> OTHER INFORMATION: n is unknown
<220> FEATURE:
<221> NAME/KEY: misc_feature
<222> LOCATION: (731)..(731)
<223> OTHER INFORMATION: n is unknown
<220> FEATURE:
<221> NAME/KEY: misc_feature
<222> LOCATION: (733)..(736)
<223> OTHER INFORMATION: n is unknown
<220> FEATURE:
<221> NAME/KEY: misc_feature
<222> LOCATION: (753)..(753)
<223> OTHER INFORMATION: n is unknown
<220> FEATURE:
<221> NAME/KEY: misc_feature
<222> LOCATION: (770)..(770)
<223> OTHER INFORMATION: n is unknown
<220> FEATURE:
<221> NAME/KEY: misc_feature
<222> LOCATION: (775)..(785)
<223> OTHER INFORMATION: n is unknown
<220> FEATURE:
<221> NAME/KEY: misc_feature
<222> LOCATION: (806)..(807)
<223> OTHER INFORMATION: n is unknown
<220> FEATURE:
<221> NAME/KEY: misc_feature
<222> LOCATION: (809)..(809)
<223> OTHER INFORMATION: n is unknown
<220> FEATURE:
<221> NAME/KEY: misc_feature
<222> LOCATION: (816)..(816)
<223> OTHER INFORMATION: n is unknown
<220> FEATURE:
<221> NAME/KEY: misc_feature
<222> LOCATION: (832)..(841)
<223> OTHER INFORMATION: n is unknown
<220> FEATURE:
<221> NAME/KEY: misc_feature
<222> LOCATION: (855)..(855)
<223> OTHER INFORMATION: n is unknown
<220> FEATURE:
<221> NAME/KEY: misc_feature
<222> LOCATION: (863)..(863)
<223> OTHER INFORMATION: n is unknown

<400> SEQUENCE: 17
cngnnangtt nntcnnngct gacaatgctg ctgcngcttc ncctcnctgt ctccacttcc 60
ttgaacaatg cgccgtcatg cttcttttgc ctcccgctgc tccagaaagc taggccgcag 120
atcanaacca ccacagtcaa tatcaccacc ttcctcttat agattcggaa tctcatgata 180
ggggctcagc ctctgtgcga gtggagagaa gttnnnnngn nagctganga ncaattgcag 240
gtgatatgat gtgctcggct caagaagcgg gcccggagnn nnnnaagnnn nnnnnnnnnt 300
aattattggc aaaacgagct cttgttnnnn nnnnnnnnnn gnnnnnnnnn nnactanngn 360
ngnncaatat tccntanngc atgatggttg ctcagaggca gnnnnnnagc aacnnanncn 420

```
atcctataaa agataaaaca taaataaaca gtcttgatta tattctgggt attaaagcca    480

caatcagaac aaatatatgc tttgtatctt nnnnngcctt cttcannnnn nanngctnnn    540

nnggccacat taagagaact tgtggtaaga taagaagata ttttattcgt tctgctgact    600

tgctggatgt cgggaaatan tctgcatttn nnnnnaggcg gttaattgca natataattg    660

gtagtgaaaa gggtcgttgc tatggtcacc gtgaagcgag tacagcagca caagaatgng    720

tgccgttctc ngnnnntatt gtttgaatat ggnaacctgt tttagtcggn ttaannnnnn    780

nnnnntctaa ccaaaaacaa cactgnngng actgantgta gtatttattt tnnnnnnnnn    840

ncttaatttt ggtgnaaaca tcnacggcgc acttcaac                            878
```

<210> SEQ ID NO 18
<211> LENGTH: 869
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (4)..(5)
<223> OTHER INFORMATION: n is unknown
<220> FEATURE:
<221> NAME/KEY: misc_feature
<222> LOCATION: (8)..(10)
<223> OTHER INFORMATION: n is unknown
<220> FEATURE:
<221> NAME/KEY: misc_feature
<222> LOCATION: (28)..(28)
<223> OTHER INFORMATION: n is unknown
<220> FEATURE:
<221> NAME/KEY: misc_feature
<222> LOCATION: (39)..(39)
<223> OTHER INFORMATION: n is unknown
<220> FEATURE:
<221> NAME/KEY: misc_feature
<222> LOCATION: (118)..(118)
<223> OTHER INFORMATION: n is unknown
<220> FEATURE:
<221> NAME/KEY: misc_feature
<222> LOCATION: (207)..(213)
<223> OTHER INFORMATION: n is unknown
<220> FEATURE:
<221> NAME/KEY: misc_feature
<222> LOCATION: (267)..(267)
<223> OTHER INFORMATION: n is unknown
<220> FEATURE:
<221> NAME/KEY: misc_feature
<222> LOCATION: (270)..(271)
<223> OTHER INFORMATION: n is unknown
<220> FEATURE:
<221> NAME/KEY: misc_feature
<222> LOCATION: (281)..(292)
<223> OTHER INFORMATION: n is unknown
<220> FEATURE:
<221> NAME/KEY: misc_feature
<222> LOCATION: (323)..(333)
<223> OTHER INFORMATION: n is unknown
<220> FEATURE:
<221> NAME/KEY: misc_feature
<222> LOCATION: (335)..(345)
<223> OTHER INFORMATION: n is unknown
<220> FEATURE:
<221> NAME/KEY: misc_feature
<222> LOCATION: (349)..(352)
<223> OTHER INFORMATION: n is unknown
<220> FEATURE:
<221> NAME/KEY: misc_feature
<222> LOCATION: (354)..(354)
<223> OTHER INFORMATION: n is unknown
<220> FEATURE:
<221> NAME/KEY: misc_feature
<222> LOCATION: (356)..(357)
<223> OTHER INFORMATION: n is unknown -continued
<220> FEATURE:
<221> NAME/KEY: misc_feature
<222> LOCATION: (367)..(367)
<223> OTHER INFORMATION: n is unknown
<220> FEATURE:
<221> NAME/KEY: misc_feature
<222> LOCATION: (370)..(371)
<223> OTHER INFORMATION: n is unknown
<220> FEATURE:
<221> NAME/KEY: misc_feature
<222> LOCATION: (395)..(400)
<223> OTHER INFORMATION: n is unknown
<220> FEATURE:
<221> NAME/KEY: misc_feature
<222> LOCATION: (406)..(408)
<223> OTHER INFORMATION: n is unknown
<220> FEATURE:
<221> NAME/KEY: misc_feature
<222> LOCATION: (410)..(411)
<223> OTHER INFORMATION: n is unknown
<220> FEATURE:
<221> NAME/KEY: misc_feature
<222> LOCATION: (504)..(508)
<223> OTHER INFORMATION: n is unknown
<220> FEATURE:
<221> NAME/KEY: misc_feature
<222> LOCATION: (520)..(526)
<223> OTHER INFORMATION: n is unknown
<220> FEATURE:
<221> NAME/KEY: misc_feature
<222> LOCATION: (529)..(529)
<223> OTHER INFORMATION: n is unknown
<220> FEATURE:
<221> NAME/KEY: misc_feature
<222> LOCATION: (538)..(538)
<223> OTHER INFORMATION: n is unknown
<220> FEATURE:
<221> NAME/KEY: misc_feature
<222> LOCATION: (623)..(628)
<223> OTHER INFORMATION: n is unknown
<220> FEATURE:
<221> NAME/KEY: misc_feature
<222> LOCATION: (724)..(729)
<223> OTHER INFORMATION: n is unknown
<220> FEATURE:
<221> NAME/KEY: misc_feature
<222> LOCATION: (746)..(746)
<223> OTHER INFORMATION: n is unknown
<220> FEATURE:
<221> NAME/KEY: misc_feature
<222> LOCATION: (769)..(769)
<223> OTHER INFORMATION: n is unknown
<220> FEATURE:
<221> NAME/KEY: misc_feature
<222> LOCATION: (771)..(777)
<223> OTHER INFORMATION: n is unknown
<220> FEATURE:
<221> NAME/KEY: misc_feature
<222> LOCATION: (785)..(785)
<223> OTHER INFORMATION: n is unknown
<220> FEATURE:
<221> NAME/KEY: misc_feature
<222> LOCATION: (805)..(805)
<223> OTHER INFORMATION: n is unknown
<220> FEATURE:
<221> NAME/KEY: misc_feature
<222> LOCATION: (808)..(812)
<223> OTHER INFORMATION: n is unknown
<220> FEATURE:
<221> NAME/KEY: misc_feature
<222> LOCATION: (816)..(816)
<223> OTHER INFORMATION: n is unknown
<220> FEATURE:
<221> NAME/KEY: misc_feature
<222> LOCATION: (830)..(841)
<223> OTHER INFORMATION: n is unknown
<220> FEATURE:
<221> NAME/KEY: misc_feature
<222> LOCATION: (849)..(849)
<223> OTHER INFORMATION: n is unknown

<400> SEQUENCE: 18
gttnntcnnn gctgacaatg ctgctgcngc ttctcctcnc tgtctccact tccttgaaca 60
atgcgccgtc atgcttcttt tgcctcccgc tgctccagaa agctaggccg cagatcanaa 120
ccaccacagt caatatcacc accttcctct tatagattcg gaatctcatg ataggggctc 180
agcctctgtg cgagtggaga gaagttnnnn nnngagctga ggagcaattg caggtgatat 240
gatgtgctcg gctcaagaag cgggccnggn naggaagaag nnnnnnnnnn nntaattatt 300
ggcaaaacga gctcttgttg tannnnnnnn nnngnnnnnn nnnnnactnn nngngnncaa 360
tattccntan ngcatgatgg ttgctcagag gcagnnnnnn agcaannnan ncgatcctat 420
aaaagataaa acataaataa acagtcttga ttatattctg ggtattaaag ccacaatcag 480
aacaaatata tgctttgtat cttnnnnngc cttcttcatn nnnnnntgnt tccgcggnca 540
cattaagaga acttgtggta agataagaag atattttatt cgttctgctg acttgctgga 600
tgtcgggaaa tattctgcat ttnnnnnnag gcggttaatt gcagatataa ttggtagtga 660
aaagggtcgt tgctatggtc accgtgaagc gagtacagca gcacaagaat gtgtgccgtt 720
ctcnnnnnnt attgtttgaa tatggnaacc tgttttagtc ggtttaaang nnnnnnntct 780
aaccnaaaac aacactgcag tgacngannn nngtanttat ttttttactn nnnnnnnnnn 840
ntttggtgna aacatcaacg gcgcacttc 869

<210> SEQ ID NO 19
<211> LENGTH: 874
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (7)..(7)
<223> OTHER INFORMATION: n is unknown
<220> FEATURE:
<221> NAME/KEY: misc_feature
<222> LOCATION: (18)..(18)
<223> OTHER INFORMATION: n is unknown
<220> FEATURE:
<221> NAME/KEY: misc_feature
<222> LOCATION: (41)..(41)
<223> OTHER INFORMATION: n is unknown
<220> FEATURE:
<221> NAME/KEY: misc_feature
<222> LOCATION: (209)..(209)
<223> OTHER INFORMATION: n is unknown
<220> FEATURE:
<221> NAME/KEY: misc_feature
<222> LOCATION: (269)..(269)
<223> OTHER INFORMATION: n is unknown
<220> FEATURE:
<221> NAME/KEY: misc_feature
<222> LOCATION: (271)..(274)
<223> OTHER INFORMATION: n is unknown
<220> FEATURE:
<221> NAME/KEY: misc_feature
<222> LOCATION: (276)..(278)
<223> OTHER INFORMATION: n is unknown
<220> FEATURE:
<221> NAME/KEY: misc_feature
<222> LOCATION: (285)..(286)
<223> OTHER INFORMATION: n is unknown
<220> FEATURE:
<221> NAME/KEY: misc_feature
<222> LOCATION: (288)..(288)
<223> OTHER INFORMATION: n is unknown
<220> FEATURE:
<221> NAME/KEY: misc_feature
<222> LOCATION: (291)..(291)
<223> OTHER INFORMATION: n is unknown
<220> FEATURE:
<221> NAME/KEY: misc_feature
<222> LOCATION: (325)..(335)
<223> OTHER INFORMATION: n is unknown
<220> FEATURE:
<221> NAME/KEY: misc_feature
<222> LOCATION: (337)..(347)
<223> OTHER INFORMATION: n is unknown
<220> FEATURE:
<221> NAME/KEY: misc_feature
<222> LOCATION: (351)..(352)
<223> OTHER INFORMATION: n is unknown
<220> FEATURE:
<221> NAME/KEY: misc_feature
<222> LOCATION: (354)..(357)
<223> OTHER INFORMATION: n is unknown
<220> FEATURE:
<221> NAME/KEY: misc_feature
<222> LOCATION: (361)..(361)
<223> OTHER INFORMATION: n is unknown
<220> FEATURE:
<221> NAME/KEY: misc_feature
<222> LOCATION: (369)..(369)
<223> OTHER INFORMATION: n is unknown
<220> FEATURE:
<221> NAME/KEY: misc_feature
<222> LOCATION: (373)..(373)
<223> OTHER INFORMATION: n is unknown
<220> FEATURE:
<221> NAME/KEY: misc_feature
<222> LOCATION: (396)..(396)
<223> OTHER INFORMATION: n is unknown
<220> FEATURE:
<221> NAME/KEY: misc_feature
<222> LOCATION: (398)..(401)
<223> OTHER INFORMATION: n is unknown
<220> FEATURE:
<221> NAME/KEY: misc_feature
<222> LOCATION: (408)..(408)
<223> OTHER INFORMATION: n is unknown
<220> FEATURE:
<221> NAME/KEY: misc_feature
<222> LOCATION: (411)..(411)
<223> OTHER INFORMATION: n is unknown
<220> FEATURE:
<221> NAME/KEY: misc_feature
<222> LOCATION: (506)..(506)
<223> OTHER INFORMATION: n is unknown
<220> FEATURE:
<221> NAME/KEY: misc_feature
<222> LOCATION: (508)..(509)
<223> OTHER INFORMATION: n is unknown
<220> FEATURE:
<221> NAME/KEY: misc_feature
<222> LOCATION: (521)..(528)
<223> OTHER INFORMATION: n is unknown
<220> FEATURE:
<221> NAME/KEY: misc_feature
<222> LOCATION: (530)..(530)
<223> OTHER INFORMATION: n is unknown
<220> FEATURE:
<221> NAME/KEY: misc_feature
<222> LOCATION: (538)..(541)
<223> OTHER INFORMATION: n is unknown
<220> FEATURE:
<221> NAME/KEY: misc_feature
<222> LOCATION: (624)..(628)
<223> OTHER INFORMATION: n is unknown
<220> FEATURE:
<221> NAME/KEY: misc_feature
<222> LOCATION: (725)..(730)
<223> OTHER INFORMATION: n is unknown
<220> FEATURE:
<221> NAME/KEY: misc_feature
<222> LOCATION: (769)..(779)
<223> OTHER INFORMATION: n is unknown
<220> FEATURE:
<221> NAME/KEY: misc_feature
<222> LOCATION: (803)..(803)
<223> OTHER INFORMATION: n is unknown -continued
<220> FEATURE:
<221> NAME/KEY: misc_feature
<222> LOCATION: (806)..(808)
<223> OTHER INFORMATION: n is unknown
<220> FEATURE:
<221> NAME/KEY: misc_feature
<222> LOCATION: (811)..(813)
<223> OTHER INFORMATION: n is unknown
<220> FEATURE:
<221> NAME/KEY: misc_feature
<222> LOCATION: (828)..(838)
<223> OTHER INFORMATION: n is unknown
<220> FEATURE:
<221> NAME/KEY: misc_feature
<222> LOCATION: (850)..(850)
<223> OTHER INFORMATION: n is unknown
<220> FEATURE:
<221> NAME/KEY: misc_feature
<222> LOCATION: (852)..(852)
<223> OTHER INFORMATION: n is unknown
<220> FEATURE:
<221> NAME/KEY: misc_feature
<222> LOCATION: (860)..(860)
<223> OTHER INFORMATION: n is unknown
<220> FEATURE:
<221> NAME/KEY: misc_feature
<222> LOCATION: (870)..(870)
<223> OTHER INFORMATION: n is unknown
<220> FEATURE:
<221> NAME/KEY: misc_feature
<222> LOCATION: (872)..(874)
<223> OTHER INFORMATION: n is unknown

<400> SEQUENCE: 19
gttgctncta ctgctganaa tgctgctgct gcttctcctc nctgtctcca cttccttgaa 60
caatgcgccg tcatgcttct tttgcctccc gctgctccag aaagctaggc cgcagatcag 120
aaccaccaca gtcaatatca ccaccttcct cttatagatt cggaatctca tgataggggc 180
tcagcctctg tgcgagtgga gagaagttng caggcgagct gaggagcaat tgcaggtgat 240
atgatgtgct cggctcaaga agcgggccng nnnngnnnga agtcnngncg nggctaatta 300
ttggcaaaac gagctcttgt tgtannnnnn nnnnngnnnn nnnnnnncta nngnnnnatc 360
natattccnt aangcatgat ggttgctcag aggcangnnn nagcaacnaa nacgatccta 420
taaaagataa aacataaata aacagtcttg attatattct gggtattaaa gccacaatca 480
gaacaaatat atgctttgta tctttncnng ccttcttcat nnnnnnnngn ttccgcgnnn 540
ncattaagag aacttgtggt aagataagaa gatattttat tcgttctgct gacttgctgg 600
atgtcgggaa atattctgca tttnnnnnga ggcggttaat tgcagatata attggtagtg 660
aaaagggtcg ttgctatggt caccgtgaag cgagtacagc agcacaagaa tgtgtgccgt 720
tctcnnnnnn tattgtttga atatggtaac ctgttttagt cggtttaann nnnnnnnnnt 780
ctaaccaaaa acaacactgc agnggnnngg nnngtagtat ttattttnnn nnnnnnnnct 840
taattttggn gnaaacatcn acggcgcacn tnnn 874

<210> SEQ ID NO 20
<211> LENGTH: 868
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (5)..(5)
<223> OTHER INFORMATION: n is unknown
<220> FEATURE:
<221> NAME/KEY: misc_feature
<222> LOCATION: (7)..(7)
<223> OTHER INFORMATION: n is unknown
<220> FEATURE:
<221> NAME/KEY: misc_feature
<222> LOCATION: (9)..(10)
<223> OTHER INFORMATION: n is unknown
<220> FEATURE:
<221> NAME/KEY: misc_feature
<222> LOCATION: (13)..(14)
<223> OTHER INFORMATION: n is unknown
<220> FEATURE:
<221> NAME/KEY: misc_feature
<222> LOCATION: (18)..(18)
<223> OTHER INFORMATION: n is unknown
<220> FEATURE:
<221> NAME/KEY: misc_feature
<222> LOCATION: (30)..(32)
<223> OTHER INFORMATION: n is unknown
<220> FEATURE:
<221> NAME/KEY: misc_feature
<222> LOCATION: (34)..(36)
<223> OTHER INFORMATION: n is unknown
<220> FEATURE:
<221> NAME/KEY: misc_feature
<222> LOCATION: (103)..(103)
<223> OTHER INFORMATION: n is unknown
<220> FEATURE:
<221> NAME/KEY: misc_feature
<222> LOCATION: (105)..(105)
<223> OTHER INFORMATION: n is unknown
<220> FEATURE:
<221> NAME/KEY: misc_feature
<222> LOCATION: (107)..(108)
<223> OTHER INFORMATION: n is unknown
<220> FEATURE:
<221> NAME/KEY: misc_feature
<222> LOCATION: (130)..(132)
<223> OTHER INFORMATION: n is unknown
<220> FEATURE:
<221> NAME/KEY: misc_feature
<222> LOCATION: (135)..(135)
<223> OTHER INFORMATION: n is unknown
<220> FEATURE:
<221> NAME/KEY: misc_feature
<222> LOCATION: (138)..(138)
<223> OTHER INFORMATION: n is unknown
<220> FEATURE:
<221> NAME/KEY: misc_feature
<222> LOCATION: (174)..(175)
<223> OTHER INFORMATION: n is unknown
<220> FEATURE:
<221> NAME/KEY: misc_feature
<222> LOCATION: (178)..(179)
<223> OTHER INFORMATION: n is unknown
<220> FEATURE:
<221> NAME/KEY: misc_feature
<222> LOCATION: (218)..(218)
<223> OTHER INFORMATION: n is unknown
<220> FEATURE:
<221> NAME/KEY: misc_feature
<222> LOCATION: (224)..(224)
<223> OTHER INFORMATION: n is unknown
<220> FEATURE:
<221> NAME/KEY: misc_feature
<222> LOCATION: (232)..(232)
<223> OTHER INFORMATION: n is unknown
<220> FEATURE:
<221> NAME/KEY: misc_feature
<222> LOCATION: (234)..(239)
<223> OTHER INFORMATION: n is unknown
<220> FEATURE:
<221> NAME/KEY: misc_feature
<222> LOCATION: (265)..(265)
<223> OTHER INFORMATION: n is unknown
<220> FEATURE:
<221> NAME/KEY: misc_feature
<222> LOCATION: (267)..(271)
<223> OTHER INFORMATION: n is unknown
<220> FEATURE:
<221> NAME/KEY: misc_feature
<222> LOCATION: (273)..(274)
<223> OTHER INFORMATION: n is unknown
<220> FEATURE:
<221> NAME/KEY: misc_feature
<222> LOCATION: (328)..(330)
<223> OTHER INFORMATION: n is unknown
<220> FEATURE:
<221> NAME/KEY: misc_feature
<222> LOCATION: (341)..(351)
<223> OTHER INFORMATION: n is unknown
<220> FEATURE:
<221> NAME/KEY: misc_feature
<222> LOCATION: (517)..(523)
<223> OTHER INFORMATION: n is unknown
<220> FEATURE:
<221> NAME/KEY: misc_feature
<222> LOCATION: (525)..(525)
<223> OTHER INFORMATION: n is unknown
<220> FEATURE:
<221> NAME/KEY: misc_feature
<222> LOCATION: (527)..(527)
<223> OTHER INFORMATION: n is unknown
<220> FEATURE:
<221> NAME/KEY: misc_feature
<222> LOCATION: (529)..(529)
<223> OTHER INFORMATION: n is unknown
<220> FEATURE:
<221> NAME/KEY: misc_feature
<222> LOCATION: (552)..(552)
<223> OTHER INFORMATION: n is unknown
<220> FEATURE:
<221> NAME/KEY: misc_feature
<222> LOCATION: (554)..(554)
<223> OTHER INFORMATION: n is unknown
<220> FEATURE:
<221> NAME/KEY: misc_feature
<222> LOCATION: (662)..(662)
<223> OTHER INFORMATION: n is unknown
<220> FEATURE:
<221> NAME/KEY: misc_feature
<222> LOCATION: (664)..(665)
<223> OTHER INFORMATION: n is unknown
<220> FEATURE:
<221> NAME/KEY: misc_feature
<222> LOCATION: (686)..(686)
<223> OTHER INFORMATION: n is unknown
<220> FEATURE:
<221> NAME/KEY: misc_feature
<222> LOCATION: (795)..(798)
<223> OTHER INFORMATION: n is unknown
<220> FEATURE:
<221> NAME/KEY: misc_feature
<222> LOCATION: (800)..(802)
<223> OTHER INFORMATION: n is unknown
<220> FEATURE:
<221> NAME/KEY: misc_feature
<222> LOCATION: (811)..(815)
<223> OTHER INFORMATION: n is unknown
<220> FEATURE:
<221> NAME/KEY: misc_feature
<222> LOCATION: (817)..(821)
<223> OTHER INFORMATION: n is unknown
<220> FEATURE:
<221> NAME/KEY: misc_feature
<222> LOCATION: (827)..(827)
<223> OTHER INFORMATION: n is unknown
<220> FEATURE:
<221> NAME/KEY: misc_feature
<222> LOCATION: (833)..(833)
<223> OTHER INFORMATION: n is unknown
<220> FEATURE:
<221> NAME/KEY: misc_feature
<222> LOCATION: (836)..(836)
<223> OTHER INFORMATION: n is unknown
<220> FEATURE:
<221> NAME/KEY: misc_feature
<222> LOCATION: (845)..(845)
<223> OTHER INFORMATION: n is unknown

<400> SEQUENCE: 20

```
gntcncngnn gannatgntg ctgctgcttn nngnnnctgt ctccacttcc ttgaacaatg     60

cgccgtcatg cttcttttgc ctcccgctgc tccagaaagc tangncnnag atcagaacca    120

ccacagtcan nntcnccncc ttcctcttat agattcggaa tctcatgata gggnntcnnc    180

ctctgtgcga gtggagagaa gtttgcaggc gagctganga gcanttgcag gngnnnnnnt    240

gtgctcggct caagaagcgg gcccngnnnn nannaagtcg tgccggggct aattattggc    300

aaaacgagct cttgttgtaa acattgannn gggggggggg nnnnnnnnnn natcaatatt    360

ccataaggca tgatggttgc tcagaggcag gagaagagca acgaatacga tcctataaaa    420

gataaaacat aaataaacag tcttgattat attctgggta ttaaagccac aatcagaaca    480

aatatatgct ttgtatcttt tcttgccttc ttcattnnnn nnngntncng cggccacatt    540

aagagaactt gngntaagat aagaagatat tttattcgtt ctgctgactt gctggatgtc    600

gggaaatatt ctgcatttga taagaggcgg ttaattgcag atataattgg tagtgaaaag    660

gngnnttgct atggtcaccg tgaagngagt acagcagcac aagaatgtgt gccgttctca    720

gttaatattg tttgaatatg gtaacctgtt ttagtcggtt taaaggtaag aagatctaac    780

caaaaacaac actgnnnngn nngattgtag nnnnnannnn ntttacntaa tcntantttt    840

ggtgnaaaca tcaacggcgc acttcaac                                       868
```

<210> SEQ ID NO 21
<211> LENGTH: 876
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (2)..(3)
<223> OTHER INFORMATION: n is unknown
<220> FEATURE:
<221> NAME/KEY: misc_feature
<222> LOCATION: (8)..(8)
<223> OTHER INFORMATION: n is unknown
<220> FEATURE:
<221> NAME/KEY: misc_feature
<222> LOCATION: (14)..(14)
<223> OTHER INFORMATION: n is unknown
<220> FEATURE:
<221> NAME/KEY: misc_feature
<222> LOCATION: (16)..(16)
<223> OTHER INFORMATION: n is unknown
<220> FEATURE:
<221> NAME/KEY: misc_feature
<222> LOCATION: (21)..(21)
<223> OTHER INFORMATION: n is unknown
<220> FEATURE:
<221> NAME/KEY: misc_feature
<222> LOCATION: (37)..(43)
<223> OTHER INFORMATION: n is unknown
<220> FEATURE:
<221> NAME/KEY: misc_feature
<222> LOCATION: (68)..(68)
<223> OTHER INFORMATION: n is unknown
<220> FEATURE:
<221> NAME/KEY: misc_feature
<222> LOCATION: (110)..(110)
<223> OTHER INFORMATION: n is unknown
<220> FEATURE:
<221> NAME/KEY: misc_feature
<222> LOCATION: (112)..(115)
<223> OTHER INFORMATION: n is unknown
<220> FEATURE:
<221> NAME/KEY: misc_feature
<222> LOCATION: (134)..(134)
<223> OTHER INFORMATION: n is unknown
<220> FEATURE:
<221> NAME/KEY: misc_feature
<222> LOCATION: (136)..(139)
<223> OTHER INFORMATION: n is unknown
<220> FEATURE:
<221> NAME/KEY: misc_feature
<222> LOCATION: (141)..(141)
<223> OTHER INFORMATION: n is unknown
<220> FEATURE:
<221> NAME/KEY: misc_feature
<222> LOCATION: (145)..(145)
<223> OTHER INFORMATION: n is unknown
<220> FEATURE:
<221> NAME/KEY: misc_feature
<222> LOCATION: (181)..(182)
<223> OTHER INFORMATION: n is unknown
<220> FEATURE:
<221> NAME/KEY: misc_feature
<222> LOCATION: (185)..(186)
<223> OTHER INFORMATION: n is unknown
<220> FEATURE:
<221> NAME/KEY: misc_feature
<222> LOCATION: (218)..(218)
<223> OTHER INFORMATION: n is unknown
<220> FEATURE:
<221> NAME/KEY: misc_feature
<222> LOCATION: (225)..(225)
<223> OTHER INFORMATION: n is unknown
<220> FEATURE:
<221> NAME/KEY: misc_feature
<222> LOCATION: (231)..(231)
<223> OTHER INFORMATION: n is unknown
<220> FEATURE:
<221> NAME/KEY: misc_feature
<222> LOCATION: (239)..(239)
<223> OTHER INFORMATION: n is unknown
<220> FEATURE:
<221> NAME/KEY: misc_feature
<222> LOCATION: (241)..(243)
<223> OTHER INFORMATION: n is unknown
<220> FEATURE:
<221> NAME/KEY: misc_feature
<222> LOCATION: (245)..(246)
<223> OTHER INFORMATION: n is unknown
<220> FEATURE:
<221> NAME/KEY: misc_feature
<222> LOCATION: (263)..(263)
<223> OTHER INFORMATION: n is unknown
<220> FEATURE:
<221> NAME/KEY: misc_feature
<222> LOCATION: (269)..(269)
<223> OTHER INFORMATION: n is unknown
<220> FEATURE:
<221> NAME/KEY: misc_feature
<222> LOCATION: (275)..(275)
<223> OTHER INFORMATION: n is unknown
<220> FEATURE:
<221> NAME/KEY: misc_feature
<222> LOCATION: (334)..(359)
<223> OTHER INFORMATION: n is unknown
<220> FEATURE:
<221> NAME/KEY: misc_feature
<222> LOCATION: (522)..(522)
<223> OTHER INFORMATION: n is unknown
<220> FEATURE:
<221> NAME/KEY: misc_feature
<222> LOCATION: (560)..(560)
<223> OTHER INFORMATION: n is unknown
<220> FEATURE:
<221> NAME/KEY: misc_feature
<222> LOCATION: (562)..(562)
<223> OTHER INFORMATION: n is unknown
<220> FEATURE:
<221> NAME/KEY: misc_feature
<222> LOCATION: (670)..(670)
<223> OTHER INFORMATION: n is unknown
<220> FEATURE:
<221> NAME/KEY: misc_feature
<222> LOCATION: (694)..(694)
<223> OTHER INFORMATION: n is unknown
<220> FEATURE:
<221> NAME/KEY: misc_feature
<222> LOCATION: (801)..(801)
<223> OTHER INFORMATION: n is unknown
<220> FEATURE:
<221> NAME/KEY: misc_feature
<222> LOCATION: (816)..(817)
<223> OTHER INFORMATION: n is unknown
<220> FEATURE:
<221> NAME/KEY: misc_feature
<222> LOCATION: (819)..(827)
<223> OTHER INFORMATION: n is unknown
<220> FEATURE:
<221> NAME/KEY: misc_feature
<222> LOCATION: (835)..(836)
<223> OTHER INFORMATION: n is unknown
<220> FEATURE:
<221> NAME/KEY: misc_feature
<222> LOCATION: (838)..(838)
<223> OTHER INFORMATION: n is unknown
<220> FEATURE:
<221> NAME/KEY: misc_feature
<222> LOCATION: (862)..(862)
<223> OTHER INFORMATION: n is unknown

<400> SEQUENCE: 21
tnngttgntc tacngntgac natgctgctg ctgcttnnnn nnnctgtctc cacttccttg 60
aacaatgngc cgtcatgctt cttttgcctc ccgctgctcc agaaagctan gnnnnagatc 120
agaaccacca cagncnnnnt naccnccttc ctcttataga ttcggaatct catgataggg 180
nntcnncctc tgtgcgagtg gagagaagtt tgcaggcnag ctgangagca nttgcaggng 240
nnngnntgtg ctcggctcaa gangcgggnc cgganaggaa gaagtcgtgc cggggctaat 300
tattggcaaa acgagctctt gttgtaaaca ttgnnnnnnn nnnnnnnnnn nnnnnnnnna 360
tcaatattcc ataaggcatg atggttgctc agaggcagga gaagagcaac gaatacgatc 420
ctataaaaga taaaacataa ataaacagtc ttgattatat tctgggtatt aaagccacaa 480
tcagaacaaa tatatgcttt gtatcttttc ttgccttctt cnttaccaac tgcttccgcg 540
gccacattaa gagaacttgn gntaagataa gaagatattt tattcgttct gctgacttgc 600
tggatgtcgg gaaatattct gcatttgata agaggcggtt aattgcagat ataattggta 660
gtgaaaaggn gcgttgctat ggtcaccgtg aagngagtac agcagcacaa gaatgtgtgc 720
cgttctcagt taatattgtt tgaatatggt aacctgtttt agtcggttta aaggtaagaa 780
gatctaacca aaaacaacac ngcagtgact gattgnngnn nnnnnnnttt tttanntnat 840
cttaattttg gtgtaaacat cnacggcgca cttcaa 876

<210> SEQ ID NO 22
<211> LENGTH: 880
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (17)..(17)
<223> OTHER INFORMATION: n is unknown
<220> FEATURE:
<221> NAME/KEY: misc_feature
<222> LOCATION: (24)..(24)
<223> OTHER INFORMATION: n is unknown
<220> FEATURE:
<221> NAME/KEY: misc_feature
<222> LOCATION: (41)..(42)
<223> OTHER INFORMATION: n is unknown
<220> FEATURE:
<221> NAME/KEY: misc_feature
<222> LOCATION: (44)..(46)
<223> OTHER INFORMATION: n is unknown
<220> FEATURE:
<221> NAME/KEY: misc_feature
<222> LOCATION: (71)..(71)
<223> OTHER INFORMATION: n is unknown
<220> FEATURE:
<221> NAME/KEY: misc_feature
<222> LOCATION: (115)..(115)
<223> OTHER INFORMATION: n is unknown
<220> FEATURE:
<221> NAME/KEY: misc_feature
<222> LOCATION: (117)..(118)
<223> OTHER INFORMATION: n is unknown
<220> FEATURE:
<221> NAME/KEY: misc_feature
<222> LOCATION: (137)..(137)
<223> OTHER INFORMATION: n is unknown
<220> FEATURE:
<221> NAME/KEY: misc_feature
<222> LOCATION: (139)..(140)
<223> OTHER INFORMATION: n is unknown
<220> FEATURE:
<221> NAME/KEY: misc_feature
<222> LOCATION: (145)..(145)
<223> OTHER INFORMATION: n is unknown
<220> FEATURE:
<221> NAME/KEY: misc_feature
<222> LOCATION: (148)..(148)
<223> OTHER INFORMATION: n is unknown
<220> FEATURE:
<221> NAME/KEY: misc_feature
<222> LOCATION: (184)..(185)
<223> OTHER INFORMATION: n is unknown
<220> FEATURE:
<221> NAME/KEY: misc_feature
<222> LOCATION: (188)..(189)
<223> OTHER INFORMATION: n is unknown
<220> FEATURE:
<221> NAME/KEY: misc_feature
<222> LOCATION: (228)..(228)
<223> OTHER INFORMATION: n is unknown
<220> FEATURE:
<221> NAME/KEY: misc_feature
<222> LOCATION: (244)..(248)
<223> OTHER INFORMATION: n is unknown
<220> FEATURE:
<221> NAME/KEY: misc_feature
<222> LOCATION: (328)..(328)
<223> OTHER INFORMATION: n is unknown
<220> FEATURE:
<221> NAME/KEY: misc_feature
<222> LOCATION: (333)..(333)
<223> OTHER INFORMATION: n is unknown
<220> FEATURE:
<221> NAME/KEY: misc_feature
<222> LOCATION: (335)..(335)
<223> OTHER INFORMATION: n is unknown
<220> FEATURE:
<221> NAME/KEY: misc_feature
<222> LOCATION: (337)..(339)
<223> OTHER INFORMATION: n is unknown
<220> FEATURE:
<221> NAME/KEY: misc_feature
<222> LOCATION: (348)..(362)
<223> OTHER INFORMATION: n is unknown
<220> FEATURE:
<221> NAME/KEY: misc_feature
<222> LOCATION: (563)..(563)
<223> OTHER INFORMATION: n is unknown
<220> FEATURE:
<221> NAME/KEY: misc_feature
<222> LOCATION: (673)..(676)
<223> OTHER INFORMATION: n is unknown
<220> FEATURE:
<221> NAME/KEY: misc_feature
<222> LOCATION: (770)..(770)
<223> OTHER INFORMATION: n is unknown
<220> FEATURE:
<221> NAME/KEY: misc_feature
<222> LOCATION: (792)..(793)
<223> OTHER INFORMATION: n is unknown
<220> FEATURE:
<221> NAME/KEY: misc_feature
<222> LOCATION: (797)..(798)
<223> OTHER INFORMATION: n is unknown
<220> FEATURE:
<221> NAME/KEY: misc_feature
<222> LOCATION: (809)..(810)
<223> OTHER INFORMATION: n is unknown
<220> FEATURE:
<221> NAME/KEY: misc_feature
<222> LOCATION: (816)..(824)
<223> OTHER INFORMATION: n is unknown
<220> FEATURE:
<221> NAME/KEY: misc_feature
<222> LOCATION: (828)..(833)
<223> OTHER INFORMATION: n is unknown
<220> FEATURE:
<221> NAME/KEY: misc_feature
<222> LOCATION: (870)..(870)
<223> OTHER INFORMATION: n is unknown
<220> FEATURE:
<221> NAME/KEY: misc_feature
<222> LOCATION: (880)..(880)
<223> OTHER INFORMATION: n is unknown

<400> SEQUENCE: 22

```
cngttatgtt gctctcngct gacnatgctg ctgctgcttc nngnnnctgt ctccacttcc      60

ttgaacaatg ngccgtcatg cttcttttgc ctcccgctgc tccagaaagc taggncnnag     120

atcagaacca ccacagncnn tatcnccncc ttcctcttat agattcggaa tctcatgata     180

gggnntcnnc ctctgtgcga gtggagagaa gtttgcaggc gagctganga gcaattgcag     240

gtgnnnnnat gtgctcggct caagaagcgg gcccggagag gaagaagtcg tgccggggct     300

aattattggc aaaacgagct cttgttgnaa acntngnnng gggggggnnn nnnnnnnnnn     360

nnatcaatat tccataaggc atgatggttg ctcagaggca ggagaagagc aacgaatacg     420

atcctataaa agataaaaca taaataaaca gtcttgatta tattctgggt attaaagcca     480

caatcagaac aaatatatgc tttgtatctt ttcttgcctt cttcattacc aactgcttcc     540

gcggccacat taagagaact tgnggtaaga taagaagata ttttattcgt tctgctgact     600

tgctggatgt cgggaaatat tctgcatttg ataagaggcg gttaattgca gatataattg     660

gtagtgaaaa ggnnnnttgc tatggtcacc gtgaagcgag tacagcagca caagaatgtg     720

tgccgttctc agttaatatt gtttgaatat ggtaacctgt tttagtcggn ttaaaggtaa     780

gaagatctaa cnnaaannca acactgcann gactgnnnnn nnnnattnnn nnntttttac     840

ttaatcttaa ttttggtgta aacatcaacn ggcgcacttn                           880
```

<210> SEQ ID NO 23
<211> LENGTH: 868
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (5)..(5)
<223> OTHER INFORMATION: n is unknown
<220> FEATURE:
<221> NAME/KEY: misc_feature
<222> LOCATION: (8)..(10)
<223> OTHER INFORMATION: n is unknown
<220> FEATURE:
<221> NAME/KEY: misc_feature
<222> LOCATION: (17)..(17)
<223> OTHER INFORMATION: n is unknown -continued
<220> FEATURE:
<221> NAME/KEY: misc_feature
<222> LOCATION: (33)..(35)
<223> OTHER INFORMATION: n is unknown
<220> FEATURE:
<221> NAME/KEY: misc_feature
<222> LOCATION: (37)..(39)
<223> OTHER INFORMATION: n is unknown
<220> FEATURE:
<221> NAME/KEY: misc_feature
<222> LOCATION: (61)..(61)
<223> OTHER INFORMATION: n is unknown
<220> FEATURE:
<221> NAME/KEY: misc_feature
<222> LOCATION: (106)..(106)
<223> OTHER INFORMATION: n is unknown
<220> FEATURE:
<221> NAME/KEY: misc_feature
<222> LOCATION: (108)..(108)
<223> OTHER INFORMATION: n is unknown
<220> FEATURE:
<221> NAME/KEY: misc_feature
<222> LOCATION: (110)..(111)
<223> OTHER INFORMATION: n is unknown
<220> FEATURE:
<221> NAME/KEY: misc_feature
<222> LOCATION: (130)..(130)
<223> OTHER INFORMATION: n is unknown
<220> FEATURE:
<221> NAME/KEY: misc_feature
<222> LOCATION: (132)..(135)
<223> OTHER INFORMATION: n is unknown
<220> FEATURE:
<221> NAME/KEY: misc_feature
<222> LOCATION: (138)..(138)
<223> OTHER INFORMATION: n is unknown
<220> FEATURE:
<221> NAME/KEY: misc_feature
<222> LOCATION: (141)..(141)
<223> OTHER INFORMATION: n is unknown
<220> FEATURE:
<221> NAME/KEY: misc_feature
<222> LOCATION: (178)..(178)
<223> OTHER INFORMATION: n is unknown
<220> FEATURE:
<221> NAME/KEY: misc_feature
<222> LOCATION: (181)..(182)
<223> OTHER INFORMATION: n is unknown
<220> FEATURE:
<221> NAME/KEY: misc_feature
<222> LOCATION: (227)..(227)
<223> OTHER INFORMATION: n is unknown
<220> FEATURE:
<221> NAME/KEY: misc_feature
<222> LOCATION: (237)..(241)
<223> OTHER INFORMATION: n is unknown
<220> FEATURE:
<221> NAME/KEY: misc_feature
<222> LOCATION: (328)..(328)
<223> OTHER INFORMATION: n is unknown
<220> FEATURE:
<221> NAME/KEY: misc_feature
<222> LOCATION: (330)..(355)
<223> OTHER INFORMATION: n is unknown
<220> FEATURE:
<221> NAME/KEY: misc_feature
<222> LOCATION: (357)..(358)
<223> OTHER INFORMATION: n is unknown
<220> FEATURE:
<221> NAME/KEY: misc_feature
<222> LOCATION: (521)..(527)
<223> OTHER INFORMATION: n is unknown
<220> FEATURE:
<221> NAME/KEY: misc_feature
<222> LOCATION: (667)..(670)
<223> OTHER INFORMATION: n is unknown
<220> FEATURE:
<221> NAME/KEY: misc_feature
<222> LOCATION: (773)..(773)
<223> OTHER INFORMATION: n is unknown
<220> FEATURE:
<221> NAME/KEY: misc_feature
<222> LOCATION: (803)..(803)
<223> OTHER INFORMATION: n is unknown
<220> FEATURE:
<221> NAME/KEY: misc_feature
<222> LOCATION: (827)..(835)
<223> OTHER INFORMATION: n is unknown
<220> FEATURE:
<221> NAME/KEY: misc_feature
<222> LOCATION: (838)..(839)
<223> OTHER INFORMATION: n is unknown
<220> FEATURE:
<221> NAME/KEY: misc_feature
<222> LOCATION: (867)..(868)
<223> OTHER INFORMATION: n is unknown

<400> SEQUENCE: 23

```
gttgntcnnn gctgacnatg ctgctgctgc ttnnngnnnc tgtctccact tccttgaaca     60

ntgcgccgtc atgcttcttt tgcctcccgc tgctccagaa agctangncn nagatcagaa    120

ccaccacagn cnnnntcncc nccttcctct tatagattcg gaatctcatg ataggggntc    180

nncctctgtg cgagtggaga gaagtttgca ggcgagctga ggagcanttg caggtgnnnn    240

natgtgctcg gctcaagaag cgggcccgga gaggaagaag tcgtgccggg gctaattatt    300

ggcaaaacga gctcttgttg taaacatngn nnnnnnnnnn nnnnnnnnnn nnnnngnnca    360

atattccata aggcatgatg gttgctcaga ggcaggagaa gagcaacgaa tacgatccta    420

taaaagataa aacataaata aacagtcttg attatattct gggtattaaa gccacaatca    480

gaacaaatat atgctttgta tcttttcttg ccttcttcat nnnnnnntgc ttccgcggcc    540

acattaagag aacttggggt aagataagaa gatattttat tcgttctgct gacttgctgg    600

atgtcgggaa atattctgca tttgataaga ggcggttaat tgcagatata attggtagtg    660

aaaaggnnnn ttgctatggt caccgtgaag cgagtacagc agcacaagaa tgtgtgccgt    720

tctcagttaa tattgtttga atatggtaac ctgttttagt cggtttaaag gtnagaagat    780

ctaaccaaaa acaacactgc agngactgat tgtagtattt atttttnnnn nnnnnctnna    840

ttttggtgta aacatcaacg gcgcacnn                                       868
```

<210> SEQ ID NO 24
<211> LENGTH: 877
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (4)..(5)
<223> OTHER INFORMATION: n is unknown
<220> FEATURE:
<221> NAME/KEY: misc_feature
<222> LOCATION: (7)..(7)
<223> OTHER INFORMATION: n is unknown
<220> FEATURE:
<221> NAME/KEY: misc_feature
<222> LOCATION: (12)..(12)
<223> OTHER INFORMATION: n is unknown
<220> FEATURE:
<221> NAME/KEY: misc_feature
<222> LOCATION: (15)..(17)
<223> OTHER INFORMATION: n is unknown
<220> FEATURE:
<221> NAME/KEY: misc_feature
<222> LOCATION: (23)..(25)
<223> OTHER INFORMATION: n is unknown
<220> FEATURE:
<221> NAME/KEY: misc_feature
<222> LOCATION: (40)..(41)
<223> OTHER INFORMATION: n is unknown
<220> FEATURE:
<221> NAME/KEY: misc_feature
<222> LOCATION: (44)..(45)
<223> OTHER INFORMATION: n is unknown
<220> FEATURE:
<221> NAME/KEY: misc_feature
<222> LOCATION: (138)..(138)
<223> OTHER INFORMATION: n is unknown
<220> FEATURE:
<221> NAME/KEY: misc_feature
<222> LOCATION: (147)..(147)
<223> OTHER INFORMATION: n is unknown
<220> FEATURE:
<221> NAME/KEY: misc_feature
<222> LOCATION: (188)..(188)
<223> OTHER INFORMATION: n is unknown
<220> FEATURE:
<221> NAME/KEY: misc_feature
<222> LOCATION: (243)..(249)
<223> OTHER INFORMATION: n is unknown
<220> FEATURE:
<221> NAME/KEY: misc_feature
<222> LOCATION: (273)..(274)
<223> OTHER INFORMATION: n is unknown
<220> FEATURE:
<221> NAME/KEY: misc_feature
<222> LOCATION: (276)..(284)
<223> OTHER INFORMATION: n is unknown
<220> FEATURE:
<221> NAME/KEY: misc_feature
<222> LOCATION: (337)..(366)
<223> OTHER INFORMATION: n is unknown
<220> FEATURE:
<221> NAME/KEY: misc_feature
<222> LOCATION: (529)..(534)
<223> OTHER INFORMATION: n is unknown
<220> FEATURE:
<221> NAME/KEY: misc_feature
<222> LOCATION: (537)..(542)
<223> OTHER INFORMATION: n is unknown
<220> FEATURE:
<221> NAME/KEY: misc_feature
<222> LOCATION: (544)..(544)
<223> OTHER INFORMATION: n is unknown
<220> FEATURE:
<221> NAME/KEY: misc_feature
<222> LOCATION: (563)..(563)
<223> OTHER INFORMATION: n is unknown
<220> FEATURE:
<221> NAME/KEY: misc_feature
<222> LOCATION: (673)..(676)
<223> OTHER INFORMATION: n is unknown
<220> FEATURE:
<221> NAME/KEY: misc_feature
<222> LOCATION: (797)..(797)
<223> OTHER INFORMATION: n is unknown
<220> FEATURE:
<221> NAME/KEY: misc_feature
<222> LOCATION: (813)..(813)
<223> OTHER INFORMATION: n is unknown
<220> FEATURE:
<221> NAME/KEY: misc_feature
<222> LOCATION: (815)..(818)
<223> OTHER INFORMATION: n is unknown
<220> FEATURE:
<221> NAME/KEY: misc_feature
<222> LOCATION: (820)..(821)
<223> OTHER INFORMATION: n is unknown
<220> FEATURE:
<221> NAME/KEY: misc_feature
<222> LOCATION: (823)..(823)
<223> OTHER INFORMATION: n is unknown
<220> FEATURE:
<221> NAME/KEY: misc_feature
<222> LOCATION: (834)..(843)
<223> OTHER INFORMATION: n is unknown -continued
<220> FEATURE:
<221> NAME/KEY: misc_feature
<222> LOCATION: (854)..(854)
<223> OTHER INFORMATION: n is unknown
<220> FEATURE:
<221> NAME/KEY: misc_feature
<222> LOCATION: (856)..(856)
<223> OTHER INFORMATION: n is unknown
<220> FEATURE:
<221> NAME/KEY: misc_feature
<222> LOCATION: (877)..(877)
<223> OTHER INFORMATION: n is unknown

<400> SEQUENCE: 24
cngnnangtt gntcnnngct gannngctgc tgctgcttcn ngtnnctgtc tccacttcct 60
tgaacaatgc gccgtcatgc ttcttttgcc tcccgctgct ccagaaagct aggccgcaga 120
tcagaaccac cacagtcnat atcaccncct tcctcttata gattcggaat ctcatgatag 180
gggctcancc tctgtgcgag tggagagaag tttgcaggcg agctgaggag caattgcagg 240
tgnnnnnnng tgctcggctc aagaagcggg ccnngnnnnn nnnnagtcgt gccggggcta 300
attattggca aaacgagctc ttgttgtaaa cattgannnn nnnnnnnnnn nnnnnnnnnn 360
nnnncnatat tccataaggc atgatggttg ctcagaggca ggagaagagc aacgaatacg 420
atcctataaa agataaaaca taaataaaca gtcttgatta tattctgggt attaaagcca 480
caatcagaac aaatatatgc tttgtatctt ttcttgcctt cttcattann nncngcnnnn 540
nngnccacat taagagaact tgnggtaaga taagaagata ttttattcgt tctgctgact 600
tgctggatgt cgggaaatat tctgcatttg ataagaggcg gttaattgca gatataattg 660
gtagtgaaaa ggnnnnttgc tatggtcacc gtgaagcgag tacagcagca caagaatgtg 720
tgccgttctc agttaatatt gtttgaatat ggtaacctgt tttagtcggt ttaaaggtaa 780
gaagatctaa ccaaaancaa cactgcagtg acngnnnngn ngnatttatt tttnnnnnnn 840
nnnttaattt tggngnaaac atcaacggcg cacttcn 877

<210> SEQ ID NO 25
<211> LENGTH: 34
<212> TYPE: DNA
<213> ORGANISM: Artificial Sequence
<220> FEATURE:
<223> OTHER INFORMATION: Primer

<400> SEQUENCE: 25
atccggcata tctcgacatt cctgattaca atcc 34

<210> SEQ ID NO 26
<211> LENGTH: 852
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (1)..(7)
<223> OTHER INFORMATION: n is unknown
<220> FEATURE:
<221> NAME/KEY: misc_feature
<222> LOCATION: (55)..(55)
<223> OTHER INFORMATION: n is unknown
<220> FEATURE:
<221> NAME/KEY: misc_feature
<222> LOCATION: (60)..(60)
<223> OTHER INFORMATION: n is unknown
<220> FEATURE:
<221> NAME/KEY: misc_feature
<222> LOCATION: (363)..(372)
<223> OTHER INFORMATION: n is unknown
<220> FEATURE:
<221> NAME/KEY: misc_feature
<222> LOCATION: (375)..(387)
<223> OTHER INFORMATION: n is unknown
<220> FEATURE:
<221> NAME/KEY: misc_feature
<222> LOCATION: (568)..(569)
<223> OTHER INFORMATION: n is unknown
<220> FEATURE:
<221> NAME/KEY: misc_feature
<222> LOCATION: (757)..(757)
<223> OTHER INFORMATION: n is unknown
<220> FEATURE:
<221> NAME/KEY: misc_feature
<222> LOCATION: (785)..(785)
<223> OTHER INFORMATION: n is unknown
<220> FEATURE:
<221> NAME/KEY: misc_feature
<222> LOCATION: (808)..(808)
<223> OTHER INFORMATION: n is unknown
<220> FEATURE:
<221> NAME/KEY: misc_feature
<222> LOCATION: (834)..(834)
<223> OTHER INFORMATION: n is unknown
<220> FEATURE:
<221> NAME/KEY: misc_feature
<222> LOCATION: (839)..(839)
<223> OTHER INFORMATION: n is unknown
<220> FEATURE:
<221> NAME/KEY: misc_feature
<222> LOCATION: (848)..(849)
<223> OTHER INFORMATION: n is unknown

<400> SEQUENCE: 26
nnnnnnnatt actgttaatg ttgctactac tgctgacaat gctgctgctg cttcncctcn 60
ctgtctccac ttccttgaac aatgcgccgt catgcttctt ttgcctcccg ctgctccaga 120
aagctaggcc gcagatcaga accaccacag tcaatatcac caccttcctc ttatagattc 180
ggaatctcat gataggggct cagcctctgt gcgagtggag agaagtttgc aggcgagctg 240
aggagcaatt gcaggtgata tgatgtgctc ggctcaagaa gcgggcccgg agaggaagaa 300
gtcgtgccgg ggctaattat tggcaaaacg agctcttgtt gtaaacattg atccaactgg 360
aannnnnnnn nnggnnnnnn nnnnnnncat aaggcatgat ggttgctcag aggcaggaga 420
agagcaacga atacgatcct ataaaagata aaacataaat aaacagtctt gattatattc 480
tgggtattaa agccacaatc agaacaaata tatgctttgt atcttttctt gccttcttca 540
ttaccaactg cttccgcggc cacattanna gaacttgtgg taagataaga agatatttta 600
ttcgttctgc tgacttgctg gatgtcggga aatattctgc atttgataag aggcggttaa 660
ttgcagatat aattggtagt gaaaagggtc gttgctatgg tcaccgtgaa gcgagtacag 720
cagcacaaga atgtgtgccg ttctcagtta atattgnttg aatatggtaa cctgttttag 780
tcggnttaaa ggtaagaaga tctaaccnaa aacaacactg cagtgactga ttgnagtant 840
tatttttnna ct 852

<210> SEQ ID NO 27
<211> LENGTH: 870
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (1)..(4)
<223> OTHER INFORMATION: n is unknown
<220> FEATURE:
<221> NAME/KEY: misc_feature
<222> LOCATION: (7)..(9)
<223> OTHER INFORMATION: n is unknown
<220> FEATURE:
<221> NAME/KEY: misc_feature
<222> LOCATION: (23)..(23)
<223> OTHER INFORMATION: n is unknown
<220> FEATURE:
<221> NAME/KEY: misc_feature
<222> LOCATION: (62)..(62)
<223> OTHER INFORMATION: n is unknown
<220> FEATURE:
<221> NAME/KEY: misc_feature
<222> LOCATION: (364)..(365)
<223> OTHER INFORMATION: n is unknown
<220> FEATURE:
<221> NAME/KEY: misc_feature
<222> LOCATION: (367)..(372)
<223> OTHER INFORMATION: n is unknown
<220> FEATURE:
<221> NAME/KEY: misc_feature
<222> LOCATION: (377)..(387)
<223> OTHER INFORMATION: n is unknown
<220> FEATURE:
<221> NAME/KEY: misc_feature
<222> LOCATION: (743)..(743)
<223> OTHER INFORMATION: n is unknown
<220> FEATURE:
<221> NAME/KEY: misc_feature
<222> LOCATION: (810)..(810)
<223> OTHER INFORMATION: n is unknown
<220> FEATURE:
<221> NAME/KEY: misc_feature
<222> LOCATION: (841)..(841)
<223> OTHER INFORMATION: n is unknown
<220> FEATURE:
<221> NAME/KEY: misc_feature
<222> LOCATION: (864)..(869)
<223> OTHER INFORMATION: n is unknown

<400> SEQUENCE: 27

```
nnnnttnnna ttactgttaa tgntgctact actgctgaca atgctgctgc tgcttctcct     60

cnctgtctcc acttccttga acaatgcgcc gtcatgcttc ttttgcctcc cgctgctcca    120

gaaagctagg ccgcagatca gaaccaccac agtcaatatc accaccttcc tcttatagat    180

tcggaatctc atgatagggg ctcagcctct gtgcgagtgg agagaagttt gcaggcgagc    240

tgaggagcaa ttgcaggtga tatgatgtgc tcggctcaag aagcgggccc ggagaggaag    300

aagtcgtgcc ggggctaatt attggcaaaa cgagctcttg ttgtaaacat tgatccaact    360

gganngnnnn nnatggnnnn nnnnnnntcc ataaggcatg atggttgctc agaggcagga    420

gaagagcaac gaatacgatc ctataaaaga taaaacataa ataaacagtc ttgattatat    480

tctgggtatt aaagccacaa tcagaacaaa tatatgcttt gtatcttttc ttgccttctt    540

cattaccaac tgcttccgcg gccacattaa gagaacttgt ggtaagataa gaagatattt    600

tattcgttct gctgacttgc tggatgtcgg gaaatattct gcatttgata agaggcggtt    660

aattgcagat ataattggta gtgaaaaggg tcgttgctat ggtcaccgtg aagcgagtac    720

agcagcacaa gaatgtgtgc cgntctcagt taatattgtt tgaatatggt aacctgtttt    780

agtcggttta aaggtaagaa gatctaaccn aaaacaacac tgcagtgact gattgtagta    840

nttatttttt tacttaatct taannnnnng                                     870
```

<210> SEQ ID NO 28
<211> LENGTH: 851
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (1)..(2)
<223> OTHER INFORMATION: n is unknown
<220> FEATURE:
<221> NAME/KEY: misc_feature
<222> LOCATION: (4)..(7)
<223> OTHER INFORMATION: n is unknown
<220> FEATURE:
<221> NAME/KEY: misc_feature
<222> LOCATION: (62)..(62)
<223> OTHER INFORMATION: n is unknown
<220> FEATURE:
<221> NAME/KEY: misc_feature
<222> LOCATION: (300)..(300)
<223> OTHER INFORMATION: n is unknown
<220> FEATURE:
<221> NAME/KEY: misc_feature
<222> LOCATION: (304)..(304)
<223> OTHER INFORMATION: n is unknown
<220> FEATURE:
<221> NAME/KEY: misc_feature
<222> LOCATION: (365)..(373)
<223> OTHER INFORMATION: n is unknown
<220> FEATURE:
<221> NAME/KEY: misc_feature
<222> LOCATION: (376)..(386)
<223> OTHER INFORMATION: n is unknown
<220> FEATURE:
<221> NAME/KEY: misc_feature
<222> LOCATION: (553)..(553)
<223> OTHER INFORMATION: n is unknown
<220> FEATURE:
<221> NAME/KEY: misc_feature
<222> LOCATION: (562)..(562)
<223> OTHER INFORMATION: n is unknown
<220> FEATURE:
<221> NAME/KEY: misc_feature
<222> LOCATION: (566)..(566)
<223> OTHER INFORMATION: n is unknown
<220> FEATURE:
<221> NAME/KEY: misc_feature
<222> LOCATION: (759)..(759)
<223> OTHER INFORMATION: n is unknown
<220> FEATURE:
<221> NAME/KEY: misc_feature
<222> LOCATION: (836)..(836)
<223> OTHER INFORMATION: n is unknown
<220> FEATURE:
<221> NAME/KEY: misc_feature
<222> LOCATION: (844)..(848)
<223> OTHER INFORMATION: n is unknown
<220> FEATURE:
<221> NAME/KEY: misc_feature
<222> LOCATION: (850)..(851)
<223> OTHER INFORMATION: n is unknown

<400> SEQUENCE: 28
nngnnnntga ttactgttaa tgttgctact actgctgaca atgctgctgc tgcttctcct 60
cnctgtctcc acttccttga acaatgcgcc gtcatgcttc ttttgcctcc cgctgctcca 120
gaaagctagg ccgcagatca gaaccaccac agtcaatatc accaccttcc tcttatagat 180
tcggaatctc atgatagggg ctcagcctct gtgcgagtgg agagaagttt gcaggcgagc 240
tgaggagcaa ttgcaggtga tatgatgtgc tcggctcaag aagcgggccc ggagaggaan 300
aagncgtgcc ggggctaatt attggcaaaa cgagctcttg ttgtaaacat tgatccaact 360
ggaannnnnn nnntgnnnnn nnnnnnttcc ataaggcatg atggttgctc agaggcagga 420
gaagagcaac gaatacgatc ctataaaaga taaaacataa ataaacagtc ttgattatat 480
tctgggtatt aaagccacaa tcagaacaaa tatatgcttt gtatcttttc ttgccttctt 540
cattaccaac tgnttccgcg gncacnttaa gagaacttgt ggtaagataa gaagatattt 600
tattcgttct gctgacttgc tggatgtcgg gaaatattct gcatttgata agaggcggtt 660
aattgcagat ataattggta gtgaaaaggg tcgttgctat ggtcaccgtg aagcgagtac 720
agcagcacaa gaatgtgtgc cgttctcagt taatattgnt tgaatatggt aacctgtttt 780
agtcggttta aaggtaagaa gatctaacca aaaacaacac tgcagtgact gattgnagta 840
tttnnnnntn n 851

<210> SEQ ID NO 29
<211> LENGTH: 892
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (7)..(13)
<223> OTHER INFORMATION: n is unknown
<220> FEATURE:
<221> NAME/KEY: misc_feature
<222> LOCATION: (62)..(63)
<223> OTHER INFORMATION: n is unknown
<220> FEATURE:
<221> NAME/KEY: misc_feature
<222> LOCATION: (364)..(364)
<223> OTHER INFORMATION: n is unknown
<220> FEATURE:
<221> NAME/KEY: misc_feature
<222> LOCATION: (366)..(366)
<223> OTHER INFORMATION: n is unknown
<220> FEATURE:
<221> NAME/KEY: misc_feature
<222> LOCATION: (368)..(368)
<223> OTHER INFORMATION: n is unknown
<220> FEATURE:
<221> NAME/KEY: misc_feature
<222> LOCATION: (372)..(375)
<223> OTHER INFORMATION: n is unknown
<220> FEATURE:
<221> NAME/KEY: misc_feature
<222> LOCATION: (377)..(383)
<223> OTHER INFORMATION: n is unknown
<220> FEATURE:
<221> NAME/KEY: misc_feature
<222> LOCATION: (760)..(760)
<223> OTHER INFORMATION: n is unknown
<220> FEATURE:
<221> NAME/KEY: misc_feature
<222> LOCATION: (771)..(771)
<223> OTHER INFORMATION: n is unknown
<220> FEATURE:
<221> NAME/KEY: misc_feature
<222> LOCATION: (778)..(778)
<223> OTHER INFORMATION: n is unknown
<220> FEATURE:
<221> NAME/KEY: misc_feature
<222> LOCATION: (811)..(811)
<223> OTHER INFORMATION: n is unknown
<220> FEATURE:
<221> NAME/KEY: misc_feature
<222> LOCATION: (827)..(827)
<223> OTHER INFORMATION: n is unknown
<220> FEATURE:
<221> NAME/KEY: misc_feature
<222> LOCATION: (837)..(837)
<223> OTHER INFORMATION: n is unknown
<220> FEATURE:
<221> NAME/KEY: misc_feature
<222> LOCATION: (839)..(840)
<223> OTHER INFORMATION: n is unknown
<220> FEATURE:
<221> NAME/KEY: misc_feature
<222> LOCATION: (849)..(853)
<223> OTHER INFORMATION: n is unknown
<220> FEATURE:
<221> NAME/KEY: misc_feature
<222> LOCATION: (855)..(858)
<223> OTHER INFORMATION: n is unknown
<220> FEATURE:
<221> NAME/KEY: misc_feature
<222> LOCATION: (861)..(861)
<223> OTHER INFORMATION: n is unknown
<220> FEATURE:
<221> NAME/KEY: misc_feature
<222> LOCATION: (863)..(869)
<223> OTHER INFORMATION: n is unknown
<220> FEATURE:
<221> NAME/KEY: misc_feature
<222> LOCATION: (871)..(871)
<223> OTHER INFORMATION: n is unknown
<220> FEATURE:
<221> NAME/KEY: misc_feature
<222> LOCATION: (881)..(881)
<223> OTHER INFORMATION: n is unknown

<400> SEQUENCE: 29
nctggtnnnn nnnactgtta atgttgctac tactgctgac aatgctgctg ctgcttctcc 60
tnnctgtctc cacttccttg aacaatgcgc cgtcatgctt cttttgcctc ccgctgctcc 120
agaaagctag gccgcagatc agaaccacca cagtcaatat caccaccttc ctcttataga 180
ttcggaatct catgataggg gctcagcctc tgtgcgagtg gagagaagtt tgcaggcgag 240
ctgaggagca attgcaggtg atatgatgtg ctcggctcaa gaagcgggcc cggagaggaa 300
gaagtcgtgc cggggctaat tattggcaaa acgagctctt gttgtaaaca ttgatccaac 360
tggnangnca cnnnngnnnn nnnaatattc cataaggcat gatggttgct cagaggcagg 420
agaagagcaa cgaatacgat cctataaaag ataaaacata aataaacagt cttgattata 480
ttctgggtat taaagccaca atcagaacaa atatatgctt tgtatctttt cttgccttct 540
tcattaccaa ctgcttccgc ggccacatta agagaacttg tggtaagata agaagatatt 600
ttattcgttc tgctgacttg ctggatgtcg ggaaatattc tgcatttgat aagaggcggt 660
taattgcaga tataattggt agtgaaaagg gtcgttgcta tggtcaccgt gaagcgagta 720
cagcagcaca agaatgtgtg ccgttctcag ttaatattgn ttgaatatgg naacctgntt 780
tagtcggttt aaaggtaaga agatctaacc naaaacaaca ctgcagngac tgattgnann 840
atttatttnn nnncnnnntc ntnnnnnnng ngtaaacatc nacggcgcac tt 892

<210> SEQ ID NO 30
<211> LENGTH: 892
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (3)..(3)
<223> OTHER INFORMATION: n is unknown
<220> FEATURE:
<221> NAME/KEY: misc_feature
<222> LOCATION: (5)..(7)
<223> OTHER INFORMATION: n is unknown
<220> FEATURE:
<221> NAME/KEY: misc_feature
<222> LOCATION: (12)..(12)
<223> OTHER INFORMATION: n is unknown
<220> FEATURE:
<221> NAME/KEY: misc_feature
<222> LOCATION: (63)..(63)
<223> OTHER INFORMATION: n is unknown
<220> FEATURE:
<221> NAME/KEY: misc_feature
<222> LOCATION: (375)..(375)
<223> OTHER INFORMATION: n is unknown
<220> FEATURE:
<221> NAME/KEY: misc_feature
<222> LOCATION: (378)..(384)
<223> OTHER INFORMATION: n is unknown
<220> FEATURE:
<221> NAME/KEY: misc_feature
<222> LOCATION: (737)..(737)
<223> OTHER INFORMATION: n is unknown
<220> FEATURE:
<221> NAME/KEY: misc_feature
<222> LOCATION: (771)..(771)
<223> OTHER INFORMATION: n is unknown
<220> FEATURE:
<221> NAME/KEY: misc_feature
<222> LOCATION: (778)..(778)
<223> OTHER INFORMATION: n is unknown
<220> FEATURE:
<221> NAME/KEY: misc_feature
<222> LOCATION: (855)..(859)
<223> OTHER INFORMATION: n is unknown
<220> FEATURE:
<221> NAME/KEY: misc_feature
<222> LOCATION: (865)..(871)
<223> OTHER INFORMATION: n is unknown
<220> FEATURE:
<221> NAME/KEY: misc_feature
<222> LOCATION: (873)..(873)
<223> OTHER INFORMATION: n is unknown
<220> FEATURE:
<221> NAME/KEY: misc_feature
<222> LOCATION: (875)..(875)
<223> OTHER INFORMATION: n is unknown
<220> FEATURE:
<221> NAME/KEY: misc_feature
<222> LOCATION: (878)..(878)
<223> OTHER INFORMATION: n is unknown

<400> SEQUENCE: 30
ncngnnnatg antactgtta atgttgctac tactgctgac aatgctgctg ctgcttctcc 60
tcnctgtctc cacttccttg aacaatgcgc cgtcatgctt cttttgcctc ccgctgctcc 120
agaaagctag gccgcagatc agaaccacca cagtcaatat caccaccttc ctcttataga 180
ttcggaatct catgataggg gctcagcctc tgtgcgagtg gagagaagtt tgcaggcgag 240
ctgaggagca attgcaggtg atatgatgtg ctcggctcaa gaagcgggcc cggagaggaa 300
gaagtcgtgc cggggctaat tattggcaaa acgagctctt gttgtaaaca ttgatccaac 360
tggaatgtca ctaanggnnn nnnnatattc cataaggcat gatggttgct cagaggcagg 420
agaagagcaa cgaatacgat cctataaaag ataaaacata aataaacagt cttgattata 480
ttctgggtat taaagccaca atcagaacaa atatatgctt tgtatctttt cttgccttct 540
tcattaccaa ctgcttccgc ggccacatta agagaacttg tggtaagata agaagatatt 600
ttattcgttc tgctgacttg ctggatgtcg ggaaatattc tgcatttgat aagaggcggt 660
taattgcaga tataattggt agtgaaaagg gtcgttgcta tggtcaccgt gaagcgagta 720
cagcagcaca agaatgngtg ccgttctcag ttaatattgt ttgaatatgg naacctgntt 780
tagtcggttt aaaggtaaga agatctaacc aaaaacaaca ctgcagtgac tgattgtagt 840
atttattttt ttacnnnnnc ttaannnnnn ngnanacntc aacggcgcac tt 892

<210> SEQ ID NO 31
<211> LENGTH: 839
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (4)..(4)
<223> OTHER INFORMATION: n is unknown
<220> FEATURE:
<221> NAME/KEY: misc_feature
<222> LOCATION: (6)..(12)
<223> OTHER INFORMATION: n is unknown
<220> FEATURE:
<221> NAME/KEY: misc_feature
<222> LOCATION: (63)..(64)
<223> OTHER INFORMATION: n is unknown
<220> FEATURE:
<221> NAME/KEY: misc_feature
<222> LOCATION: (752)..(753)
<223> OTHER INFORMATION: n is unknown
<220> FEATURE:
<221> NAME/KEY: misc_feature
<222> LOCATION: (755)..(762)
<223> OTHER INFORMATION: n is unknown
<220> FEATURE:
<221> NAME/KEY: misc_feature
<222> LOCATION: (778)..(778)
<223> OTHER INFORMATION: n is unknown
<220> FEATURE:
<221> NAME/KEY: misc_feature
<222> LOCATION: (817)..(822)
<223> OTHER INFORMATION: n is unknown
<220> FEATURE:
<221> NAME/KEY: misc_feature
<222> LOCATION: (837)..(838)
<223> OTHER INFORMATION: n is unknown

<400> SEQUENCE: 31

```
nccngnnnnn nntactgtta atgttgctac tactgctgac aatgctgctg ctgcttctcc     60

tcnntgtctc cacttccttg aacaatgcgc cgtcatgctt cttttgcctc ccgctgctcc    120

agaaagctag gccgcagatc agaaccacca cagtcaatat caccaccttc ctcttataga    180

ttcggaatct catgataggg gctcagcctc tgtgcgagtg gagagaagtt tgcaggcgag    240

ctgaggagca attgcaggtg atatgatgtg ctcggctcaa gaagcgggcc cggagaggaa    300

gaagtcgtgc cggggctaat tattggcaaa acgagctctt gttgtaaaca ttgatccaac    360

tggaatgtca ctaatggcga atcaatattc cataaggcat gatggttgct cagaggcagg    420

agaagagcaa cgaatacgat cctataaaag ataaaacata aataaacagt cttgattata    480

ttctgggtat taaagccaca atcagaacaa atatatgctt tgtatctttt cttgccttct    540

tcattaccaa ctgcttccgc ggccacatta agagaacttg tggtaagata agaagatatt    600

ttattcgttc tgctgacttg ctggatgtcg ggaaatattc tgcatttgat aagaggcggt    660

taattgcaga tataattggt agtgaaaagg gtcgttgcta tggtcaccgt gaagcgagta    720

cagcagcaca agaatgtgtg ccgttctcag tnngnnnnnn nngaatatgg taacctgntt    780

tagtcggttt aaaggtaaga agatctaacc aaaaacnnnn nngcagtgac tgattgnng     839
```

<210> SEQ ID NO 32
<211> LENGTH: 807
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (15)..(17)
<223> OTHER INFORMATION: n is unknown
<220> FEATURE:
<221> NAME/KEY: misc_feature
<222> LOCATION: (19)..(22)
<223> OTHER INFORMATION: n is unknown
<220> FEATURE:
<221> NAME/KEY: misc_feature
<222> LOCATION: (51)..(51)
<223> OTHER INFORMATION: n is unknown
<220> FEATURE:
<221> NAME/KEY: misc_feature
<222> LOCATION: (739)..(750)
<223> OTHER INFORMATION: n is unknown
<220> FEATURE:
<221> NAME/KEY: misc_feature
<222> LOCATION: (766)..(766)
<223> OTHER INFORMATION: n is unknown
<220> FEATURE:
<221> NAME/KEY: misc_feature
<222> LOCATION: (776)..(776)
<223> OTHER INFORMATION: n is unknown
<220> FEATURE:
<221> NAME/KEY: misc_feature
<222> LOCATION: (784)..(784)
<223> OTHER INFORMATION: n is unknown
<220> FEATURE:
<221> NAME/KEY: misc_feature
<222> LOCATION: (792)..(792)
<223> OTHER INFORMATION: n is unknown
<220> FEATURE:
<221> NAME/KEY: misc_feature
<222> LOCATION: (805)..(807)
<223> OTHER INFORMATION: n is unknown

<400> SEQUENCE: 32

```
tactgttaat gttgnnncnn nngctgacaa tgctgctgct gcttctcctc nctgtctcca     60

cttccttgaa caatgcgccg tcatgcttct tttgcctccc gctgctccag aaagctaggc    120

cgcagatcag aaccaccaca gtcaatatca ccaccttcct cttatagatt cggaatctca    180

tgataggggc tcagcctctg tgcgagtgga gagaagtttg caggcgagct gaggagcaat    240

tgcaggtgat atgatgtgct cggctcaaga agcgggcccg gagaggaaga agtcgtgccg    300

gggctaatta ttggcaaaac gagctcttgt tgtaaacatt gatccaactg gaatgtcact    360

aatggcgaat caatattcca taaggcatga tggttgctca gaggcaggag aagagcaacg    420

aatacgatcc tataaaagat aaaacataaa taaacagtct tgattatatt ctgggtatta    480

aagccacaat cagaacaaat atatgctttg tatcttttct tgccttcttc attaccaact    540

gcttccgcgg ccacattaag agaacttgtg gtaagataag aagatatttt attcgttctg    600

ctgacttgct ggatgtcggg aaatattctg catttgataa gaggcggtta attgcagata    660

taattggtag tgaaaagggt cgttgctatg gtcaccgtga agcgagtaca gcagcacaag    720

aatgtgtgcc gttctcagnn nnnnnnnnnn gaatatggta acctgnttta gtcggnttaa    780

aggnaagaag anctaaccaa aaacnnn                                        807
```

<210> SEQ ID NO 33
<211> LENGTH: 865
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (1)..(3)
<223> OTHER INFORMATION: n is unknown
<220> FEATURE:
<221> NAME/KEY: misc_feature
<222> LOCATION: (6)..(6)
<223> OTHER INFORMATION: n is unknown
<220> FEATURE:
<221> NAME/KEY: misc_feature
<222> LOCATION: (10)..(10)
<223> OTHER INFORMATION: n is unknown
<220> FEATURE:
<221> NAME/KEY: misc_feature
<222> LOCATION: (15)..(15)
<223> OTHER INFORMATION: n is unknown
<220> FEATURE:
<221> NAME/KEY: misc_feature
<222> LOCATION: (69)..(70)
<223> OTHER INFORMATION: n is unknown
<220> FEATURE:
<221> NAME/KEY: misc_feature
<222> LOCATION: (758)..(769)
<223> OTHER INFORMATION: n is unknown
<220> FEATURE:
<221> NAME/KEY: misc_feature
<222> LOCATION: (823)..(828)
<223> OTHER INFORMATION: n is unknown
<220> FEATURE:
<221> NAME/KEY: misc_feature
<222> LOCATION: (841)..(842)
<223> OTHER INFORMATION: n is unknown
<220> FEATURE:
<221> NAME/KEY: misc_feature
<222> LOCATION: (844)..(844)
<223> OTHER INFORMATION: n is unknown

<400> SEQUENCE: 33
nnngcngccn ggttntgatt actgttaatg ttgctactac tgctgacaat gctgctgctg 60
cttctcctnn ctgtctccac ttccttgaac aatgcgccgt catgcttctt ttgcctcccg 120
ctgctccaga aagctaggcc gcagatcaga accaccacag tcaatatcac caccttcctc 180
ttatagattc ggaatctcat gataggggct cagcctctgt gcgagtggag agaagtttgc 240
aggcgagctg aggagcaatt gcaggtgata tgatgtgctc ggctcaagaa gcgggcccgg 300
agaggaagaa gtcgtgccgg ggctaattat tggcaaaacg agctcttgtt gtaaacattg 360
atccaactgg aatgtcacta atggcgaatc aatattccat aaggcatgat ggttgctcag 420
aggcaggaga agagcaacga atacgatcct ataaaagata aaacataaat aaacagtctt 480
gattatattc tgggtattaa agccacaatc agaacaaata tatgctttgt atcttttctt 540
gccttcttca ttaccaactg cttccgcggc cacattaaga gaacttgtgg taagataaga 600
agatatttta ttcgttctgc tgacttgctg gatgtcggga aatattctgc atttgataag 660
aggcggttaa ttgcagatat aattggtagt gaaaagggtc gttgctatgg tcaccgtgaa 720
gcgagtacag cagcacaaga atgtgtgccg ttctcagnnn nnnnnnnnng aatatggtaa 780
cctgttttag tcggtttaaa ggtaagaaga tctaaccaaa aannnnnntg cagtgactga 840
nngnagtatt tattttttta cttaa 865

<210> SEQ ID NO 34
<211> LENGTH: 818
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (1)..(3)
<223> OTHER INFORMATION: n is unknown
<220> FEATURE:
<221> NAME/KEY: misc_feature
<222> LOCATION: (10)..(10)
<223> OTHER INFORMATION: n is unknown
<220> FEATURE:
<221> NAME/KEY: misc_feature
<222> LOCATION: (14)..(14)
<223> OTHER INFORMATION: n is unknown
<220> FEATURE:
<221> NAME/KEY: misc_feature
<222> LOCATION: (20)..(24)
<223> OTHER INFORMATION: n is unknown
<220> FEATURE:
<221> NAME/KEY: misc_feature
<222> LOCATION: (62)..(62)
<223> OTHER INFORMATION: n is unknown
<220> FEATURE:
<221> NAME/KEY: misc_feature
<222> LOCATION: (64)..(65)
<223> OTHER INFORMATION: n is unknown
<220> FEATURE:
<221> NAME/KEY: misc_feature
<222> LOCATION: (753)..(755)
<223> OTHER INFORMATION: n is unknown
<220> FEATURE:
<221> NAME/KEY: misc_feature
<222> LOCATION: (757)..(757)
<223> OTHER INFORMATION: n is unknown
<220> FEATURE:
<221> NAME/KEY: misc_feature
<222> LOCATION: (759)..(764)
<223> OTHER INFORMATION: n is unknown
<220> FEATURE:
<221> NAME/KEY: misc_feature
<222> LOCATION: (794)..(794)
<223> OTHER INFORMATION: n is unknown
<220> FEATURE:
<221> NAME/KEY: misc_feature
<222> LOCATION: (796)..(799)
<223> OTHER INFORMATION: n is unknown
<220> FEATURE:
<221> NAME/KEY: misc_feature
<222> LOCATION: (813)..(814)
<223> OTHER INFORMATION: n is unknown

<400> SEQUENCE: 34

```
nnnctggttn tgantactgn nnnngttgct actactgctg acaatgctgc tgctgcttct      60
cntnnctgtc tccacttcct tgaacaatgc gccgtcatgc ttcttttgcc tcccgctgct     120
ccagaaagct aggccgcaga tcagaaccac cacagtcaat atcaccacct tcctcttata    180
gattcggaat ctcatgatag gggctcagcc tctgtgcgag tggagagaag tttgcaggcg    240
agctgaggag caattgcagg tgatatgatg tgctcggctc aagaagcggg cccggagagg    300
aagaagtcgt gccggggcta attattggca aaacgagctc ttgttgtaaa cattgatcca    360
actggaatgt cactaatggc gaatcaatat tccataaggc atgatggttg ctcagaggca    420
ggagaagagc aacgaatacg atcctataaa agataaaaca taaataaaca gtcttgatta    480
tattctgggt attaaagcca caatcagaac aaatatatgc tttgtatctt ttcttgcctt    540
cttcattacc aactgcttcc gcggccacat taagagaact tgtggtaaga taagaagata    600
ttttattcgt tctgctgact tgctggatgt cgggaaatat tctgcatttg ataagaggcg    660
gttaattgca gatataattg gtagtgaaaa gggtcgttgc tatggtcacc gtgaagcgag    720
tacagcagca caagaatgtg tgccgttctc agnnngnann nnnngaatat ggtaacctgt    780
tttagtcggt ttanannnna gaagatctaa ccnnaaaa                           818
```

<210> SEQ ID NO 35
<211> LENGTH: 822
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (1)..(4)
<223> OTHER INFORMATION: n is unknown
<220> FEATURE:
<221> NAME/KEY: misc_feature
<222> LOCATION: (11)..(11)
<223> OTHER INFORMATION: n is unknown
<220> FEATURE:
<221> NAME/KEY: misc_feature
<222> LOCATION: (15)..(15)
<223> OTHER INFORMATION: n is unknown
<220> FEATURE:
<221> NAME/KEY: misc_feature -continued
<222> LOCATION: (25)..(25)
<223> OTHER INFORMATION: n is unknown
<220> FEATURE:
<221> NAME/KEY: misc_feature
<222> LOCATION: (66)..(66)
<223> OTHER INFORMATION: n is unknown
<220> FEATURE:
<221> NAME/KEY: misc_feature
<222> LOCATION: (353)..(353)
<223> OTHER INFORMATION: n is unknown
<220> FEATURE:
<221> NAME/KEY: misc_feature
<222> LOCATION: (357)..(357)
<223> OTHER INFORMATION: n is unknown
<220> FEATURE:
<221> NAME/KEY: misc_feature
<222> LOCATION: (359)..(359)
<223> OTHER INFORMATION: n is unknown
<220> FEATURE:
<221> NAME/KEY: misc_feature
<222> LOCATION: (754)..(765)
<223> OTHER INFORMATION: n is unknown
<220> FEATURE:
<221> NAME/KEY: misc_feature
<222> LOCATION: (781)..(781)
<223> OTHER INFORMATION: n is unknown
<220> FEATURE:
<221> NAME/KEY: misc_feature
<222> LOCATION: (791)..(791)
<223> OTHER INFORMATION: n is unknown
<220> FEATURE:
<221> NAME/KEY: misc_feature
<222> LOCATION: (817)..(817)
<223> OTHER INFORMATION: n is unknown
<220> FEATURE:
<221> NAME/KEY: misc_feature
<222> LOCATION: (821)..(822)
<223> OTHER INFORMATION: n is unknown

<400> SEQUENCE: 35
nnnnctggtt ntgantactg ttaangttgc tactactgct gacaatgctg ctgctgcttc 60
tcctcnctgt ctccacttcc ttgaacaatg cgccgtcatg cttcttttgc ctcccgctgc 120
tccagaaagc taggccgcag atcagaacca ccacagtcaa tatcaccacc ttcctcttat 180
agattcggaa tctcatgata ggggctcagc ctctgtgcga gtggagagaa gtttgcaggc 240
gagctgagga gcaattgcag gtgatatgat gtgctcggct caagaagcgg gcccggagag 300
gaagaagtcg tgccggggct aattattggc aaaacgagct cttgttgtaa acnttgntnc 360
aactggaatg tcactaatgg cgaatcaata ttccataagg catgatggtt gctcagaggc 420
aggagaagag caacgaatac gatcctataa aagataaaac ataaataaac agtcttgatt 480
atattctggg tattaaagcc acaatcagaa caaatatatg ctttgtatct tttcttgcct 540
tcttcattac caactgcttc cgcggccaca ttaagagaac ttgtggtaag ataagaagat 600
attttattcg ttctgctgac ttgctggatg tcgggaaata ttctgcattt gataagaggc 660
ggttaattgc agatataatt ggtagtgaaa agggtcgttg ctatggtcac cgtgaagcga 720
gtacagcagc acaagaatgt gtgccgttct cagnnnnnnn nnnnngaata tggtaacctg 780
ntttagtcgg nttaaaggta agaagatcta accaaanaca nn 822

<210> SEQ ID NO 36
<211> LENGTH: 844
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (4)..(4)
<223> OTHER INFORMATION: n is unknown
<220> FEATURE:
<221> NAME/KEY: misc_feature
<222> LOCATION: (16)..(20)
<223> OTHER INFORMATION: n is unknown
<220> FEATURE:
<221> NAME/KEY: misc_feature
<222> LOCATION: (59)..(59)
<223> OTHER INFORMATION: n is unknown
<220> FEATURE:
<221> NAME/KEY: misc_feature
<222> LOCATION: (371)..(380)
<223> OTHER INFORMATION: n is unknown
<220> FEATURE:
<221> NAME/KEY: misc_feature
<222> LOCATION: (498)..(509)
<223> OTHER INFORMATION: n is unknown
<220> FEATURE:
<221> NAME/KEY: misc_feature
<222> LOCATION: (511)..(511)
<223> OTHER INFORMATION: n is unknown
<220> FEATURE:
<221> NAME/KEY: misc_feature
<222> LOCATION: (526)..(529)
<223> OTHER INFORMATION: n is unknown
<220> FEATURE:
<221> NAME/KEY: misc_feature
<222> LOCATION: (588)..(588)
<223> OTHER INFORMATION: n is unknown
<220> FEATURE:
<221> NAME/KEY: misc_feature
<222> LOCATION: (591)..(591)
<223> OTHER INFORMATION: n is unknown
<220> FEATURE:
<221> NAME/KEY: misc_feature
<222> LOCATION: (603)..(609)
<223> OTHER INFORMATION: n is unknown
<220> FEATURE:
<221> NAME/KEY: misc_feature
<222> LOCATION: (674)..(685)
<223> OTHER INFORMATION: n is unknown
<220> FEATURE:
<221> NAME/KEY: misc_feature
<222> LOCATION: (716)..(718)
<223> OTHER INFORMATION: n is unknown
<220> FEATURE:
<221> NAME/KEY: misc_feature
<222> LOCATION: (721)..(726)
<223> OTHER INFORMATION: n is unknown
<220> FEATURE:
<221> NAME/KEY: misc_feature
<222> LOCATION: (730)..(730)
<223> OTHER INFORMATION: n is unknown
<220> FEATURE:
<221> NAME/KEY: misc_feature
<222> LOCATION: (733)..(733)
<223> OTHER INFORMATION: n is unknown
<220> FEATURE:
<221> NAME/KEY: misc_feature
<222> LOCATION: (735)..(735)
<223> OTHER INFORMATION: n is unknown
<220> FEATURE:
<221> NAME/KEY: misc_feature
<222> LOCATION: (738)..(739)
<223> OTHER INFORMATION: n is unknown
<220> FEATURE:
<221> NAME/KEY: misc_feature
<222> LOCATION: (741)..(749)
<223> OTHER INFORMATION: n is unknown
<220> FEATURE:
<221> NAME/KEY: misc_feature
<222> LOCATION: (756)..(756)
<223> OTHER INFORMATION: n is unknown
<220> FEATURE:
<221> NAME/KEY: misc_feature
<222> LOCATION: (767)..(769)
<223> OTHER INFORMATION: n is unknown
<220> FEATURE:
<221> NAME/KEY: misc_feature
<222> LOCATION: (774)..(774)
<223> OTHER INFORMATION: n is unknown
<220> FEATURE:
<221> NAME/KEY: misc_feature
<222> LOCATION: (784)..(784)
<223> OTHER INFORMATION: n is unknown
<220> FEATURE:
<221> NAME/KEY: misc_feature
<222> LOCATION: (807)..(807)
<223> OTHER INFORMATION: n is unknown
<220> FEATURE:
<221> NAME/KEY: misc_feature
<222> LOCATION: (836)..(836)
<223> OTHER INFORMATION: n is unknown
<220> FEATURE:
<221> NAME/KEY: misc_feature
<222> LOCATION: (838)..(844)
<223> OTHER INFORMATION: n is unknown

<400> SEQUENCE: 36
nttntgatta ctgttnnnnn tgctactact gctgacaatg ctgctgctgc ttctcctcnc 60
tgtctccact tccttgaaca atgcgccgtc atgcttcttt tgcctcccgc tgctccagaa 120
agctaggccg cagatcagaa ccaccacagt caatatcacc accttcctct tatagattcg 180
gaatctcatg ataggggctc agcctctgtg cgagtggaga gaagtttgca ggcgagctga 240
ggagcaattg caggtgatat gatgtgctcg gctcaagaag cgggcccgga gaggaagaag 300
tcgtgccggg gctaattatt ggcaaaacga gctcttgttg taaacattga tccaactgga 360
atgtcactaa nnnnnnnnnn atattccata aggcatgatg gttgctcaga ggcaggagaa 420
gagcaacgaa tacgatccta taaaagataa aacataaata aacagtcttg attatattct 480
gggtattaaa gccacaannn nnnnnnnnnt ntgctttgta tctttnnnng ccttcttcat 540
taccaactgc ttccgcggcc acattaagag aacttgtggt aagataanaa natattttat 600
tcnnnnnnnt gacttgctgg atgtcgggaa atattctgca tttgataaga ggcggttaat 660
tgcagatata attnnnnnnn nnnnnggtcg ttgctatggt caccgtgaag cgagtnnngc 720
nnnnnnagan tgngnggnng nnnnnnnnna tattgnttga atatggnnnc ctgntttagt 780
cggnttaaag gtaagaagat ctaaccnaaa acaacactgc agtgactgat tgtagnannn 840 nnnn 844

<210> SEQ ID NO 37
<211> LENGTH: 851
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (1)..(6)
<223> OTHER INFORMATION: n is unknown
<220> FEATURE:
<221> NAME/KEY: misc_feature
<222> LOCATION: (11)..(11)
<223> OTHER INFORMATION: n is unknown
<220> FEATURE:
<221> NAME/KEY: misc_feature
<222> LOCATION: (65)..(66)
<223> OTHER INFORMATION: n is unknown
<220> FEATURE:
<221> NAME/KEY: misc_feature
<222> LOCATION: (378)..(388)
<223> OTHER INFORMATION: n is unknown
<220> FEATURE:
<221> NAME/KEY: misc_feature
<222> LOCATION: (504)..(516)
<223> OTHER INFORMATION: n is unknown
<220> FEATURE:
<221> NAME/KEY: misc_feature
<222> LOCATION: (532)..(536)
<223> OTHER INFORMATION: n is unknown
<220> FEATURE:
<221> NAME/KEY: misc_feature
<222> LOCATION: (538)..(538)
<223> OTHER INFORMATION: n is unknown
<220> FEATURE:
<221> NAME/KEY: misc_feature
<222> LOCATION: (540)..(540)
<223> OTHER INFORMATION: n is unknown
<220> FEATURE:
<221> NAME/KEY: misc_feature
<222> LOCATION: (610)..(616)
<223> OTHER INFORMATION: n is unknown
<220> FEATURE:
<221> NAME/KEY: misc_feature
<222> LOCATION: (683)..(692)
<223> OTHER INFORMATION: n is unknown
<220> FEATURE:
<221> NAME/KEY: misc_feature
<222> LOCATION: (694)..(694)
<223> OTHER INFORMATION: n is unknown
<220> FEATURE:
<221> NAME/KEY: misc_feature
<222> LOCATION: (744)..(755)
<223> OTHER INFORMATION: n is unknown
<220> FEATURE:
<221> NAME/KEY: misc_feature
<222> LOCATION: (763)..(763)
<223> OTHER INFORMATION: n is unknown
<220> FEATURE:
<221> NAME/KEY: misc_feature
<222> LOCATION: (814)..(814)
<223> OTHER INFORMATION: n is unknown
<220> FEATURE:
<221> NAME/KEY: misc_feature
<222> LOCATION: (820)..(820)
<223> OTHER INFORMATION: n is unknown
<220> FEATURE:
<221> NAME/KEY: misc_feature
<222> LOCATION: (840)..(840)
<223> OTHER INFORMATION: n is unknown
<220> FEATURE:
<221> NAME/KEY: misc_feature
<222> LOCATION: (846)..(851)
<223> OTHER INFORMATION: n is unknown

<400> SEQUENCE: 37
nnnnnnggtt ntgattactg ttaatgttgc tactactgct gacaatgctg ctgctgcttc 60
tcctnnctgt ctccacttcc ttgaacaatg cgccgtcatg cttcttttgc ctcccgctgc 120
tccagaaagc taggccgcag atcagaacca ccacagtcaa tatcaccacc ttcctcttat 180
agattcggaa tctcatgata ggggctcagc ctctgtgcga gtggagagaa gtttgcaggc 240
gagctgagga gcaattgcag gtgatatgat gtgctcggct caagaagcgg gcccggagag 300
gaagaagtcg tgccggggct aattattggc aaaacgagct cttgttgtaa acattgatcc 360
aactggaatg tcactaannn nnnnnnnnta ttccataagg catgatggtt gctcagaggc 420
aggagaagag caacgaatac gatcctataa aagataaaac ataaataaac agtcttgatt 480
atattctggg tattaaagcc acannnnnnn nnnnnntatg ctttgtatct tnnnnngncn 540
tcttcattac caactgcttc cgcggccaca ttaagagaac ttgtggtaag ataagaagat 600
attttattcn nnnnnntgac ttgctggatg tcgggaaata ttctgcattt gataagaggc 660
ggttaattgc agatataatt ggnnnnnnnn nngntcgttg ctatggtcac cgtgaagcga 720
gtacagcagc acaagaatgt gtgnnnnnnn nnnnnaatat tgnttgaata tggtaacctg 780
ttttagtcgg tttaaaggta agaagatcta accnaaaacn acactgcagt gactgattgn 840
agtatnnnnn n 851

<210> SEQ ID NO 38
<211> LENGTH: 890
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (4)..(7)
<223> OTHER INFORMATION: n is unknown
<220> FEATURE:
<221> NAME/KEY: misc_feature
<222> LOCATION: (18)..(21)
<223> OTHER INFORMATION: n is unknown
<220> FEATURE:
<221> NAME/KEY: misc_feature
<222> LOCATION: (61)..(62)
<223> OTHER INFORMATION: n is unknown
<220> FEATURE:
<221> NAME/KEY: misc_feature
<222> LOCATION: (374)..(381)
<223> OTHER INFORMATION: n is unknown
<220> FEATURE:
<221> NAME/KEY: misc_feature
<222> LOCATION: (383)..(383)
<223> OTHER INFORMATION: n is unknown
<220> FEATURE:
<221> NAME/KEY: misc_feature
<222> LOCATION: (416)..(416)
<223> OTHER INFORMATION: n is unknown
<220> FEATURE:
<221> NAME/KEY: misc_feature
<222> LOCATION: (499)..(507)
<223> OTHER INFORMATION: n is unknown
<220> FEATURE:
<221> NAME/KEY: misc_feature
<222> LOCATION: (510)..(511)
<223> OTHER INFORMATION: n is unknown
<220> FEATURE:
<221> NAME/KEY: misc_feature
<222> LOCATION: (527)..(531)
<223> OTHER INFORMATION: n is unknown
<220> FEATURE:
<221> NAME/KEY: misc_feature
<222> LOCATION: (533)..(533)
<223> OTHER INFORMATION: n is unknown
<220> FEATURE:
<221> NAME/KEY: misc_feature
<222> LOCATION: (605)..(611)
<223> OTHER INFORMATION: n is unknown
<220> FEATURE:
<221> NAME/KEY: misc_feature
<222> LOCATION: (678)..(679)
<223> OTHER INFORMATION: n is unknown
<220> FEATURE:
<221> NAME/KEY: misc_feature
<222> LOCATION: (682)..(687)
<223> OTHER INFORMATION: n is unknown
<220> FEATURE:
<221> NAME/KEY: misc_feature
<222> LOCATION: (689)..(690)
<223> OTHER INFORMATION: n is unknown
<220> FEATURE:
<221> NAME/KEY: misc_feature
<222> LOCATION: (720)..(721)
<223> OTHER INFORMATION: n is unknown
<220> FEATURE:
<221> NAME/KEY: misc_feature
<222> LOCATION: (739)..(749)
<223> OTHER INFORMATION: n is unknown
<220> FEATURE:
<221> NAME/KEY: misc_feature
<222> LOCATION: (756)..(756)
<223> OTHER INFORMATION: n is unknown
<220> FEATURE:
<221> NAME/KEY: misc_feature
<222> LOCATION: (786)..(786)
<223> OTHER INFORMATION: n is unknown
<220> FEATURE:
<221> NAME/KEY: misc_feature
<222> LOCATION: (829)..(835)
<223> OTHER INFORMATION: n is unknown
<220> FEATURE:
<221> NAME/KEY: misc_feature
<222> LOCATION: (841)..(846)
<223> OTHER INFORMATION: n is unknown
<220> FEATURE:
<221> NAME/KEY: misc_feature
<222> LOCATION: (856)..(860)
<223> OTHER INFORMATION: n is unknown
<220> FEATURE:
<221> NAME/KEY: misc_feature
<222> LOCATION: (865)..(865)
<223> OTHER INFORMATION: n is unknown
<220> FEATURE:
<221> NAME/KEY: misc_feature
<222> LOCATION: (880)..(880)
<223> OTHER INFORMATION: n is unknown

<400> SEQUENCE: 38
ctgnnnntga ttactgtnnn ngttgctact actgctgaca atgctgctgc tgcttctcct 60
nnctgtctcc acttccttga acaatgcgcc gtcatgcttc ttttgcctcc cgctgctcca 120
gaaagctagg ccgcagatca gaaccaccac agtcaatatc accaccttcc tcttatagat 180
tcggaatctc atgatagggg ctcagcctct gtgcgagtgg agagaagttt gcaggcgagc 240
tgaggagcaa ttgcaggtga tatgatgtgc tcggctcaag aagcgggccc ggagaggaag 300
aagtcgtgcc ggggctaatt attggcaaaa cgagctcttg ttgtaaacat tgatccaact 360
ggaatgtcac taannnnnnn nantattcca taaggcatga tggttgctca gaggcnggag 420
aagagcaacg aatacgatcc tataaaagat aaaacataaa taaacagtct tgattatatt 480
ctgggtatta aagccacann nnnnnnngan ntatgctttg tatcttnnnn ngncttcttc 540
attaccaact gcttccgcgg ccacattaag agaacttgtg gtaagataag aagatatttt 600
attcnnnnnn ntgacttgct ggatgtcggg aaatattctg catttgataa gaggcggtta 660
attgcagata taattggnng tnnnnnngnn cgttgctatg gtcaccgtga agcgagtacn 720
ncagcacaag aatgtgtgnn nnnnnnnnnt aatatngttt gaatatggta acctgtttta 780
gtcggnttaa aggtaagaag atctaaccaa aaacaacact gcagtgacnn nnnnnagtat 840
nnnnnntttt acttannnnn aattntggtg taaacatcan cggcgcactt 890

<210> SEQ ID NO 39
<211> LENGTH: 875
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (1)..(6)
<223> OTHER INFORMATION: n is unknown
<220> FEATURE:
<221> NAME/KEY: misc_feature
<222> LOCATION: (13)..(13)
<223> OTHER INFORMATION: n is unknown
<220> FEATURE:
<221> NAME/KEY: misc_feature
<222> LOCATION: (18)..(18)
<223> OTHER INFORMATION: n is unknown
<220> FEATURE:
<221> NAME/KEY: misc_feature
<222> LOCATION: (68)..(69)
<223> OTHER INFORMATION: n is unknown
<220> FEATURE:
<221> NAME/KEY: misc_feature
<222> LOCATION: (381)..(388)
<223> OTHER INFORMATION: n is unknown
<220> FEATURE:
<221> NAME/KEY: misc_feature
<222> LOCATION: (507)..(507)
<223> OTHER INFORMATION: n is unknown
<220> FEATURE:
<221> NAME/KEY: misc_feature
<222> LOCATION: (509)..(509)
<223> OTHER INFORMATION: n is unknown
<220> FEATURE:
<221> NAME/KEY: misc_feature
<222> LOCATION: (511)..(515)
<223> OTHER INFORMATION: n is unknown
<220> FEATURE:
<221> NAME/KEY: misc_feature
<222> LOCATION: (517)..(518)
<223> OTHER INFORMATION: n is unknown
<220> FEATURE:
<221> NAME/KEY: misc_feature
<222> LOCATION: (534)..(540)
<223> OTHER INFORMATION: n is unknown
<220> FEATURE:
<221> NAME/KEY: misc_feature
<222> LOCATION: (597)..(597)
<223> OTHER INFORMATION: n is unknown
<220> FEATURE:
<221> NAME/KEY: misc_feature
<222> LOCATION: (599)..(600)
<223> OTHER INFORMATION: n is unknown
<220> FEATURE:
<221> NAME/KEY: misc_feature
<222> LOCATION: (602)..(603)
<223> OTHER INFORMATION: n is unknown
<220> FEATURE:
<221> NAME/KEY: misc_feature
<222> LOCATION: (613)..(616)
<223> OTHER INFORMATION: n is unknown
<220> FEATURE:
<221> NAME/KEY: misc_feature
<222> LOCATION: (618)..(618)
<223> OTHER INFORMATION: n is unknown
<220> FEATURE:
<221> NAME/KEY: misc_feature
<222> LOCATION: (665)..(665)
<223> OTHER INFORMATION: n is unknown
<220> FEATURE:
<221> NAME/KEY: misc_feature
<222> LOCATION: (685)..(686)
<223> OTHER INFORMATION: n is unknown
<220> FEATURE:
<221> NAME/KEY: misc_feature
<222> LOCATION: (689)..(694)
<223> OTHER INFORMATION: n is unknown
<220> FEATURE:
<221> NAME/KEY: misc_feature
<222> LOCATION: (746)..(747)
<223> OTHER INFORMATION: n is unknown
<220> FEATURE:
<221> NAME/KEY: misc_feature
<222> LOCATION: (749)..(756)
<223> OTHER INFORMATION: n is unknown
<220> FEATURE:
<221> NAME/KEY: misc_feature
<222> LOCATION: (847)..(853)
<223> OTHER INFORMATION: n is unknown

<400> SEQUENCE: 39
nnnnnncctg gtnatganta ctgttaatgt tgctactact gctgacaatg ctgctgctgc 60
ttctcctnnc tgtctccact tccttgaaca atgcgccgtc atgcttcttt tgcctcccgc 120
tgctccagaa agctaggccg cagatcagaa ccaccacagt caatatcacc accttcctct 180
tatagattcg gaatctcatg ataggggctc agcctctgtg cgagtggaga gaagtttgca 240
ggcgagctga ggagcaattg caggtgatat gatgtgctcg gctcaagaag cgggcccgga 300
gaggaagaag tcgtgccggg gctaattatt ggcaaaacga gctcttgttg taaacattga 360
tccaactgga atgtcactaa nnnnnnnnaa tattccataa ggcatgatgg ttgctcagag 420

-continued

```
gcaggagaag agcaacgaat acgatcctat aaaagataaa acataaataa acagtcttga    480

ttatattctg ggtattaaag ccacaangng nnnnnannta tgctttgtat cttnnnnnnn    540

cttcttcatt accaactgct tccgcggcca cattaagaga acttgtggta agataanann    600

anntttttatt cgnnnngntg acttgctgga tgtcgggaaa tattctgcat ttgataagag    660

gcggntaatt gcagatataa ttggnngtnn nnnnggtcgt tgctatggtc accgtgaagc    720

gagtacagca gcacaagaat gtgtgnngnn nnnnnntaat attgtttgaa tatggtaacc    780

tgttttagtc ggtttaaagg taagaagatc taaccaaaaa caacactgca gtgactgatt    840

gtagtannnn nnnttttact taatcttaat tttgg                               875
```

```
<210> SEQ ID NO 40
<211> LENGTH: 838
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (1)..(5)
<223> OTHER INFORMATION: n is unknown
<220> FEATURE:
<221> NAME/KEY: misc_feature
<222> LOCATION: (9)..(9)
<223> OTHER INFORMATION: n is unknown
<220> FEATURE:
<221> NAME/KEY: misc_feature
<222> LOCATION: (58)..(58)
<223> OTHER INFORMATION: n is unknown
<220> FEATURE:
<221> NAME/KEY: misc_feature
<222> LOCATION: (370)..(378)
<223> OTHER INFORMATION: n is unknown
<220> FEATURE:
<221> NAME/KEY: misc_feature
<222> LOCATION: (496)..(504)
<223> OTHER INFORMATION: n is unknown
<220> FEATURE:
<221> NAME/KEY: misc_feature
<222> LOCATION: (507)..(508)
<223> OTHER INFORMATION: n is unknown
<220> FEATURE:
<221> NAME/KEY: misc_feature
<222> LOCATION: (530)..(530)
<223> OTHER INFORMATION: n is unknown
<220> FEATURE:
<221> NAME/KEY: misc_feature
<222> LOCATION: (603)..(604)
<223> OTHER INFORMATION: n is unknown
<220> FEATURE:
<221> NAME/KEY: misc_feature
<222> LOCATION: (606)..(608)
<223> OTHER INFORMATION: n is unknown
<220> FEATURE:
<221> NAME/KEY: misc_feature
<222> LOCATION: (675)..(676)
<223> OTHER INFORMATION: n is unknown
<220> FEATURE:
<221> NAME/KEY: misc_feature
<222> LOCATION: (679)..(684)
<223> OTHER INFORMATION: n is unknown
<220> FEATURE:
<221> NAME/KEY: misc_feature
<222> LOCATION: (735)..(746)
<223> OTHER INFORMATION: n is unknown
<220> FEATURE:
<221> NAME/KEY: misc_feature
<222> LOCATION: (806)..(806)
<223> OTHER INFORMATION: n is unknown
<220> FEATURE:
<221> NAME/KEY: misc_feature
<222> LOCATION: (832)..(833)
<223> OTHER INFORMATION: n is unknown
```

<220> FEATURE:
<221> NAME/KEY: misc_feature
<222> LOCATION: (835)..(835)
<223> OTHER INFORMATION: n is unknown
<220> FEATURE:
<221> NAME/KEY: misc_feature
<222> LOCATION: (837)..(838)
<223> OTHER INFORMATION: n is unknown

<400> SEQUENCE: 40

```
nnnnnattnc tgttaatgtt gctactactg ctgacaatgc tgctgctgct tctcctcnct      60

gtctccactt ccttgaacaa tgcgccgtca tgcttctttt gcctcccgct gctccagaaa     120

gctaggccgc agatcagaac caccacagtc aatatcacca ccttcctctt atagattcgg     180

aatctcatga taggggctca gcctctgtgc gagtggagag aagtttgcag gcgagctgag     240

gagcaattgc aggtgatatg atgtgctcgg ctcaagaagc gggcccggag aggaagaagt     300

cgtgccgggg ctaattattg gcaaaacgag ctcttgttgt aaacattgat ccaactggaa     360

tgtcactaan nnnnnnnnaa tattccataa ggcatgatgg ttgctcagag gcaggagaag     420

agcaacgaat acgatcctat aaaagataaa acataaataa acagtcttga ttatattctg     480

ggtattaaag ccacannnnn nnnngannta tgctttgtat cttttcttgn cttcttcatt     540

accaactgct tccgcggcca cattaagaga acttgtggta agataagaag atattttatt     600

cgnncnnntg acttgctgga tgtcgggaaa tattctgcat ttgataagag gcggttaatt     660

gcagatataa ttggnngtnn nnnnggtcgt tgctatggtc accgtgaagc gagtacagca     720

gcacaagaat gtgtnnnnnn nnnnnntaat attgtttgaa tatggtaacc tgttttagtc     780

ggtttaaagg taagaagatc taaccnaaaa caacactgca gtgactgatt gnngnann       838
```

<210> SEQ ID NO 41
<211> LENGTH: 865
<212> TYPE: DNA
<213> ORGANISM: Artificial Sequence
<220> FEATURE:
<223> OTHER INFORMATION: S. cerevisiae PCR reaction /DNA sequence standard
<220> FEATURE:
<221> NAME/KEY: misc_feature
<222> LOCATION: (1)..(5)
<223> OTHER INFORMATION: n is unknown
<220> FEATURE:
<221> NAME/KEY: misc_feature
<222> LOCATION: (8)..(9)
<223> OTHER INFORMATION: n is unknown
<220> FEATURE:
<221> NAME/KEY: misc_feature
<222> LOCATION: (15)..(15)
<223> OTHER INFORMATION: n is unknown
<220> FEATURE:
<221> NAME/KEY: misc_feature
<222> LOCATION: (24)..(24)
<223> OTHER INFORMATION: n is unknown
<220> FEATURE:
<221> NAME/KEY: misc_feature
<222> LOCATION: (58)..(59)
<223> OTHER INFORMATION: n is unknown
<220> FEATURE:
<221> NAME/KEY: misc_feature
<222> LOCATION: (244)..(246)
<223> OTHER INFORMATION: n is unknown
<220> FEATURE:
<221> NAME/KEY: misc_feature
<222> LOCATION: (347)..(355)
<223> OTHER INFORMATION: n is unknown
<220> FEATURE:
<221> NAME/KEY: misc_feature
<222> LOCATION: (359)..(359)
<223> OTHER INFORMATION: n is unknown
<220> FEATURE:

<221> NAME/KEY: misc_feature
<222> LOCATION: (378)..(381)
<223> OTHER INFORMATION: n is unknown
<220> FEATURE:
<221> NAME/KEY: misc_feature
<222> LOCATION: (383)..(387)
<223> OTHER INFORMATION: n is unknown
<220> FEATURE:
<221> NAME/KEY: misc_feature
<222> LOCATION: (393)..(394)
<223> OTHER INFORMATION: n is unknown
<220> FEATURE:
<221> NAME/KEY: misc_feature
<222> LOCATION: (424)..(426)
<223> OTHER INFORMATION: n is unknown
<220> FEATURE:
<221> NAME/KEY: misc_feature
<222> LOCATION: (428)..(428)
<223> OTHER INFORMATION: n is unknown
<220> FEATURE:
<221> NAME/KEY: misc_feature
<222> LOCATION: (433)..(437)
<223> OTHER INFORMATION: n is unknown
<220> FEATURE:
<221> NAME/KEY: misc_feature
<222> LOCATION: (493)..(493)
<223> OTHER INFORMATION: n is unknown
<220> FEATURE:
<221> NAME/KEY: misc_feature
<222> LOCATION: (499)..(500)
<223> OTHER INFORMATION: n is unknown
<220> FEATURE:
<221> NAME/KEY: misc_feature
<222> LOCATION: (502)..(503)
<223> OTHER INFORMATION: n is unknown
<220> FEATURE:
<221> NAME/KEY: misc_feature
<222> LOCATION: (533)..(550)
<223> OTHER INFORMATION: n is unknown
<220> FEATURE:
<221> NAME/KEY: misc_feature
<222> LOCATION: (602)..(608)
<223> OTHER INFORMATION: n is unknown
<220> FEATURE:
<221> NAME/KEY: misc_feature
<222> LOCATION: (611)..(616)
<223> OTHER INFORMATION: n is unknown
<220> FEATURE:
<221> NAME/KEY: misc_feature
<222> LOCATION: (659)..(659)
<223> OTHER INFORMATION: n is unknown
<220> FEATURE:
<221> NAME/KEY: misc_feature
<222> LOCATION: (674)..(684)
<223> OTHER INFORMATION: n is unknown
<220> FEATURE:
<221> NAME/KEY: misc_feature
<222> LOCATION: (720)..(728)
<223> OTHER INFORMATION: n is unknown
<220> FEATURE:
<221> NAME/KEY: misc_feature
<222> LOCATION: (799)..(799)
<223> OTHER INFORMATION: n is unknown
<220> FEATURE:
<221> NAME/KEY: misc_feature
<222> LOCATION: (832)..(832)
<223> OTHER INFORMATION: n is unknown
<220> FEATURE:
<221> NAME/KEY: misc_feature
<222> LOCATION: (835)..(835)
<223> OTHER INFORMATION: n is unknown
<220> FEATURE:
<221> NAME/KEY: misc_feature
<222> LOCATION: (837)..(837)
<223> OTHER INFORMATION: n is unknown
<220> FEATURE:
<221> NAME/KEY: misc_feature
<222> LOCATION: (860)..(860)
<223> OTHER INFORMATION: n is unknown
<220> FEATURE:

<221> NAME/KEY: misc_feature
<222> LOCATION: (863)..(864)
<223> OTHER INFORMATION: n is unknown

<400> SEQUENCE: 41

```
nnnnnatnnc tgttnatgtt gctnctactg ctgacaatgc tgctgctgct tctcctcnnt      60

gtctccactt ccttgaacaa tgcgccgtca tgcttctttt gcctcccgct gctccagaaa     120

gctaggccgc agatcagaac caccacagtc aatatcacca ccttcctctt atagattcgg     180

aatctcatga taggggctca gcctctgtgc gagtggagag aagtttgcag gcgagctgag     240

gagnnnttgc aggtgatatg atgtgctcgg ctcaagaagc gggcccggag aggaagaagt     300

cgtgccgggg ctaattattg gcaaaacgag ctcttgttgt aaacatnnnn nnnnntggna     360

tgtcactaat ggcgaatnnn nannnnntaa ggnntgatgg ttgctcagag gcaggagaag     420

agcnnngnat acnnnnntat aaaagataaa acataaataa acagtcttga ttatattctg     480

ggtattaaag ccncaatcnn annaaatata tgctttgtat cttttcttgc ctnnnnnnnn     540

nnnnnnnnnn tccgcggcca cattaagaga acttgtggta agataagaag atattttatt     600

cnnnnnnntg nnnnnntgga tgtcgggaaa tattctgcat ttgataagag gcggttaant     660

gcagatataa ttgnnnnnnn nnnnggtcgt tgctatggtc accgtgaagc gagtacagcn     720

nnnnnnnnat gtgtgccgtt ctcagttaat attgtttgaa tatggtaacc tgttttagtc     780

ggtttaaagg taagaaganc taaccaaaaa caacactgca gtgactgatt gnagnantta     840

tttttttact taatcttaan ttnng                                           865
```

<210> SEQ ID NO 42
<211> LENGTH: 888
<212> TYPE: DNA
<213> ORGANISM: Artificial Sequence
<220> FEATURE:
<223> OTHER INFORMATION: S. cerevisiae PCR reaction /DNA sequence standard
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (4)..(5)
<223> OTHER INFORMATION: n is unknown
<220> FEATURE:
<221> NAME/KEY: misc_feature
<222> LOCATION: (19)..(20)
<223> OTHER INFORMATION: n is unknown
<220> FEATURE:
<221> NAME/KEY: misc_feature
<222> LOCATION: (22)..(23)
<223> OTHER INFORMATION: n is unknown
<220> FEATURE:
<221> NAME/KEY: misc_feature
<222> LOCATION: (25)..(25)
<223> OTHER INFORMATION: n is unknown
<220> FEATURE:
<221> NAME/KEY: misc_feature
<222> LOCATION: (58)..(59)
<223> OTHER INFORMATION: n is unknown
<220> FEATURE:
<221> NAME/KEY: misc_feature
<222> LOCATION: (348)..(357)
<223> OTHER INFORMATION: n is unknown
<220> FEATURE:
<221> NAME/KEY: misc_feature
<222> LOCATION: (380)..(386)
<223> OTHER INFORMATION: n is unknown
<220> FEATURE:
<221> NAME/KEY: misc_feature
<222> LOCATION: (388)..(388)
<223> OTHER INFORMATION: n is unknown
<220> FEATURE:
<221> NAME/KEY: misc_feature
<222> LOCATION: (394)..(396)
<223> OTHER INFORMATION: n is unknown
<220> FEATURE:
<221> NAME/KEY: misc_feature
<222> LOCATION: (398)..(398)
<223> OTHER INFORMATION: n is unknown
<220> FEATURE:
<221> NAME/KEY: misc_feature
<222> LOCATION: (425)..(427)
<223> OTHER INFORMATION: n is unknown
<220> FEATURE:
<221> NAME/KEY: misc_feature
<222> LOCATION: (429)..(429)
<223> OTHER INFORMATION: n is unknown
<220> FEATURE:
<221> NAME/KEY: misc_feature
<222> LOCATION: (435)..(438)
<223> OTHER INFORMATION: n is unknown
<220> FEATURE:
<221> NAME/KEY: misc_feature
<222> LOCATION: (534)..(551)
<223> OTHER INFORMATION: n is unknown
<220> FEATURE:
<221> NAME/KEY: misc_feature
<222> LOCATION: (580)..(580)
<223> OTHER INFORMATION: n is unknown
<220> FEATURE:
<221> NAME/KEY: misc_feature
<222> LOCATION: (603)..(609)
<223> OTHER INFORMATION: n is unknown
<220> FEATURE:
<221> NAME/KEY: misc_feature
<222> LOCATION: (611)..(617)
<223> OTHER INFORMATION: n is unknown
<220> FEATURE:
<221> NAME/KEY: misc_feature
<222> LOCATION: (660)..(660)
<223> OTHER INFORMATION: n is unknown
<220> FEATURE:
<221> NAME/KEY: misc_feature
<222> LOCATION: (718)..(720)
<223> OTHER INFORMATION: n is unknown
<220> FEATURE:
<221> NAME/KEY: misc_feature
<222> LOCATION: (722)..(729)
<223> OTHER INFORMATION: n is unknown
<220> FEATURE:
<221> NAME/KEY: misc_feature
<222> LOCATION: (797)..(798)
<223> OTHER INFORMATION: n is unknown
<220> FEATURE:
<221> NAME/KEY: misc_feature
<222> LOCATION: (800)..(801)
<223> OTHER INFORMATION: n is unknown
<220> FEATURE:
<221> NAME/KEY: misc_feature
<222> LOCATION: (831)..(831)
<223> OTHER INFORMATION: n is unknown
<220> FEATURE:
<221> NAME/KEY: misc_feature
<222> LOCATION: (833)..(833)
<223> OTHER INFORMATION: n is unknown
<220> FEATURE:
<221> NAME/KEY: misc_feature
<222> LOCATION: (864)..(864)
<223> OTHER INFORMATION: n is unknown
<220> FEATURE:
<221> NAME/KEY: misc_feature
<222> LOCATION: (866)..(867)
<223> OTHER INFORMATION: n is unknown
<220> FEATURE:
<221> NAME/KEY: misc_feature
<222> LOCATION: (869)..(869)
<223> OTHER INFORMATION: n is unknown
<220> FEATURE:
<221> NAME/KEY: misc_feature
<222> LOCATION: (878)..(878)
<223> OTHER INFORMATION: n is unknown
<220> FEATURE:
<221> NAME/KEY: misc_feature
<222> LOCATION: (882)..(884)
<223> OTHER INFORMATION: n is unknown
<220> FEATURE:
<221> NAME/KEY: misc_feature
<222> LOCATION: (886)..(886)
<223> OTHER INFORMATION: n is unknown

<400> SEQUENCE: 42

```
nttnngatta ctgttaatnn tnntnctact gctgacaatg ctgctgctgc ttctcctnnc     60

tgtctccact tccttgaaca atgcgccgtc atgcttcttt tgcctcccgc tgctccagaa    120

agctaggccg cagatcagaa ccaccacagt caatatcacc accttcctct tatagattcg    180

gaatctcatg ataggggctc agcctctgtg cgagtggaga gaagtttgca ggcgagctga    240

ggagcaattg caggtgatat gatgtgctcg gctcaagaag cgggcccgga gaggaagaag    300

tcgtgccggg gctaattatt ggcaaaacga gctcttgttg taaacatnnn nnnnnnngga    360

atgtcactaa tggcgaatcn nnnnnncnta aggnnngntg gttgctcaga ggcaggagaa    420

gagcnnngna tacgnnnnta taaaagataa aacataaata aacagtcttg attatattct    480

gggtattaaa gccacaatca gaacaaatat atgctttgta tcttttcttg cctnnnnnnn    540

nnnnnnnnnn ntccgcggcc acattaagag aacttgtggn aagataagaa gatattttat    600

tcnnnnnnnt nnnnnnntgg atgtcgggaa atattctgca tttgataaga ggcggttaan    660

tgcagatata attggtagtg aaaagggtcg ttgctatggt caccgtgaag cgagtacnnn    720

gnnnnnnnna tgtgtgccgt tctcagttaa tattgtttga atatggtaac ctgttttagt    780

cggtttaaag gtaagannan ntaaccaaaa acaacactgc agtgactgat ngnagtattt    840

attttttac ttaatcttaa tttngnngna aacatcancg gnnngntt                  888
```

<210> SEQ ID NO 43
<211> LENGTH: 695
<212> TYPE: DNA
<213> ORGANISM: Artificial Sequence
<220> FEATURE:
<223> OTHER INFORMATION: S. cerevisiae PCR reaction /DNA sequence
standard
<220> FEATURE:
<221> NAME/KEY: misc_feature
<222> LOCATION: (1)..(3)
<223> OTHER INFORMATION: n is unknown
<220> FEATURE:
<221> NAME/KEY: misc_feature
<222> LOCATION: (6)..(7)
<223> OTHER INFORMATION: n is unknown
<220> FEATURE:
<221> NAME/KEY: misc_feature
<222> LOCATION: (13)..(13)
<223> OTHER INFORMATION: n is unknown
<220> FEATURE:
<221> NAME/KEY: misc_feature
<222> LOCATION: (16)..(16)
<223> OTHER INFORMATION: n is unknown
<220> FEATURE:
<221> NAME/KEY: misc_feature
<222> LOCATION: (71)..(71)
<223> OTHER INFORMATION: n is unknown
<220> FEATURE:
<221> NAME/KEY: misc_feature
<222> LOCATION: (259)..(259)
<223> OTHER INFORMATION: n is unknown
<220> FEATURE:
<221> NAME/KEY: misc_feature
<222> LOCATION: (360)..(372)
<223> OTHER INFORMATION: n is unknown
<220> FEATURE:
<221> NAME/KEY: misc_feature
<222> LOCATION: (374)..(374)

<223> OTHER INFORMATION: n is unknown
<220> FEATURE:
<221> NAME/KEY: misc_feature
<222> LOCATION: (390)..(394)
<223> OTHER INFORMATION: n is unknown
<220> FEATURE:
<221> NAME/KEY: misc_feature
<222> LOCATION: (396)..(400)
<223> OTHER INFORMATION: n is unknown
<220> FEATURE:
<221> NAME/KEY: misc_feature
<222> LOCATION: (406)..(407)
<223> OTHER INFORMATION: n is unknown
<220> FEATURE:
<221> NAME/KEY: misc_feature
<222> LOCATION: (436)..(439)
<223> OTHER INFORMATION: n is unknown
<220> FEATURE:
<221> NAME/KEY: misc_feature
<222> LOCATION: (441)..(441)
<223> OTHER INFORMATION: n is unknown
<220> FEATURE:
<221> NAME/KEY: misc_feature
<222> LOCATION: (446)..(451)
<223> OTHER INFORMATION: n is unknown
<220> FEATURE:
<221> NAME/KEY: misc_feature
<222> LOCATION: (546)..(563)
<223> OTHER INFORMATION: n is unknown
<220> FEATURE:
<221> NAME/KEY: misc_feature
<222> LOCATION: (616)..(621)
<223> OTHER INFORMATION: n is unknown
<220> FEATURE:
<221> NAME/KEY: misc_feature
<222> LOCATION: (624)..(629)
<223> OTHER INFORMATION: n is unknown
<220> FEATURE:
<221> NAME/KEY: misc_feature
<222> LOCATION: (663)..(663)
<223> OTHER INFORMATION: n is unknown
<220> FEATURE:
<221> NAME/KEY: misc_feature
<222> LOCATION: (668)..(668)
<223> OTHER INFORMATION: n is unknown
<220> FEATURE:
<221> NAME/KEY: misc_feature
<222> LOCATION: (672)..(672)
<223> OTHER INFORMATION: n is unknown
<220> FEATURE:
<221> NAME/KEY: misc_feature
<222> LOCATION: (675)..(675)
<223> OTHER INFORMATION: n is unknown
<220> FEATURE:
<221> NAME/KEY: misc_feature
<222> LOCATION: (677)..(677)
<223> OTHER INFORMATION: n is unknown
<220> FEATURE:
<221> NAME/KEY: misc_feature
<222> LOCATION: (682)..(682)
<223> OTHER INFORMATION: n is unknown
<220> FEATURE:
<221> NAME/KEY: misc_feature
<222> LOCATION: (688)..(689)
<223> OTHER INFORMATION: n is unknown
<220> FEATURE:
<221> NAME/KEY: misc_feature
<222> LOCATION: (691)..(691)
<223> OTHER INFORMATION: n is unknown

<400> SEQUENCE: 43
nnntgnngcc tgnttntgat tactgttaat gttgctacta ctgctgacaa tgctgctgct 60
gcttctcctc nctgtctcca cttccttgaa caatgcgccg tcatgcttct tttgcctccc 120
gctgctccag aaagctaggc cgcagatcag aaccaccaca gtcaatatca ccaccttcct 180
cttatagatt cggaatctca tgataggggc tcagcctctg tgcgagtgga gagaagtttg 240

```
caggcgagct gaggagcant tgcaggtgat atgatgtgct cggctcaaga agcgggcccg    300

gagaggaaga agtcgtgccg gggctaatta ttggcaaaac gagctcttgt tgtaaacatn    360

nnnnnnnnnn nnangtcact aatggcgaan nnnnannnnn taaggnntga tggttgctca    420

gaggcaggag aagagnnnng natacnnnnn nataaaagat aaaacataaa taaacagtct    480

tgattatatt ctgggtatta aagccacaat cagaacaaat atatgctttg tatcttttct    540

tgcctnnnnn nnnnnnnnnn nnntccgcgg ccacattaag agaacttgtg gtaagataag    600

aagatatttt attcgnnnnn ntgnnnnnnt ggatgtcggg aaatattctg catttgataa    660

gangcggnta antgnanata tnattggnng ngaaa                               695
```

<210> SEQ ID NO 44
<211> LENGTH: 873
<212> TYPE: DNA
<213> ORGANISM: Artificial Sequence
<220> FEATURE:
<223> OTHER INFORMATION: S. cerevisiae PCR reaction /DNA sequence standard
<220> FEATURE:
<221> NAME/KEY: misc_feature
<222> LOCATION: (9)..(9)
<223> OTHER INFORMATION: n is unknown
<220> FEATURE:
<221> NAME/KEY: misc_feature
<222> LOCATION: (12)..(12)
<223> OTHER INFORMATION: n is unknown
<220> FEATURE:
<221> NAME/KEY: misc_feature
<222> LOCATION: (18)..(18)
<223> OTHER INFORMATION: n is unknown
<220> FEATURE:
<221> NAME/KEY: misc_feature
<222> LOCATION: (20)..(22)
<223> OTHER INFORMATION: n is unknown
<220> FEATURE:
<221> NAME/KEY: misc_feature
<222> LOCATION: (24)..(24)
<223> OTHER INFORMATION: n is unknown
<220> FEATURE:
<221> NAME/KEY: misc_feature
<222> LOCATION: (63)..(63)
<223> OTHER INFORMATION: n is unknown
<220> FEATURE:
<221> NAME/KEY: misc_feature
<222> LOCATION: (350)..(350)
<223> OTHER INFORMATION: n is unknown
<220> FEATURE:
<221> NAME/KEY: misc_feature
<222> LOCATION: (352)..(361)
<223> OTHER INFORMATION: n is unknown
<220> FEATURE:
<221> NAME/KEY: misc_feature
<222> LOCATION: (383)..(392)
<223> OTHER INFORMATION: n is unknown
<220> FEATURE:
<221> NAME/KEY: misc_feature
<222> LOCATION: (438)..(443)
<223> OTHER INFORMATION: n is unknown
<220> FEATURE:
<221> NAME/KEY: misc_feature
<222> LOCATION: (539)..(555)
<223> OTHER INFORMATION: n is unknown
<220> FEATURE:
<221> NAME/KEY: misc_feature
<222> LOCATION: (583)..(583)
<223> OTHER INFORMATION: n is unknown
<220> FEATURE:
<221> NAME/KEY: misc_feature
<222> LOCATION: (607)..(613)
<223> OTHER INFORMATION: n is unknown
<220> FEATURE:
<221> NAME/KEY: misc_feature
<222> LOCATION: (616)..(621)
<223> OTHER INFORMATION: n is unknown
<220> FEATURE:
<221> NAME/KEY: misc_feature
<222> LOCATION: (722)..(733)
<223> OTHER INFORMATION: n is unknown
<220> FEATURE:
<221> NAME/KEY: misc_feature
<222> LOCATION: (760)..(761)
<223> OTHER INFORMATION: n is unknown
<220> FEATURE:
<221> NAME/KEY: misc_feature
<222> LOCATION: (788)..(788)
<223> OTHER INFORMATION: n is unknown
<220> FEATURE:
<221> NAME/KEY: misc_feature
<222> LOCATION: (827)..(827)
<223> OTHER INFORMATION: n is unknown
<220> FEATURE:
<221> NAME/KEY: misc_feature
<222> LOCATION: (837)..(837)
<223> OTHER INFORMATION: n is unknown
<220> FEATURE:
<221> NAME/KEY: misc_feature
<222> LOCATION: (873)..(873)
<223> OTHER INFORMATION: n is unknown

<400> SEQUENCE: 44
cctggttang antactgntn nngntgctac tactgctgac aatgctgctg ctgcttctcc 60
tcnctgtctc cacttccttg aacaatgcgc cgtcatgctt cttttgcctc ccgctgctcc 120
agaaagctag gccgcagatc agaaccacca cagtcaatat caccaccttc ctcttataga 180
ttcggaatct catgataggg gctcagcctc tgtgcgagtg gagagaagtt tgcaggcgag 240
ctgaggagca attgcaggtg atatgatgtg ctcggctcaa gaagcgggcc cggagaggaa 300
gaagtcgtgc cggggctaat tattggcaaa acgagctctt gttgtaaacn tnnnnnnnnn 360
nggaatgtca ctaatggcga atnnnnnnnn nntaaggcat gatggttgct cagaggcagg 420
agaagagcaa cgaatacnnn nnnataaaag ataaaacata aataaacagt cttgattata 480
ttctgggtat taaagccaca atcagaacaa atatatgctt tgtatctttt cttgccttnn 540
nnnnnnnnnn nnnnntccgc ggccacatta agagaacttg tgntaagata agaagatatt 600
ttattcnnnn nnntgnnnnn ntggatgtcg ggaaatattc tgcatttgat aagaggcggt 660
taattgcaga tataattggt agtgaaaagg gtcgttgcta tggtcaccgt gaagcgagta 720
cnnnnnnnnn nnnatgtgtg ccgttctcag ttaatattgn ntgaatatgg taacctgttt 780
tagtcggntt aaaggtaaga agatctaacc aaaaacaaca ctgcagngac tgattgnagt 840
atttattttt ttacttaatc ttaattttgg ggn 873

<210> SEQ ID NO 45
<211> LENGTH: 862
<212> TYPE: DNA
<213> ORGANISM: Artificial Sequence
<220> FEATURE:
<223> OTHER INFORMATION: S. cerevisiae PCR reaction /DNA sequence
standard
<220> FEATURE:
<221> NAME/KEY: misc_feature
<222> LOCATION: (5)..(9)
<223> OTHER INFORMATION: n is unknown
<220> FEATURE:
<221> NAME/KEY: misc_feature
<222> LOCATION: (63)..(63)
<223> OTHER INFORMATION: n is unknown
<220> FEATURE:
<221> NAME/KEY: misc_feature
<222> LOCATION: (352)..(361)
<223> OTHER INFORMATION: n is unknown
<220> FEATURE:
<221> NAME/KEY: misc_feature
<222> LOCATION: (382)..(392)

<223> OTHER INFORMATION: n is unknown
<220> FEATURE:
<221> NAME/KEY: misc_feature
<222> LOCATION: (398)..(398)
<223> OTHER INFORMATION: n is unknown
<220> FEATURE:
<221> NAME/KEY: misc_feature
<222> LOCATION: (440)..(440)
<223> OTHER INFORMATION: n is unknown
<220> FEATURE:
<221> NAME/KEY: misc_feature
<222> LOCATION: (443)..(444)
<223> OTHER INFORMATION: n is unknown
<220> FEATURE:
<221> NAME/KEY: misc_feature
<222> LOCATION: (539)..(555)
<223> OTHER INFORMATION: n is unknown
<220> FEATURE:
<221> NAME/KEY: misc_feature
<222> LOCATION: (608)..(613)
<223> OTHER INFORMATION: n is unknown
<220> FEATURE:
<221> NAME/KEY: misc_feature
<222> LOCATION: (616)..(621)
<223> OTHER INFORMATION: n is unknown
<220> FEATURE:
<221> NAME/KEY: misc_feature
<222> LOCATION: (662)..(664)
<223> OTHER INFORMATION: n is unknown
<220> FEATURE:
<221> NAME/KEY: misc_feature
<222> LOCATION: (667)..(667)
<223> OTHER INFORMATION: n is unknown
<220> FEATURE:
<221> NAME/KEY: misc_feature
<222> LOCATION: (725)..(725)
<223> OTHER INFORMATION: n is unknown
<220> FEATURE:
<221> NAME/KEY: misc_feature
<222> LOCATION: (727)..(733)
<223> OTHER INFORMATION: n is unknown
<220> FEATURE:
<221> NAME/KEY: misc_feature
<222> LOCATION: (768)..(768)
<223> OTHER INFORMATION: n is unknown
<220> FEATURE:
<221> NAME/KEY: misc_feature
<222> LOCATION: (771)..(776)
<223> OTHER INFORMATION: n is unknown
<220> FEATURE:
<221> NAME/KEY: misc_feature
<222> LOCATION: (827)..(827)
<223> OTHER INFORMATION: n is unknown
<220> FEATURE:
<221> NAME/KEY: misc_feature
<222> LOCATION: (850)..(857)
<223> OTHER INFORMATION: n is unknown

<400> SEQUENCE: 45
cctgnnnnng attactgtta atgttgctac tactgctgac aatgctgctg ctgcttctcc 60
tcnctgtctc cacttccttg aacaatgcgc cgtcatgctt cttttgcctc ccgctgctcc 120
agaaagctag gccgcagatc agaaccacca cagtcaatat caccaccttc ctcttataga 180
ttcggaatct catgataggg gctcagcctc tgtgcgagtg gagagaagtt tgcaggcgag 240
ctgaggagca attgcaggtg atatgatgtg ctcggctcaa gaagcgggcc cggagaggaa 300
gaagtcgtgc cggggctaat tattggcaaa acgagctctt gttgtaaaca tnnnnnnnnn 360
nggaatgtca ctaatggcga annnnnnnnn nntaaggnat gatggttgct cagaggcagg 420
agaagagcaa cgaatacgan gcnntaaaag ataaaacata aataaacagt cttgattata 480
ttctgggtat taaagccaca atcagaacaa atatatgctt tgtatctttt cttgccttnn 540
nnnnnnnnnn nnnnntccgc ggccacatta agagaacttg tggtaagata agaagatatt 600

-continued

```
ttattcgnnn nnntgnnnnn ntggatgtcg ggaaatattc tgcatttgat aagaggcggt    660

tnnntgnaga tataattggt agtgaaaagg gtcgttgcta tggtcaccgt gaagcgagta    720

cagcngnnnn nnnatgtgtg ccgttctcag ttaatattgt ttgaatangg nnnnnngttt    780

tagtcggttt aaaggtaaga agatctaacc aaaaacaaca ctgcagngac tgattgtagt    840

atttattttn nnnnnnnatc tt                                             862
```

```
<210> SEQ ID NO 46
<211> LENGTH: 867
<212> TYPE: DNA
<213> ORGANISM: Artificial Sequence
<220> FEATURE:
<223> OTHER INFORMATION: S. aureus PCR reaction /DNA sequence standard
      consensus sequence
<220> FEATURE:
<221> NAME/KEY: misc_feature
<222> LOCATION: (10)..(10)
<223> OTHER INFORMATION: n is unknown
<220> FEATURE:
<221> NAME/KEY: misc_feature
<222> LOCATION: (17)..(17)
<223> OTHER INFORMATION: n is unknown
<220> FEATURE:
<221> NAME/KEY: misc_feature
<222> LOCATION: (33)..(35)
<223> OTHER INFORMATION: n is unknown
<220> FEATURE:
<221> NAME/KEY: misc_feature
<222> LOCATION: (37)..(39)
<223> OTHER INFORMATION: n is unknown
<220> FEATURE:
<221> NAME/KEY: misc_feature
<222> LOCATION: (64)..(64)
<223> OTHER INFORMATION: n is unknown
<220> FEATURE:
<221> NAME/KEY: misc_feature
<222> LOCATION: (106)..(106)
<223> OTHER INFORMATION: n is unknown
<220> FEATURE:
<221> NAME/KEY: misc_feature
<222> LOCATION: (108)..(108)
<223> OTHER INFORMATION: n is unknown
<220> FEATURE:
<221> NAME/KEY: misc_feature
<222> LOCATION: (110)..(111)
<223> OTHER INFORMATION: n is unknown
<220> FEATURE:
<221> NAME/KEY: misc_feature
<222> LOCATION: (130)..(130)
<223> OTHER INFORMATION: n is unknown
<220> FEATURE:
<221> NAME/KEY: misc_feature
<222> LOCATION: (132)..(133)
<223> OTHER INFORMATION: n is unknown
<220> FEATURE:
<221> NAME/KEY: misc_feature
<222> LOCATION: (135)..(135)
<223> OTHER INFORMATION: n is unknown
<220> FEATURE:
<221> NAME/KEY: misc_feature
<222> LOCATION: (138)..(138)
<223> OTHER INFORMATION: n is unknown
<220> FEATURE:
<221> NAME/KEY: misc_feature
<222> LOCATION: (141)..(141)
<223> OTHER INFORMATION: n is unknown
<220> FEATURE:
<221> NAME/KEY: misc_feature
<222> LOCATION: (177)..(178)
<223> OTHER INFORMATION: n is unknown
<220> FEATURE:
<221> NAME/KEY: misc_feature
<222> LOCATION: (181)..(182)
<223> OTHER INFORMATION: n is unknown
<220> FEATURE:
<221> NAME/KEY: misc_feature
```

-continued

<222> LOCATION: (221)..(221)
<223> OTHER INFORMATION: n is unknown
<220> FEATURE:
<221> NAME/KEY: misc_feature
<222> LOCATION: (227)..(227)
<223> OTHER INFORMATION: n is unknown
<220> FEATURE:
<221> NAME/KEY: misc_feature
<222> LOCATION: (237)..(241)
<223> OTHER INFORMATION: n is unknown
<220> FEATURE:
<221> NAME/KEY: misc_feature
<222> LOCATION: (328)..(328)
<223> OTHER INFORMATION: n is unknown
<220> FEATURE:
<221> NAME/KEY: misc_feature
<222> LOCATION: (330)..(355)
<223> OTHER INFORMATION: n is unknown
<220> FEATURE:
<221> NAME/KEY: misc_feature
<222> LOCATION: (556)..(556)
<223> OTHER INFORMATION: n is unknown
<220> FEATURE:
<221> NAME/KEY: misc_feature
<222> LOCATION: (666)..(669)
<223> OTHER INFORMATION: n is unknown
<220> FEATURE:
<221> NAME/KEY: misc_feature
<222> LOCATION: (763)..(763)
<223> OTHER INFORMATION: n is unknown
<220> FEATURE:
<221> NAME/KEY: misc_feature
<222> LOCATION: (802)..(802)
<223> OTHER INFORMATION: n is unknown
<220> FEATURE:
<221> NAME/KEY: misc_feature
<222> LOCATION: (812)..(813)
<223> OTHER INFORMATION: n is unknown
<220> FEATURE:
<221> NAME/KEY: misc_feature
<222> LOCATION: (815)..(816)
<223> OTHER INFORMATION: n is unknown
<220> FEATURE:
<221> NAME/KEY: misc_feature
<222> LOCATION: (819)..(823)
<223> OTHER INFORMATION: n is unknown

<400> SEQUENCE: 46
gttgctctcn gctgacnatg ctgctgctgc ttnnngnnnc tgtctccact tccttgaaca 60
atgngccgtc atgcttcttt tgcctcccgc tgctccagaa agctangncn nagatcagaa 120
ccaccacagn cnntntcncc nccttcctct tatagattcg gaatctcatg atagggnntc 180
nncctctgtg cgagtggaga gaagtttgca ggcgagctga ngagcanttg caggtgnnnn 240
natgtgctcg gctcaagaag cgggcccgga gaggaagaag tcgtgccggg gctaattatt 300
ggcaaaacga gctcttgttg taaacatngn nnnnnnnnnn nnnnnnnnnn nnnnnatcaa 360
tattccataa ggcatgatgg ttgctcagag gcaggagaag agcaacgaat acgatcctat 420
aaaagataaa acataaataa acagtcttga ttatattctg ggtattaaag ccacaatcag 480
aacaaatata tgctttgtat cttttcttgc cttcttcatt accaactgct tccgcggcca 540
cattaagaga acttgnggta agataagaag atattttatt cgttctgctg acttgctgga 600
tgtcgggaaa tattctgcat ttgataagag gcggttaatt gcagatataa ttggtagtga 660
aaaggnnnnt tgctatggtc accgtgaagc gagtacagca gcacaagaat gtgtgccgtt 720
ctcagttaat attgtttgaa tatggtaacc tgttttagtc ggnttaaagg taagaagatc 780
taaccaaaaa caacactgca gngactgatt gnngnnttnn nnnttttttta cttaatctta 840 attttggtgt aaacatcaac ggcgcac 867

<210> SEQ ID NO 47
<211> LENGTH: 819
<212> TYPE: DNA
<213> ORGANISM: Artificial Sequence
<220> FEATURE:
<223> OTHER INFORMATION: S. aureus PCR reaction /DNA sequence standard consensus sequence
<220> FEATURE:
<221> NAME/KEY: misc_feature
<222> LOCATION: (1)..(3)
<223> OTHER INFORMATION: n is unknown
<220> FEATURE:
<221> NAME/KEY: misc_feature
<222> LOCATION: (10)..(10)
<223> OTHER INFORMATION: n is unknown
<220> FEATURE:
<221> NAME/KEY: misc_feature
<222> LOCATION: (14)..(14)
<223> OTHER INFORMATION: n is unknown
<220> FEATURE:
<221> NAME/KEY: misc_feature
<222> LOCATION: (24)..(24)
<223> OTHER INFORMATION: n is unknown
<220> FEATURE:
<221> NAME/KEY: misc_feature
<222> LOCATION: (64)..(65)
<223> OTHER INFORMATION: n is unknown
<220> FEATURE:
<221> NAME/KEY: misc_feature
<222> LOCATION: (753)..(764)
<223> OTHER INFORMATION: n is unknown
<220> FEATURE:
<221> NAME/KEY: misc_feature
<222> LOCATION: (818)..(819)
<223> OTHER INFORMATION: n is unknown

<400> SEQUENCE: 47
nnnctggttn tgantactgt taangttgct actactgctg acaatgctgc tgctgcttct 60
cctnnctgtc tccacttcct tgaacaatgc gccgtcatgc ttcttttgcc tcccgctgct 120
ccagaaagct aggccgcaga tcagaaccac cacagtcaat atcaccacct tcctcttata 180
gattcggaat ctcatgatag gggctcagcc tctgtgcgag tggagagaag tttgcaggcg 240
agctgaggag caattgcagg tgatatgatg tgctcggctc aagaagcggg cccggagagg 300
aagaagtcgt gccggggcta attattggca aaacgagctc ttgttgtaaa cattgatcca 360
actggaatgt cactaatggc gaatcaatat tccataaggc atgatggttg ctcagaggca 420
ggagaagagc aacgaatacg atcctataaa agataaaaca taaataaaca gtcttgatta 480
tattctgggt attaaagcca caatcagaac aaatatatgc tttgtatctt ttcttgcctt 540
cttcattacc aactgcttcc gcggccacat taagagaact tgtggtaaga taagaagata 600
ttttattcgt tctgctgact tgctggatgt cgggaaatat tctgcatttg ataagaggcg 660
gttaattgca gatataattg gtagtgaaaa gggtcgttgc tatggtcacc gtgaagcgag 720
tacagcagca caagaatgtg tgccgttctc agnnnnnnnn nnnngaatat ggtaacctgt 780
tttagtcggt ttaaaggtaa gaagatctaa ccaaaaann 819

<210> SEQ ID NO 48
<211> LENGTH: 887
<212> TYPE: DNA
<213> ORGANISM: Artificial Sequence
<220> FEATURE:
<223> OTHER INFORMATION: S. cerevisiae PCR reaction /DNA sequence standard consensus sequence
<220> FEATURE:
<221> NAME/KEY: misc_feature
<222> LOCATION: (4)..(4)
<223> OTHER INFORMATION: n is unknown
<220> FEATURE:
<221> NAME/KEY: misc_feature
<222> LOCATION: (44)..(44)
<223> OTHER INFORMATION: n is unknown
<220> FEATURE:
<221> NAME/KEY: misc_feature
<222> LOCATION: (49)..(49)
<223> OTHER INFORMATION: n is unknown
<220> FEATURE:
<221> NAME/KEY: misc_feature
<222> LOCATION: (79)..(79)
<223> OTHER INFORMATION: n is unknown
<220> FEATURE:
<221> NAME/KEY: misc_feature
<222> LOCATION: (81)..(81)
<223> OTHER INFORMATION: n is unknown
<220> FEATURE:
<221> NAME/KEY: misc_feature
<222> LOCATION: (107)..(107)
<223> OTHER INFORMATION: n is unknown
<220> FEATURE:
<221> NAME/KEY: misc_feature
<222> LOCATION: (111)..(111)
<223> OTHER INFORMATION: n is unknown
<220> FEATURE:
<221> NAME/KEY: misc_feature
<222> LOCATION: (113)..(113)
<223> OTHER INFORMATION: n is unknown
<220> FEATURE:
<221> NAME/KEY: misc_feature
<222> LOCATION: (140)..(140)
<223> OTHER INFORMATION: n is unknown
<220> FEATURE:
<221> NAME/KEY: misc_feature
<222> LOCATION: (154)..(154)
<223> OTHER INFORMATION: n is unknown
<220> FEATURE:
<221> NAME/KEY: misc_feature
<222> LOCATION: (157)..(158)
<223> OTHER INFORMATION: n is unknown
<220> FEATURE:
<221> NAME/KEY: misc_feature
<222> LOCATION: (266)..(267)
<223> OTHER INFORMATION: n is unknown
<220> FEATURE:
<221> NAME/KEY: misc_feature
<222> LOCATION: (271)..(292)
<223> OTHER INFORMATION: n is unknown
<220> FEATURE:
<221> NAME/KEY: misc_feature
<222> LOCATION: (349)..(350)
<223> OTHER INFORMATION: n is unknown
<220> FEATURE:
<221> NAME/KEY: misc_feature
<222> LOCATION: (353)..(358)
<223> OTHER INFORMATION: n is unknown
<220> FEATURE:
<221> NAME/KEY: misc_feature
<222> LOCATION: (363)..(363)
<223> OTHER INFORMATION: n is unknown
<220> FEATURE:
<221> NAME/KEY: misc_feature
<222> LOCATION: (365)..(367)
<223> OTHER INFORMATION: n is unknown
<220> FEATURE:
<221> NAME/KEY: misc_feature
<222> LOCATION: (369)..(372)
<223> OTHER INFORMATION: n is unknown
<220> FEATURE:
<221> NAME/KEY: misc_feature
<222> LOCATION: (375)..(375)
<223> OTHER INFORMATION: n is unknown
<220> FEATURE:
<221> NAME/KEY: misc_feature
<222> LOCATION: (377)..(380)
<223> OTHER INFORMATION: n is unknown
<220> FEATURE:
<221> NAME/KEY: misc_feature
<222> LOCATION: (480)..(481)
<223> OTHER INFORMATION: n is unknown
<220> FEATURE:
<221> NAME/KEY: misc_feature
<222> LOCATION: (483)..(485)
<223> OTHER INFORMATION: n is unknown
<220> FEATURE:
<221> NAME/KEY: misc_feature
<222> LOCATION: (487)..(487)
<223> OTHER INFORMATION: n is unknown
<220> FEATURE:
<221> NAME/KEY: misc_feature
<222> LOCATION: (508)..(515)
<223> OTHER INFORMATION: n is unknown
<220> FEATURE:
<221> NAME/KEY: misc_feature
<222> LOCATION: (517)..(517)
<223> OTHER INFORMATION: n is unknown
<220> FEATURE:
<221> NAME/KEY: misc_feature
<222> LOCATION: (520)..(520)
<223> OTHER INFORMATION: n is unknown
<220> FEATURE:
<221> NAME/KEY: misc_feature
<222> LOCATION: (522)..(523)
<223> OTHER INFORMATION: n is unknown
<220> FEATURE:
<221> NAME/KEY: misc_feature
<222> LOCATION: (525)..(545)
<223> OTHER INFORMATION: n is unknown
<220> FEATURE:
<221> NAME/KEY: misc_feature
<222> LOCATION: (552)..(556)
<223> OTHER INFORMATION: n is unknown
<220> FEATURE:
<221> NAME/KEY: misc_feature
<222> LOCATION: (567)..(573)
<223> OTHER INFORMATION: n is unknown
<220> FEATURE:
<221> NAME/KEY: misc_feature
<222> LOCATION: (593)..(593)
<223> OTHER INFORMATION: n is unknown
<220> FEATURE:
<221> NAME/KEY: misc_feature
<222> LOCATION: (719)..(720)
<223> OTHER INFORMATION: n is unknown
<220> FEATURE:
<221> NAME/KEY: misc_feature
<222> LOCATION: (745)..(746)
<223> OTHER INFORMATION: n is unknown
<220> FEATURE:
<221> NAME/KEY: misc_feature
<222> LOCATION: (763)..(763)
<223> OTHER INFORMATION: n is unknown
<220> FEATURE:
<221> NAME/KEY: misc_feature
<222> LOCATION: (789)..(789)
<223> OTHER INFORMATION: n is unknown
<220> FEATURE:
<221> NAME/KEY: misc_feature
<222> LOCATION: (810)..(815)
<223> OTHER INFORMATION: n is unknown
<220> FEATURE:
<221> NAME/KEY: misc_feature
<222> LOCATION: (817)..(819)
<223> OTHER INFORMATION: n is unknown
<220> FEATURE:
<221> NAME/KEY: misc_feature
<222> LOCATION: (825)..(836)
<223> OTHER INFORMATION: n is unknown
<220> FEATURE:
<221> NAME/KEY: misc_feature
<222> LOCATION: (841)..(849)
<223> OTHER INFORMATION: n is unknown
<220> FEATURE:
<221> NAME/KEY: misc_feature
<222> LOCATION: (852)..(854)
<223> OTHER INFORMATION: n is unknown
<220> FEATURE:
<221> NAME/KEY: misc_feature
<222> LOCATION: (857)..(857)
<223> OTHER INFORMATION: n is unknown
<220> FEATURE:
<221> NAME/KEY: misc_feature
<222> LOCATION: (859)..(859)
<223> OTHER INFORMATION: n is unknown
<220> FEATURE:
<221> NAME/KEY: misc_feature
<222> LOCATION: (867)..(867)
<223> OTHER INFORMATION: n is unknown
<220> FEATURE:
<221> NAME/KEY: misc_feature
<222> LOCATION: (871)..(878)
<223> OTHER INFORMATION: n is unknown
<220> FEATURE:
<221> NAME/KEY: misc_feature
<222> LOCATION: (887)..(887)
<223> OTHER INFORMATION: n is unknown

<400> SEQUENCE: 48
ctgntaatgt tgctactact gctgacaatg ctgctgctgc ttcncctcnc tgtctccact 60
tccttgaaca atgcgccgnc ntgcttcttt tgcctcccgc tgctccngag ngntaggccg 120
cagatcagaa ccaccacagn caatatcacc accntcnnct tatagattcg gaatctcatg 180
ataggggctc agcctctgtg cgagtggaga gaagtttgca ggcgagctga ggagcaattg 240
caggtgatat gatgtgctcg gctcannggg nnnnnnnnnn nnnnnnnnnn nntgccgggg 300
ctaattattg gcaaaacgag ctcttgttgt aaacattgat ccaactggnn ggnnnnnnat 360
ggngnnngnn nntgncnnnn ggcatgatgg ttgctcagag gcaggagaag agcaacgaat 420
acgatcctat aaaagataaa acataaataa acagtcttga ttatattctg ggtattaaan 480
ncnnngncag aacaaatata tgctttgnnn nnnnncntgn cnncnnnnnn nnnnnnnnnn 540
nnnnnggcca cnnnnngaga acttgtnnnn nnntaagaag atattttatt cgntctgctg 600
acttgctgga tgtcgggaaa tattctgcat ttgataagag gcggttaatt gcagatataa 660
ttggtagtga aaagggtcgt tgctatggtc accgtgaagc gagtacagca gcacaagann 720
gtgtgccgtt ctcagttaat attgnntgaa tatggtaacc tgntttagtc ggtttaaagg 780
taagaaganc taaccaaaaa caacactgcn nnnnngnnng ggggnnnnnn nnnnnntact 840
nnnnnnnnnt tnnnggngna aacatcnacg nnnnnnnnca accaatn 887

<210> SEQ ID NO 49
<211> LENGTH: 687
<212> TYPE: DNA
<213> ORGANISM: Artificial Sequence
<220> FEATURE:
<223> OTHER INFORMATION: S. cerevisiae PCR reaction /DNA sequence
standard consensus sequence
<220> FEATURE:
<221> NAME/KEY: misc_feature
<222> LOCATION: (5)..(9)
<223> OTHER INFORMATION: n is unknown
<220> FEATURE:
<221> NAME/KEY: misc_feature
<222> LOCATION: (63)..(63)
<223> OTHER INFORMATION: n is unknown
<220> FEATURE:
<221> NAME/KEY: misc_feature
<222> LOCATION: (251)..(251)
<223> OTHER INFORMATION: n is unknown
<220> FEATURE:
<221> NAME/KEY: misc_feature
<222> LOCATION: (352)..(361)
<223> OTHER INFORMATION: n is unknown
<220> FEATURE:
<221> NAME/KEY: misc_feature
<222> LOCATION: (364)..(364)
<223> OTHER INFORMATION: n is unknown
<220> FEATURE:
<221> NAME/KEY: misc_feature
<222> LOCATION: (382)..(386)
<223> OTHER INFORMATION: n is unknown
<220> FEATURE:

<221> NAME/KEY: misc_feature
<222> LOCATION: (388)..(392)
<223> OTHER INFORMATION: n is unknown
<220> FEATURE:
<221> NAME/KEY: misc_feature
<222> LOCATION: (398)..(399)
<223> OTHER INFORMATION: n is unknown
<220> FEATURE:
<221> NAME/KEY: misc_feature
<222> LOCATION: (429)..(431)
<223> OTHER INFORMATION: n is unknown
<220> FEATURE:
<221> NAME/KEY: misc_feature
<222> LOCATION: (433)..(433)
<223> OTHER INFORMATION: n is unknown
<220> FEATURE:
<221> NAME/KEY: misc_feature
<222> LOCATION: (438)..(443)
<223> OTHER INFORMATION: n is unknown
<220> FEATURE:
<221> NAME/KEY: misc_feature
<222> LOCATION: (538)..(555)
<223> OTHER INFORMATION: n is unknown
<220> FEATURE:
<221> NAME/KEY: misc_feature
<222> LOCATION: (608)..(613)
<223> OTHER INFORMATION: n is unknown
<220> FEATURE:
<221> NAME/KEY: misc_feature
<222> LOCATION: (616)..(621)
<223> OTHER INFORMATION: n is unknown
<220> FEATURE:
<221> NAME/KEY: misc_feature
<222> LOCATION: (664)..(664)
<223> OTHER INFORMATION: n is unknown
<220> FEATURE:
<221> NAME/KEY: misc_feature
<222> LOCATION: (667)..(667)
<223> OTHER INFORMATION: n is unknown
<220> FEATURE:
<221> NAME/KEY: misc_feature
<222> LOCATION: (680)..(681)
<223> OTHER INFORMATION: n is unknown
<220> FEATURE:
<221> NAME/KEY: misc_feature
<222> LOCATION: (683)..(683)
<223> OTHER INFORMATION: n is unknown

<400> SEQUENCE: 49
cctgnnnnng attactgtta atgttgctac tactgctgac aatgctgctg ctgcttctcc 60
tcnctgtctc cacttccttg aacaatgcgc cgtcatgctt cttttgcctc ccgctgctcc 120
agaaagctag gccgcagatc agaaccacca cagtcaatat caccaccttc ctcttataga 180
ttcggaatct catgataggg gctcagcctc tgtgcgagtg gagagaagtt tgcaggcgag 240
ctgaggagca nttgcaggtg atatgatgtg ctcggctcaa gaagcgggcc cggagaggaa 300
gaagtcgtgc cggggctaat tattggcaaa acgagctctt gttgtaaaca tnnnnnnnnn 360
nggnatgtca ctaatggcga annnnnannn nntaaggnnt gatggttgct cagaggcagg 420
agaagagcnn ngnatacnnn nnnataaaag ataaaacata aataaacagt cttgattata 480
ttctgggtat taaagccaca atcagaacaa atatatgctt tgtatctttt cttgcctnnn 540
nnnnnnnnnn nnnnntccgc ggccacatta agagaacttg tggtaagata agaagatatt 600
ttattcgnnn nnntgnnnnn ntggatgtcg ggaaatattc tgcatttgat aagaggcggt 660
taantgnaga tataattggn ngngaaa 687

<210> SEQ ID NO 50
<211> LENGTH: 859
<212> TYPE: DNA
<213> ORGANISM: Artificial Sequence
<220> FEATURE:

<223> OTHER INFORMATION: S. enterica PCR reaction /DNA sequence standard
consensus sequence
<220> FEATURE:
<221> NAME/KEY: misc_feature
<222> LOCATION: (18)..(18)
<223> OTHER INFORMATION: n is unknown
<220> FEATURE:
<221> NAME/KEY: misc_feature
<222> LOCATION: (29)..(29)
<223> OTHER INFORMATION: n is unknown
<220> FEATURE:
<221> NAME/KEY: misc_feature
<222> LOCATION: (108)..(108)
<223> OTHER INFORMATION: n is unknown
<220> FEATURE:
<221> NAME/KEY: misc_feature
<222> LOCATION: (197)..(203)
<223> OTHER INFORMATION: n is unknown
<220> FEATURE:
<221> NAME/KEY: misc_feature
<222> LOCATION: (257)..(257)
<223> OTHER INFORMATION: n is unknown
<220> FEATURE:
<221> NAME/KEY: misc_feature
<222> LOCATION: (260)..(262)
<223> OTHER INFORMATION: n is unknown
<220> FEATURE:
<221> NAME/KEY: misc_feature
<222> LOCATION: (264)..(266)
<223> OTHER INFORMATION: n is unknown
<220> FEATURE:
<221> NAME/KEY: misc_feature
<222> LOCATION: (271)..(282)
<223> OTHER INFORMATION: n is unknown
<220> FEATURE:
<221> NAME/KEY: misc_feature
<222> LOCATION: (313)..(323)
<223> OTHER INFORMATION: n is unknown
<220> FEATURE:
<221> NAME/KEY: misc_feature
<222> LOCATION: (325)..(335)
<223> OTHER INFORMATION: n is unknown
<220> FEATURE:
<221> NAME/KEY: misc_feature
<222> LOCATION: (339)..(344)
<223> OTHER INFORMATION: n is unknown
<220> FEATURE:
<221> NAME/KEY: misc_feature
<222> LOCATION: (346)..(347)
<223> OTHER INFORMATION: n is unknown
<220> FEATURE:
<221> NAME/KEY: misc_feature
<222> LOCATION: (357)..(357)
<223> OTHER INFORMATION: n is unknown
<220> FEATURE:
<221> NAME/KEY: misc_feature
<222> LOCATION: (360)..(361)
<223> OTHER INFORMATION: n is unknown
<220> FEATURE:
<221> NAME/KEY: misc_feature
<222> LOCATION: (385)..(390)
<223> OTHER INFORMATION: n is unknown
<220> FEATURE:
<221> NAME/KEY: misc_feature
<222> LOCATION: (396)..(398)
<223> OTHER INFORMATION: n is unknown
<220> FEATURE:
<221> NAME/KEY: misc_feature
<222> LOCATION: (400)..(401)
<223> OTHER INFORMATION: n is unknown
<220> FEATURE:
<221> NAME/KEY: misc_feature
<222> LOCATION: (494)..(498)
<223> OTHER INFORMATION: n is unknown
<220> FEATURE:
<221> NAME/KEY: misc_feature
<222> LOCATION: (510)..(517)
<223> OTHER INFORMATION: n is unknown
<220> FEATURE:
<221> NAME/KEY: misc_feature
<222> LOCATION: (519)..(519)
<223> OTHER INFORMATION: n is unknown
<220> FEATURE:
<221> NAME/KEY: misc_feature
<222> LOCATION: (528)..(528)
<223> OTHER INFORMATION: n is unknown
<220> FEATURE:
<221> NAME/KEY: misc_feature
<222> LOCATION: (613)..(618)
<223> OTHER INFORMATION: n is unknown
<220> FEATURE:
<221> NAME/KEY: misc_feature
<222> LOCATION: (714)..(719)
<223> OTHER INFORMATION: n is unknown
<220> FEATURE:
<221> NAME/KEY: misc_feature
<222> LOCATION: (736)..(736)
<223> OTHER INFORMATION: n is unknown
<220> FEATURE:
<221> NAME/KEY: misc_feature
<222> LOCATION: (759)..(768)
<223> OTHER INFORMATION: n is unknown
<220> FEATURE:
<221> NAME/KEY: misc_feature
<222> LOCATION: (776)..(776)
<223> OTHER INFORMATION: n is unknown
<220> FEATURE:
<221> NAME/KEY: misc_feature
<222> LOCATION: (792)..(792)
<223> OTHER INFORMATION: n is unknown
<220> FEATURE:
<221> NAME/KEY: misc_feature
<222> LOCATION: (796)..(796)
<223> OTHER INFORMATION: n is unknown
<220> FEATURE:
<221> NAME/KEY: misc_feature
<222> LOCATION: (799)..(800)
<223> OTHER INFORMATION: n is unknown
<220> FEATURE:
<221> NAME/KEY: misc_feature
<222> LOCATION: (815)..(825)
<223> OTHER INFORMATION: n is unknown
<220> FEATURE:
<221> NAME/KEY: misc_feature
<222> LOCATION: (839)..(839)
<223> OTHER INFORMATION: n is unknown
<220> FEATURE:
<221> NAME/KEY: misc_feature
<222> LOCATION: (847)..(847)
<223> OTHER INFORMATION: n is unknown

<400> SEQUENCE: 50
gctgacaatg ctgctgcngc ttctcctcnc tgtctccact tccttgaaca atgcgccgtc 60
atgcttcttt tgcctcccgc tgctccagaa agctaggccg cagatcanaa ccaccacagt 120
caatatcacc accttcctct tatagattcg gaatctcatg ataggggctc agcctctgtg 180
cgagtggaga gaagttnnnn nnngagctga ggagcaattg caggtgatat gatgtgctcg 240
gctcaagaag cgggccnggn nngnnngaag nnnnnnnnnn nntaattatt ggcaaaacga 300
gctcttgttg tannnnnnnn nnngnnnnnn nnnnnactnn nnnngnncaa tattccntan 360
ngcatgatgg ttgctcagag gcagnnnnnn agcaannnan ncgatcctat aaaagataaa 420
acataaataa acagtcttga ttatattctg ggtattaaag ccacaatcag aacaaatata 480
tgctttgtat cttnnnnngc cttcttcatn nnnnnnngnt tccgcggnca cattaagaga 540
acttgtggta agataagaag atattttatt cgttctgctg acttgctgga tgtcgggaaa 600
tattctgcat ttnnnnnnag gcggttaatt gcagatataa ttggtagtga aaagggtcgt 660
tgctatggtc accgtgaagc gagtacagca gcacaagaat gtgtgccgtt ctcnnnnnnt 720
attgtttgaa tatggnaacc tgttttagtc ggtttaaann nnnnnnnntc taaccnaaaa 780
caacactgca gngacngann gtagtattta ttttnnnnnn nnnnncttaa ttttggtgna 840
aacatcnacg gcgcacttc 859

<210> SEQ ID NO 51
<211> LENGTH: 843
<212> TYPE: DNA
<213> ORGANISM: Artificial Sequence
<220> FEATURE:
<223> OTHER INFORMATION: S. enterica PCR reaction /DNA sequence standard consensus sequence
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (4)..(4)
<223> OTHER INFORMATION: n is unknown
<220> FEATURE:
<221> NAME/KEY: misc_feature
<222> LOCATION: (16)..(18)
<223> OTHER INFORMATION: n is unknown
<220> FEATURE:
<221> NAME/KEY: misc_feature
<222> LOCATION: (58)..(59)
<223> OTHER INFORMATION: n is unknown
<220> FEATURE:
<221> NAME/KEY: misc_feature
<222> LOCATION: (371)..(380)
<223> OTHER INFORMATION: n is unknown
<220> FEATURE:
<221> NAME/KEY: misc_feature
<222> LOCATION: (496)..(508)
<223> OTHER INFORMATION: n is unknown
<220> FEATURE:
<221> NAME/KEY: misc_feature
<222> LOCATION: (524)..(528)
<223> OTHER INFORMATION: n is unknown
<220> FEATURE:
<221> NAME/KEY: misc_feature
<222> LOCATION: (530)..(530)
<223> OTHER INFORMATION: n is unknown
<220> FEATURE:
<221> NAME/KEY: misc_feature
<222> LOCATION: (602)..(608)
<223> OTHER INFORMATION: n is unknown
<220> FEATURE:
<221> NAME/KEY: misc_feature
<222> LOCATION: (675)..(684)
<223> OTHER INFORMATION: n is unknown
<220> FEATURE:
<221> NAME/KEY: misc_feature
<222> LOCATION: (686)..(686)
<223> OTHER INFORMATION: n is unknown
<220> FEATURE:
<221> NAME/KEY: misc_feature
<222> LOCATION: (717)..(717)
<223> OTHER INFORMATION: n is unknown
<220> FEATURE:
<221> NAME/KEY: misc_feature
<222> LOCATION: (736)..(747)
<223> OTHER INFORMATION: n is unknown
<220> FEATURE:
<221> NAME/KEY: misc_feature
<222> LOCATION: (755)..(755)
<223> OTHER INFORMATION: n is unknown
<220> FEATURE:
<221> NAME/KEY: misc_feature
<222> LOCATION: (783)..(783)
<223> OTHER INFORMATION: n is unknown
<220> FEATURE:
<221> NAME/KEY: misc_feature
<222> LOCATION: (806)..(806)
<223> OTHER INFORMATION: n is unknown
<220> FEATURE:
<221> NAME/KEY: misc_feature
<222> LOCATION: (832)..(832)
<223> OTHER INFORMATION: n is unknown
<220> FEATURE:

-continued

```
<221> NAME/KEY: misc_feature
<222> LOCATION: (838)..(843)
<223> OTHER INFORMATION: n is unknown

<400> SEQUENCE: 51

nttntgatta ctgttnnngt tgctactact gctgacaatg ctgctgctgc ttctcctnnc      60

tgtctccact tccttgaaca atgcgccgtc atgcttcttt tgcctcccgc tgctccagaa     120

agctaggccg cagatcagaa ccaccacagt caatatcacc accttcctct tatagattcg     180

gaatctcatg ataggggctc agcctctgtg cgagtggaga gaagtttgca ggcgagctga     240

ggagcaattg caggtgatat gatgtgctcg gctcaagaag cgggcccgga gaggaagaag     300

tcgtgccggg gctaattatt ggcaaaacga gctcttgttg taaacattga tccaactgga     360

atgtcactaa nnnnnnnnnn tattccataa ggcatgatgg ttgctcagag gcaggagaag     420

agcaacgaat acgatcctat aaaagataaa acataaataa acagtcttga ttatattctg     480

ggtattaaag ccacannnnn nnnnnnnnta tgctttgtat cttnnnnngn cttcttcatt     540

accaactgct tccgcggcca cattaagaga acttgtggta agataagaag atattttatt     600

cnnnnnnntg acttgctgga tgtcgggaaa tattctgcat ttgataagag gcggttaatt     660

gcagatataa ttggnnnnnn nnnngntcgt tgctatggtc accgtgaagc gagtacngca     720

gcacaagaat gtgtgnnnnn nnnnnnnaat attgnttgaa tatggtaacc tgttttagtc     780

ggnttaaagg taagaagatc taaccnaaaa caacactgca gtgactgatt gnagtatnnn     840

nnn                                                                   843
```